US006410516B1

(12) United States Patent
Baltimore et al.

(10) Patent No.: US 6,410,516 B1
(45) Date of Patent: Jun. 25, 2002

(54) NUCLEAR FACTORS ASSOCIATED WITH TRANSCRIPTIONAL REGULATION

(75) Inventors: David Baltimore, New York, NY (US); Ranjan Sen, Cambridge; Phillip A. Sharp, Newton, both of MA (US); Harinder Singh, Chicago, IL (US); Louis Staudt, Silver Springs, MD (US); Jonathan H. Lebowitz, Zionsville, IN (US); Albert S. Baldwin, Jr., Chapel Hill, NC (US); Roger G. Clerc, Binningen (CH); Lynn M. Corcoran, Port Melbourne (AU); Patrick A. Baeuerle, Eichenau (DE); Michael J. Lenardo, Potomac, MD (US); Chen-Ming Fan, San Francisco; Thomas P. Maniatis, Belmont, both of MA (US)

(73) Assignees: President & Fellows of Harvard College; Massachusetts Institute of Technology; Whitehead Instittue for Biomedical Research, all of Cambridge, MA (US)

( * ) Notice: Subject to any disclaimer, the term of this patent is extended or adjusted under 35 U.S.C. 154(b) by 0 days.

(21) Appl. No.: 08/464,364

(22) Filed: Jun. 5, 1995

Related U.S. Application Data

(60) Division of application No. 08/418,266, filed on Apr. 6, 1995, now Pat. No. 5,804,374, which is a continuation of application No. 07/791,898, filed on Nov. 13, 1991, now abandoned, which is a continuation-in-part of application No. 06/946,365, filed on Dec. 24, 1986, now abandoned, application No. 08/418,266, which is a continuation-in-part of application No. 07/341,436, filed on Apr. 21, 1989, now abandoned, and a continuation-in-part of application No. 07/318,901, filed on Mar. 3, 1989, now abandoned, and a continuation-in-part of application No. 07/280,173, filed on Dec. 5, 1988, now abandoned, and a continuation-in-part of application No. 07/162,680, filed on Mar. 1, 1988, now abandoned, and a continuation-in-part of application No. 07/155,207, filed on Feb. 12, 1988, now abandoned, and a continuation-in-part of application No. 06/817,441, filed on Jan. 9, 1986, now abandoned.

(51) Int. Cl.[7] .................. A61K 31/711; C12N 5/10; C12N 15/10

(52) U.S. Cl. ............... 514/44; 435/6; 435/455; 435/325; 435/366; 435/370; 435/372; 435/372.2; 435/372.3

(58) Field of Search .................. 435/6, 172.3, 455, 435/325, 366, 370, 372, 372.2, 372.3; 514/2, 44; 935/34, 36

(56) References Cited

FOREIGN PATENT DOCUMENTS

WO 87/04170 7/1987

OTHER PUBLICATIONS

Gosh, S. and Baltimore, D., "Activation in vitro of NF–kB by phosphorylation of its inhibitor IkB," Nature, 344(6267): 678–682 (1990).

Zabel, U. and Baeurle, P., "Purified Human IkB Can Rapidly Dissociate the Complex of the NF kB Transcription Factor with it Cognate DNA," Cell, 61:255–265 (1990).

Haskill, S., et al., "Characterization of an Immediate–Early Gene Induced in Adherent Monocytes That Encodes IkB–like Activity," Cell, 65:1281–1289 (1991).

Baldwin, Jr., A.S., and Sharp, P.A., "Two transcription factors, NF–kB and H2TF1, interact with a single regulatory sequence in the class I major histocompatability complex promotor," Proc. Natl. Acad. Sci, USA, 85:723–727 (1988).

Böhnlein, E.,, et al., "The Same Inducible Nuclear Proteins Regulates Mitogen Activation of Both the Interleukin–2 Receptor–Alpha Gene and Type 1 HIV," Cell, 53:827–836 (1988).

Leung, K. and Nable, G.J., "HTLV–1 transactivator induces interleukin–2 receptor expression through an NF–kB–like factor," Nature, 333:776–778 (1988).

Ruben, S., et al., "Cellular Transcription Factors and Regulation of IL–2 Receptor Gene Expression by HTLV–1 tax Gene Product," Science, 241:89–92 (1988).

Lenardo, J.J., et al., "NF–kB protein purification from bovine spleen: Nucleotide stimulation and binding site specificity," Prod. Natl. Acad. Sci. USA, 85:8825–8829 (1988).

Wirth, T. and Baltimore, D., "Nuclear factor NF–kB can interact functionally with its cognate binding site to provide lymphoid–specific promotor function," The EMBO Journal, 7 (10):3109–3113 (1988).

Nelsen, B., et al., "The NF–kB–Binding Site Mediates Phorbol Ester–Inducible Transcription in Nonlymphoid Cells," Mol. & Cell Biol., 8:3526–3531 (1988).

Ballard, D.W., et al., "HTLV–I Tax Induces Cellular Proteins That Activate the kB Element in the IL–2 Receptor a Gene," Science, 241:1652–1657 (1988).

Blanar, M.A., et al., "Nf–kB Binds within a Region Required for B–Cell–Specific Expression of the Major Histocompatibility Complex Class II Gene Ead," Mol. & Cell. Biol., 9 (2):844–846.

Karin, M., et al., "Activation of a Heterologous Promoter in Response to Dexamethasone and Cadmium by Metallothionein Gene 5'Flanking DNA," Cell, 36:371–379 (1984).

(List continued on next page.)

*Primary Examiner*—David Guzo
(74) *Attorney, Agent, or Firm*—David L. Berstein; Matthew P. Vincent; Ropes & Gray

(57) ABSTRACT

Constitutive and tissue-specific protein factors which bind to transcriptional regulatory elements of Ig genes (promoter and enhancer) are described. The factors were identified and isolated by an improved assay for protein-DNA binding. Genes encoding factors which positively regulate transcription can be isolated and employed to enhance transription of Ig genes. In particular, NF-kB, the gene encoding NF-kB, IkB and the gene encoding IkB and uses therefor.

203 Claims, 58 Drawing Sheets

OTHER PUBLICATIONS

Davis, N., et al., "Rel–Associated pp40: An Inhibitor of the Rel Family of Transcription Factors," *Science* 253:1268–1271 (1991).

Treisman, R., "Transient Accumulation of c–fos RNA Following Serum Stimulation Requires a Conserved 5'Element and c–fos 3' Sequences," *Cell, 42*:889–902 (1985).

Queen, C. and Stafford, J., "Fine Mapping of an Immunoglobulin Gene Activator," *Mol. Cel. Biol., 4*(6):1042–1049 (1984).

Nelson, K. J., et al., "Inducible transcription of the unrearranged κ constant region locus is a common feature of pre–B cells and does not require DNA or protein synthesis," *Proc. Natl. Acad. Sci. USA, 82*:5305–5309 (1985).

Foster, J., et al., "An immunoglobulin promoter displays cell–type specificity independently of the enhancer," *Nature, 315*:423–425 (1985).

Ko, H.–S., et al., "A Human Protein Specific for the Immunoglobulin Octamer DNA Motif Contains a Functional Homeobox Domain," *Cell, 55*:135–144 (1988).

Sen, R. and Baltimore, D., "Multiple Nuclear Factors Interact with the Immunoglobulin Enhancer Sequences," *Cell, 46*:705–716 (1986).

Nabel, G. and Baltimore, D., An inducible transcription factor activates expression of human immunodeficiency virus in T cells, *Nature, 326*:711–713 (1987).

Baeuerle, P.A and Baltimore, D., "IκB: A Specific Inhibitor of the NF–κB Transcription Factor," *Science, 242*:540–546 (1988).

Baeuerle, P.A. and Baltimore, D., "Activation of DNA–Binding Activity in an Apparently Cytoplasmic Precursor of the NF–κB Transcription Factor," *Cell, 53*:211–217 (1988).

Baeurle, P.A. and Baltimore, D., "Activation of NF–κB: A Transcription Factor Controlling Expression of the Immunoglobuli κ Light–chain Gene and of HIV," *The Control of Human Retrovirus Gene Expression,* Banbury Conference, Cold Spring Harbor, NY, pp.: 217–226 (1988).

Sen, R. and Baltimore, D., Inducibility of κ Immunoglobulin Enhancer–Binding Protein NF–κB by a Posttranslational Mechanism, *Cell, 47*:921–928 (1986).

Wall, R., et al., "A labile inhibitor blocks immunoglobulin κ–light–chain–gene transcription in a pre–B leukemic cell line," *Proc. Natl. Acad. Sci. USA, 83*:295–298 (1986).

Lenardo, M., et al., "Protein–Binding Sites in Ig Gene Enhancers Determine Transcriptional Activity and Inducibility," *Science, 236*:1573–1577 (1987).

Cross, S. L., et al., "Functionally Distinct NF–κB Binding Sites in the Immunoglobulin κ and IL–2 Receptor α Chain Genes," *Science, 244*:466–469 (1989).

Kawakami, K., et al., "Identification and purification of a human immunoglobulin–enhancer–binding protein (NF–κB) that activates transcription from a human immunodeficiency virus type 1 promoter in vitro," *Proc. Natl. Acad. Sci. USA, 85*:4700–4704 (1988).

Goodbourn, S., et al., "Human β–Interferon Gene Expression Is Regulated by an Inducible Enhancer Element," *Cell, 41*:509–520 (1985).

Bergman, Y., et al., "Two regulatory elements for immunoglobulin κ light chain gene expression," *Proc. Natl. Acad. Sci. USA, 81*:7041–7045 (1984).

Mason, J. O., et al., "Transcription Cell Type Specificity Is Conferred by an Immunoglobulin $V_H$ Gene Promoter That Includes a Functional Consensus Sequence," *Cell, 41*:479–487 (1985).

Fried, M. and Crothers, D. M., "Equilibria and kinetics of lac repressor–operator interactions by polyacrylamide gel electrophoresis," *Nucleic Acids Research, 9*(23):6505–6524 (1981).

Garner, M. M. and Revzin, A., "A gel electrophoresis method for quantifying the binding of proteins to specific DNA regions: application to components of the *Escherichia coli* lactose operon regulatory system," *Nucleic Acids Research, 9*(13):3047–3060 (1981).

Strauss, F. and Varshavsky, A., "A Protein Binds to a Satellite DNA Repeat at Three Specific Sites That Would be Brought into Mutualy Proximity by DNA Folding in the Nucleosome," *Cell, 37*:889–901 (1984).

Grosschedi, R. and Baltimore, D., "Cell–Type Specificity of Immunoglobulin Gene Expression is Regulated by at Least Three DNA Sequence Elements," *Cell, 41*:885–897 (1985).

Banerji, J., et al., "A Lymphocyte–Specific Cellular Enhancer Is Located Downstream of the Joining Region in Immunoglobulin Heavy Chain Genes," *Cell, 33*:729–740 (1983).

Queen, C. and Baltimore, D., "Immunoglobulin Gene Transcription Is Activated by Downstream Sequence Elements," *Cell, 33*:741–748 (1983).

Church, G. M., et al., "Cell–type–specific contacts to immunoglobulin enhancers in nuclei," *Nature, 313*:798–801 (1985).

Gerster, T., et al., "Cell type–specificity elements of the immunoglobulin heavy chain gene enhancer," *EMBO Journal, 6*(5):1323–1330 (1987).

Landolfi, N. F., et al., "Interaction of cell–type–specific nuclear proteins with immunoglobulin $V_H$ promoter region sequences," *Nature, 323*:548–551 (1986).

Staudt, L. M., et al., "A Lymphoid–specific protein binding to the octamer motif of immunoglobulin genes," *Nature, 323*:640–643 (1986).

Fletcher, C., et al., "Purification and Characterizaiton of OTF–1, a Transcription Factor Regulating Cell Cycle Expression of a Human Histone H2b Gene," *Cell, 51*:773–781 (1987).

Scheidereit, C., et al., "Identification and Purification of a Human Lymphoid–Specific Octamer–Binding Protein (OTF–2) That Activates Transcription of an Immunoglobulin Promoter In Vitro," *Cell, 51*:783–793 (1987).

Sassone–Corsi, P., et al., "A trans–acting factor is responsible for the simian virus 40 enhancer activity in vitro," *Nature, 313*:458–463 (1985).

Singh, H., et al., "A nuclear factor that binds to a conserved sequence motif in transcriptional control elements of immunoglobulin genes," *Nature, 319*:154–158 (1986).

Baldwin, A. and Sharp, P., et al., "Binding of a Nuclear Factor to a Regulatory Sequence in the Promoter of the Mouse H–2K$^b$ Class I Major Histocompatibility Gene," *Mol. & Cell. Biol., 7*(1):305–313 (1987).

Mercola, M., et al., "Transcriptional Enhancer Elements in the Mouse Immunoglobulin Heavy Chain Locus," *Science, 221*:663–665 (1983).

Picard, D. and Schaffner, W., "A lymphocyte–specific enhancer in the mouse immunoglobulin κ gene," *Nature, 307*:80–82 (1984).

Mercola, M., et al., "Immunoglobulin Heavy–Chain Enhancer Requires One or More Tissue–Specific Factors," *Science, 227*:266–270 (1985).

Staudt, L., et al., "Cloning of a Lymphoid–Specific cDNA Encoding a Protein Binding the Regulatory Octamer DNA Motif," *Science, 241:*577–580 (1988).

Wu et al. (1988) Purification of the human immunodeficiency virus type 1 enhancer and TAR binding protiens EBP–1 and UBP–1, EMBO J. 7:2117–2129.*

Leonard et al. (1985) Interleukin 2 receptor gene expression in normal human T lymphocytes. Proc. Natl. Acad. Sci. USA 82:6281–6285.*

Johnston et al. (1993) Present Status and future prospects for HIV therapies. Science 260:1286–1293.*

* cited by examiner

Figure 9A
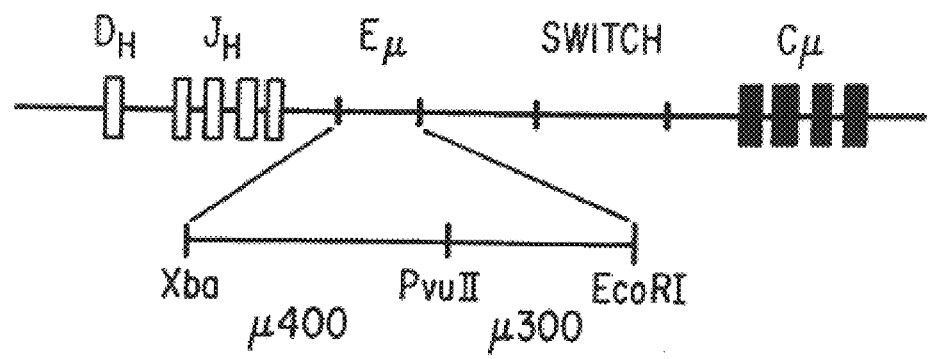
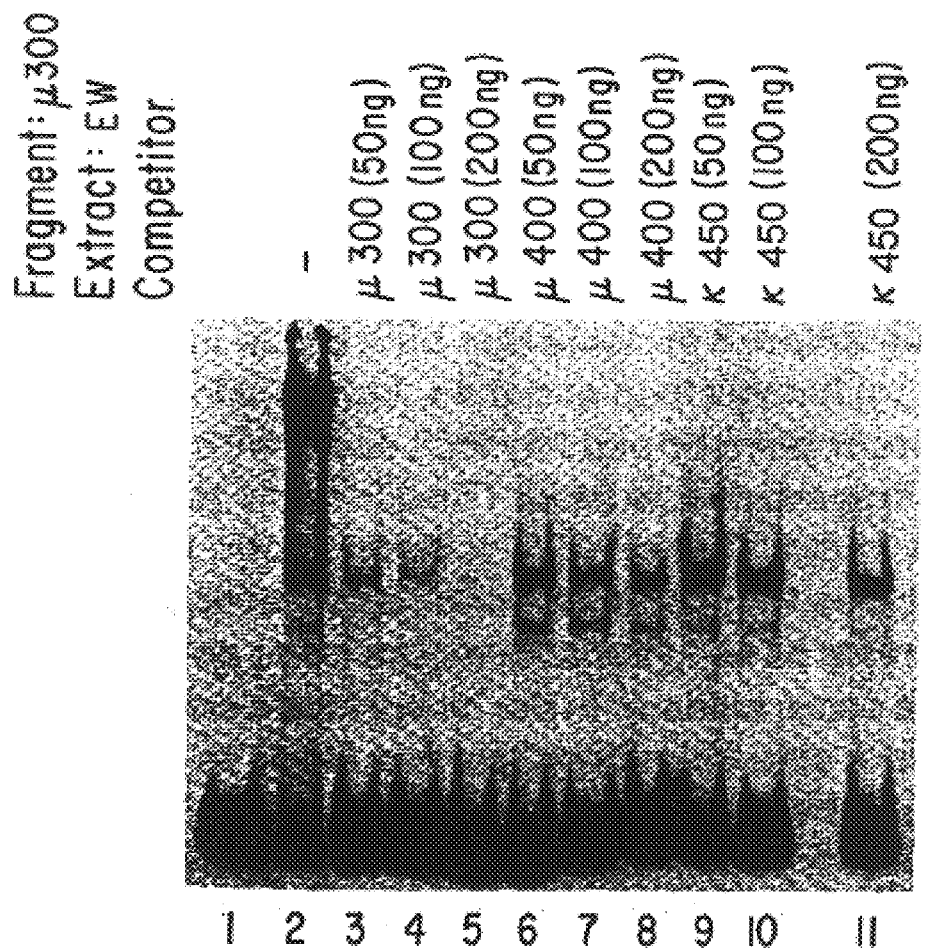
Figure 9B

```
    CTGGGGCCCCCAGAGAGGGTGGGGAGATGACACAGTTGTTCCCCCAGCCCTGGCGGGGCG
  1 ---------+---------+---------+---------+---------+---------+

GGCAGCATGGTTCACTCCAGCATGGGGGCTCCAGAAATAAGAATGTCTAAGCCCCTGGAG
 61 ---------+---------+---------+---------+---------+---------+
          M  V  H  S  S  M  G  A  P  E  I  R  M  S  K  P  L  E

GCCGAGAAGCAAGGTCTGGACTCCCCATCAGAGCACACAGACACCGAAAGAAATGGACCA
121 ---------+---------+---------+---------+---------+---------+
     A  E  K  Q  G  L  D  S  P  S  E  M  T  D  T  E  R  N  G  P

GACACTAATCATCAGAACCCCCAAAATAAGACCTCCCCATTCTCCGTGTCCCCAACTGGC
181 ---------+---------+---------+---------+---------+---------+
     D  T  N  H  Q  N  P  Q  N  R  T  S  P  F  S  V  S  P  T  G

CCCAGTACAAAGATCAAGGCTGAAGACCCCAGTGGCGATTCAGCCCCAGCAGCACCCCTG
241 ---------+---------+---------+---------+---------+---------+
     P  S  T  K  I  K  A  E  D  P  S  G  D  S  A  P  A  A  P  L

CCCCCTCAGCCGGCCCAGCCTCATCTGCCCCAGGCCCAACTCATGTTGACGGGCAGCCAG
301 ---------+---------+---------+---------+---------+---------+
     P  P  Q  P  A  Q  P  N  L  P  Q  A  Q  L  M  L  T  G  S  Q

CTAGCTGGGGACATACAGCAGCTCCTCCAGCTCCAGCAGCTGGTGCTTGTGCCAGGCCAC
361 ---------+---------+---------+---------+---------+---------+
     L  A  G  D  I  Q  Q  L  L  Q  L  Q  Q  L  V  L  V  P  G  H

CACCTCCAGCCACCTGCTCAGTTCCTGCTACCGCAGGCCCAGCAGAGCCAGCCAGGCCTG
421 ---------+---------+---------+---------+---------+---------+
     H  L  Q  P  P  A  Q  F  L  L  P  Q  A  Q  Q  S  Q  P  G  L

CTACCGACACCAAATCTATTCCAGCTACCTCAGCAAACCCAGGGAGCTCTTCTGACCTCC
481 ---------+---------+---------+---------+---------+---------+
     L  P  T  P  H  L  F  Q  L  P  Q  Q  T  Q  G  A  L  L  T  S

CAGCCCCGGGCCGGGCTTCCCACACAGGCCGTGACCCGCCCTACGCTGCCCGACCCGCAC
541 ---------+---------+---------+---------+---------+---------+
     Q  P  R  A  G  L  P  T  Q  A  V  T  R  P  T  L  P  D  P  H

CTCTCGCACCCGCAGCCCCCCAAATGCTTGGAGCCACCATCCCACCCCGAGGAGCCCAGT
601 ---------+---------+---------+---------+---------+---------+
     L  S  H  P  Q  P  P  K  C  L  E  P  P  S  H  P  E  E  P  S

GATCTGGAGGAGCTGGAGCAATTGGCCCGCACCTTCAAGCAACGCCGCATCAAGCTGGGC
661 ---------+---------+---------+---------+---------+---------+
     D  L  E  E  L  E  Q  F  A  R  T  F  K  Q  R  R  I  K  L  G

TTCACGCAGGGTGATGTGGGCCTGGCCATGGGCAAGCTCTACGCCAACGACTTCAGCCAG
721 ---------+---------+---------+---------+---------+---------+
     F  T  Q  G  D  V  G  L  A  M  G  K  L  Y  A  N  D  F  S  Q
        C  G  P  G  H  G  Q  A  L  R  Q  R  L  Q  P  D
```

Fig. 18A

```
        ACGACCATTTCCCGCTTCGAGGCCCTCAACCTGAGCTTCAAGAACATGTGCAAACTCAAG
781     ----------+---------+---------+---------+---------+---------+
         T  T  I  S  R  F  E  A  L  N  L  S  F  K  N  M  C  K  L  K
           D  H  F  P  L  R  G  P  Q  P  E  L  Q  E  H  V  Q  T  Q  A

CCCCTCCTGGAGAAGTGGCTCAACGATGCAGAGACTATGTCTGTGGACTCAAGCCTGCCC
841     ----------+---------+---------+---------+---------+---------+
         P  L  L  E  K  W  L  N  D  A  E  T  M  S  V  D  S  S  L  P
           P  P  G  E  V  A  Q  R  C  R  D  Y  V  C  G  L  K  P  A  Q

AGCCCCAACCAGCTGAGCAGCCCCAGCCTGGGTTTCGAGCCTGCCGGCCGGAGACGCAAG
901     ----------+---------+---------+---------+---------+---------+
         S  P  N  Q  L  S  S  P  S  L  G  F  E  P  A  G  R  R  R  K
           P  Q  P  A  E  Q  P  Q  P  G  F  R  A  C  M  P  E  T  Q  E

AAGAGGACCAGCATCGAGACAAACGTCCGCTTCGCCTTAGAGAAGAGTTTTCTAGCGAAC
961     ----------+---------+---------+---------+---------+---------+
         K  R  T  S  I  E  T  N  V  R  F  A  L  E  K  S  F  L  A  N
           E  D  Q  M  R  D  K  R  P  L  R  L  R  E  E  F  S  S  E  P

CAGAAGCCTACCTCAGAGGAGATCCTGCTGATCGCCGAGCAGCTGCACATGGAGAAGGAA
1021    ----------+---------+---------+---------+---------+---------+
         Q  K  P  T  S  E  E  I  L  L  I  A  E  Q  L  H  M  E  K  E
           E  A  Y  L  R  G  D  P  A  D  R  R  A  A  A  H  G  E  G  S

GTGATCCGCGTCTGGTTCTGCAACCGGCCCCAGAAGGACAAACGCATCAACCCCTGCAGT
1081    ----------+---------+---------+---------+---------+---------+
         V  I  R  V  W  F  C  N  R  R  Q  K  E  K  R  I  H  P  C  S
           D  P  R  L  V  L  Q  P  A  P  E  G  E  T  H  Q  P  L  Q  C

GCGGCCCCCATGCTGCCCAGCCCAGGGAAGCCGGCCAGCTACAGCCCCCATATGGTCACA
1141    ----------+---------+---------+---------+---------+---------+
         A  A  P  M  L  P  S  P  G  K  P  A  S  Y  S  P  H  M  V  T
           G  P  H  A  A  Q  P  R  E  A  G  Q  L  Q  P  P  Y  G  H  T

CCCCAAGGCGGCGCGGGGACCTTACCGTTGTCCCAAGCTTCCAGCAGTCTGAGCACAACA
1201    ----------+---------+---------+---------+---------+---------+
         P  Q  G  G  A  G  T  L  P  [L] S  Q  A  S  S  S  [L] S  T  T
           P  A  G  R  G  D  L  T  V  V  P  S  F  Q  Q  S  E  H  N  S
```

Fig. 18A
(CONTINUED)

```
       GTTACTACCTTATCCTCAGCTGTGGGGACGCTCCACCCCAGCCGGACAGCTGGAGGGGGT
1261   ------------+---------+---------+---------+---------+---------+
       V  T  T [L] S  S  A  V  G  T [L] H  P  S  R  T  A  G  G  G
         Y  Y  L  I  L  S  C  G  D  A  P  P  Q  P  D  S  N  M  G  W

GGGGGCGGGGGCGGGGCTGCGCCCCCCCTCAATTCCATCCCCTCTGTCACTCCCCCACCC
1321   ------------+---------+---------+---------+---------+---------+
       G  G  G  G  A  A  P  P  L  N  S  I  P  S  V  T  P  P  P
         G  M  G  R  G  C  A  P  P  Q  F  H  P  L  C  H  S  P  T  P

CCGGCCACCACCAACAGCACAAACCCCAGCCCTCAAGGCAGCCACTCGGCTATCGGCTTG
1381   ------------+---------+---------+---------+---------+---------+
       P  A  T  T  N  S  T  N  P  S  P  Q  G  S  H  S  A  I  G  L
         G  H  N  Q  Q  H  K  P  Q  P  S  R  Q  P  L  G  Y  M  L  V

TCAGGCCTGAACCCCAGCACGGGGTAAGTGGGTGCACGTGGGAAGCTGTGGGGAGAAGCA
1441   ------------+---------+---------+---------+---------+---------+
       S  G  L  H  P  S  T  G  +
         A  P  E  P  Q  N  G  V  S  G  C  T  W  E  A  V  G  R  S  R

GCGTCGCTGCTCCTTCTAGGGTGGGGAGCGGCACCCCAGTTATGTTGGCAGGTCCCTGCC
1501   ------------+---------+---------+---------+---------+---------+
         V  A  A  A  S  R  V  G  S  G  T  P  V  M  L  A  G  P  C  P

CCTGCTAATGCCTCTGCTTTGCCTCTTGCAGAAGCACAATGGTGGGGTTGAGCTCCGGCT
1561   ------------+---------+---------+---------+---------+---------+
         C  +

GAGTCCAGCCCTCATGAGCAACAACCCTTTGGCCACTATCCAAGGTGCGTGCTGCCTCAT
1621   ------------+---------+---------+---------+---------+---------+

GTCACACCCATCGTCACCAGCCCCGGAATTCGAG
1681   ------------+---------+----
```

Fig. 18A
(CONTINUED)

```
      CCTCAAGGCAGCCACTCGGCTATCGGCTTGTCAGGCCTGAACCCCAGCACGGGCCCTGGC
1411  ---------+---------+---------+---------+---------+---------+
      P  Q  G  S  H  S  A  I  G  L  S  G  L  N  P  S  T  G  P  G
        S  A  Q  P  L  G  Y  R  L  V  M  P  E  P  Q  M  G  P  N  P

CTCTGGTGGAACCCTGCCCCTTACCAGCCTTGATGGCAGCGGGAATCTGGTGCTGGGGGC
1471  ---------+---------+---------+---------+---------+---------+
      L  W  W  N  P  A  P  Y  Q  P  .
        L  V  E  P  C  P  L  P  A  L  M  A  A  G  I  W  C  W  G  Q

AGCCGGTGCAGCCCCGGGGAGCCCTGGCCTGGTGACCTCGCCGCTCTTCTTGAATCATGC
1531  ---------+---------+---------+---------+---------+---------+
        P  V  Q  P  R  G  A  L  A  W  .

TGGGCTGCCCCTGCTCAGCACCCCGCCTGGTGTGGGCCTGGTCTCAGCAGCGGCTGCGGG
1591  ---------+---------+---------+---------+---------+---------+

TGTGGCAGCCTCCATCTCCAGCAAGTCTCCTGGCCTCTCCTCCTCATCCTCTTCATCCTC
1651  ---------+---------+---------+---------+---------+---------+

ATCCTCCTCCTCCTCCACTTGCAGCGAGACGGCAGCACAGACCCTGGAGGTCCAGGGGGG
1711  ---------+---------+---------+---------+---------+---------+

CCCGAGGCAGGGTCCAAACCTGAGTGAGGGCCAGCCATGCCTCCCCTCCCATTCCTCTGG
1771  ---------+---------+---------+---------+---------+---------+

TCCCTGCCCCGGAATTC
1831  ---------+-------
```

Fig. 18B

```
                        helix   turn  helix
                        <------->     <------->

Oct-2   RRKKRTSIETNVRFALEKSFLANQKPTSEEILLIAEQLHMEKEVIRVWFCNRRQKEKRINPC
                    *                             * a1      SPKGKSSISPQARAFLEQVFRRKQSLNSKEKEEVAKKCGITPLQVRVWFINKRMRSK
                    *                             *

α2      KPYRGHRFTKENVRILESWFAKNPYLDTKGLENLMKNTSLSRIQIKNWVSNRRRKEKTIT
                    *                             * pho2    QRPKRTRAKGEALDVLKRKFEINPTPSLVERKKISDLIGMPEKNVRIWFQNRRAKLRKKQ
                    *                             * mec-3   RRGPRTTIKQNQLDVLNEMFSNTPKPSKHARAKLALETGLSMRVIQVWFQNRRSKERRLK
                    *                             * cut     SKKQRVLFSEEQKEALRLAFALDPYPNVGTIEFLANELGLATRTITNWFHNHRMRLKQQV
                    *                             * en      EKRPRTAFSSEQLARLKREFNENRYLTERRRQQLSSELGLNEAQIKIWFQNKRAKIKKST
                    *                             *

Antp    RKRGRQTYTRYQTLELEKEFHFNRYLTRRRRIEIAHALCLTERQIKIWFQNRRMKWKKEN
                    *                             *

R    Q  L              Y           L      WF N R      (conserved
                                                                residues in
                                                                homeo-box
                                                                family)
```

Fig. 20

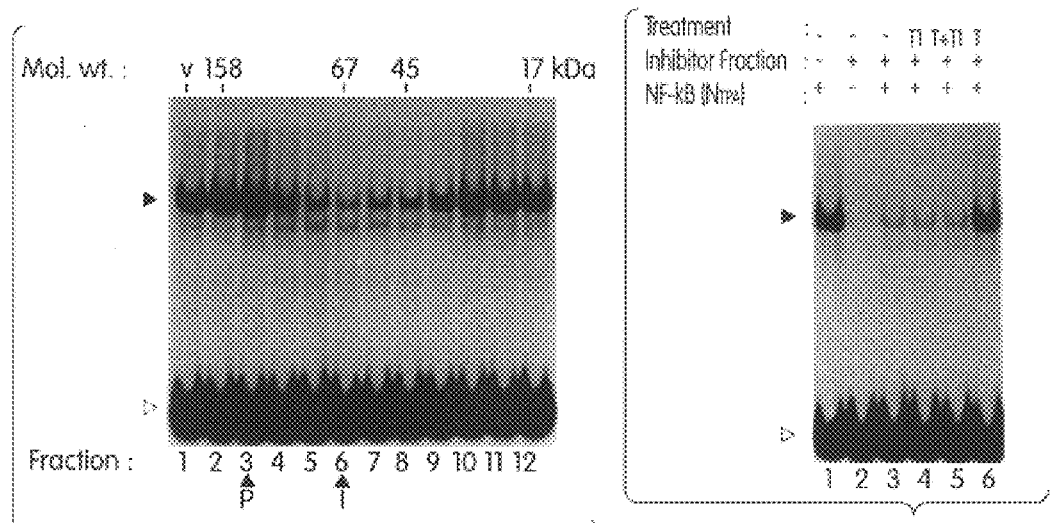
Fig. 35A
Fig. 35B
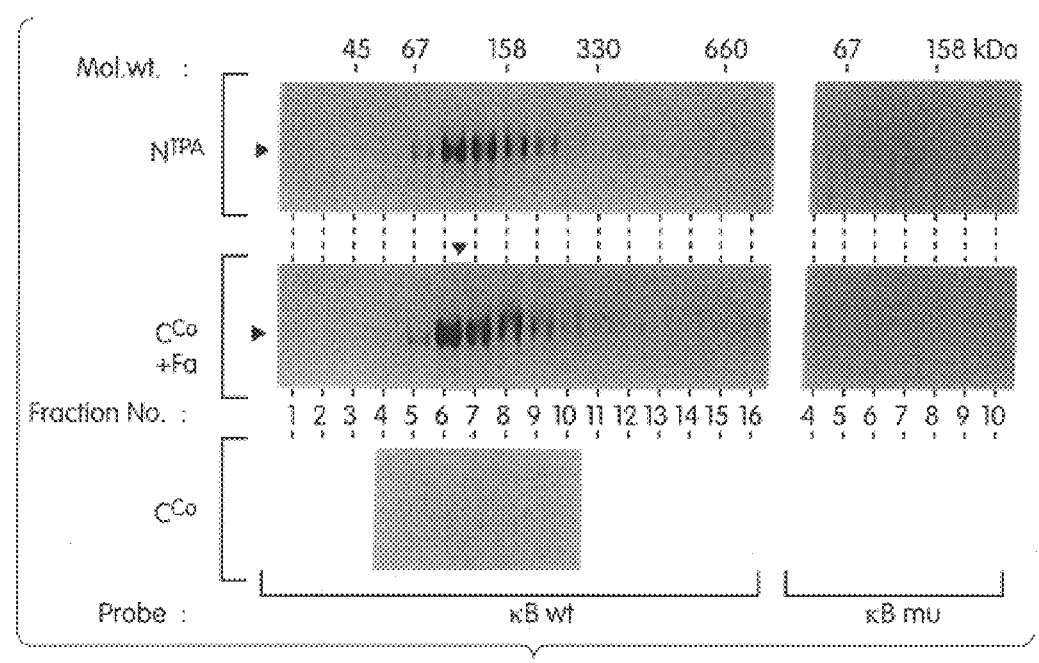
Fig. 35C

Figure 43

```
AACATTGCAACCTTATAAAAAATTAACTATTTCGACAATGCCGCAGAAGGAAATTCTGTGTTAGGTGCTGGTGGG
AAAACACTATCTCCAGCTTGTAGGTTTGAGCATCACCAGAACCACTTGATGAAATCACACACAGAACAAGTAGAG
AGGCAACTGTGAATCGTGGGGCTATAAAGCCATCAACAAGTGGCTGCTACACCGTCTTGTTAAAACACTACGTC
CCCCACAACAGATCGGCACCCCAGAGTTCAACAAGTGGCTGCTACACCGTCTGTTTGCTAAAACACTACGTAGTC
CCGGATCAGTAGTTGCACAGCCCCCCGTTCTGCTCCTGTCCCTGCGGCGCTGAATGAACCGCACACAAGTCTGCATCTGCACGAA
CCTCCCAGGCCCCCCGTTCTGCTCCTGTCCCTGCGGCGCTGAATGAACCGCACACAAGTCTGCATCTGCACGAA
TTCTCATGGGAGCCACGTCATGAGGTACGTGGTTGCACACCTATCACACAAGAAGTCTTGCAGTTCTGACTCTCCTGA
GCTCGGTGTGGGAAAGTCTGGATAGTACCTCCCCCCCCCCTTGTCAAACACACCTGAGGGGGAGTCTCACCTCTCCCCAGC
CAGGTCTATTGAGTTTCTCTTCAGAGCGAGCTTTAATGCTCCGGCCCAATCCTGAGGTGCTGGTTTGTGGGCTGCGTTTGT
AACTCAGATCAGTGCCTTATTTTTAATGCTCCGGCCCAATCCTGAGGTGCTGGTTTGTGGGCCAAATTCAAGCCA
TGAACCCTCCCCCCTCCCAACGCCCTGGAGCTCAAAGCAGAGTTGCACCTGACCCCCAGCTGAACGGCCAATTGGTTCACCCAGAG
GAGTGAGCAGTAGGATGTGGAGCTCAAAGCAGAGTTGCACCTGACCCCCAGCTGAACGGCCAATTGGTTCACCCAGAG
ACTACAAGTGGGAAGGCATGTTTAGAGAAGAAGAAGAGATCCATAGAGATGTGAACCAGAATCAGTCGTGTTGAGC
GCACAGTGGGAAGGCTGGACAGAAGAAGAAGAGATCCATAGAGATGTGAACCAGAATCAGTCGTGTTGAGC
TCTGGGTATATCACTACATGTTTAACTCTTGCAAGACCGTTTGCCCAGGGCTTTGGTACCACAGGGTTAGAGTTAC
ATTAACCACAACCAGAGAGAGGAACTGAGGTTTATGACCCCCCCCAAAGGTTAGATTTCTGCCGAGTATA
                     M  T  P  P  P  P  K  V  R  F  L  P  S  I

AAGGGGGGAAGGGGGGGGGGTCCTTGGTTCATTTCCCTTCACTGTGTGACCGAAGTTTGCTTTTATTTGTAAACA
 K  G  G  E  G  G  G  G  P  W  F  I  S  L  H  C  V  T  E  V  L  L  L  F  V  N  I

TCTTGAATTACCCGTCGTTTCCAGTCTTCATCGTGTGCTGTCAGGCCACTGGAGGAATTCCCCGTCTCGGAAC
 L  N  Y  P  S  F  S  S  L  H  R  A  V  V  R  P  L  E  G  I  P  R  L  G  T

GCCGCCGCCAGCAGCCGCGCCGCCAGCCGCTCCGCGCCATGCTCAGCGCCCACCGCCCCGCC
 P  P  P  A  P  A  A  P  R  R  P  A  S  S  A  A  M  L  S  A  H  R  P  A
```

Figure 43 (continued)

```
GAGCCGCCCCGCCTGTGGAGGGCTGCGAGCCCCCGCCGCGCAAGGAACGGCAAGGGCTGTGCCGCGACCGCC
 E  P  P  A  V  E  G  C  E  P  P  R  K  E  R  Q  G  G  L  L  P  P  D  D  R  H
ACGACAGCGGGGCTGGACTCCATGAAGGAGGAGGAGTACAGGCAGCTGGTGCGGGAGCTGGAGGACATCCGCCTGCA
 D  S  G  L  D  S  M  K  E  E  E  Y  R  Q  L  V  R  E  L  E  D  I  R  L  Q
GCCCCGAGCGCGCCCCGGCCCACGCCTGGGCCCAGCAGCTCACCGAGGACGGCGACACTTTTCTCCACTTG
 P  R  E  P  P  A  R  P  H  A  W  A  Q  Q  L  T  E  D  G  D  T  F  L  H  L
GCGATCATTCACGAGGAAAAGGCCCTGAGCCTGGAGGTGATCCGGCAGGCCGCTGGGACGCCGCCTTCCTGAACT
 A  I  I  H  E  E  K  A  L  S  L  E  V  I  R  Q  A  A  G  D  A  A  F  L  N  F
 Ank. I
TCCAGAACAACCTCAGCCAGACTCCGCTCCACCTGGCGGTGATCACGGACCAGGCCGAAATCGCCGAGCACCTGCT
 Q  N  N  L  S  Q  T  P  L  H  L  A  V  I  T  D  Q  A  E  I  A  E  H  L  L
                                                          Ank. II
GAAGGCTGGCTGCGACCTGGATGTCAGGGACTTCCGTGGGAACACCCCGCTCCACATCGCCTGCCAGGGCTCG
 K  A  G  C  D  L  D  V  R  D  F  R  G  N  T  P  L  H  I  A  C  Q  Q  G  S
                                                 Ank. III
CTCCGCAGGTCAGTGTCCTCACGGCAGCACTGCCAGCCCCACCACCTCCTGCTGGCTGTGTTGCAATACCTACA
 L  R  S  V  S  V  L  T  Q  H  C  Q  P  H  H  L  L  A  V  L  Q  A  T  N  Y  N
ACGGCCATACACATGTCTCCATTTGGCATCTATTCAAGGATACCTGGCTGTGGTAGAATACTACTGCTGTCCTTAGGAGC
 G  H  T  C  L  H  L  A  S  I  Q  G  Y  L  A  V  V  E  Y  L  L  S  L  G  A
                           Ank. IV
AGATGTAAATGCTCAGGAGCCATGCAATGGGAGAACAGCACTACACTTGGCCGTAGACCTTCAGAACTCAGACCTG
 D  V  N  A  Q  E  P  C  N  G  R  T  A  L  H  L  A  V  D  L  Q  N  S  D  L
                                         Ank. V
```

Figure 43 (continued)

```
GTGTCACTTCTGGTGAAACACGGGCCAGATGTGAACAAAGTGACCTACCCAGGGCTACTCCCCATACCAGCTTACAT
 V  S  L  L  V  K  H  G  P  D  V  N  K  V  T  Y  Q  G  Y  S  P  Y  Q  L  T  W

GGGCAGAGACAACGCCAGCATACAGGAGCAGCTGAAGCTGCTGACCACAGCTGACCTGCAGATACTGCCCGAAAGT
 A  E  T  T  P  A  Y  R  S  S     354

GAGGATGAGGAGAGCAGTGAATCAGAGCCAGAGTTCACAGAGGATGAACTTATGTATGATGACTGCTGTATTGGAG
GAAGACAGCTGACATTTTAAAGCAGAGGTTTCTGTGAAGAAGTGACTGTGTACATATGTATAGAGAAAAAAGCTGA
CTTTCTTCATTTAAAAGAAAAGTCTATACTGCTCTGACCTGTGTACTAACGGATGGATGGTGTAACATCGTTAAGAGATC
ACATCATGCTAACAGGTTCCATGTGTTTGAGATGGTGTGTAACATCGTTAAGAGATC
AGTGAACATGCACACCATCTGATAAAGAGCCACGTTATCTAATTCTCTGCCACATGAGGATAACGGACTGCACGT
CCAATGTGCTGTGTTGCAAGACAGCTTGCACAAACGTCCCATCTGCTTGAAGACTGTGAGGTTGGCATTAGGTTGAGGCACTGCT
CGGTGGCAAGACAGGCTTGCACAAACGTCCCATCTGCTTGAAGACTGTCCGACCATGGGAGAGGTGACCTGGCTGCTGGGAGG
GTGCCCTGCTCCCTGACCCTGGCTGCTCAGGTTGAGAAACTGTGTGTTTCACACCATGTGTGTACCTGTCATAATTGCTACACTT
AAGTAGCAATGATGTATAGAATACTGTAAATACTGTACATCTTTGTTTATAATTATTTTGGTACCTGTGAGATATGTATTTA
TTTAGCAACTGTATAGAATGTAAATACTGTACATCTTTGTTTATAATTATTTTGGTACCTGTGAGATATGTATTTA
TTAAAAAGGCAGATTTCTGTAAAAAA
```

NUCLEAR FACTORS ASSOCIATED WITH TRANSCRIPTIONAL REGULATION

Related Applications

This application is a division of application Ser. No. 08/418,266 filed Apr. 6, 1995, U.S. Pat. No. 5,804,374 which is a continuation of U.S. Ser. No. 07/791,898, filed Nov. 13, 1991, abandoned which is a continuation-in-part of U.S. Ser. No. 06/946,365, filed Dec. 24, 1986, abandoned and of U.S. Ser. No. 07/318,901, filed Mar. 3, 1989, abandoned and of U.S. Ser. No. 07/162,680, filed Mar. 1, 1988, abandoned and of U.S. Ser. No. 07/341,436, filed Apr. 21, 1989, abandoned and of U.S. Ser. No. 06/817,441, filed Jan. 9, 1986, abandoned and of U.S. Ser. No. 07/155,207, filed Feb. 12, 1988, abandoned and of U.S. Ser. No. 07/280,173, filed Dec. 5, 1988, abandoned. All of the above applications are incorporated herein by reference in their entirety.

GOVERNMENT SUPPORT

The work leading to this invention was supported in part by a grant from the National Cancer Institute. The Government has certain rights in this invention.

BACKGROUND OF THE INVENTION

Trans-acting factors that mediate B cell specific transcription of immunoglobulin (Ig) genes have been postulated based on an analysis of the expression of exogenously introduced Ig gene recombinants in lymphoid and non-lymphoid cells. Two B cell-specific, cis-acting transcriptional regulatory elements have been identified. One element is located in the intron between the variable and constant regions of both heavy and kappa light chain genes and acts as a transcriptional enhancer. The second element is found upstream of both heavy chain and kappa light chain gene promoters. This element directs lymphoid-specific transcription even in the presence of viral enhancers.

Mouse and human light chain promoters contain the octamer sequence ATTTGCAT approximately 70 base pairs upstream from the site of initiation. Heavy chain gene promoters contain the identical sequence in inverted orientation, ATGCAAAT, at the same position. This element appears to be required for the efficient utilization of Ig promoters in B cells. The high degree of sequence and positional conservation of this element as well as its apparent functional requirement suggests its interaction with a sequence-specific transcription factor but no such factor has been identified.

DISCLOSURE OF THE INVENTION

This invention pertains to human lymphoid-cell nuclear factors which bind to gene elements associated with regulation of the transcription of Ig genes and to methods for identification and for isolation of such factors. The factors are involved in the regulation of transcription of Ig genes. The invention also pertains to the nucleic acid encoding the regulatory factors, to methods of cloning factor-encoding genes and to methods of altering transcription of Ig genes in lymphoid cells or lymphoid derived cells, such as hybridoma cells, by transfecting or infecting cells with nucleic acid encoding the factors.

Four different factors which bind to transcriptional regulatory DNA elements of Ig genes were identified and isolated in nuclear extracts of lymphoid cells. Two of the factors, IgNF-A and E, are constitutive; two IgNF-B and κ-3 (hereinafter NF-κB) are lymphoid cell specific. Each factor is described below.

IgNF-A (NF-A1)

IgNF-A binds to DNA sequences in the upstream regions of both the murine heavy and kappa light chain gene promoters and also to the murine heavy chain gene enhancer. The binding is sequence specific and is probably mediated by a highly conserved sequence motif, ATTTGCAT, present in all three transcriptional elements. A factor with binding specificity similar to IgNF-A is also present in human HeLa cells indicating that IgNF-A may not be tissue specific.

E Factors

The E factors are expressed in all cell types and bind to the light and heavy chain enhancers.

IgNF-B (NF-A2)

IgNF-B exhibits the same sequence-specificity as IgNF-A; it binds to upstream regions of murine heavy and kappa light chain gene promoters and to murine heavy chain gene enhancer. This factor, however, is lymphoid specific; it is restricted to B and T cells.

NF-κB (Previously Kappa-3)

NF-κB binds exclusively to the kappa light chain gene enhancer (the sequence TGGGGATTCCCA). Initial work provided evidence that NF-kB is specific to B-lymphocytes (B-cells) and also to be B-cell stage specific. NF-kB was originally defected because it stimulates transcription of genes encoding kappa immunoglobulins in B lymphocytes. As described herein, it has subsequently been shown that transcription factor NF-kB, previously thought to be limited in its cellular distribution, is, in fact, present and inducible in many, if not all, cell types and that it acts as an intracellular messenger capable of playing a broad role in gene regulation as a mediator of inducible signal transduction. It has now been demonstrated that NF-kB has a central role in regulation of intercellular signals in many cell types. For example, NF-kB has not been shown to positively regulate the human β-interferon (β-IFN) gene in many, if not all, cell types. As described below, it is now clear not only that NF-kB is not tissue specific in nature, but also that in the wide number of types of cells in which it is present, it serves the important function of acting as an intracellular transducer of external influences. NF-kB has been shown to interact with a virus inducible element, called PRDII, in the β-IFN gene and to be highly induced by virus infection or treatment of cells with double-stranded RNA. In addition, NF-kB controls expression of the human immunodeficiency virus (HIV).

As further described, it has been shown that a precursor of NF-KB is present in a variety of cells, that the NF-KB precursor in cytosolic fractions is inhibited in its DNA binding activity and that inhibition can be removed by appropriate stimulation, which also results in translocation of NF-KB to the nucleus. A protein inhibitor of NF-KB, designated IkB, has been shown to be present in the cytosol and to convert NF-KB into an inactive form in a reversible, saturable and specific reaction. Release of active NF-kB from the IkB-NF-kB complex has been shown to result from stimulation of cells by a variety of agents, such as bacterial lipopolysaccharide, extracellular polypeptides and chemical agents, such as phorbel esters, which stimulate intracellular phosphokinases. IkB and NF-KB appear to be present in a stoichiometric complex and dissociation of the two complex components results in two events: activation (appearance of NF-KB binding activity) and translocation of NF-KB to the nucleus.

Identification and Isolation of the Transcriptional Regulatory Factors

The transcription regulatory factors of the present invention were identified and isolated by means of a modified DNA binding assay. The assay has general applicability for analysis of protein DNA interactions in eukaryotic cells. In performing the assay, DNA probes embodying the relevant DNA elements or segments thereof are incubated with cellular nuclear extracts. The incubation is performed under conditions which allows the formation of protein-DNA complexes. Protein-DNA complexes are resolved from uncomplexed DNA by electrophoresis through polyacrylamide gels in low ionic strength buffers. In order to minimize binding of protein in a sequence nonspecific fashion, a competitor DNA species can be added to the incubation mixture of the extract and DNA probe. In the present work with eukaryotic cells the addition of alternating copolymer duplex poly(dI-dC)-poly(dI-dC) as a competitor DNA species provided for an enhancement of sensitivity in the detection of specific protein-DNA complexes and facilitated detection of the regulatory factors described herein.

This invention pertains to the transcriptional regulatory factors, the genes encoding the four factors associated with transcriptional regulation, reagents (e.g., oligonucleotide probes, antibodies) which include or are reactive with the genes or the encoded factors and uses for the genes, factors and reagents. It further relates to NF-KB inhibitors, including isolated IkB, the gene encoding IkB and agents or drugs which enhance or block the activity of NF-KB or of the NF-KB inhibitor (e.g., IkB).

The invention also pertains to a method of cloning DNA encoding the transcriptional regulatory factors or other related transcriptional regulatory factors. The method involves screening for expression of the part of the binding protein with binding-site DNA probes. Identification and cloning of the genes can also be accomplished by conventional techniques. For example, the desired factor can be purified from crude cellular nuclear extracts. A portion of the protein can then be sequenced and with the sequence information, oligonucleotide probes can be constructed and used to identify the gene coding the factor in a cDNA library. Alternatively, the polymerase chain reaction (PCR) can be used to identify genes encoding transcriptional regulatory factors.

The present invention further relates to a method of inducing expression of a gene in a cell. In the method, a gene of interest (i.e., one to be expressed) is linked to the enhancer sequence containing the NF-KB binding site in such a manner that expression of the gene of interest is under the influence of the enhancer sequence. The resulting construct includes the kappa enhancer or a kappa enhancer portion containing at least the NF-KB binding site, the gene of interest, and a promoter appropriate for the gene of interest. Cells are transfected with the construct and, at an appropriate time, exposed to an appropriate inducer of NF-KB, resulting in induction of NF-KB and expression of the gene of interest.

The subject invention further relates to methods of regulating (inducing or preventing) activation of NF-KB, controlling expression of the immunoglobulin kappa light chain gene and of other genes whose expression is controlled by NF-KB (e.g., HIV).

As a result of this finding, it is now possible to alter or modify the activity of NF-κB as an intracellular messenger and, as a result, to alter or modify the effect of a variety of external influences, referred to as inducing substances, whose messages are transduced within cells through NF-κB activity. Alteration or modification, whether to enhance or reduce NF-κB activity or to change its binding activity (e.g., affinity, specificity), is referred to herein as regulation of NF-κB activity. The present invention relates to a method of regulating or influencing transduction, by NF-κB, of extracellular signals into specific patterns of gene expression and, thus, of regulating NF-κB-mediated gene expression in the cells and systems in which it occurs.

In particular, the present invention relates to a method of regulating (enhancing or diminishing) the activity of NF-κB in cells in which it is present and capable of acting as an intracellular messenger, as well as to substances or composition useful in such a method. Such methods and compositions are designed to make use of the role of NF-κB as a mediator in the expression of genes in a variety of cell types. The expression of a gene having a NF-κB binding recognition sequence can be regulated, either positively or negatively, to provide for increased or decreased production of the protein whose expression is mediated by NF-κB. NF-κB-mediated gene expression can also be selectively regulated by altering the binding domain of NF-κB in such a manner that binding specificity and/or affinity are modified. In addition, genes which do not normally possess NF-κB binding recognition sequences can be placed under the control of NF-κB by inserting an NF-κB binding site in an appropriate position, to produce a construct which is then regulated by NF-κB. As a result of the present invention, cellular interactions between NF-κB and a gene or genes whose expression is mediated by NF-κB activity and which have, for example, medical implications (e.g., NF-κB/cytokine interactions; NF-κB/HTLV-I tax gene product interactions) can be altered or modified.

Genes encoding the regulatory factors can be used to alter cellular transcription. For example, positive acting lymphoid specific factors involved in Ig gene transcription can be inserted into Ig-producing cells in multiple copies to enhance Ig production. Genes encoding tissue specific factors can be used in conjunction with genes encoding constitutive factors, where such combinations are determined necessary or desirable. Modified genes, created by, for example, mutagenesis techniques, may also be used. Further, the sequence-specific DNA binding domain of the factors can be used to direct a hybrid or altered protein to the specific binding site.

DNA sequences complementary to regions of the factor-encoding genes can be used as DNA probes to determine the presence of DNA encoding the factors for diagnostic purposes and to help identify other genes encoding transcriptional regulatory factors. Antibodies can be raised against the factors and used as probes for factor expression. In addition, the cloned genes permit development of assays to screen for agonists or antagonists of gene expression and/or of the factors themselves. Further, because the binding site for NF-kB in the kappa gene is clearly defined, an assay for blockers or inhibitors of binding is available, as is an assay to determinte whether active NF-kB is present.

BRIEF DESCRIPTION OF THE DRAWINGS

FIG. 9A shows a restriction map of the μ-enhancer; FIG. 9B shows an autoradiograph binding assay carried out with μ-enhancer fragments.

FIG. 18A shows the nucleotide sequence of the oct-2 gene derived from cDNA and the predicted amino acid sequence of encoded proteins.

FIG. 18B shows the nucleotide sequence of the 3' terminus and predicted the amino acid sequence of the C-terminus derived from clone pass-3.

FIG. 20 shows amino acid sequence alignment of the DNA binding domain of oct-2 factor with homeo-boxes of several other genes.

FIG. 26A represents determination of the molecular weight of NF-kB. Nuclear extract (300 ug of protein) from TPA-stimulated 70Z/3 pre-B cells was denatured and subjected to reducing SDS-polyacrylamide gel electrophoresis (SDS-PAGE). Protein in the molecular weight fractions indicated by dashed lines was eluted and renatured prior to mobility shift assays as described. A fluorogram of a native gel is shown. The filled arrowhead indicates the position of a specific protein DNA-complex only detected in the 62–55 kDa fraction with a wild type (wt) but not with a mutant (mu) kappa enhancer fragment. The open arrowhead indicates the position of unbound DNA-fragments. FIG. 26B is a representation of glycerol gradient centrifugation of NF-kB. Nuclear extract (400 ug of protein) from TPA-stimulated 70Z/3 cells was subjected to ultracentrifugation on a continuous 10–30% glycerol gradient for 20 hours at 150,000×g in buffer D(+). Co-sedimented molecular weight standards (ovalbumin, 45 kDa; bovine serum albumin, 67 kDa; immunoglobulin G, 158 kDa; thyroglobulin monomer, 330 kDa and dimer 660 kDa) were detected in the fractions by SDS-PAGE, followed by Coomassie Blue staining. The distribution of NF-kB activity was determined by electrophoretic mobility shift assays using an end-labelled kappa enhancer fragment. Fluorograms of native gels are shown. The specificity of binding was tested using a kappa enhancer fragment with a mutation in the NF-kB binding site.

FIG. 27A represents analysis of subcellular fractions for NF-kB DNA-binding activity. Nuclear extracts (N), cytosolic (C) and postnuclear membrane fractions (P) from control and TPA-stimulated 70Z/3 pre-B cells were analyzed by gel-shift assays. The filled arrowhead indicates the position of the specific protein-DNA complex seen only with a wild type but not with a mutant kappa enhancer fragment. FIG. 27B represents activation of a cytosolic NF-kB precursor after treatment with dissociating agents. Subcellular fractions were treated with 25% formamide followed by dilution and addition of 0.2% sodium desoxycholate as described. FIG. 27C represents detection of a cytosolic NF-kB precursor after denaturation, SDS-PAGE and renaturation of protein. Nuclear extract (N) and cytosolic fraction (C) from unstimulated (control) 70Z/3 cells was subjected to the treatment outlined in FIG. 26A. For details of illustration, see FIG. 27A.

FIG. 31A: cell-free activation of a NF-kB precursor in the cytosolic fraction by desoxycholate. FIG. 31B: cell-free activation of a NF-kB precursor in the cytosolic fraction by formamide and by a combined treatment with formamide and desoxycholate.

FIG. 34A: Release of DOC-independent NF-kB activity. Equal proportions of load, flow-through (FT), washings, and eluates were analyzed by EMSA, with (+) or without (−) excess DOC. The $^{32}$P-radioactivity in the NF-kB-DNA complexes was counted by liquid scintillation and the percentage of NF-kB activity recovered in the various fractions was calculated. FIG. 34B: Release of an inhibitory activity. NF-kB contained in the 0.2M NaCl fraction (31 ng of protein) or NF-kB in a nuclear extract from TPA-treated 70Z/3 cells (1.1 μg of protein) was incubated under non dissociating conditions with the indicated amounts (in microliters) of either cytosol which was DOC-treated but not passed over DNA-cellulose (lanes 4 to 6 and 13 to 15) or the flow-through fraction (referred to as NF-kB-depleted cytosol; lanes 7 to 9 and 16 to 18).

FIGS. 35A–35C shows-characterization of IkB and its complex with NF-kB. In the fluorograms shown, the filled arrowheads indicate the position of the NF-kB-DNA complex and the open arrowheads the position of free DNA probe. FIG. 35A: For size determination of IkB, the flow-through from the DNA-cellulose column was passed over a G-200 Sephadex column. Portions of fractions were incubated with NF-kB contained in nuclear extracts from TPA-stimulated 70Z/3 cells (N TPA), and analyzed by EMSA. v, void volume; P, fraction where remaining NF-kB precursor (FIG. 34A, lane 4) peaked after gel filtration as assayed with excess DOC in the absence of added NF-kB; I, fraction where the inhibiting activity peaked. FIG. 35B: The effect of trypsin treatment on the inhibiting activity of IkB. NF-kB in a nuclear extract (lane 1) was incubated with a fraction containing inhibitor (lane 2) without any addition (−; lane 3) or with bovine pancreas trypsin inhibitor (TI; lane 4), trypsin that had been incubated with BPTI (T+TI; lane 5), or with trypsin alone (T; lane 6). Samples were then used in the inhibitor assay. FIG. 35C: Glycerol gradient sedimentation of NF-kB and its complex with IkB. Nuclear extract from TPA-stimulated 70Z/3 cells (N TPA) and cytosol from unstimulated cells (C Co) were subjected to sedimentation through a glycerol gradient. Cosedimented size markers were ovalbumin (45 kD), BSA (67 kD), immunoglobulin G (158 kD) and thyroglobulin (330 and 660 kD). NF-kB activity was detected in the fractions by EMSA with a wild type k enhancer fragment (kB wt, left panels). The specificity was tested with a mutant fragment (kB mu, right panels). The inactive cytosolic NF-κB precursor (lower panel) was activated by formamide treatment (Fa; middle panel).

FIG. 36A: The effect of DOC treatment on in vitro inactivated NF-kB. NF-kB contained in nuclear extracts from TPA-stimulated 70Z/3 cells (N TPA; 1.1 μg of protein) was inactivated by addition of a gel filtration fraction containing IkB (2.5 μg of protein). A duplicate sample was treated after the inhibition reaction with 0.8% DOC followed by addition of DNA binding reaction mixture containing 0.7% NP-40. Samples were analyzed by EMSA. In the fluorograms shown, the filled arrowhead indicates the position of the NF-kB-DNA complex and the open arrowhead the position of unbound DNA probe. FIG. 36B: A titration and kinetic analysis of the in vitro inactivation of NF-kB. NF-kB contained in nuclear extracts from TPA-treated 70Z/3 cells (2.2 μg of protein) was incubated with increasing amounts (0.25 to 2.25 μg of protein) of a gel filtration fraction containing IkB. After the DNA binding reaction, samples were analyzed by EMSA. The $^{32}$P-radioactivity in the NF-kB-DNA complexes visualized by fluorography was determined by liquid scintillation counting. All reactions were performed in triplicates. The bars represent standard deviations.

FIG. 37A: Influence of IkB on the DNA binding activity of various nuclear factors. The probes were: NF-kB; H2TF1, an oligonucleotide subcloned into pUC containing the H2TF1 binding site from the H-2 promoter; OCTA, an oligonucleotide subcloned into pUC containing the common binding site for the ubiquitous (upper filled arrowhead) and lymphoid-specific (lower filled arrowhead) octamer-binding proteins; NF-μE1; NF-kE2; and AP-1, EcoRI-HindIII fragment of the yeast HIS4 promoter containing three binding sites recognized by mammalian AP-1/jun. In the fluorograms shown, filled arrowheads indicate the positions of specific protein-DNA complexes. Open arrowheads indicate the positions of uncomplexed DNA fragments. FIG. 37B: Interaction of IkB with NF-kB from different cell lines. The filled arrowheads indicate the positions of the NF-kB-DNA complexes from the various cell lines and the open arrowhead indicates the position of uncomplexed DNA probe.

FIG. 38A: Phase contrast and fluoresence microscopy of enucleated HeLa cells. From 612 cells counted on photographic prints, 63 showed nuclear staining. A representative micrograph is shown. The arrow indicates a cell that retained its nucleus. FIG. 38B: Analysis of complete and enucleated cells for NF-kB activity. Total cell extracts (1.2 μg of protein) from control (Co) and TPA-treated complete and enucleated cells were analyzed by EMSA with a labeled k enhancer fragment (kB) or HIS4 promoter fragment (AP-1), 3 μg of poly(dI-dC), 1 μg of BSA, 1.2% NP-40 and the binding buffer in a final volume of 20 μl. In lanes 5 to 8, extracts were treated with DOC followed by the addition of the DNA binding mixture to give final concentrations of 0.8% DOC and 1.2% NP-40. Samples were analyzed by EMSA. In the fluorograms shown, the filled arrowheads indicate the positions of specific protein-DNA complexes and the open arrowheads the positions of uncomplexed DNA probe.

FIG. 40A shows the results of mobility shift electrophoresis assays using as radiolabelled probe an IRE DNA fragment (IRE, lanes 1–3, 10–14, 20–24, 30 and 31), an oligonucleotide containing two copies of the PRDII sequence (PRDII$_2$, lanes 4–6) or a κB site oligonucleotide (κB, lanes 7–9, 15–19, 25–29, 32 and 33). Assays contained either no protein (φ, lanes 1, 4 and 7); 5 μg of unstimulated Jurkat nuclear extract (−, lanes 2, 5 and 8) or 5 μg of nuclear extract from Jurkat cells stimulated with PHA and PMA (+, lanes 3, 6, 9 and 10–29). Competitions used either the κB oligonucleotide (κB; lanes 10–19) or the PRDII oligonucleotide (PRD II$_2$, lanes 20–29) in the ng amounts shown above each lane. Cytosol (8 μg) from unstimulated Jurkat cells was tested either before (−, lanes 30 and 32) or following treatment with 0.8% deoxycholate (DC, lanes 31 and 33).

FIG. 40B shows that mutations within PRDII that reduce β-IFN induction in vivo decrease the affinity of NF-κB for PRDII in vitro. IRE sequences bearing the mutations indicated (for positions refer to FIG. 39) were tested. The mutations were previously shown to have either high (+) or low (−) inducibility. Goodbourn and Maniatis, *Proc. Natl. Acad. Sci. USA*, 85:1447–1451 (1988). Binding and competition were carried out, as described for FIG. 2A, using 5 μg of nuclear extract from virus infected 70Z/3 cells. Competitor was 10 ng of either the wild-type (WT) or mutant (MUT) κB oligonucleotide (lanes 7,8).

FIG. 41A is an autoradiogram showing the results of CAT assays of extracts prepared from L929 and S194 myeloma cells transfected with the reporter genes illustrated in FIG. 41B.

FIG. 41B is a diagram of the reporter genes containing multiple copies of PRDII or κB. Two or four PRDII sites [(P)$_2$ and (P)$_4$, respectively] were inserted upstream of the truncated −41 human β-globin promoter/CAT fusion gene (−41β) using an oligonucleotide containing two copies of PRDII (PRDII×2, as described in the Exemplification). Two copies of a synthetic wild-type KB site, or mutant κB site (B and B⁻, respectively) were inserted upstream of the mouse c-fos promoter/CAT fusion gene in which the promoter was truncated to nucleotide −56 (Δ56).

FIG. 42A represents the results of a binding assay which shows complexes formed with the Ig κB site using 5 μg of nuclear extract from unstimulated cells (lanes 1, 9 and 17) and 5 μg (lanes 2–6, 10–14 and 18–22) or 1 μg (lanes 7, 8, 15, 16, 23 and 24) of nuclear extract from cells after virus infection. Extracts were prepared from Namalwa cells (lanes 1–8), 70Z/3 cells (lanes 7–16), and L929 cells (lanes 17–28). Competitions used either 5 or 20 ng of the wild-type (WT) or mutant (MUT)κB oligonucleotide. GTP stimulation was tested by addition directly to the binding assay to a final concentration of 3 mM. Cytosol was obtained from L929 cells either prior to (lanes 25, 26) or after (lanes 27, 28) viral treatment and tested before (−) and after (DC) treatment with deoxycholate.

FIG. 42B presents a comparison of methylation interference footprints of virus-induced complexes from Namalwa and L929 cell extracts with NF-κB complexes derived from PHA/PMA-stimulated Jurkat cells. The cleavage pattern resulting from methylation of guanine or adenine residues is shown for DNA extracted from the free probe (F) or the DNA-protein complex (B) observed following mobility shift electrophoresis. The sequence of the κB site presented at the sides and methylated residues that interfere with binding are indicated by a solid circle.

FIG. 42C presents results of Northern blot analyses of 70Z/3 cells treated with various inducers. The upper panel shows the induction (from 0 to 20 hr as indicated) of κ (κ) mRNA by treatment with 50 ng/ml PMA (PMA, lanes 1–4), 15 μg/ml LPS (LPS, lanes 5–8) or Sendai virus (V, lanes 9–12). The lower panel shows the same blot hybridized to a β-IFN DNA fragment.

FIG. 43 is the nucleotide sequence and the amino acid sequence of IkB-α.

CLONE DEPOSITS

Figure 1A:
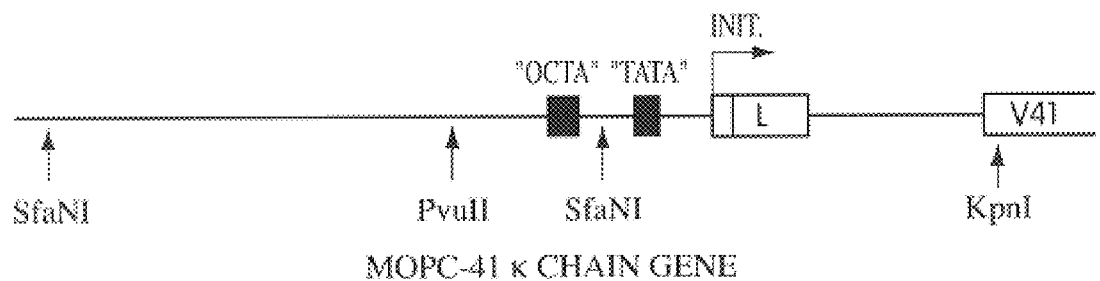
FIG. 1A is a schematic depiction of the 5' region of the MOPC 41 $V_\kappa$ gene segment.

Clones λh3 and λ3-1 were deposited (Feb. 12, 1988) at the AMerican Type Culture Collection (12301 Parklawn Drive; Rockville, Md. 20852), under the terms of the Budapest Treaty. They were assigned ATCC Designationals 67629 and 67630, respectively. Upon issue of a U.S. patent from the subject application, all restrictions upon the availability of these clones will be irrevocably removed.

DETAILED DESCRIPTION OF THE INVENTION

The present invention relates to the identification, isolation and characterization of human transcriptional regulatory factors, to genes encoding the factors, methods of isolating DNA encoding transcriptional regulatory factors and the encoded factors, uses of the DNA, encoded factors, and antibodies against the encoded factors, inhibitors of the transcriptional regulatory factors. In particular, it relates to the transcriptional regulatory factor NF-kB (previously designated Kappa-3); its inhibitor; IkB, DNA encoding each, methods of altering interactions of NF-kB and IkB and methods of regulating the activity of NF-kB. As described herein, NF-kB, was initially thought to be a B-cell specific factor involved in immunoglobulin gene regulation and has since been shown to be inducible in many, if not all, cell types and to act as an intracellular transducer or mediator of a variety of external influences. The following is a description of the discovery and characterization of four transcriptional regulatory factors, assessment of the function of NF-kB and its role, in many cell types, as an intracellular mediator or transducer of a variety of external influences, discovery of the NF-kB inhibitor IkB and demonstration that NF-kB and IkB exist in the cytoplasm as a NF-kB-IkB complex whose dissociation results in activation of NF-kB and its translocation into the nucleus. The following is also a description of the uses of the genes, regulatory factors and related products and reagents.

The transcriptional regulatory factors described herein can be broadly classified as constitutive (non-lymphoid) or tissue (lymphoid) specific. All factors are believed to play a role in transcription of immunoglobulin (Ig) genes. Constitutive factors, which are present in non-lymphoid cells, may have a role in regulating transcription of genes other than Ig genes; lymphoid-specific factors might also play a role in regulating transcription of genes in addition to Ig genes.

Four transcriptional regulatory factors were identified, as described below and in the Examples. The presence of constitutive factors rendered the detection of tissue specific factors more difficult. A sensitive DNA binding assay, described below, was employed in all studies to facilitate detection of tissue specific factors.

The characteristics of the transcriptional regulatory factors IgNF-A, E, IgNFB and Kappa-3 (or NF-κB) are summarized in Table 1 below.

TABLE 1

CHARACTERISTICS OF FOUR TRANSCRIPTIONAL REGULATORY FACTORS

| Factor Designation | Ig Regulatory Sequence | | | | | |
|---|---|---|---|---|---|---|
| | Promoter | | Enhancer | | | |
| | $V_H$ | $V_\kappa$ | $U_E$ | $K_E$ | Lymphoid | Nonlymphoid |
| IgNF-A (NF-A1) | + | + | + | − | + | + |
| E factors | − | − | + | + | + | + |
| IgNF-B (NF-A2) | + | + | + | − | + | − |
| Kappa-3 (NF-κB) | − | − | − | + | + | + |

Factor Ig NF-A

As indicated in Table 1, IgNF-A binds to Ig regulatory DNA elements in the region of mouse heavy and kappa light chain gene promoters and also to mouse heavy chain gene enhancer. DNAase I footprint analysis indicates that the binding is mediated by the octamer sequence (ATTTGCAT) which occurs in mouse and human light chain gene promoters approximately 70 base pairs upstream from the site of initation and in heavy chain gene promoters at about the same position (in inverted sequence).

Deletion or disruption of the IgNF-A binding site in Ig promoters significantly reduces the level of accurately initiated transcripts in vivo. See, e.g., Bergman, Y. et al. PNAS USA 81 7041–7045 (1984); Mason, J. O. et al. Cell 41 479–487 (1985). As demonstrated in Example 2, this also occurs in an in vitro transcription system. IgNF-A appears to be a positive transacting factor.

The IgNF-A binding site appears to be a functional component of the B-cell-specific Ig promoter. For example, sequences from this promoter containing the IgNF-A binding site specify accurate transcription in B-cells but not in Hela cells. IgNF-A however, may not be restricted to B-cells because a factor was detected in Hela cell extracts which generated complexes with similar mobilities and sequence specificity (as tested by competition analysis). Interestingly, the Ig octamer motif in the IgNF-A binding site has recently been shown to be present in the upstream region (about 225 bp) of vertebrate U1 and U2 snRNA genes. More importantly, this element dramatically stimulates (20 to 50 fold) transcription of U2 snRNA genes in Xenopus oocytes. Therefore, IgNF-A may be a constitutive activator protein that also functions in the high level expression of U1 and U2 snRNA genes in vertebrate cells.

The presence of an IgNF-A binding site in the mouse heavy chain enhancer suggests the additional involvement of IgNF-A in enhancer function. It is known that deletion of an 80 bp region of the enhancer containing the putative binding site reduces activity approximately tenfold. The occupation of the binding site, in vivo, has been inferred from the fact that the G residue in the enhancer octamer is protected from dimethyl sulfate modification only in cell of the B lineage. Furthermore, IgNF-A also binds in a sequence-specific manner to the SV40 enhancer (J. Weinberger, personal communication), which contains the Ig octamer motif, thereby strengthening the notion that the factor participates in enhancer function.

E Factors

The E factors are constitutive factors which bind to the Ig light and heavy chain enhancer.

Factor Ig NF-B

Factor IgNF-B binds to the same regulatory elements as IgNF-A. Indeed, the binding site for IgNF-B appears to be the octamer motif. In contrast to IgNF-A, IgNF-B is lymphoid cell specific. It was. found in nuclear extracts from pre-B, mature B and myeloma cell lines and in nuclear extracts from some T cell lymphomas. IgNF-B was undetectable in nuclear extracts of several non-lymphoid cells. The gene encoding Ig NF-B has been cloned (oct-2 clone below) and its nucleotide sequence has been determined (See FIG. 18a).

Factor NF-κB

NF-κB (previously referred to as Kappa-3) binds only to the Ig light chain enhancer. The binding is mediated by the sequence TGGGATTCCCA. The factor initially was characterized as lymphoid cell specific and also as lymphoid stage specific; that is, work showed that it is expressed only by mature B-cells. Thus, it is a marker of B cell maturation (e.g. the factor can be used to type B cell lymphomas). Additional work, described in Examples 8–15 in particular, has shown that NF-kB is an inducible factor in cells, both pre-B and non pre-B, in which it is not constitutively present (Example 8), that it is present in the cytoplasm as an inactive precursor (Examples 10 and 11), and that the inactive precursor is a complex of NF-kB and an inhibitor, referred to as IkB, which converts NF-kB to an inactive form in a reversible saturable and specific reaction. Dissociation of the complex results in activation of NF-kB (appearance of NF-kB binding activity) and translocation of the NF-kB into the nucleus.

As discussed below, it is now evident that this DNA binding protein, initially thought to be a B-cell specific factor and subsequently implicated in gene regulation in T lymphocytes, is present in many, if not all, cell types and that it acts as an important intracellular transducer or mediator of a variety of external influences. That is, NF-κB is now known to be involved in a variety of induction processes in essentially all types of cells and is thought to participate in a system through which multiple induction pathways work, in much the same manner as "second messengers" (e.g., cAMP, $IP_3$) act, resulting in transduction of a variety of extra-cellular signals into specific patterns of gene expression. Different cell types and different genes respond to this one signal, which serves as a central "control", whose activity can be altered by means of the present invention. As used, the terms altering and modifying mean changing the activity or function of NF-κB in such a manner that it differs from the naturally-occurring activity of NF-κB under the same conditions (e.g., is greater than or less than, including no activity, the naturally-occurring NF-κB activity; is of different specificity in terms of binding, etc.).

It has been shown that NF-κB participates in gene expression (e.g., cytokine gene expression) which is activated by a specific influence or extracellular signal (e.g., infection by a virus) in many, if not all types of cells. In particular, it has now been demonstrated that NF-κB has a central role in virus induction of human β-interferon (β-IFN) gene expression. Virus infection has been shown to potently activate the binding and nuclear localization of NF-κB and, in pre-B lymphocytes, to result in expression of both the β-IFN gene and the Ig kappa gene. The wide variety of cell types in which β-interferon can be induced and the divergent set of gene induction processes which involve NF-κB provide evidence that NF-κB plays a broad role in gene regulation as a mediator of inducible signal transduction.

The following is a description and exemplification of work (Example 15) which clearly demonstrates the role of NF-κB in virus-induced human β-IFN gene expression; of the evidence that there is a single NF-κB which serves many roles in many different cell types and how it acts as an intracellular messenger in a variety of different gene induction processes, particularly several which have important effects on cell physiology in health and disease; and of the use of methods and compositions of the present invention.

Role of NF-κB in Cytokine Gene Regulation

The role of NFκB as a mediator or messenger in cytokine gene regulation has been demonstrated, as explained in greater detail in the Exemplification, through assessment of the viral induction of human β-IFN gene expression. The human β-IFN gene has been shown to be positively regulated by NF-κB, which was, in turn, shown to interact with a virus inducible element, called PRDII, in the β-IFN gene. As described below, NF-κB has been shown to be highly induced in lymphoid and non-lymphoid cells by either virus infection or treatment of cells with double-stranded RNA [poly (rI:rC)]. It has also been shown to bind specifically to PRDII, which is one of two positive regulatory domains of the interferon gene regulatory element (IRE) which, together with the release of a negative influence over a site called NRDI, are necessary and sufficient for virus induction of the β-IFN gene.

It is known that the human β-interferon (β-IFN) gene is highly inducible by virus or synthetic double-stranded RNA poly(rI:rC) in many, if not all, cell types. DeMaeyer, E. and J. DeMaeyer-Guignard, "Interferons and Other Regulatory Cytokines", John Wiley and Sons, New York (1988). Extensive characterization of the β-IFN gene promoter has revealed a complex arrangement of positive and negative regulatory elements. Taniguchi, T., *Ann. Rev. Immunol.*, 6:439–464 (1988). A 40 base pair DNA sequence designated the IRE (Interferon gene Regulatory Element) is both necessary and sufficient for virus induction. Goodbourn et al., *Cell*, 41: 509–520 (1985). The IRE contains two distinct positive regulatory domains (PRDI and PRDII) and one negative regulatory domain (NRDI). Goodbourn et al., *Cell*, 45:601–610 (1986); Goodbourn, S. and T. Maniatis, *Proc. Natl. Acad. Sci. USA*, 85:1447–1451 (1988). Virus induction apparently requires cooperative interactions between PRDI and PRDII. Goodbourn, S. and T. Maniatis, *Proc. Natl. Acad. Sci. USA*, 85:1447–1451 (1988). Single copies of PRDI or PRDII alone are not sufficient for virus or poly (rI:rC) induction, but two or more copies of PRDI (Fujita et al., *Cell*, 49:357–367 (1987)) or PRDII (Fan, C. M. and T. Maniatis, *EMBO J.*, 8:101–110 (1989)) confer inducibility on heterologous promoters.

The PRDII sequence binds a nuclear factor, designated PRDII-BF, that is present in extracts from both uninduced and induced MG63 cells. Keller, A. and T. Maniatis, *Proc. Natl. Acad. Sci. USA*, 85:3309–3313 (1988). A cDNA clone encoding a PRDII binding factor (designated PRDII-BF1) was isolated. DNA sequence analysis revealed that PRDII-BF1 is similar, if not identical, to a cDNA clone encoding a protein that binds to related sites in both the MHC class I H-2K$^b$ gene and the Ig κ enhancer. Singh et al., *Cell* 52:415–423 (1988). This observation suggested that PDRII might be functionally related to the H2-K$^b$ and κ enhancer sites.

The site in the H-2K$^b$ promoter is required for its constitutive and interferon-induced expression and binds a factor designated H2TF1 and possibly similar factors KBF1 and EBP-1 which are constitutively expressed in most cell types. (Baldwin, A. S. and P. A. Sharp, *Proc. Natl. Acad. Sci. USA*, 85:723–727 (1988); Yano et al., *EMBO J.*, 6:3317–3324 (1988); Clark et al., *Genes & Dev.*, 2:991–1002 (1988)). The Ig κ enhancer site, termed κB, binds NF-κB, which is required for κ enhancer function. Sen, R. and D. Baltimore, *Cell*, 46:705–716 (1986); Atchison, M. and R. P. Perry, *Cell*, 48:121–128 (1987); Lenardo, M. et al., *Science*, 236:1573–1577 (1987). The transcriptional activities and in vitro binding of the κB site and PRDII were compared and results showed that the two regulatory sequences are interchangeable in vivo, and that PRDII specifically binds NF-κB in vitro. A binding activity indistinguishable from NF-κB in nuclear extracts from virus-infected cells was also identified. Viral treatment of 70Z/3 pre-B lymphocytes induced κ gene expression as well as β-IFN gene expression. These results show that NF-κB plays an important role in the virus induction of the β-IFN gene and indicate that NF-κB acts similarly to second messenger systems in that it transduces a variety of extracellular signals into specific patterns of gene expression.

It has been shown, by all available criteria, that the κB and the PRDII DNA elements—one from the Ig κ light chain gene and one from the β-IFN gene—are interchangeable. They drive transcription of reporter genes in response to the same set of inducers, cross-compete for binding in vitro and have closely-related DNA sequences. Another indication of the identity of the two elements is that release of NF-κB from a complex with its inhibitor, I-κB, correlates with the induction of β-IFN in L929 cells and that, conversely, a β-IFN inducer (Sendai virus) induces κ gene transcription in 70Z/3 cells. This relationship is strengthened by the correlation between the ability of mutations in PRDII to decrease β-IFN gene inducibility in vivo and reduce binding to NF-κB in vitro. Evidence that double-stranded RNA induces a factor resembling NF-κB has also been recently obtained by Visvanathan, K. V. and S. Goodbourn, *EMBO J.*, 8:1129–1138 (1989).

Results described in the Exemplification strongly imply that β-IFN gene expression is activated, at least in part, by induction of NF-κB. The ability of NF-κB to be activated by a protein synthesis-independent pathway is consistent with the fact that induction of β-IFN is not blocked by cycloheximide. In fact, the β-IFN gene, like the κ gene, can be induced by cycloheximide. Ringold et al., *Proc. Natl. Acad. Sci. USA*, 81:3964–3968 (1984); Enoch et al., *Mol. Cell Biol.*, 6:801–810 (1987); and Wall et al., *Proc. Natl. Acad. Sci. USA*, 83:295–298 (1986). In addition to the interaction between NF-κB and PRDII, virus induction of β-IFN involves activation through PRDI and the release of repression at NRDI. The present data revealing a role for NF-κB in β-IFN regulation is a striking example of how it is used in many, if not all, cell types.

Evidence for the Existence of a Single NF-κB

As shown in Table 1, sites present in a variety of genes form a mobility shift electrophoretic complex which resembles NF-κB, as reported by Sen, and Baltimore, upon incubation of the Ig κ enhancer with B-cell extracts, Sen, R. and D. Baltimore, (*Cell* 46:705–716 (1986)). The biochemical evidence suggests the involvement of a single NF-κB in all cell types and not a family of factors in which individual members are specifically inducible in particular cell types.

This evidence includes the fact that purification of NF-κB to homogeneity from both human and bovine sources yields a single polypeptide chain of approximately 44 to 50 kD (although this could be a fragment of a larger protein).

Kawakami et al., *Proc. Natl. Acad. Sci. USA* 85:4700–4704 (1988); and Lenardo et al., *Proc. Natl. Acad. Sci. USA,* 85:8825–8829 (1988). NF-κB adopts an oligomeric structure in solution; based on the size of the complex, it exists either as a homodimer or associates with a heterologous subunit of approximately equal molecular weight. Baeuerle, P. et al., *Cold Spring Harbor Symposium,* 53:789–798 (1988); Lenardo et al., *Proc. Natl. Acad. Sci. USA,* 85:8825–8829 (1988). NF-κB has the unique property that nucleoside triphosphates dramatically stimulate its ability to bind DNA in vitro. Lenardo et al., *Proc. Natl. Acad. Sci. USA,* 85:8825–8829 (1988). NF-κB is further distinguished by the fact that it can be released as an active binding species from an inactive cytosolic form that is completed with IκB. Baeuerle, P. and D. Baltimore, *Cell,* 53:211–217 (1988); Baeuerle, P. and D. Baltimore, *Science,* 242:540–545 (1988). All of these features are shared by the NF-κB complex irrespective of the cell-type from which it is derived.

More importantly, no differences in binding specificity have been detected between the NF-κB complexes from different cell types. That is, the NF-κB complex induced in T cells has no preference for sites from genes activated in T cells rather than those from genes activated in B cells and vice-versa. Lenardo et al., *Proc. Natl. Acad. Sci. USA,* 85:8825–8829 (1988). An identical pattern of base contacts is characteristic of complexes between DNA and NF-κB from different cell types, further decreasing the possibility that the NF-κB complex in different cell types is due to heterogeneous proteins.

It is clear that NF-κB binding sites are recognized by other obviously distinct transcription factors. The best examples are the H2-TF1 and KBF-1 proteins, which bind to an NF-κB-like site in the H2-K$^b$ MHC class I gene (Baldwin, A. S. and P. A. Sharp, *Mol. Cell. Biol.,* 7:305–313 (1987); and Yano et al., *EMBO J.,* 6:3317–3324 (1987)). However, these factors are constitutively active nuclear binding proteins in many different cell types and no evidence implicates them in inducible gene expression. Other examples include the factor EBP-1 which binds to the SV40 κB site but has a different molecular size than NF-κB and is also not inducible (Clark et al., *Genes & Development,* 2:991–1002 (1988); HIVEN86A, an 86 kD factor identified in activated T cell extracts by DNA affinity chromatography (Franza et al., *Nature,* 330:391–395 (1987)); and finally, a protein encoded by a cDNA (λh3 or PRDII-BF1) selected from λgt11 expression libraries (Singh et al., *Cell,* 52:415–523 (1988)). Recent evidence has made it unlikely that the λh3 clone encodes NF-κB because several cell types that have abundant expression of NF-κB lack the transcript for λh3. Taken together these findings indicate that there is only one NF-κB that serves multiple roles in many different cell types.

NF-κB Acts as an Intracellular Messenger

A salient feature of the induction of NF-κB is that it takes place in the absence of new protein synthesis. Sen, R. and D. Baltimore, *Cell,* 47:921–928 (1986). In fact, the protein synthesis inhibitor cycloheximide can alone activate NF-κB. Sen, R. and D. Baltimore, *Cell,* 47:921–928 (1986). It appears, therefore, that NF-κB induction involves the conversion of a pre-existing precursor into an active form.

Inactive NF-κB is complexed with a labile inhibitor protein, I-κB. Cytosolic extracts from uninduced cells can be treated in vitro with dissociating agents such as formamide and deoxycholate to unmask very high levels of NF-κB activity. Baeuerle, P. and D. Baltimore, *Cell,* 53:211–217 (1988). These treatments by and large do not work on nuclear extracts from uninduced cells. Conversely, NF-κB activated normally in the cell is detected in nuclear but not cytosolic extracts implying a nuclear translocation step following activation in vivo. The inhibitory activity has been shown to be due to a protein of 68 kD that can be separated chromatographically from NF-κB. Baeuerle, P. and D. Baltimore, *Science,* 242:540–545 (1988). This protein is able to inhibit the binding of NF-κB but not other DNA-binding proteins and has therefore been named "I-κB" (Inhibitor-κB).

Notably, crude preparations of I-κB efficiently inhibit binding of NF-κB derived from mature B cells or other cell-types that have been induced. Baeuerle, P. and D. Baltimore, *Science,* 242:540–545 (1988). The implicaton is that activation of NF-κB involves a modification of I-κB and not NF-κB. This distinguishes NF-κB activation from a similar phenomenon involving the glucocorticoid receptor. In the latter, a direct interaction of glucocorticoid with the receptor is required to release it from a cytoplasmic complex with the heat shock protein, hsp90. Picard, D. and K. R. Yamamoto, *EMBO J.,* 6:3333–3340 (1987).

The model which ties together these observations is that NF-κB is initially located in the cytoplasm in a form unable to bind DNA because it is complexed with I-κB. Various inducers then cause an alteration in I-κB allowing NF-κB to be released from the complex. Free NF-κB then travels to the nucleus and interacts with its DNA recognition sites to facilitate gene transcription. The complex formation of NF-κB with I-κB appears to be rapidly and efficiently reversible in vitro which lends itself well to the shut-off as well as turn-on of NF-κB binding. Moreover, this model resolves a major question in signal transduction: NF-κB, like the glucocorticoid receptor, acts as a messenger to transmit the gene induction signal from the plasma membrane to the nucleus.

The model presented above is not unlike the well known role of cAMP as a second messenger in the action of many hormones; in the case of cAMP, the first messenger is the hormone itself. (see, eg., Pastan, *Sci. Amer.,* 227:97–105 (1972)). The essential features of the cAMP model are that cells contain receptors for hormones in the plasma membrane. The combination of a hormone with its specific membrane receptor stimulates the enzyme adenylate cyclase which is also bound to the plasma membrane. The concomitant increase in adenylate cyclase activity increases the amount of cAMP inside the cell which serves to alter the rate of one or more cellular processes. An important feature of this second messenger or mediator model is that the hormone (the first messenger) need not enter the cell.

The participation of NF-κB in gene expression that is activated in specific cells by specific influences calls for a level of regulation in addition to the inducibility of NF-κB binding. How is "cross-talk" between the various paths employing NF-κB avoided? Factors acting upon other sequences within a transcriptional control element appear to govern the response to the NF-κB signal, as described herein for β-IFN. Studies of β-IFN expression have shown that virus induction works through three events: two virus-inducible positive signals, one of which is NF-κB, and the release of a single negative regulator. The two positive signals work through distinct DNA sites (PRDI and PRDII), but must act together to facilitate transcription. Either site alone is not inducible.

The theme of multiple signals that generate specificity is further supported by studies of the Ig κ gene and the IL-2 receptor gene. The NF-κB site from the κ light chain enhancer alone on a short oligonucleotide will stimulate transcription in B and T lymphocytes as well as in non-lymphoid cells. Pierce, J. W. et al., *Proc. Natl. Acad. Sci. USA*, 85:1482–1486 (1988). Its function depends solely on the presence of NF-κB. By contrast, the entire κ enhancer is inducible only in B lymphocytes and is unresponsive to NF-κB in other cell types. The restricted response to NF-κB by the κ enhancer has now been attributed to a repressor sequence. The repressor sequence resides in the enhancer some distance away from the NF-κB binding site and acts to suppress transcriptional effects of NF-κB in non-B cell types. The activation of the IL-2 receptor gene specifically in T lymphocytes is attained by a slightly different means. Full induction of this gene depends on NF-κB as well as a positively-acting sequence immediately downstream. The downstream element has now been found to bind a T cell specific protein called NF-ILT. Though NF-ILT is not itself inducible, its presence only in T cells seems to contribute to T cell specific induction of the IL-2 receptor gene.

Role of NF-κB in Other Inducible Systems

Recently, NF-κB has been implicated in several other inducible systems. For example, NF-κB is induced in T-cells by a trans-activator (tax) of HTLV-1 or by PMA/PHA treatment and thereby activates the IL-2 receptor α gene and possibly the IL-2 gene. Bohnlein et al., *Cell*, 53:827–836 (1988); Leung, K. and G. Nabel, *Nature*, 333:776–778 (1988); Ruben et al., *Science*, 241:89–92 (1988); Cross et al., *Science*, (1989); and Lenardo et al., *Proc. Natl. Acad. Sci. USA*, 85:8825–8829 (1988). NF-κB also appears to take part in gene activation during the acute phase response of the liver. Edbrooke et al., (1989). Results described here suggest that inducibility of NF-κB plays a prominent role in interactions between cytokines. IL-1 and TNF-α activate NF-κB binding and both have been shown known to induce β-IFN. Osborn et al., *Proc. Natl. Acad. Sci. USA*, 86:2336–2340 (1989); and DeMaeyer, E. and J. DeMaeyer-Guignard, "Interferons and Other Regulatory Cytokines", John Wiley and Sons, New York (1988). Finally, NF-κB has been shown to play a role in the transcription of human immunodeficiency virus (HIV). Nabel, G. and D. Baltimore, *Nature*, 326:711–713 (1987). Significantly, herpes simplex virus has recently been shown to increase HIV LTR transcription through NF-κB/core sequences. Gimble et al., *J. Virol.*, 62:4104–4112 (1988). Thus, NF-κB induction may lead to the propagation of HIV in cells infected with other viruses.

NF-κB is unique among transcription regulatory proteins in its role as a major intracellular transducer of a variety of external influences in many cell types. In the cases studied thus far, it appears that the actual target of induction is I-κB, which becomes modified to a form that no longer binds to NF-κB. Baeuerle, P. and D. Baltimore, *Science*, 242:540–545 (1988). The released NF-κB then displays DNA binding activity and translocates to the nucleus.

Role of NF-kB in HIV Expression

Figure 25:
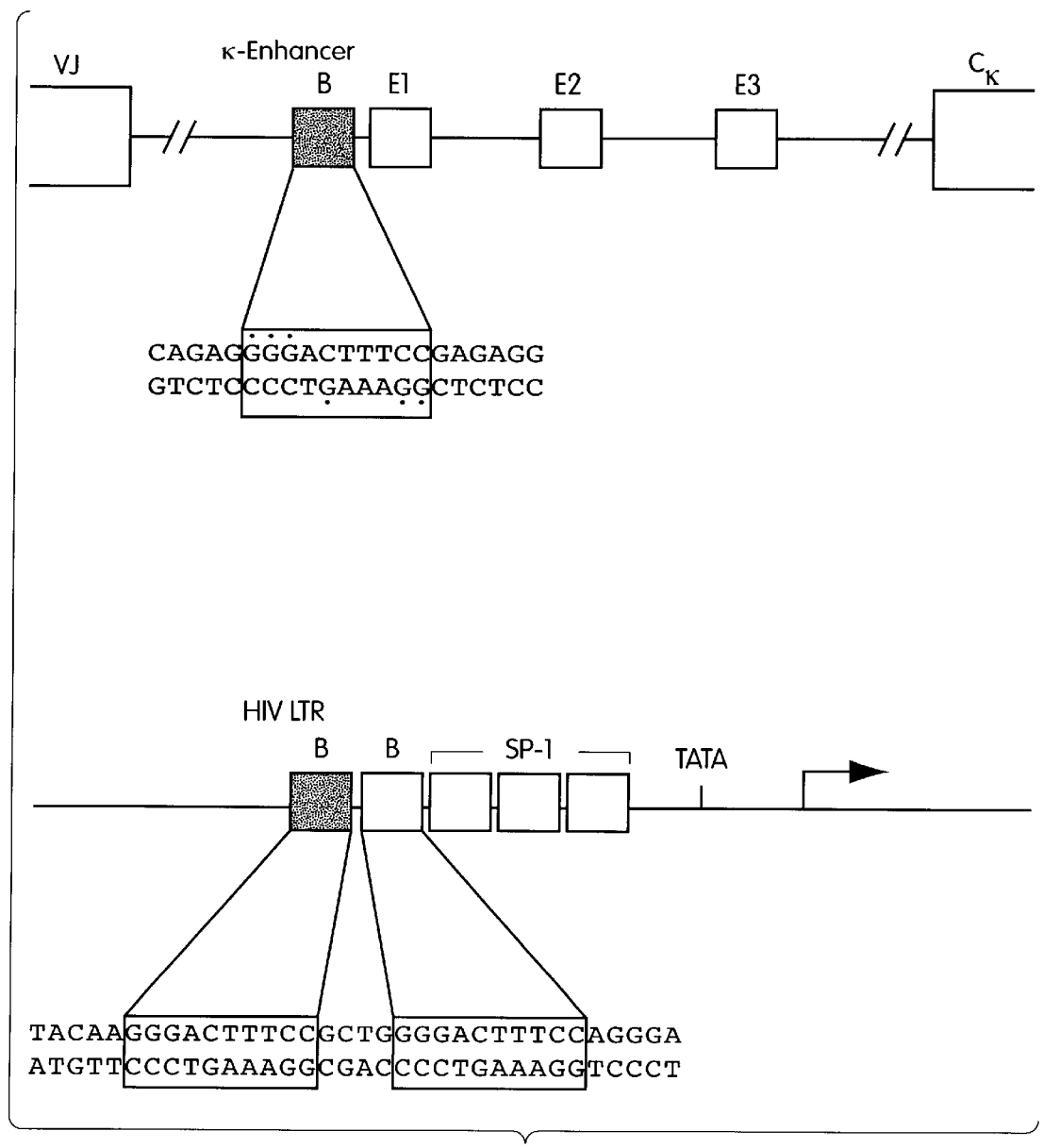
FIG. 25 is a representation of binding sites for the NF-kB transcription factor in the immunoglobulin kappa light chain enhancer and the HIV enhancer. Boxes indicate the binding sites for NF-kB (B); other regulatory sites are referred to as E1, E2 and E3 and Spl. Dots indicate guanosine residues in the kappa enhancer whose methylation interfered with binding of NF-kB.

Treatment of latently HIV-infected T-cells with phorbol ester (12-O-tetradecanoylphorbol 13-acetate; TPA) and with phytohaemaglutinin (PHA) results in the onset of virus production. Harada, S. et al., *Virology*, 154:249–258 (1986); Zagury, D. J. et al., *Science*, 232:755–759 (1986). The same treatments induce NF-kB activity in the human T-lymphoma cell line Jurkat. Sen, R. and D. Baltimore, *Cell*, 47:921–928 (1896). This correlation and the finding that two NF-kB binding sites are present upstream of the transcriptional start site in the HIV enhancer, (FIG. 25) suggested a direct role for NF-kB in the activation of the viral enhancer, an event ultimately leading to the production of virus. Nabel, G. and D. Baltimore, *Nature*, 326:711–713 (1987). This possibility was tested by transient transfection of a plasmid containing an HIV LTR-controlled CAT gene into a human T-lymphoma cell line. Nabel, G. and D. Baltimore, *Nature*, 326:711–713 (1987). The viral cis-acting elements rendered the transcriptional activity of the CAT gene responsive to TPA/PHA treatment of cells. This inducible transcriptional stimulation of the CAT gene was completely dependent on intact binding sites for NF-kB in the HIV enhancer because mutation of the two binding sites abolished inducibility. A protein-DNA complex with a fragment of the HIV enhancer containing the two NF-kB binding sites was observed in mobility shift assays only with nuclear extracts from TPA/PHA-stimulated T-cells and not with control extracts. These observations provided strong evidence that HIV expression in latently infected T-cells is induced by the same transcription factor that regulates kappa gene expression, NF-kB. A precursor of NF-kB is constitutively present in T-cells. Its activity can be induced by a treatment that mimicks antigenic T-cell activation and, after induction, NF-kB is able to bind to and subsequently enhance the activity of HIV transcriptional control elements. Thus, it is reasonable to conclude that NF-kB is the physiological transactivator responsible for initial expression of dormant HIV-DNA following stimulation of T-lymphocytes.

Other factors have also been implicated in the control of HIV expression including the HIV-encoded tat-III protein, the cellular transcription factor Spl, and viral proteins encoded by the ElA gene of adenovirus and the ICPO gene of the Herpes Simplex Virus. Muesing, M. A. et al., *Cell*, 48:691–701 (1987); Jones, K. A. et al., *Science*, 232:755–759 (1986); Gendelman, H. E. et al., *Proc. of the Natl. Acad. of Sc., USA*, 83:9759–9763 (1986); Nabel, G. J. et al., *Science* (1988); Rando, R. F. et al., *Oncogene*, 1:13–19 (1987); Mosca, J. D. et al., *Nature*, 325:67–70 (1987). It is doubtful whether the tat-III and Spl proteins are responsible for an initial induction of HIV expression. Although the tat-III protein functions as a strong positive feedback regulator of HIV expression, full expression of the tat-III protein appears to depend on NF-kB. Muesing, M. A. et al., *Cell*, 48:691–701 (1987); Nabel, G. and D. Baltimore, *Nature*, 326:711–713 (1987). It is unlikely that Spl initiates HIV expression because it is constitutively active. Dynan, W. S. and R. Tjian, *Cell*, 32:669–680 (1983). The viral ElA and ICPO gene products might lead to induction of HIV expression. This, however, is independent of T-cell activation by antigenic stimulation and of NF-kB, as shown by cotransfection experiments into human T-lymphoma cells of plasmids with an HIV enhancer-controlled CAT gene and plasmids encoding the viral genes. The increase in CAT activity induced by the viral gene products was unchanged when the NF-kB binding sites in the HIV enhancer were inactivated by mutation.

Improved DNA Binding Assay with Enhanced Sensitivity for Identification of Regulatory Factors The transcriptional regulatory factors described above were identified in extracts of cellular nuclear protein by means of an improved gel electrophoresis DNA binding assay with enhanced sensitivity. This improved assay is a modification of an original assay based on the altered mobility of protein-DNA complexes during gel electrophoresis. In the improved assay of this invention, the simple alternating copolymer, duplex poly(dI-dC)-poly(dI-dC) was used as the competitor DNA species. The use of this copolymer as competitor resulted in an enhancement of sensitivity for detection of specific protein-DNA complexes. The original assay has been extensively employed in equilibrium and kinetic analyses of purified prokaryotic gene regulatory proteins. See, e.g., Fried, M. and Crothers, D. M.,

*Nucleic Acid Res.* 9 6505–6525 (1981); Garner, M. M. and Revzin A., *Nucleic Acids Res.* 9 3047–3060 (1981). More recently it has been used to identify and isolate a protein that binds to satellite DNA from a nuclear extract of eukaryotic cells (monkey cells). See Strauss, R. and Varshavsky, A., *Cell* 37 889–901 (1984). In the latter study an excess of heterologous competitor DNA (*E. coli*) was included with the specific probe fragment to bind the more abundant, sequence non-specific DNA binding proteins in the extract.

The assay is performed essentially as described by Strauss and Varshavky, supra, except for the addition of the poly (dI-dC)-poly(dI-dC). An extract of nuclear protein is prepared, for example, by the method of Dingnam, J. D. et al., *Nucleic Acids Research* 11:1475–1489 (1983). The extract is incubated with a radiolabelled DNA probe (such as an end-labeled DNA probe) that is to be tested for binding to nuclear protein present in the extract. Incubation is carried out in the presence of the poly(dI-dC)-poly(dI-dC) competitor in a pysiological buffer. DNA protein complexes are resolved from (separated from) free DNA probes by electrophoresis through a polyacrylamide gel in a low ionic strength buffer and visualized by autoradiography.

In a preferred embodiment of the method, protein samples (about 10 μg protein) are incubated with approximately 10,000 cpm (about 0.5 ηg) of an end-labeled $^{32}$P double-stranded DNA probe fragment in the presence of about 0.8–4 ηg poly(dI-dC)-poly(dI-dC) (Pharmacia) in a final volume of about 25 μl. Incubations are carried out at 30° for 30–60 minutes in 10 mM Tris HCl (pH 7.5), 50 mM NaCl, 1 mM DTT, 1 mM EDTA. Protein-DNA complexes are resolved on low-ionic strength polyacrylamide gels. Samples are layered onto low ionic-strength 4% polyacrylamide gels (0.15×16 cm; acrylamide:bisacrylamide weight ratio of 30:1). Gels are pre-electrophoresed for about 30 min at 11 V/cm in buffer consisting of 6.7 mM TrisHCl, (pH 7.5), 3.3 mM NaOAc, and 1 mM EDTA. Buffer is recirculated between compartments. Gels are electrophoresed at the same voltage at room temperature, transferred to Whatman 3MM, dried and autoradiographed.

Figure 1B:
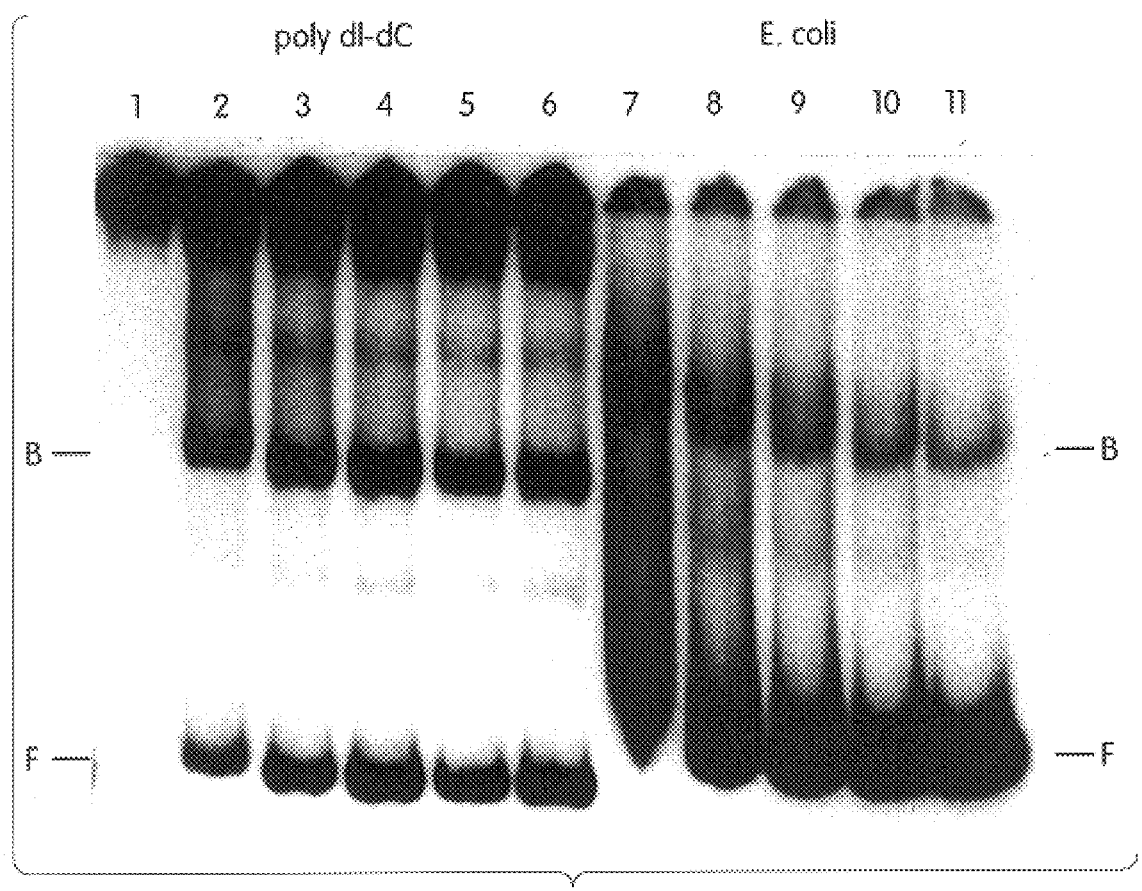
FIG. 1B is an autoradiograph of gel electrophoresis DNA binding assays with the SfaNI-SfaNI κ promoter fragment of the MOPC 41 $V_\kappa$ gene.

The enhanced sensitivity of the assay of the present invention is evident in the initial work which led to identification of the factor IgNF-A. A radiolabelled SfaNI-SfaNI DNA fragment derived from the upstream region of the MOPC 41 κ light chain gene (FIG. 1*a*) was incubated with a nuclear extract of a human B cell line, in the absence or in the presence of *E. coli* chromosomal DNA or poly(dI-dC)-poly(dI-dC). The resulting complexes were resolved from the free fragment by electrophoresis through a low ionic strength, non-denaturing polyacrylamide gel and visualized by autoradiography (FIG. 1*b*). In the absence of competitor DNA, all of the labeled fragment was retained at the top of the gel (lane 1), probably due to the binding of an excess of non sequence-specific proteins. With addition of increasing amounts of either poly(dI-dC)-poly(dI-dC) (lanes 2–6) or *E. coli* chromosomal DNA (lanes 7–11) as competitors, putative protein-DNA complexes which migrated slower than the free fragment were detected. The relative abundance of the major species of complex (B) as well as that of minor species was significantly greater in the presence of the alternating copolymer competitor DNA.

The use of a sensitive gel electrophoresis DNA binding assay in conjunction with the copolymer competitor poly (dI-dC)-poly(dI-dC) facilitated the identification of the regulatory factors described herein. The simple alternating copolymer probably competes less effectively than heterologous DNA sequences for binding of a sequence-specific factor, thereby significantly increasing the sensitivity of the assay. The assay has general applicability for elucidation of mammalian gene regulatory proteins.

A further increase in sensitivity in this assay is obtained by the use of small DNA probes (about 100 bp or less) which minimize non-specific binding interactions in a crude extract. (See Example 1).

Employing this assay, binding competition tests can be performed to analyze the sequence specificity of protein-DNA interactions. For this purpose, an unlabeled DNA fragment to be examined for competitive binding to the protein factor can be added to the incubation mixture of protein extract and labeled DNA probe (along with the poly(dI-dC)-poly(dI-dC)). The disappearance of protein-DNA probe complex, or its diminishment, indicates that the unlabeled fragments compete for binding of the protein factor. In addition, relative binding affinity of the protein to a probe sequence can be assessed by examining the ability of a competitor to displace the protein at varying concentrations.

In conjunction with the competition assays, DNase I footprint analysis (See Galas, D. and Schmitz A., *Nucl. Acids Res.* 5 3157–3170 (1978) and Example 1) and methylation interference experiments (See, e.g., Ephrussi, A. et al., *Science* 227:134–140 (1985) can be used to refine analysis of the binding domain of the protein factors.

Assessment of the Functional Role of Factors Described Herein in Regulation of Transcription The functional role of the factors in the regulation of the transcription can be assessed in several ways. A preferred technique for lymphoid cell factors entails the use of the in vitro transcription system developed from cells of lymphoid cell lineage. This system is described in detail in the Example 2. The function of a factor can be indirectly assessed in this system by employing as templates for transcription, nucleotide sequences from which the binding domain of the factor has been deleted. As has been noted above, deletion of the upstream sequence located between −44 and −79 bp from the cap site of the MOPC41 κ gene disrupts transcriptions in this system (This has also been noted in in vivo systems). The deleted region includes the IgNF-A binding site. This indicates that transcription of the template is dependent upon the factor—binding site and, inferentially, upon the factor itself.

A direct way to assess the function of the factors is to show that transcription can be modulated by removal and replacement of the factor in the in vitro transcription system with an appropriate template. For example, the intact MOPC41 κ promoter gene can be used as a template in the in vitro system described and transcription of this template can be assessed in the presence and absence of a factor (for instance, NF-κB, a lymphoid specific factor). The factor can be removed from the lymphoid cell extract by chromatographic fractionation and then replaced. If the level of transcription is diminished in the absence and restored by replacement of the factor, a direct indication of the factors involvement in transcription is provided.

In an alternative approach, antisera or monoclonal antibody can be raised against a purified or enriched preparation of the factor. The antibody can be used to probe for expression of the factor in a library of cDNA of cells known to express the factor.

Cloning of Genes Encoding Sequence-Specific DNA Binding Proteins, Particularly Genes Encoding Transcriptional Regulatory Factors Genes encoding transcriptional regulatory factors can be isolated by a novel method for cloning genes that encode sequence-specific DNA binding proteins. The method involves screening a library of recombinant expression vectors for expression of the factor with a DNA probe comprising the recognition (binding) site for the factor. Expression of the factor is identified by the presence of complex between the DNA probe and the expressed binding protein. The approach has general applicability to the cloning of sequence-specific DNA binding proteins.

According to the method, an expression library is created by inserting DNA (e.g., cDNA from a cell which expresses the sequence specific binding protein) into an appropriate expression vector to establish an expression library. A preferred expression vector is the bacteriophage λgt11 which is capable of expressing foreign DNA inserts within *E. coli*. See e.g., Young, R. A. and Davis, R. W. in *Genetic Engineering: Principles and Techniques*, vol 7 (eds Setlow, J. & Hollaender, A.) 29–41 (Plenum, New York 1985). Alternatively, plasmid vectors may be used.

The expression library is screened with a binding-site DNA probe. The probe comprises the DNA sequence recognized by the binding protein, such as an appropriate transcriptional regulatory element (e.g., the octamer or κ-element). In preferred embodiments, the probe is less than 150 bp in length, to reduce nonspecific binding. The probe can be an oligomer of the binding site. Multiple copies of the site provide for multiple protein binding to the probe. The DNA probe is generally detectably labeled DNA. A particularly useful label is $^{32}P$.

In the present method, the binding site probe is incubated with host cell protein under conditions which allow the probe to complex with the any cognate binding protein expressed in the cell. The formation of such complexes is determined by detecting label associated with the protein. In a preferred mode, the screening is performed by generating a replica of host cell lysates and by screening the replicated protein with the probe. For example, when the bacteriophage λgt11 is used, recombinant viruses are plated in arrays onto a lawn of *E. coli* and a replica of the resulting viral plaques is made by transferring plaque protein onto an appropriate adsorbtive surface (e.g. protein replica filters). The adsorbed plaque protein is contacted with the probe under conditions which permit the formation of complexes between adsorbed protein and the probe. The replica is then washed to remove unbound probe and then examined for associated label. The protein can be examined autoradiograghically for the presence of label.

In other embodiments, a nonspecific competitor DNA can be used along with the recognition site probe, to reduce nonspecific binding to the probe. Examples of such nonspecific competitor DNA include poly (dI-dC)-poly(dI-dC) and denatured calf thymus DNA. In addition, the protein-probe complexes can be stabilized covalently for detection, for example, by uv irradiation.

This method of screening for sequence specific binding proteins is dependent, inter alia, upon:
i) the functional expression of the binding domain of the desired binding protein in the host cell;
ii) a strong and selective interaction between the binding domain and the DNA probe; and
iii) a sufficiently high level of expression of the binding protein.

These parameters can be optimimized for different proteins by routine experimentation. Some factors relevant to such optimization are discussed in detail in the exemplification of the cloning of transcriptional regulatory factor NF-κB given below.

Other modes of cloning genes encoding sequence-specific DNA binding proteins, such as genes encoding transcriptional regulatory factors, may be used. For example, the factor can be purified chromatographically by, for example, ion exchange, gel filtration and affinity chromatography or combinations thereof. Once the factor is sufficiently purified, it can be partially sequenced and from the sequence information, oligodeoxy-nucleotide probes can be made and used to identify the gene encoding the factor in a cDNA library.

Occurrence and Activation of NF-kB and Demonstration of the Role of an NF-kB Inhibitor (IkB)

The following is a description of the occurrence and activation of NF-kB in cells which do not express k immunoglobulin light chain genes (and, in which NF-kB is not evident in either cytoplasmic or nuclear fractions). In particular, the following is a description of localization of NF-kB in the cytosolic fraction; of activation of NF-kB in cytosolic fractions by dissociating agents; of redistribution of NF-kB into the nuclear fraction upon TPA stimulation; of demonstration of the appearance of NF-kB binding ability; and of the occurrence and characterization of an NF-kB inhibitor.

NF-kB Occurrence and Activation in 70Z/3 Cells

NF-kB is Virtually Undetectable in Unstimulated 70Z/3 Cells

To determine where in the cell NF-kB or its inactive precursor are located, subcellular fractions from control and TPA-stimulated 70Z/3 cells were analyzed for kB-specific DNA-binding activity. Nuclear extracts, cytosolic and postnuclear membrane fractions were analyzed at equal amounts of protein in an electrophoretic mobility shift assay, described in Example 1, followed by fluorography. (Sen, R. and D. Baltimore, *Cell*, 46:705–716 (1986). The specificity of protein-binding to a fragment of the kappa light chain enhancer was controlled by using a fragment with a mutation in the binding motif for NF-kB. This mutation has been shown to prevent binding of NF-kB. Lenardo, M. et al., *Science*, 236:1573–1577 (1987). Thus, any complexes formed on the wild type, but not on the mutant fragment, are considered specific for the NF-kB site.

Figure 29:
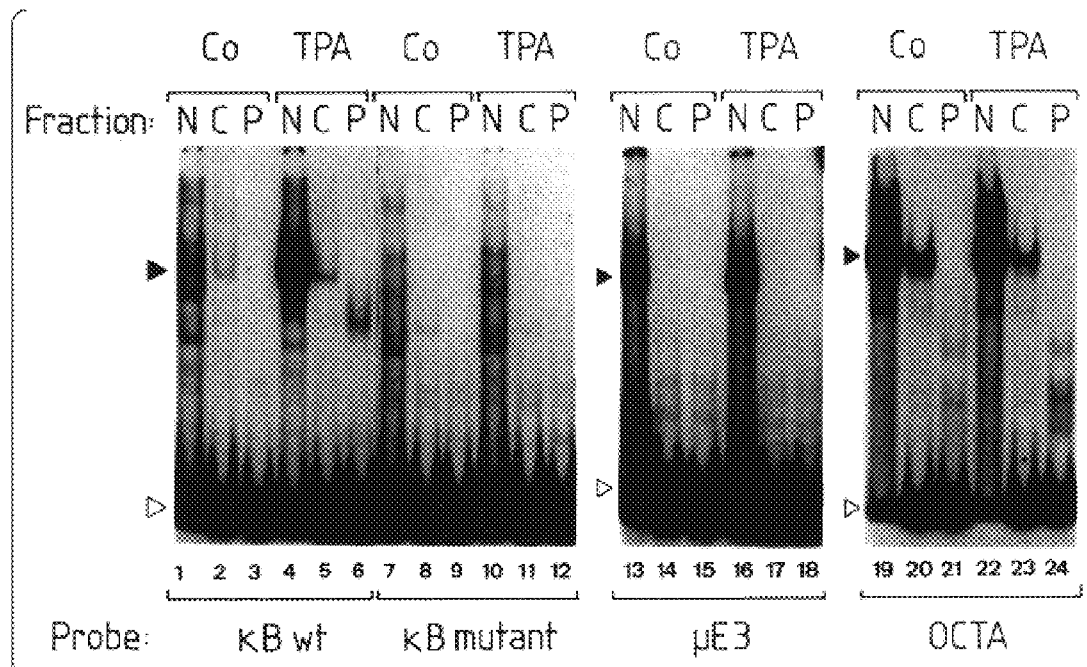
FIG. 29 represents results of electrophoretic mobility shift analysis of subcellular fraction of 70Z/3 cells.

Nuclear extracts from control cells contained very little kB-specific binding activity (FIG. 29, compare lanes 1 and 7). This is in agreement with results reported previously by Sen and Baltimore. Sen, R. and D. Baltimore, *Cell*, 46:705–716 (1986); Sen, R. and D. Baltimore, *Cell*, 47:921–928 (1986). Similarly, the ctyosolic fraction produced only a faint, but specific and reproducible, signal co-migrating with the signal from the nuclear extract (FIG. 29, compare lanes 2 and 8). The fraction containing post-nuclear membranes did not exhibit any detectable DNA-binding activity (FIG. 29, lane 3).

Figure 8:
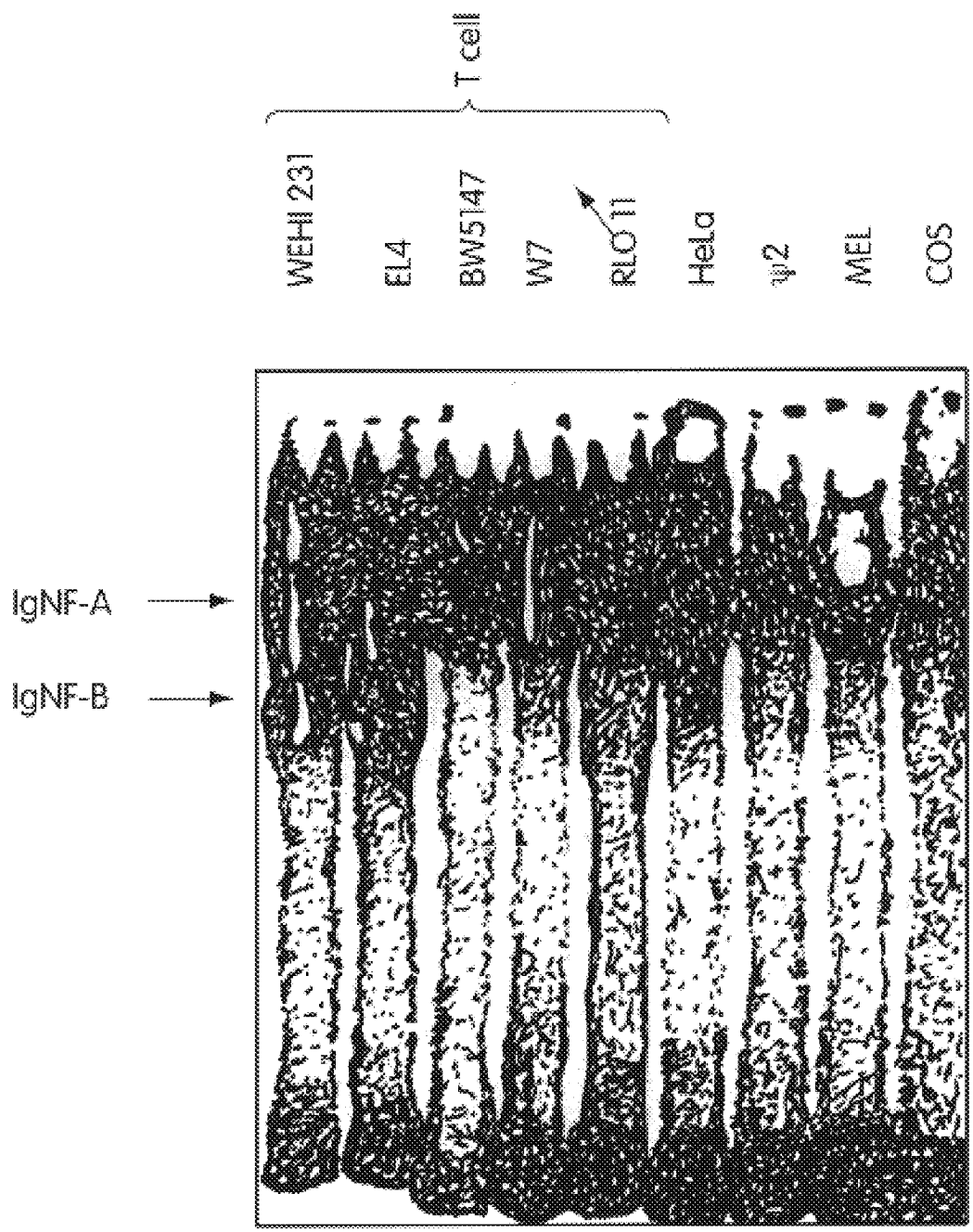
FIG. 8 shows the binding of T cell and nonlymphoid cell nuclear extracts to the MOPC-41 κ promoter region.

Upon treatment of cells with TPA for 30 minutes, the nuclear NF-kB activity was dramatically increased (FIG. 8, compare lanes 4 and 10). Almost no increase of the specific signal in the cytosolic fraction was observed (FIG. 29, compare lanes 5 and 11). The post-nuclear membrane fraction gave raise to an apparently kB-specific complex with a mobility higher than that formed by nuclear NF-kB (FIG. 29, compare lanes 6 and 12). None of the fractions had inhibitors of binding because added authentic NF-kB was fully recovered in all fractions, indicating that the results reflect a true activation of binding specificity.

NF-kB is Detectable in the Cytosolic Fraction after Denaturation and Renaturation To examine whether active NF-kB might be present but masked in fractions from unstimulated 70Z/3 cells, proteins from nuclear extracts and cytosolic fractions of control and TPA-stimulated cells were precipitated, denatured by boiling in SDS plus 2-mercaptoethanol and fractionated by electrophoresis through SDS-polyacrylamide gels. 300 ug of protein of nuclear extracts (N) and cytosolic fractions (C) from control (Co) and TPA-stimulated cells (TPA) were subjected to reducing SDS-polyacrylamide gel electrophoresis. Proteins eluted from different molecular weight fractions of the gel (i.e., corresponding to approximately 70–62 kDa (gel slice No. 6), 62–55 kDa (gel slice No. 7) and 55–48 kDa (gel slice No. 8)) were subjected to a renaturation protocol after removal of SDS. Hager, D. A. and R. R. Burgess, *Anal. Biochem.*, 109:76–86 (1980) and Example 10. Renatured fractions were tested for kB-specific DNA-binding activity in mobility shift assays using wild type and mutant kappa light chain enhancer fragments. DNA-binding reactions were performed with 11 ul of the renatured fractions in the presence of 80 ng poly(d[I-c]) in a final volume of 15 ul. Assays with wild type (WT) and mutant (mu) k enhancer fragments were loaded in adjacent lanes.

Figure 30:
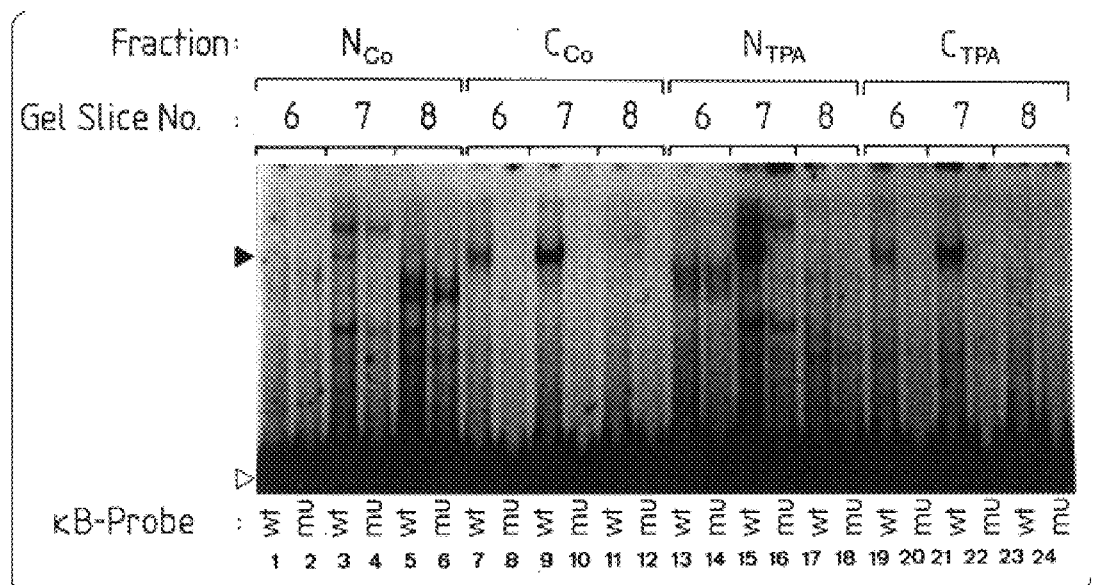
FIG. 30 shows the effect of denaturation and renaturation of kB-specific DNA-binding activity in nuclear extracts and cytosolic fractions of 70Z/3 cells.

In nuclear extracts from TPA-stimulated cells, NF-kB activity was exclusively found in a molecular weight region of 62–55 kDa. The efficiency of renaturation of the nuclear NF-kB activity was about one percent. In FIG. 30, the active and two adjacent fractions are shown for the nuclear extract from TPA-stimulated cells (lanes 13 to 18). In nuclear extracts from control cells, much less NF-kB activity was found in the same molecular weight fraction after renaturation (FIG. 30, lanes 3 and 4). Both the cytosolic fractions from control and TPA-stimulated cells, however, gave rise to a strong NF-kB-specific signal (FIG. 30, lanes 9, 10 and 21, 22). The specificity of the signal was shown by several criteria. First, it was only present when the wild type, but not the mutant, DNA fragment was used in mobility shift assays (FIG. 30, lanes 9, 10 and 21, 22). Second, it was generated with protein eluted from the same molecular weight fraction that contained authentic nuclear NF-kB. Third, upon mixing, the complex formed by the putative cytoplasmic NF-kB co-migrated exactly in native polyacrylamide gels with the complex formed by interaction of the nuclear form of NF-kB with its cognate DNA.

Assuming that NF-kB from the various fractions had a similar recovery and efficiency of renaturation, the data suggest that significant amounts of NF-kB can be activated in unstimulated 70Z/3 cells by denaturation, followed by fractionation and renaturation. Furthermore, in unstimulated cells, the in vitro activated NF-kB activity was almost exclusively recovered in the cytosolic fraction.

The subcellular distribution of two noninducible DNA-binding proteins, NF-uE3 and the octamer-binding protein were also examined in mobility shift assays, in order to determine whether other DNA-binding factors also partition into cytoplasmic fractions. Sen, R. and D. Baltimore, *Cell*, 46:705–716 (1986); Singh, H. et al., *Nature*, 319:154–158 (1986); and Staudt, L. M. et al., *Nature*, 323:640–643 (1986). The vast majority of both DNA-binding activities was found in nuclear extracts; cytosolic and postnuclear membrane fractions contained only very little activities (FIG. 29, lanes 13 to 24). No significant change in the complex formation by the two factors was observed when fractions from control and TPA-stimulated cells were compared. Thus, although subcellular fractionation can produce artificial redistribution of proteins, the fractions used in this study do well reflect nuclear localization of a number of DNA-binding proteins.

NF-kB in the Cytosolic Fraction Can be Activated by Dissociating Agents

Figure 31A:
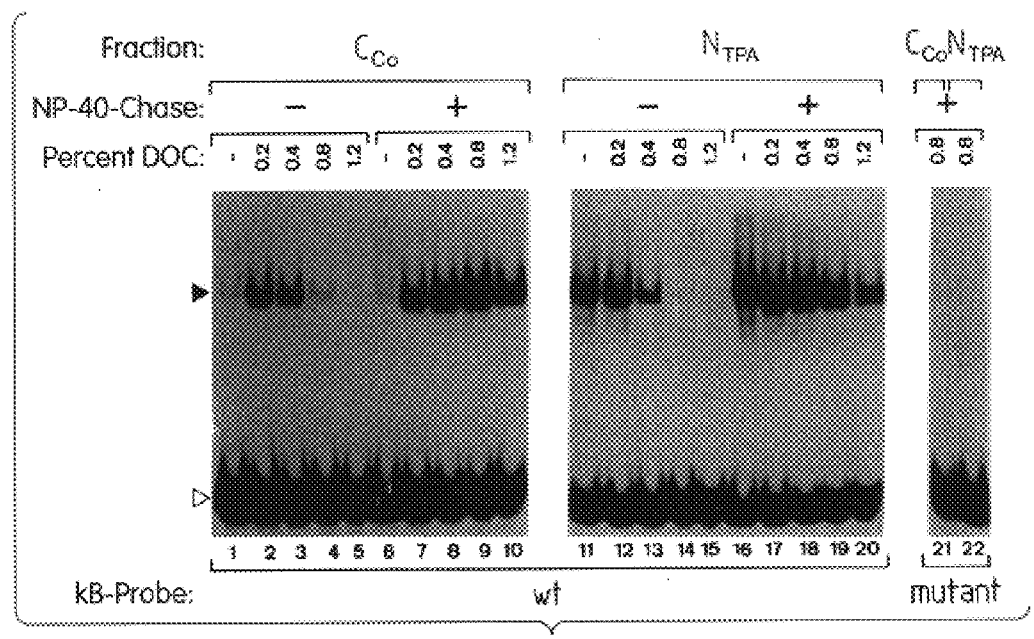
FIGS. 31A–31B show the effects of dissociating agents on the activity of NF-kB in subcellular fractions of 70Z/3 cells.
Figure 31B:
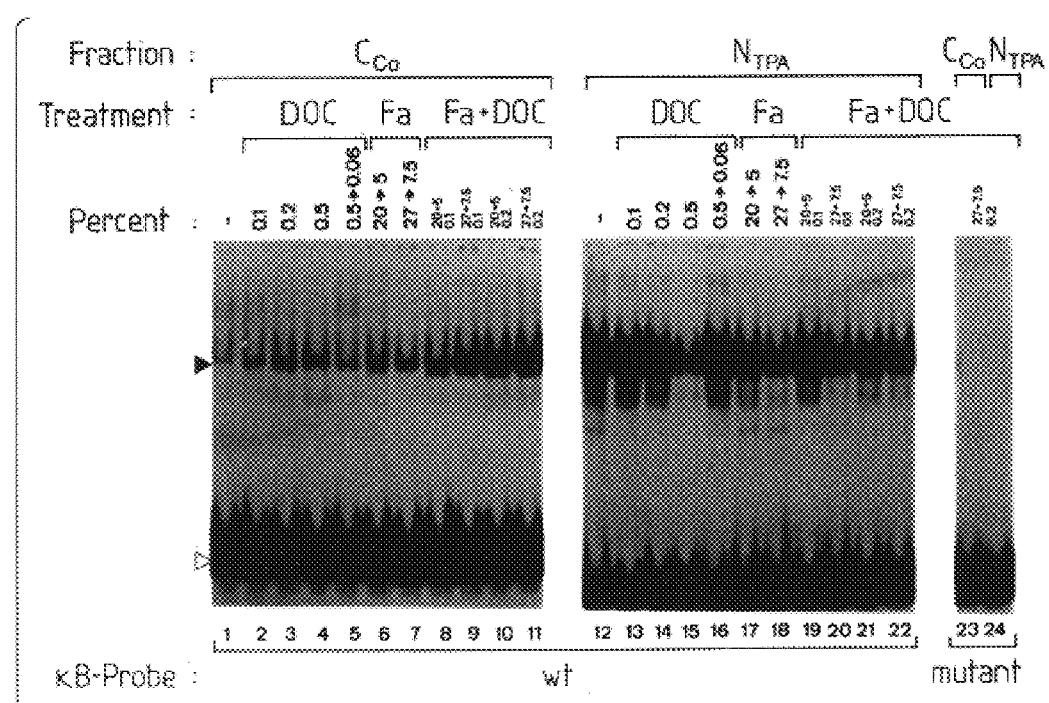

The ability to reveal cytosolic NF-kB by simply denaturation and renaturation suggested that NF-kB might be bound to an inhibitor and therefore several compounds that might dissociate protein complexes were tested for their ability to directly activate kB-specific DNA-binding activity in fractions of 70Z/3 cells. The cytosolic fraction from unstimulated cells and, as a control, the nuclear extract from TPA-treated cells were incubated with the compounds prior to electrophoretic separation of the protein-DNA complexes. Incubation of the cytosolic fraction with 0.2% sodium desoxycholate (DOC) (in the presence of 0.2% NP-40) resulted in the activation of DNA-binding activity (FIG. 31, lane 2). The induced complex had the same mobility in native gels as the one formed by nuclear NF-kB. It appeared to be specific for the kB site of the kappa light chain enhancer because it was not formed when the mutant fragment was used in the mobility shift assay (FIG. 31, lane 21). Higher concentrations of DOC led to the inactivation of the newly activated kB-binding activity (FIG. 31, lanes 3 to 5) as well as of the authentic nuclear factor (FIG. 31, lanes 13 to 15).

DOC can be sequestered out of a solution by the addition of excess nonionic detergent, presumably by inclusion of the DOC into micelles formed by the nonionic detergent. When treatment of the cytosolic fraction with up to 0.8% DOC was followed by the addition of 1% of the nonionic detergent NP-40, a quite efficient activation of the cytosolic kB-binding activity was achieved (FIG. 31, lanes 7 to 9). The DNA-binding activity of in vivo activated NF-kB from nuclear extracts was not significantly increased at low concentrations of DOC (FIG. 31, lanes 11, 12 and 16, 17). Elevated concentrations of DOC showed inhibitory effects on the DNA-binding activity of TPA-activated NF-kB that paralleled those observed for the in vitro activated kB-binding activity (FIG. 31, compare lanes 3, 4, 5 with lanes 13, 14, 15 and lanes 9, 10 with lanes 19, 20).

A partial activation of the cytosolic kB-binding activity was observed after treatment of the cytosolic fraction with 27% formamide followed by dilution (FIG. 31, lane 7). With the further addition of 0.2% DOC—a condition that alone also leads only to partial activation (FIG. 31, lane 3)—a very potent activation was observed (FIG. 31, lane 11). A titration showed that formamide and DOC activated in a synergistic manner (FIG. 31, lanes 2 to 11). The DNA-binding activity of in vivo activated NF-kB from nuclear extracts was not enhanced by any of the treatments (FIG. 31, lanes 13 to 22). On the contrary, partial inhibition of DNA-binding of NF-kB was observed under some conditions.

No in vitro activation of NF-kB was achieved by treatment with guanidinium hydrochloride (between 0.3 and 3M), urea (between 0.5 and 5M), and SDS (between 0.1 and 1%), in the presence of 0.2% NP-40). Exhaustive dialysis of the cytosolic fraction using dialysis membranes with a cut-off of 25 kDa did not lead to an activation of DNA-binding activity. In the dialyzed fraction, NF-kB-activity could still be efficiently induced by formamide/DOC treatment, suggesting that no freely diffusible cofactors smaller than 25 kDa were required for the in vitro activation.

TPA Stimulation Causes Redistribution of NF-kB into the Nuclear Fraction

To examine whether the form of NF-kB detected after in vitro activation in the cytosolic fraction could quantitatively account for the NF-kB found in nuclear extracts after TPA stimulation of cells, subcellular fractions of 70Z/3 cells were reinvestigated in mobility shift assays after treatment with formamide and DOC using equal cell-equivalents of subcellular fractions. Equal cell-equivalents of nuclear extracts (N) and cytosolic (C) and post-nuclear membrane fractions (P) from control (Co) and TPA-stimulated cells (TPA) were left untreated (lanes 1–6 and 13–18) or subjected to a formamide/desoxycholate treatment (Fa+DOC; lanes 7–12 and 19–24; for conditions see FIG. 31, lane 11). This treatment was preferred over the DOC/NP-40 chase treatment because it gave a higher resolution of bands in mobility shift assays. DNA-binding reactions were performed in the presence of 3.2 ug poly(d[I-C]) using 4.4 ug of protein from nuclear extracts, 8.8 ug of protein from cytosolic fractions or 2.2 ug of protein from postnuclear membrane fractions (all in 4 ul buffer D(+)). Fluorograms of native gels are shown. The specificity of protein-DNA complexes was controlled using wild type (kB wt) and mutant kappa enhancer fragments (kB mutant; see legend to FIG. 29). The filled arrowhead indicates the position of kB-specific protein-DNA complexes and the open arrowhead the positions of unbound DNA-fragments.

Figure 32:
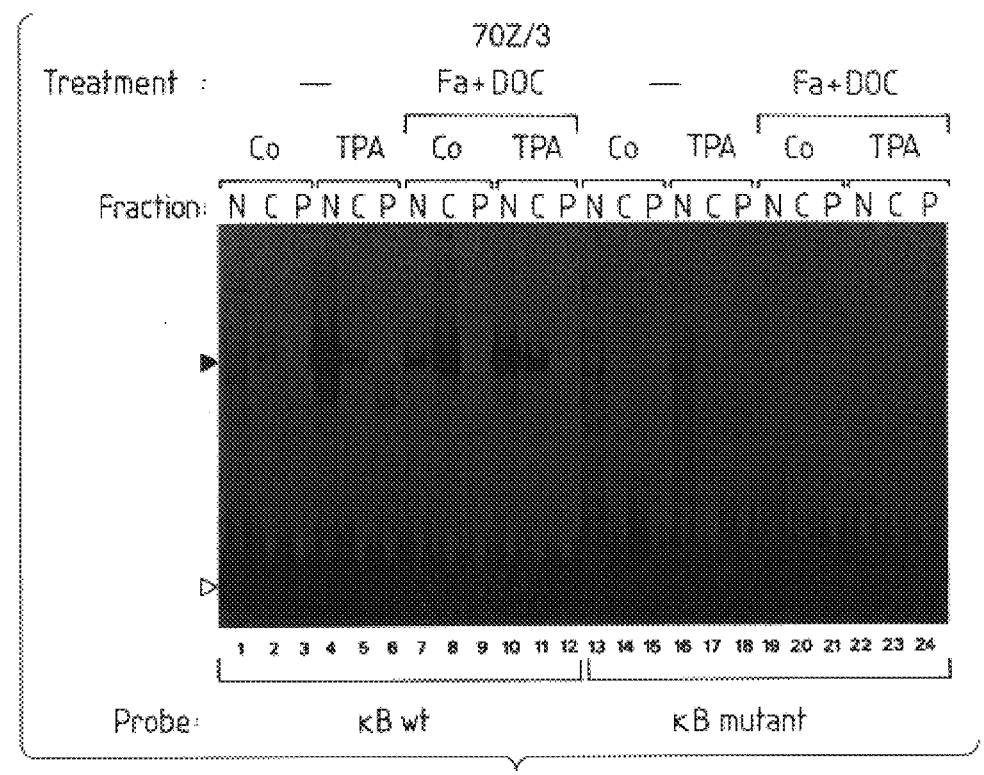
FIG. 32 shows the effect of TPA stimulation on the subcellular distribution of NF-kB in 70Z/3 cells.

Densitometric scanning of fluorograms showed that in control cells, more than 92% of the total cellular kB-specific DNA-binding activity was recovered in the cytosolic fraction following treatment with formamide and COD (FIG. 32, lanes 7 to 9). In TPA-stimulated cells, 80% of the kB-specific DNA-binding activity was found in nuclear extracts (FIG. 32, lanes 10 to 12). The remaining activity was largely recovered in the cytosolic fraction (FIG. 32, lane 11). All DNA-binding activities described were specific for the kB site, as shown by their absence when the mutant kappa enhancer fragment was used in the mobility shift assays (FIG. 32, lanes 13 to 24).

When the total cellular NF-kB activity that was activated in vitro in control cells was compared to the total cellular activity found in TPA-stimulated cells after the same treatment, virtually identical amounts of activity were observed. The equal amounts of NF-kB activity found in control and TPA-treated cells suggest that the treatment with formamide and DOC resulted in the complete conversion of an inactive precursor of NF-kB into a form of NF-kB with high DNA-binding affinity. Furthermore, these results provide evidence for a TPA-inducible translocation of NF-kB from the cytosol into the nucleus.

NF-kB Occurrence and Activation in HeLa Cells

NF-kB activity can also be induced in HeLa cells after TPA treatment, as shown by the appearance of a kB-specific DNA-binding activity in nuclear extracts. Sen, R. and D. Baltimore, Cell, 47:921–928 (1986). Therefore, induction of NF-kB in the cytosolic fraction of HeLa cells was tested by treatment with formamide and DOC. To equal cell-equivalents of fractions, 17% formamide was added and diluted to 10% by the addition of the DNA-binding reaction mixture containing 4 ug poly(d[I-C]). DOC was then added to a final concentration of 0.6% to give a reaction volume of 20 ul. Assays contained either 1.35 ug of protein from nuclear extracts, 9 ug of protein from the cytosolic fractions of 0.9 ug of protein from the postnuclear membrane fractions (all in 10 ul buffer D(+)).

Figure 33:
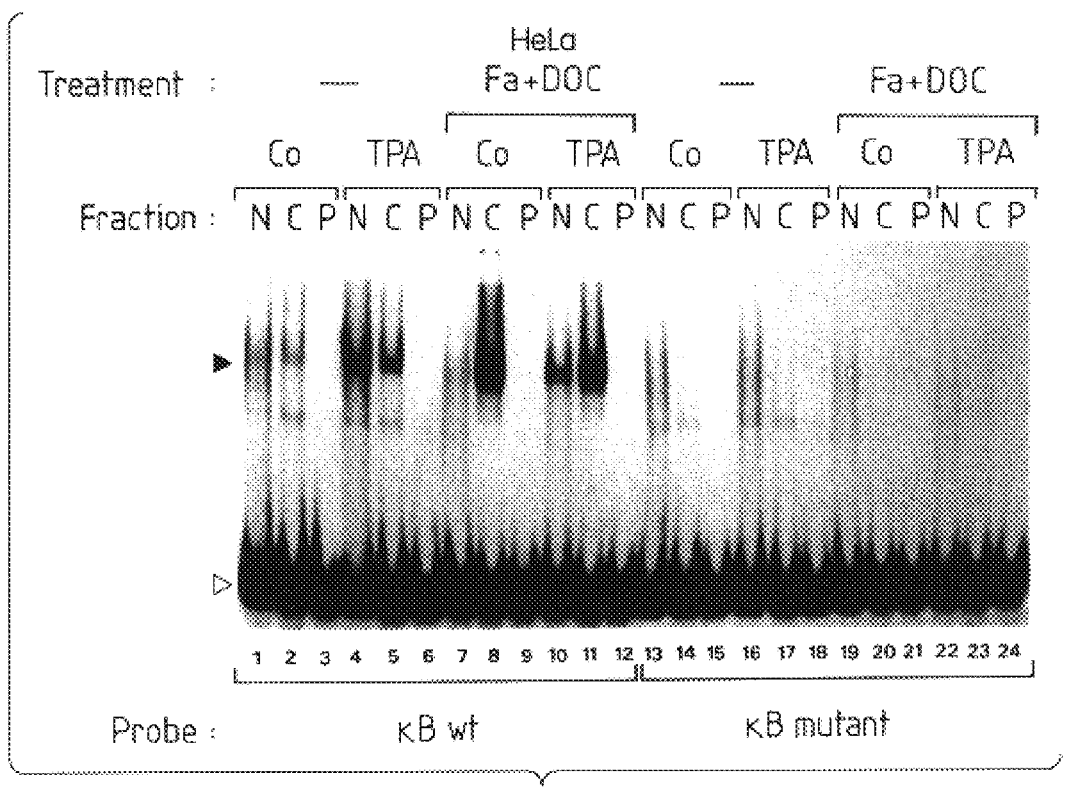
FIG. 33 shows the effect of TPA stimulation on the subcellular distribution of NF-kB in HeLa cells.

Redistribution of NF-kB activity in the subcellular fractions upon TPA stimulation of cells, was also assessed, using the procedure described for 70Z/3 cells. Mobility shift assays were performed with equal cell-equivalents of the subcellular fractions. Because HeLa cells had about ten times as much cytosolic protein as nuclear protein—as opposed to the 2:1 ratio in 70Z/3 cells—the use of equal cell-equivalents of fractions gave very different quantitative results from those obtained with equal amounts of protein. Without any treatment, only traces of a kB-specific DNA-binding activity were detected in the nuclear and cytosolic fractions of HeLa cells and no activity was observed in the postnuclear membrane fraction (FIG. 33, lanes 1 to 3). Upon TPA stimulation of cells under the same conditions as for 70Z/3 cells, NF-kB activity was strongly increased in the nuclear extract (FIG. 33, lane 4). Also, in the cytosolic fraction, a significant increase of NF-kB activity was found (FIG. 33, lane 5). This was not an artifact of fractionation because the activity of AP-1, another nuclear factor (Lee, W. et al., Cell, 49:741–752 (1987), was highly enriched in nuclear extracts and almost not detectable in the cytosolic fraction of HeLa cells before and after TPA stimulation.

The treatment of control fractions of HeLa cells with formamide and DOC revealed large amounts of kB-specific DNA-binding activity in the cytosolic fraction (FIG. 33, compare lanes 8 and 20). The concentrations of formamide and DOC required for an optimal in vitro activation of NF-kB in HeLa cells were different from those required for 70Z/3 cells; less formamide and more DOC was needed. All DNA-binding activities described were specific for the kB-binding site in the kappa enhancer fragment (FIG. 33, lanes 13 to 24).

Almost no activity was detected in the HeLa nuclear extract and the postnuclear membrane fraction after in vitro activation (FIG. 33, lanes 7 and 9). Large amounts of NF-kB activity could still be activated in the cytosolic fraction of TPA-stimulated HeLa cells (FIG. 33, lane 11). This suggests that in vivo in HeLa cells—as contrasted to 70Z/3 cells—only a minor portion of the total cellular NF-kB is activated upon a TPA stimulus. The NF-kB activity in formamide/DOC-treated nuclear extracts of TPA-stimulated cells was less, compared to untreated nuclear extracts (FIG. 33, compare lanes 4 and 10), reflecting a partial inhibition of the DNA-binding activity of in vivo activated NF-kB. As in 70Z/3 cells, the total cellular NF-kB activity in HeLa cells, as revealed after in vitro activation, remained constant before and after TPA treatment of cells. These data imply that NF-kB is activated by the same mechanism in HeLa cells as it is in the pre-B cell line 70Z/3. However, in HeLa cells, TPA is much less complete in its activation than it is in 70Z/3 cells.

NF-kB Occurrence and Activation in Other Cell Types

NF-kB occurrence and activation in several additional cell types, including two T cell lines (H9, Jurkat) and fibroblasts, and in tissues, including human placenta and mice kidney, liver, spleen, lung, muscle and brain, were also assessed, as described above. In each case, NF-kB in a DOC-activatable form was shown to be present in the cytosolic fraction.

Appearance of Binding Activity

Results described above suggested that the appearance of binding activity may be due to separation of NF-kB from an inhibitor. Size fractionation and denaturing agents were both shown to be capable of separating NF-kB from such an inhibitor, which was apparently of low molecular weight. This provides a reasonable explanation for how NF-kB is induced in pre-B cells, HeLa cells and other inducible cells, such as T cells.

Whether the DOC-dependence of cytosolic NF-kB results from its association with an inhibitor, was investigated by probing for activity in cytosolic fractions that would specifically prevent DNA binding to NF-kB in electrophoretic mobility shift assays (EMSA). This work demonstrated the existence of a protein inhibitor, called IkB, in cytosolic fractions of unstimulated pre-B cells, that can convert NF-kB into an inactive DOC-dependent form by a reversible, saturable, and specific reaction. The inhibitory activity becomes evident after selective removal of the endogenous cytosolic NF-kB under dissociating conditions, suggesting that NF-kB and IkB were present in a stoichiometric complex. Enucleation experiments showed that the complex of NF-kB and IkB is truly cytoplasmic. The data are consistent with a molecular mechanism of inducible gene expression by which a cytoplasmic transcription factor-inhibitor complex is dissociated by the action of TPA, presumably through activation of protein kinase C. The dissociation event results in activation and apparent nuclear translocation of the transcription factor. It would appear that IkB is the target for the TPA-induced dissociation reaction. The following is a description of this investigation, which is described in greater detail in Example 12.

Separation of an Inhibitor from NF-kB

Figure 34A:
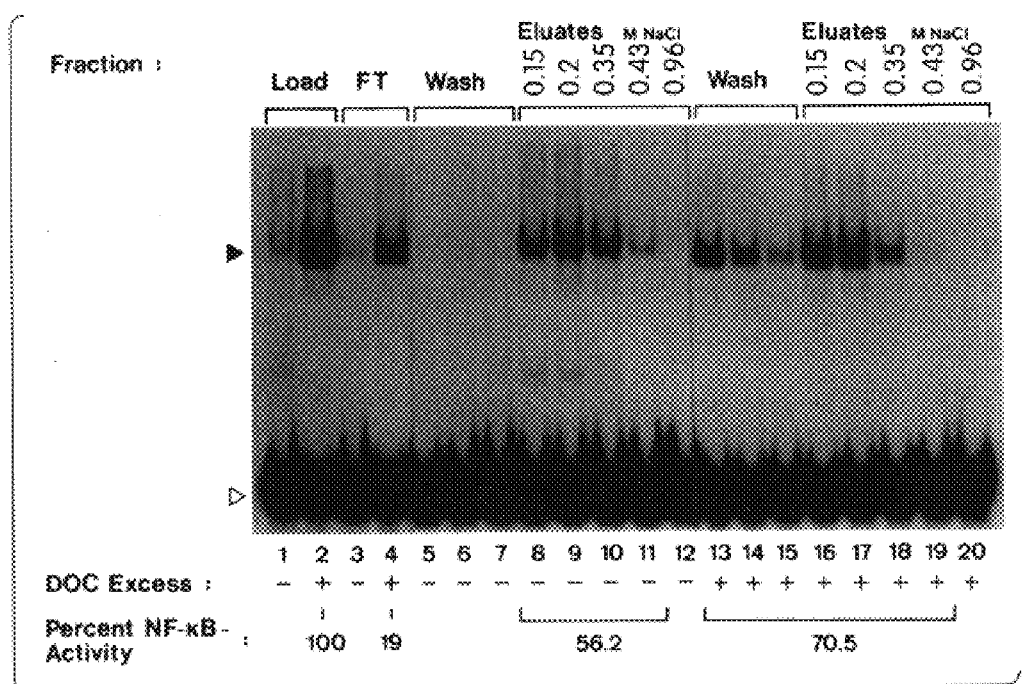
FIGS. 34A–34B show results of DNA-cellulose chromatography of DOC-treated cytosol. Cytosol was prepared from unstimulated 70Z/3 pre-B cells and protein concentrations determined. In the fluorograms of native gels shown, the filled arrowheads indicate the position of the NF-kB-k enhancer fragment complex and the open arrowheads the position of unbound DNA probe.

Cytosolic fractions from unstimulated 70Z/3 pre-B cells were examined for an activity that would impair the DNA binding activity of added NF-kB in an EMSA. Baeuerle, P. A., and D. Baltimore, Cell 53: 211 (1988). Increasing amounts of cytosol from unstimulated cells did not significantly influence the formation of a protein-DNA complex between NF-kB and a k enhancer fragment (FIG. 34, lanes 13 to 15). This indicated the absence of free inhibitor, presumably because all of it is complexed with endogenous NF-kB. DNA-cellulose was used to selectively remove the endogenous NF-kB from DOC-treated cytosol, in an attempt to liberate the inhibitor. Almost all NF-kB was present in a DOC-dependent form, prior to DOC activation and chromatography (FIG. 34A, lanes 1 and 2). In the presence of excess DOC, about 80% of the NF-kB activity was retained by DNA-cellulose (FIG. 34A, compare lanes 2 and 4), most of which eluted from the DNA-cellulose between 0.15 and 0.35M NaCl (FIG. 34A, lanes 8 to 10 and 16 to 18). The NF-kB activity eluting at high salt was detectable in mobility shift assays in the absence of excess DOC (FIG. 34A, lanes 8 to 11), indicating that NF-kB had been separated from an activity that caused its DOC-dependent DNA binding activity. In contrast, the small percentage of NF-kB activity contained in the washings was still dependent on DOC (FIG. 34A, compare lanes 5 to 7 and 13 to 15). These results show that affinity chromatography is sufficient to convert DOC-dependent NF-kB precursor into DOC-independent active NF-kB, similar to that found in nuclear extracts from TPA-stimulated cells.

Figure 34B:
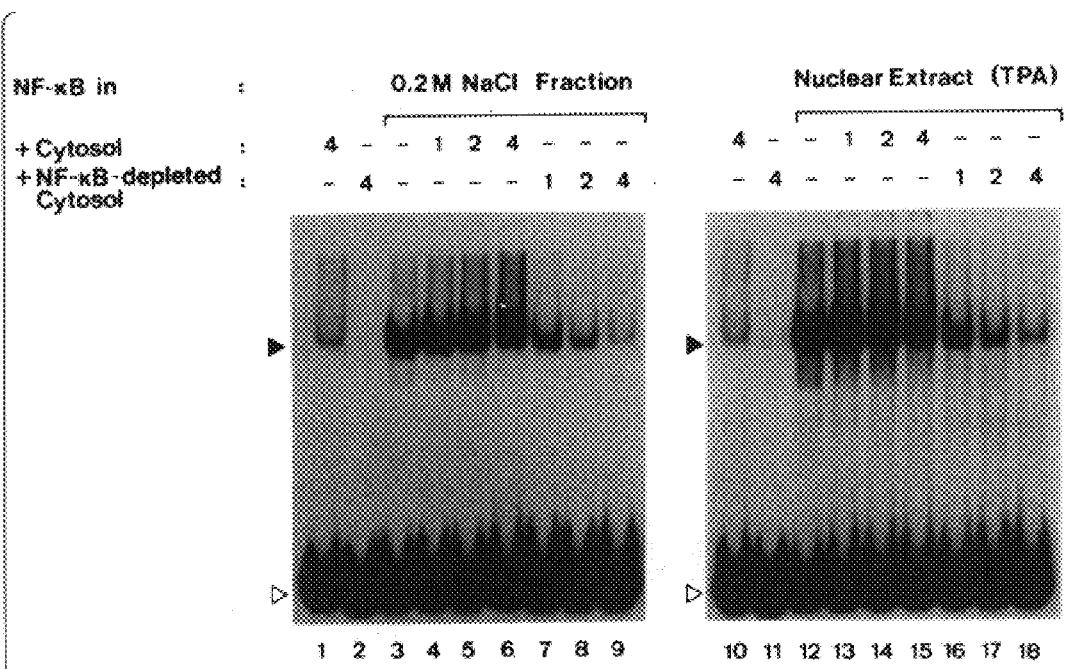

The flow-through fraction from the DNA-cellulose was assayed for an activity that, after neutralization of DOC by non-ionic detergent, would inactivate added NF-kB from the 0.2M NaCl-fraction from nuclear extracts of TPA-stimulated cells. Increasing amounts of cytosol from which the endogenous NF-kB was removed inhibited the formation of an NF-kB—DNA complex as monitored by EMSA (FIG. 34B, lanes 7 to 9 and 16 to 18). DOC-treated cytosol that was not passed over DNA-cellulose had no effect (FIG. 34B, lanes 4 to 6 and 13 to 15), even if cells had been treated with TPA. The fact that, after DNA-cellulose chromatography of DOC-treated cytosol, both DOC-independent NF-kB and an inhibitory activity were observed made it reasonable to believe that NF-kB had been separated from an inhibitor. This inhibitor is referred to as IkB.

IkB Characterization

IkB fractionates as a 60 to 70 kD protein. The flow-through fraction from the DNA-cellulose column was subjected to gel filtration through G-200 Sephadex and the fractions were assayed for an activity that would interfere with the DNA binding activity of added NF-kB contained in a nuclear extract from TPA-stimulated 70Z/3 cells (FIG. 35A). The 67 kD fraction had the highest activity: it virtually completely prevented interaction of NF-kB and DNA (FIG. 35A, lanes 6). In fractions from a G-75 Sephadex column, no additional inhibitor of low molecular size was detectable indicating that NF-kB was inactivated by a macromolecule of defined size. No significant inhibitory activity could be demonstrated after gel filtration of a DNA-cellulose flow-through of DOC-treated cytosol from TPA-stimulated 70Z/3 cells, implying that TPA treatment of cells inactivated IkB.

The inhibitor fraction was treated with trypsin to test whether IkB is a protein (FIG. 35B). Tryptic digestion was stopped by the addition of bovine pancreas trypsin inhibitor (BPTI) and samples were analyzed for NF-kB inhibition. Trypsin treatment interfered with the activity of IkB, as shown by the complete inability of the treated sample to inhibit NF-kB activity (FIG. 35B, compare lanes 1 and 6). Trypsin that had been treated with BPTI had no effect (FIG. 35B, lane 5), demonstrating that the inactivation of IkB was specifically caused by the proteolytic activity of trypsin. It appears that IkB requires an intact polypeptide structure for its activity. The nucleotide sequence of the IkB-α gene and the amino acid sequence of IkB-α are shown in FIG. 43.

The cytosolic complex of IkB and NF-kB showed an apparent size of about 120 to 130 kD, both after gel filtration (FIG. 35A, lane 3) and after sedimentation through a glycerol gradient (FIG. 35C, lanes 6 and 7). For both methods, cytosol from unstimulated cells was analyzed under non-dissociating conditions. NF-kB was activated in fractions by either DOC (FIG. 35A) or formamide (FIG. 35C, middle panel) prior to analysis by EMSA. Baeuerle, P. A. and D. Baltimore, Cell, 53:211 (1988). The specificity of complexes was tested with a mutant DNA probe (FIG. 35C, right panels). Lenardo, M. et al., Science, 236:1573 (1987). The apparent release of a 60 to 70 kD inhibitory protein from the cytosolic NF-kB precursor, its sedimentation velocity in glycerol gradients, and its size seen by gel filtration suggest that the inactive NF-kB precursor is a heterodimer composed of a 55 to 62 kD NF-kB molecule and a 60 to 70 kD IkB molecule. Nuclear NF-kB was found to cosediment with the cytosolic complex of IkB and NF-kB (FIG. 35C, upper panel). Native gel electrophoresis, a method that allows resolution of size differences of protein-DNA complexes, provided evidence that the 120 kD form of nuclear NF-kB seen in glycerol gradients comes from the formation of a homodimer. Hope, I. A. and K. Struhl, EMBO J., 6:2781 (1987). By these interpretations, activation of NF-kB would include an additional step (i.e., formation of a NF-kB homodimer). This is consistent with the observation that the protein-DNA complexes formed with in vitro-activated NF-kB have the same mobility in native gels as those formed with nuclear NF-kB. Baeuerle, P. A. and D. Baltimore, Cell, 53:211 (1988).

Figure 36A:
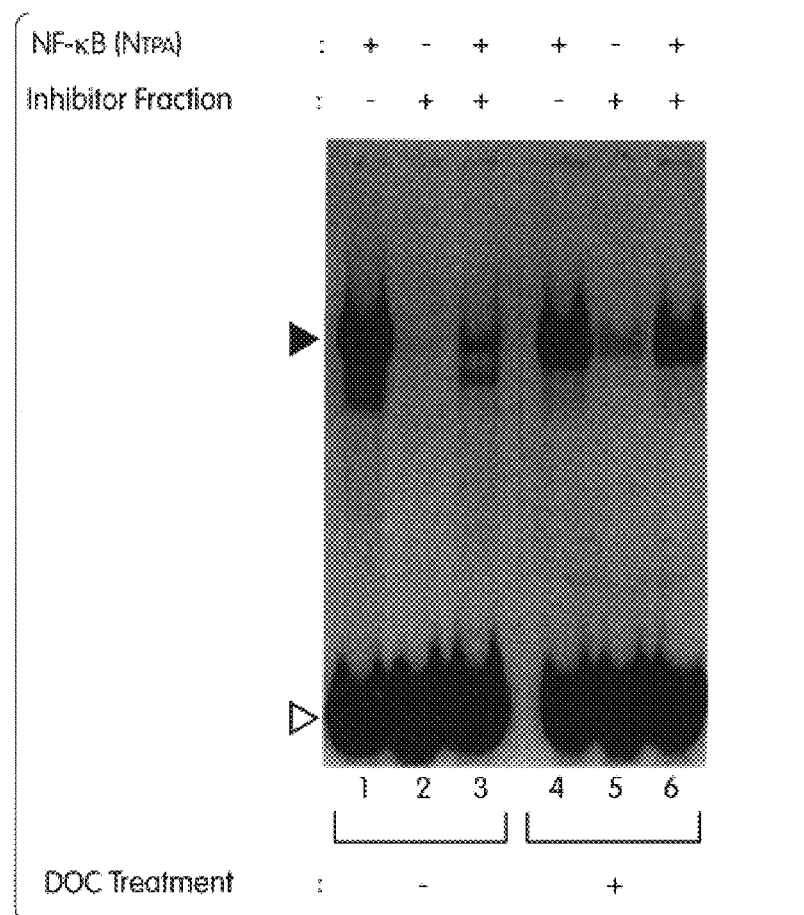
FIGS. 36A–36B show the reversibility and kinetics of the inactivation of NF-kB.

The inactivation of NF-kB by IkB is reversible, saturable and specific. Incubation with the inhibitor fraction can inhibit the DNA binding activity of NF-kB by more than 90% (FIG. 36A, lanes 1 and 3). Treatment of a duplicate sample with DOC after the inhibition reaction reactivated 66% of the added NF-kB activity (FIG. 36A; compare lanes 3, 4 and 6). This showed that a DOC-dependent form of NF-kB can be reconstituted in vitro by the addition of a fraction containing IkB to nuclear NF-kB. The incomplete activation of NF-kB by DOC might be due to the DOC-neutralizing effect of non-ionic detergent which was still present in the sample from the preceding inhibition reaction.

Figure 36B:
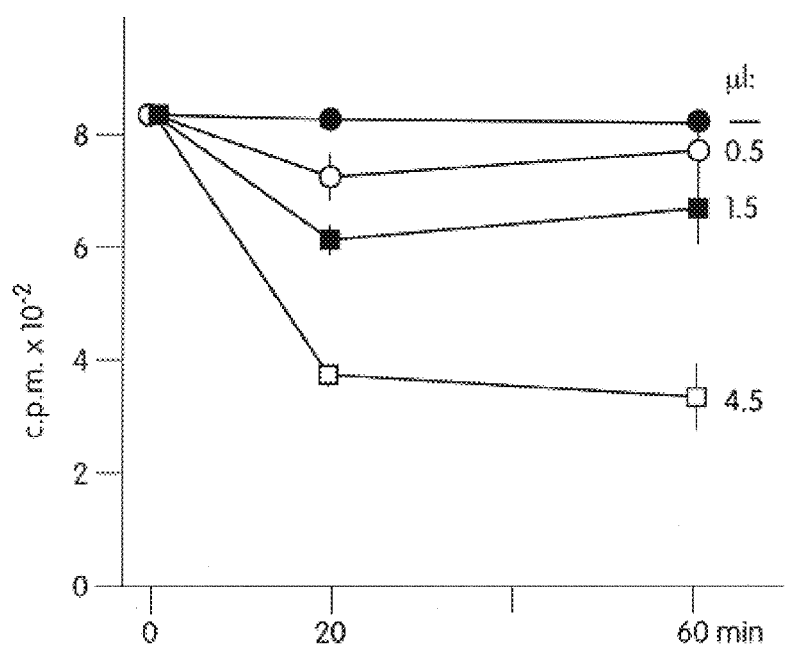

A titration and kinetic analysis showed that IkB stoichiometrically interacts with NF-kB (FIG. 36B). Increasing amounts of inhibitor fraction were added to an excess amount of NF-kB and incubated for 20 or 60 minutes. After the DNA binding reaction, NF-kB-DNA complexes were separated on native gels and quantified by liquid scintillation counting. The relationship between amount of IkB fraction added and extent of inhibition was linear. The amount of NF-kB inactivated after 20 minutes of incubation was not increased after 60 minutes (FIG. 36B). These kinetics were probably not the result of a rapid decay of a catalytically active inhibitor because the fractions were incubated prior to the reaction. The data are consistent with rapid formation of an inactive complex by addition of IkB to NF-kB. The fraction containing IkB does not appear to catalytically or covalently inactivate NF-kB: neither the reversibility nor the kinetics support such a model.

Figure 13A:
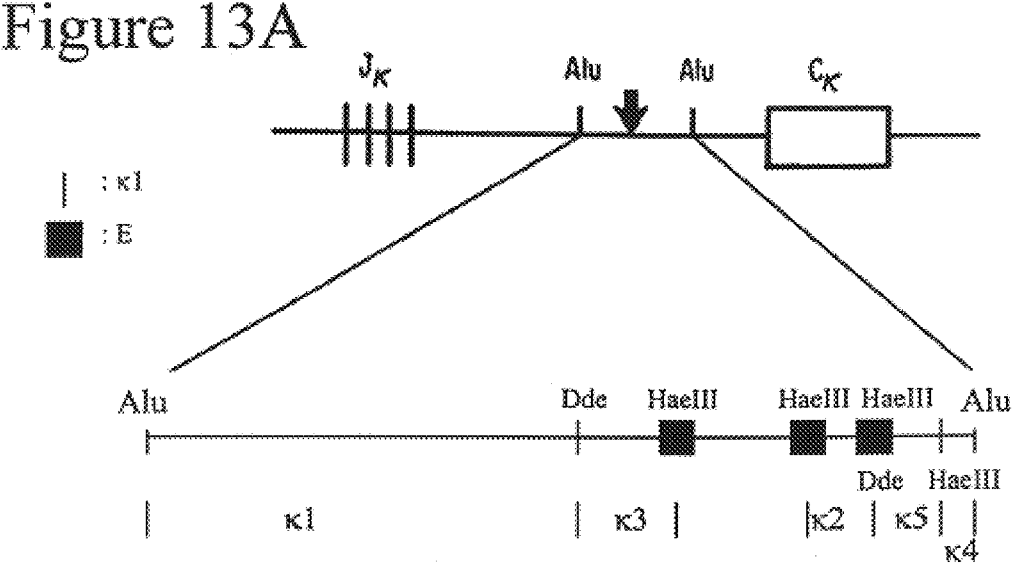
FIG. 13A is a restriction map of κ enhancer.

IkB was tested for its influence on the DNA binding activity of other defined nuclear factors (FIG. 13A). These factors were contained in nuclear extracts that had essentially no active NF-kB, which otherwise could have inactivated IkB by complex formation. The DNA binding activity of H2TF1, a transcription factor thought to be related to NF-kB, was not affected by the inhibitor fraction. Baeuerle, P. A. et al., unpublished observation). Ubiquitous and lymphoid-specific octamer-binding proteins (OCTA) (Sive, H. L. and R. G. Roeder, *Proc. Natl. Acad. Sci. USA*, 83:6382 (1986) and Staudt, L. M. et al., *Nature*, 323:640 (1986)) were unaffected in their DNA binding activities, as were two E-box binding factor, NF-$\mu$E1 (Weinberger, J. et al., *Nature*, 322:846 (1986)) and NF-kE2 (Lenardo, M. et al., *Science*, 236:1573 (1987)), interacting with $\mu$ heavy chain and k light chain enhancers, respectively. AP-1, another TPA-inducible transcription factor (Lee, W. et al., *Cell*, 49:741 (1987); Angel, P. et al., *Cell*, 49:729 (1987)), also showed equal complex formation after incubation in the presence and absence of the inhibitor fraction. Furthermore, none of the undefined DNA binding activities seen in the EMSA showed any inactivation by IkB. These results show that IkB is a specific inhibitor of the DNA binding activity of NF-kB.

Figure 37A:
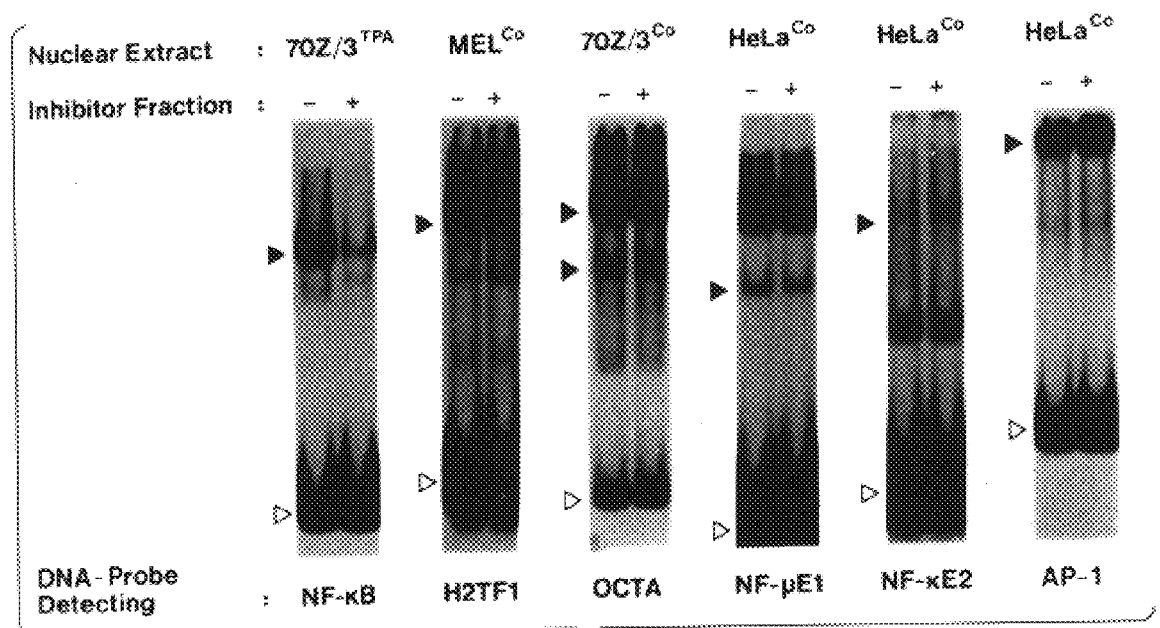
FIGS. 37A–37B show the specificity of IkB. Nuclear extracts from unstimulated (Co) or TPA-treated cells were incubated with 5 μl of buffer G (−) or with 5 μl of a gel filtration fraction containing IkB (+) (A, in the presence of 150 mM NaCl). After DNA binding reactions, samples were analyzed by EMSA.
Figure 37B:
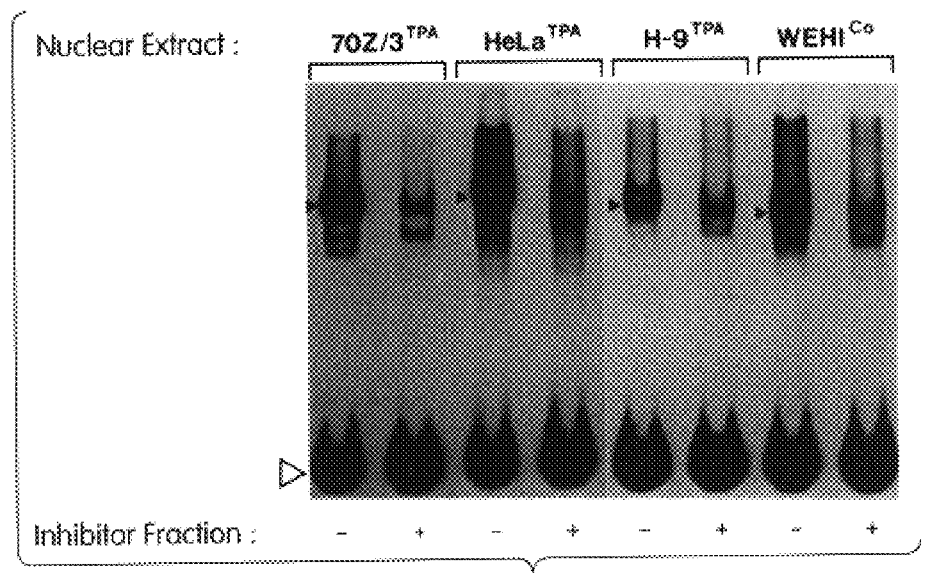

In vivo activated NF-κB is responsive to IkB. IkB prepared from the mouse pre-B cell line 70Z/3 was tested for inactivation of NF-kB contained in nuclear extracts from other cell lines. Human NF-kB contained in nuclear extracts from TPA-stimulated HeLa cells and H-9 T-lymphoma cells was efficiently inactivated (FIG. 37B). When excess amounts of the various NF-kB activities were used in the inhibitor assay, the extent of reduction of NF-kB activities by a fixed amount of IkB was very similar, as quantified by liquid scintillation counting. NF-kB from nuclear extracts of TPA-stimulated Madin-Darby bovine kidney (MDBK) cells was also inactivated suggesting that the control of NF-kB activity by IkB is conserved among different mammalian species.

NF-kB is constitutively active in cell lines derived from mature B cells. Sen, R. and D. Baltimore, *Cell*, 46:705 (1986). Nuclear extracts from the mouse B cell line WEHI 231 were tested in the inhibitor assay to examine whether NF-kB has undergone a modification in those cell lines that prevented its inactivation by IkB. NF-kB from B cells was as efficiently inactivated as NF-kB from pre-B cells (FIG. 37B), suggesting that NF-kB is not stably modified in B cells (or in other cells after TPA stimulation) in such a way that it cannot respond to inactivation by IkB.

Figure 38A:
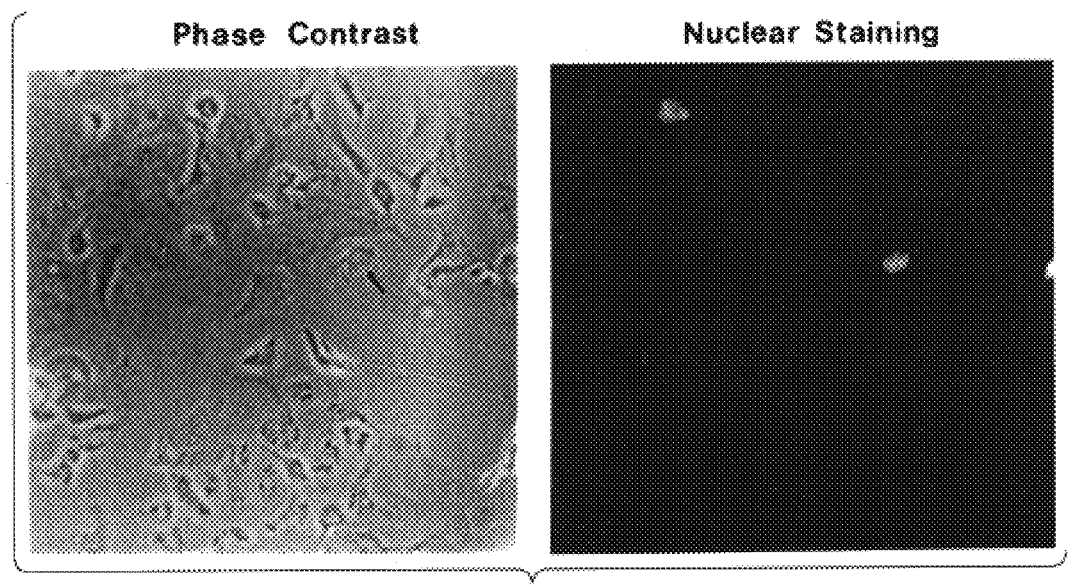
FIGS. 38A–38B show the presence of NF-kB in enucleated cells.

The NF-kB—IkB complex is present in enucleated cells. The NF-kB—IkB complex shows a cytosolic localization on subcellular fractionation (FIG. 38A). This procedure may, however, cause artifacts. Hypotonic lysis of cells may result in partitioning of nuclear proteins into the cytosol, especially, when they are not tightly associated with nuclear components. Li, J. J. and T. J. Kelly, *Proc. Natl. Acad. Sci, USA*, 81:6973 (1984). Detection of the complex of IkB and NF-kB in enucleated cells was attempted. Enucleation is performed with living cells at 37° C. and should therefore not interfere with active nuclear import of proteins, which is ATP-dependent and blocked at low temperature. Prescott, D. M. and J. B. Kirkpatrick, In: *Methods Cell Biol.*, D. M. Prescott, ed. (Academic Press, New York, 1973), p. 189; Newmeyer, D. D. and D. J. Forbes, *Cell*, 52:641 (1987); Richardson, W. D. et al., *Cell*, 52:655 (1988).

Figure 38B:
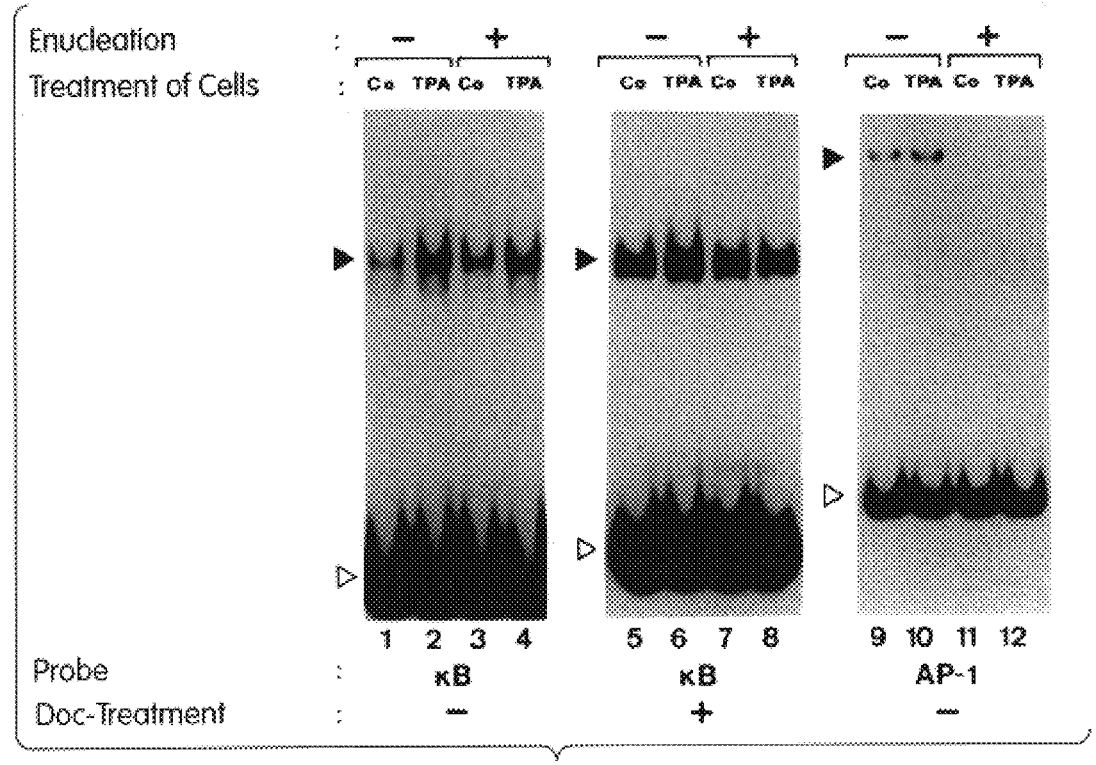

Using cytochalasin B-treated HeLa cells, an enucleation efficiency of about 90% was obtained (FIG. 38A). Enucleated and cytochalasin B-treated complete cells were incubated in the absence and presence of TPA, solubilized by detergent and proteins were extracted with high salt. Because of the small number of cells analyzed, this procedure is different from the standard one. Total cell extracts were analyzed for NF-kB specific DNA binding activity by EMSA (FIG. 38B). In both enucleated and complete cells, similar amounts of NF-kB activity were found after TPA stimulation (FIG. 38B, lanes 1 to 4). The activity was specific for NF-kB because it was not observed with a mutant k enhancer fragment. Lenardo, M. et al., *Science*, 236:1573 (1987); These results suggest that TPA-inducible NF-kB in HeLa cells is predominantly cytoplasmic because it was still present in enucleated cells. The NF-kB activity seen under control conditions (FIG. 38B, lanes 1 and 3) was most likely activated by the lysis conditions used because it was also observed in extracts from HeLa cells that were not treated with cytochalasin B, but not in fractions obtained after hypotonic lysis. Baeuerle, P. A. and D. Baltimore, *Cell*, 53:211 (1988). It was still evident, however, that TPA could activate NF-kB in enucleated cells (FIG. 38B, lanes 3 and 4).

After treatment with DOC, total extracts from complete and enucleated control cells showed about a 2-fold increase in the amount of NF-kB activity (FIG. 38B, compare lanes 1 and 3 with 5 and 7). The demonstration of DOC-activatable NF-kB in enucleated cells, as well as the presence of similar amounts of total NF-kB in enucleated and complete cells (FIG. 38B, compare lanes 5 to 8), shows that a substantial amount of the total cellular NF-kB—IkB complex was cytoplasmic. In contrast to NF-kB, most of the DNA binding activity of AP-1, a bona fide nuclear protein, was apparently lost by enucleation of cells (FIG. 38B, lanes 9 to 12). Lee, W. et al., *Cell*, 49:741 (1987); Angel, P. et al., *Cell*, 49:729 (1987).

Mechanism of NF-kB Activation

Thus, it has been shown that the NF-kB nuclear transcription factor exists in unstimulated pre-B cells in a cytoplasmic complex with a specific inhibitory protein, IκB. In this complex, NF-kB does not exhibit DNA binding activity in EMSA and partitions upon subcellular fractionation into the cytosol. The complex is apparently a heterodimer consisting of about a 60 kD NF-kB molecule and a 60 to 70 kD IkB molecule. Upon TPA stimulation of cells, or after treatment with dissociating agents in vitro, the NF-kB—IkB complex dissociates. This releases NF-kB, which appears now to form a homodimer and can translocate into the nucleus. Whether dimerization is required for activation of NF-kB is not known.

The inhibitory effect of IkB on the DNA binding activity and nuclear localization properties of NF-kB appears to arise from a simple physical affinity of the two proteins. The complex freely dissociates and the components readily associate under in vitro conditions. Even in vivo, dissociation by short-term TPA treatment and reassociation after long-term TPA treatment is evident. The latter presumably results from the degradation of protein kinase C after TPA activation and implies that NF-kB can move back to the cytoplasm after being active in the nucleus.

The effect of TPA appears to involve an alteration of IkB, but not of NF-kB. After TPA stimulation, no active IkB was found—implying its alteration—while the nuclear NF-κB remained sensitive to unmodified IkB when tested in vitro. Whether inactive IkB can be regenerated is unclear; in experiments using cycloheximide (Baeuerle, P. A. et al., *Cold Spring Harbor Symp. Quant. Biol.,* 53, In Press), irreversible loss of IkB activity was the only demonstrable effect after 8 hours of TPA treatment. Given the ability of TPA to activate protein kinase C, it is a reasonable hypothesis that direct or indirect phosphorylation of IkB results in its dissociation from NF-kB.

It had previously been found that the NF-kB—IkB complex is recovered in the cytosol. It is now shown directly that the complex is not removed from the cell by enucleation and, therefore, is truly cytoplasmic. Welshons, W. V. et al., *Nature,* 307:747 (1984). Because active protein kinase C is bound to the plasma membrane (Kraft, A. S. et al., *J. Biol. Chem.,* 257:13193 (1983); Wolf, M. et al., *Nature,* 317:546 (1985); Kikkawa, U. and Y. Nishizuka, *Ann. Rev. Cell. Biol.,* 2:149 (1986)), it becomes increasingly attractive to suggest that the cytoplasmic complex interacts in the cytoplasm (maybe near the plasma membrane) with protein kinase C and the liberated NF-kB carries the signal from cytoplasm to nucleus. Under a number of conditions, active NF-kB is found in the cytoplasm. This fact and the reversibility of NF-kB activation in vivo suggests that the protein may freely move in and out of the nucleus, bringing to the nucleus information reflecting the cytoplasmic activation state of protein kinase C and possibly of other signalling systems.

The response of NF-kB to activated protein kinase C occurs apparently indirectly through modification and subsequent release of associated IkB. The inducibility of NF-kB by TPA is thus dependent on the presence and state of activity of IkB. Changes in amount or activity of IkB should therefore influence the TPA inducibility of NF-kB. NF-kB can indeed exist not only in TPA-inducible but also in constitutively active form (e.g., in mature B cells; Sen, R. and D. Baltimore, *Cell,* 46:705 (1986). Because constitutive NF-kB from B cells is still responsive to IkB in vitro, it is thought that IkB, and not NF-kB, is altered during differentiation of pre-B into B cells.

IkB is apparently unstable when not complexed with NF-kB. This is suggested by the absence of excess active inhibitor in the cytosol from unstimulated cells. In a situation where the production of new inhibitor is impaired, the decay of occasionally released inhibitor could activate NF-kB. This would explain the partial activation of NF-kB seen after treatment with the protein synthesis inhibitors cycloheximide and anisomycin. Sen R. and D. Baltimore, *Cell,* 47:921 (1987). The demonstration of a specific inhibitory protein of NF-kB and the interpretation that cycloheximide treatment can activate NF-kB, presumably because cells become depleted of inhibitor, suggest that IkB is the putative labile repressor of k gene expression (Wall, R. et al., *Proc. Natl. Acad. Sci. USA,* 83:295 (1986)) and of NF-kB activity. Sen, R. and D. Baltimore, *Cell,* 47:921 (1987).

As a result of the work described herein, the IκB gene is now available, as is IκB itself, antibodies specific for the IκB gene-encoded product, and probes which include all or a portion of the IκB gene sequence. Also available are methods of using the IκB gene, the encoded protein and IκB-specific antibodies for such purposes as identifying and isolating other IκB genes, IκB "like" genes, and IκB-encoded products. Altering NF-κB activity and altering NF-κB-mediated gene expression. In particular, it is now possible, through the method of the present invention, to block or inhibit NF-κB passage into the nucleus of cells in which it occurs and, thus, block (partially or totally) binding of NF-κB to NF-κB binding sites on genes which include such recognition sites. Such a method is useful for altering expression of genes which is mediated by NF-κB; such genes include cellular genes (e.g., cytokine genes) and genes introduced into host cells (e.g., viral genes, such as cytomegalovirus gene, HIV-1 genes (e.g., the tax gene), and the SV40 gene). This method of altering NF-κB-mediated gene expression is useful, for example, for inhibiting viral gene expression in infected cells, such as in an individual infected with the HIV-1 or cytomegalovirus.

The IκB gene and the encoded IκB protein can be used to negatively regulate NF-κB activity in cells. For example, the IκB gene can be incorporated into an appropriate vector (e.g., a retroviral vector or capable of expressing the IκB gene and introduced into cells in which NF-κB activity is to be inhibited (partially or totally). For example, a vector capable of expressing IκB can be introduced into HIV-1 infected cells (e.g, T cells) in order to inhibit HIV-1 gene expression and activity in the cells. IκB expressed in the cells binds NF-κB (e.g., free NF-κB such as that released from its inactive complex with Iκ-β) and limits its ability to act as a messenger by inhibiting its translocation into the nucleus. For this purpose, all or a portion of the IκB-encoding DNA or DNA encoding an IκB-like protein is used. If a portion is used, it must encode at least that region of the IκB (or other rel-associated protein) molecule sufficient to bind NF-κB and prevent it from passing into the cell nucleus. The IκB-encoding DNA or DNA encoding an IκB-like protein used can be obtained from a source in which it naturally occurs, can be produced by genetic engineering or recombinant techniques or can be synthesized using known chemical methods. For convenience, DNA from all three types of sources is referred to herein as "essentially pure". The DNA used can have all or a portion of the DNA sequence of clone MAD-3, all or a portion of pp40 or all or a portion of another sequence which encodes a rel-associated or IκB-like protein capable of inhibiting NF-κB. In a similar manner, DNA encoding a rel-associated or IκB-like protein can be introduced into cells to inhibit a rel-related protein other than NF-κB.

Cells in which IκB (or other rel-associated protein) is to be expressed in this manner to inhibit NF-κB (or other rel-related protein) can be removed from the body, the IκB-expressing vector can be introduced, using known methods, and the resulting cells, which contain the IκB-expressing vector, then reintroduced into the body. For example, T-cells or bone marrow cells can be removed from an HIV-1 infected individual, IκB-expressing vectors can be introduced into them, and they can then be replaced in the individual. Alternatively, the expression vector containing IκB-encoding DNA can be introduced into an individual, using known techniques, by any of a variety of routes, such as intramuscular, intravenous, intraperitoneal administration. IκB itself (or other rel-associated protein) can also be introduced into cells to inhibit NF-κB (or other rel-related protein). The entire IκB molecule or a portion sufficient to bind NF-κB and prevent its passage into the nucleus can be used for this purpose. IκB or an appropriate IκB portion can be obtained from naturally-occurring sources, can be produced using known genetic engineering methods or, particularly in the case of an IκB portion, can be synthesized chemically. For convenience, proteins (or portions thereof) of all three types are referred to herein as "essentially pure".

Uses of Genes Encoding Transcriptional Regulatory Factors, the Encoded Factors and Related Products The genes encoding positive transcriptional regulatory factors provide a means for enhancing gene expression.

Lymphoid-specific factors involved in positive regulation of Ig gene transcription provide a method for enhancing immunoglobulin production in lymphoid cells. Lymphoid cells, such as monoclonal antibody-producing hybridomas or myelomas, can be transfected with multiple copies of a gene encoding a regulatory factory to induce greater production of Ig. For this purpose, the gene encoding a regulatory factor can be linked to a strong promoter. In addition, the construct can include DNA encoding a selectable marker. Multiple copies of the contruct can be inserted into the cell, using known transfection procedures, such as electroporation. The cell can be transfected with multiple regulatory factors, including constitutive factors; this is particularly useful in the case of factors determined to act in conjunction, possibly synergistically. Amplification of genes encoding transcriptional regulatory factors in this manner results in enhanced or increased production of the regulatory factors and, consequently, production of immunoglobulin is enhanced in these cells.

The present invention also relates to a method for transiently expressing a gene product in a eukaryotic cell, in which the inducibility of the NF-kB factor is used to advantage. This phenomenon can be exploited to provide for the transient overexpression of a gene product produced by a transfected gene in a eukaryotic cell at a chosen time.

According to the method of this invention, a gene of interest is placed under influence of the κ enhancer sequence containing the binding site for NF-kB (i.e., the entire enhancer sequence or a portion containing at least the NF-κB site). The κ-enhancer sequence is linked to a structural gene of interest to provide an gene inducible by NF-kB. A gene construct is thus provided comprising 1) a κ-enhancer sequence or a portion of the κ enhancer sequence containing at least the sequence to which the factor NF-kB binds; 2) a promoter; and in 3) structural gene of interest.

Conventional recombinant DNA techniques can be used to prepare the construct. The κ enhancer sequence can be obtained from lymphoid cells which express the κ-light chain. The κ enhancer can also be obtained from clones containing the sequence. The construct can be prepared in or inserted into a transfection vehicle such as a plasmid.

The structural gene can be any gene or gene segment which encodes a useful protein for which transient overexpression is desired. Such proteins are, for example, those that are damaging to cells when produced constitutively. The structural gene can be used with its endogenous promoter or other eukaryotic promoter.

Cells for transfection can be any eukaryotic cells used for the expression of eukaryotic proteins. Transfection procedures, such as the calcium precipitation technique are well known in the art.

As the desired time, the transfected cells can be stimulated with the appropriate inducer in an amount sufficient to induce production of NF-kB. The preferred inducer is a phorbol ester which acts rapidly and directly to activate protein kinase C and induces production of NF-kB. If the transfected cell is a lymphoid cell (e.g., B cell) responsive to a mitogen such as LPS or PHA the mitogen may be used alone or in combination with phorbol ester.

Genes encoding transcriptional regulatory factors can be modified for a variety of purposes, such as to encode factors with activity equivalent to the naturally-occurring factor, factors with enhanced ability to regulate transcription (e.g., to cause enhanced transcription of genes, relative to transcription resulting from regulation by or the effects of the normal/unmodified factor), or factors with decreased ability to regulate transcription. This can be carried out, for example, by mutagenesis of factor-encoding DNA or by producing DNA (e.g., by recombinant DNA methods or synthetic techniques) which encodes a modified or mutant transcriptional regulatory factor (i.e., a transcriptional regulatory factor with an amino acid sequence different from the normal or naturally-occurring transcription factor amino acid sequence). These modified DNA sequences and encoded modified factors are intended to be encompassed by the present invention.

The gene encoding IgNF-b, for example, has been cloned and sequenced and the nucleotide sequence is shown in FIG. 18A. For the various utilities discussed below, the modified nucleotide sequence can be obtained either naturally (e.g., polymorphic variants) or by mutagenesis to yield substantially complementary sequences having comparable or improved biological activity. Fragments of the sequence may also be used. This invention encompasses nucleic acid sequences to which the sequence of FIG. 18A hybridizes in a specific fashion.

In addition, the DNA binding domain of the factors, which is responsible for the binding sequence-specificity, can be combined with different "activators" (responsible for the effect on transcription) to provide modified or hybrid proteins for transcriptional regulation. For example, with recombinant DNA techniques, DNA sequences encoding the binding domain can be linked to DNA sequences encoding the activator to form a gene encoding a hybrid protein. The activator portion can be derived from one of the factors or from other molecules. The DNA binding region of the hybrid protein serves to direct the protein to the cognate DNA sequence. For example, in this way, stronger activators of RNA polymerases can be designed and linked to the appropriate DNA binding domain to provide for stronger enhancement of transcription.

DNA probes for the genes encoding the regulatory factors can be used to determine the presence, absence or copy number of regulatory factor-encoding genes or to identify related genes, by hybridization techniques or a polymerase chain amplification method (e.g., PCR). The ability to detect and quantify genes encoding transcriptional regulatory factors can be used in diagnostic applications, such as to assess conditions relating to aberrant expression of a regulatory factor. Cells can be typed as positive or negative for the occurrence of a particular gene and, in addition, can be analyzed for the copy number of the gene. The DNA probes are labeled DNA sequences complementary to at least a portion of a nucleic acid encoding a transcriptional regulatory factor. The labeled probe is contacted with a sample to be tested (e.g., a cell lysate) and incubated under stringent hybridization conditions which permit the labeled probe to hybridize with only DNA or RNA containing the sequence to which the probe is substantially complementary. The unhybridized probe is then removed and the sample is analyzed for hybridized probe.

The DNA probes can also be used to identify genes encoding related transcriptional regulatory factors. For this purpose, hybridization conditions may be relaxed in order to make it possible to detect related DNA sequences which are not completely homologous to the probe.

Antibodies can be raised against the transcriptional regulatory factors of this invention. The antibodies can be polyclonal or monoclonal and they can be used as diagnostic reagents in assays to determine whether a factor is expressed by particular cells or to quantitate expression levels of a factor.

A gene encoding a transcriptional regulatory factors can also be used to develop in vivo or in vitro assays to screen for agonists or antagonists of a factor-encoding gene or of the factor encoded by the gene. For example, genetic constructs can be created in which a reporter gene (e.g., the CAT gene) is made dependent upon the activity of a factor-encoding gene. These constructs introduced into host cells provide a means to screen for agonists or antagonists of the factor-encoding gene. The antagonists may be used to decrease the activity of the factors and thus may be useful in the therapy of diseases associated with overactivity of a transcriptional regulatory factor. Such agonists or antagonists identified by assays employing the factor-encoding genes of this invention are within the scope of this invention.

The present invention is useful as a means of controlling activation in a host cell of an NF-kB precursor, which results in formation of activated NF-kB, which, in turn, plays a key role in transcriptional activation of other sequences, such as the k light chain enhancer, the HIV enhancer and the interleukin-2 receptor α-chain gene. NF-kB has been shown to be a ubiquitous inducible transcription factor; it has been shown, as described herein, to be present in many types of cells (i.e., all cell types assessed to date). It serves to make immediate early responses which it is capable of effecting because it is post-translationally activated. As a result, the method and composition of the present invention can be used to control transcriptional activation of genes encoding a selected cellular protein. Changes in expression of genes transcribed by RNA polymerase II in response to agents, such as steroid hormones, growth factors, interferon, tumor promoters, heavy metal ions and heat shock are mediated through cis-acting DNA sequence elements such as enhancers. Binding of NF-kB transcription factor has been shown to confer transcriptional activity on several genes. Expression of these genes and others similarly affected can be controlled by the present method. For example, it has been shown that expression of one of the two elements of the cell surface receptor specific for IL-2 is controlled by NF-kB. Thus, in T cells, which produce IL-2, production can be controlled (enhanced, reduced) by controlling activation of NF-kB. In a similar manner, the method of the present invention can be used to control expression of human immunodeficiency virus in infected host cells.

Methods and compositions of the present invention are based on use of the role of NF-κB as a second messenger, or mediator, in the expression of genes in a wide variety of cell types. The expression of a gene having an NF-κB binding recognition sequence can be positively or negatively regulated to provide, respectively, for increased or decreased production of the protein whose expression is mediated by NF-κB. Furthermore, genes which do not, in their wild type form, have NF-κB,recognition sequences can be placed under the control of NF-κB by inserting NF-κB binding site in an appropriate position, using techniques known to those skilled in the art.

DNA sequences known to contain NF-κB binding domains are shown in Table 2. According to the methods described herein, the expression of genes under the control of one of these elements is subject to modulation by alteration of the concentration or availability of NF-κB. This can also be carried out, according to the present method, for any gene which contains an NF-κB binding site. Furthermore, genes which do not naturally contain NF-κB binding sites can be modified, using known techniques, to subject these genes to NF-κB modulation. First, an appropriate expression vector is selected for use in a biological system of interest, the vector having a gene of interest and restriction enzyme recognition sequences to facilitate the insertion of a DNA fragment carrying the NF-κB binding sites.

For example, the sequences of the κ immunoglobulin enhancer, the SV40 70 base pair repeat, the HIV long terminal repeat, the MHC class I H2-kb gene and the interferon β PRDII gene, all possess NF-κB binding sites (Table 2). By comparing sequences to which NF-κB binds specifically, a consensus sequence has been determined:

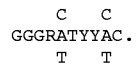

DNA sequences which flank the binding site are scanned for convenient restriction enzyme recognition sequences to facilitate removal of the fragment from the longer sequence in which occurs and its subsequent insertion into the expression vector. If such sequences are present, the transfer of the fragment carrying the binding site, to the expression vector, is straight forward. If convenient sites do not exist, fragment transfer is facilitated through the introduction of such restriction enzyme recognition sequences using well known, site-directed mutagenic techniques. The construct, prepared as described, can then be introduced into a biological system of interest.

The expression of such constructs in a biological system is subject to modulation by NF-κB. For example, purified NF-κB could be introduced into the system in an effective amount such that any inhibitory molecule present in the system would be titrated out and uninhibited NF-κB could interact with its binding recognition sequence, thereby increasing the rate of transcription. This is an example of positive regulation.

Similarly, a copy of the NF-κB gene, cloned in an appropriate expression vector, could be introduced into the biological system, thereby providing for internal expression of the NF-κB molecule, preferably at relatively high levels. Again, high levels of NF-κB would function to titrate out any inhibitor molecule present, and also to increase the rate of transcription from a gene possessing a NF-κB binding site.

A level of discrimination among members of a related family of NF-κB binding sites, by a modified NF-κB molecule, can also be introduced. Referring to Table 1, for example, there are apparent differences among the various NF-κB binding sites from various genes. A copy of a cloned NF-κB gene can be mutagenized to alter the binding domain by well known techniques, such as site or region directed mutagenesis. Alternatively, DNA fragments encoding a modified NF-κB binding domain can be made synthetically, having appropriate cohesive or blunt termini to facilitate insertion into the NF-κB gene to replace the existing sequences encoding the corresponding portion of the binding domain. Such restriction fragments can be synthesized having any desired nucleotide changes. Mutated proteins encoded by such genes can be expressed and assayed for preferential binding to, for example, one of the 10 different DNA binding sites shown in Table 1 or related members of the family of NF-κB binding sites. An example of an assay which can be used to screen large numbers of recombinant clones in order to identify binding domain mutants is that described by Singh et al., (*Cell*, 52:415–423 (1988)). Once such a mutant is identified, a DNA expression vector encoding this mutant protein can be introduced into a cell. The mutant protein will preferentially bind to the selected member or members of the family of DNA binding sites, such as those shown in Table 2, thereby preferentially enhancing transcription from only those genes which contain that particular binding site.

TABLE 2

Sequences recognized by NF-κB.

| Gene | Sequence |
|---|---|
| Ig κ enhancer - mouse<br>SV40 enhancer<br>HIV-1 (-91)<br>CMV (4)[1,2] | GGGGACTTTCC |
| HIV-1 (-105)<br>HIV-2<br>CMV (1)[1]<br>β2-microglobulin<br>serum amyloid A -g9 | AGGGACTTTCC |
| Ig κ enhancer - human<br>CMV (3)[1] | GGGGATTTCC |
| Interferon-β- PRDII | GGGAAATTCC |
| CMV(2)[1] | GGGACTTTCC |
| MHC class II-$E_\alpha$[d] | GGGACTTCCC |
| IL-2 lymphokine | GGGATTTCAC |
| mouse IL-2Rα | GGGGATTCCT |
| human IL-2Rα | GGGAATCTCC |
| MHC class I - H2 - $K^b$<br>HLA - A2, A11, B7<br>B27, B51 | GGGATTCCCC |
| CONSENSUS[3]: |    C C<br>GGGRATYYAC<br>   T T |

[1] In this particular element, the sequence has not been tested in a binding assay. All others have been proven by direct binding and usually by inhibition of binding to the Ig κ sequence.
[2] Since there are four putative NF-KB recognition sites in the cytomegalovirus enhancer, these have been numbered 1–4 as they are found from 5' to 3' on the coding strand.
[3] Consensus is based on all sequences though the assignments of the sixth and tenth positions ignore one deviant.

Negative regulation can be effected in an analogous manner. For example, a specific inhibitor molecule which is able to block (reduce or eliminate) NF-κB binding can be added to the biological system in an effective amount. Preferably, this inhibitor is specific for NF-κB and does not interact with other cell constituents. An example of such a molecule is I-κB.

Alternatively, negative regulation can be effected using "decoy" molecules, which are designed to mimic a region of the gene whose expression would normally be induced by NF-κB. In this case, NF-κB would bind the decoy and, thus, not be available to bind its natural target.

Furthermore, in the case of an inhibitor molecule which is also a protein, the gene encoding the inhibitor molecule can be identified, isolated, and cloned into an appropriate expression vector using common methodology. When introduced into an appropriate biological system, the inhibitor molecule is synthesized and functions to interact with NF-κB with its binding site and as a consequence reducing the level of transcription of the gene containing the NF-κB binding site.

Yet another method for negatively regulating the expression of a gene containing an NF-κB binding domain involves the introduction of an effective amount of a decoy sequence encoding the NF-κB binding domain. The decoy sequence serves as an unproductive binding domain with which the NF-κB molecule binds. As the finite number of NF-κB molecules bind to the decoy sequences, the number which bind productively (result in increased transcription) with an intact gene, decreases.

Negative regulation can also be effected by the introduction of "dominantly interfering" molecules (see e.g., Friedman et al., Nature, 335:452–454 (1988). For example, if the DNA binding domain and the DNA polymerase activating domain of NF-κB are spatially distinct in the molecule, a truncated form of the NF-κB molecule can be synthesized, using well known techniques. A preferred embodiment would be a truncated molecule retaining the DNA binding domain, but lacking the RNA polymerase activating domain. Such a "dominantly interfering" molecule would recognize and bind to the NF-κB binding site, however, the binding would be non-productive. Because the activation portion of NF-κB would be required for enhanced transcription, the truncated molecule would exert no positive effect. Furthermore, its occupation of the NF-κB binding site effectively blocks access to any intact NF-κB molecule which may be present in the cell.

The invention is further illustrated by the following examples, which are not intended to be limiting in any way.

EXAMPLES

Example 1

Identification of Nuclear Factor IgNF-A

Methods

1. Gel Electrophoresis DNA Binding Assays with the SfaNI-SfaNI X Promoter Fragment The SfaNI fragment was subcloned into the SmaI site of pS64 (pSPIgV$_\kappa$, provided by N. Speck). For binding analysis this fragment was excised from pSPIgV$_\kappa$ by digesting with Hind III and Eco RI. These latter sites flank the Sma I site in the polylinker of pSP64. After end-labeling with [$\alpha$-$^{32}$P]dATP and the large fragment of E. coli DNA polymerase I, the radiolabeled fragment was isolated by polyacrylamide gel electrophoresis. Binding reactions were performed and the reaction mixtures resolved by electrophoresis (FIG. 1b). The $^{32}$Plabeled fragment (about 0.5 ng, 10,000 cpm) was incubated with a nuclear extract of a human B lymphoma cell line (EW)(prepared by the method of Dignam, J. D. et al. Nucl. Acids Res. 11 1475–1489 (1983)) in the absence (lane 1) or presence of two different non-specific competitor DNAs (lanes 2–11). Binding reactions (25 μl) contained 10 mM Tris.HCl (pH 7.5), 50 mM NaCl, 1 mM DTT, 1 mM EDTA, 5% glycerol and 8 μg EW nuclear extract protein. Reactions 2–6 additionally contained 800, 1600, 2400, 3200 and 4000 ηg, respectively, of poly(dI-dC)-poly(dI-dC). Reactions 7–11 contained 300, 600, 900, 1200 and 1500 ηg, respectively, of Hinf I digested E. coli chromosomal DNA. After a 30 min incubation at room temperature, the resulting complexes were resolved in a low ionic strength 4% polyacrylamide gel (acrylamide:bisacrylamide weight ratio of 30:1) containing 6.7 mM Tris.HCl (pH 7.5), 3.3 mM Na-acetate and 1 mM Na-EDTA. See Strauss, F. and Varshavsky, A. Cell 37 889–901 (1984). The gel was preelectrophoresed for 30 min at 11V/cm. Electrophoresis was carried out at the same voltage gradient for 90 min at room temperature with buffer recirculation. The gel was then dried and auto-radiographed at −70° C. with a screen. In FIG. 1b, F and B indicate positions of free and bound fragments respectively.

Binding assays were performed as detailed above using 2400 ng poly(dI-dC)-poly(dI-dC)) and the following DNA fragments: κ SfaNI-SfaNI (~0.5 ηg, 10,000 cpm, lane 1), κ PvuII-KpnI (~0.5 ηg, 10,000 cpm, lane 2), κ PvuII-SfaNI (~0.1 ηg, 5000 cpm, lane 3) and pSP64 PvuII-EcoRI (~0.2 ng, 5000 cpm, lane 4). The κ PvuII-SfaNI fragment was derived from the plasmid pSPIgV$_K$ by digesting with PvuII and EcoRI. The EcoRI site is in the polylinker and therefore this fragment contains 16 bp of polylinker sequence.

2. Binding Competition Analysis in Nuclear Extracts of Human EW and HeLa Cells

Figure 2A:
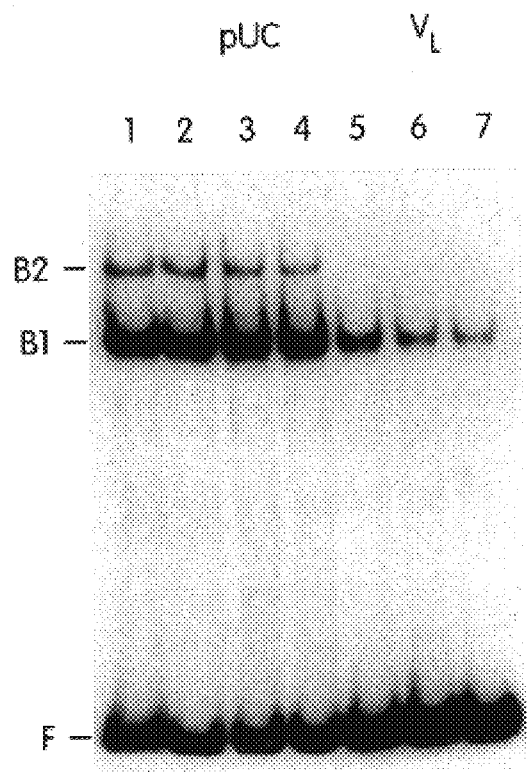
FIGS. 2A–2B show autoradiographs of binding competition analysis in nuclear extracts of human (a) EW and (b) HeLa nuclear extracts.

EW nuclear extract, FIG. 2a. Binding assays were performed as detailed above using radiolabeled K PvuII-SfaNI fragment (~0.1 ηg, 5000 cpm) and 2400 ηg poly(dI-dC)-poly(dI-dC). Reactions 2–4 additionally contained 50, 100 and 200 ηg, respectively, of the bacterial plasmid pSP64 whereas 5–7 contained 50, 100 and 200 ηg, respectively, of the recombinant plasmid pSPIgV$_K$. Assuming that a molecule of pSPIgV$_K$ contains a single high affinity site whereas a molecule of pSP64 (3000 bp) contains 6000 non-specific sites, the apparent affinity ratio of the factor for these two types of sites is greater than $6000 \times 200/50 = 12.4 \times 10^4$ Hela nuclear extract, FIG. 2b. Binding assays were performed as detailed above using radiolabeled κ PvuII-SfaNI fragment (about 0.1 ng, 5000 cpm), 2400 ng poly(dI-dC)-poly(dI-dC) and 6 μg Hela nuclear extract protein (provided by P. Grabowski). Reactions 1 and 2 additionally contained 100 ηg of pSP64 and pSPIgV$_K$, respectively.

Figure 3:
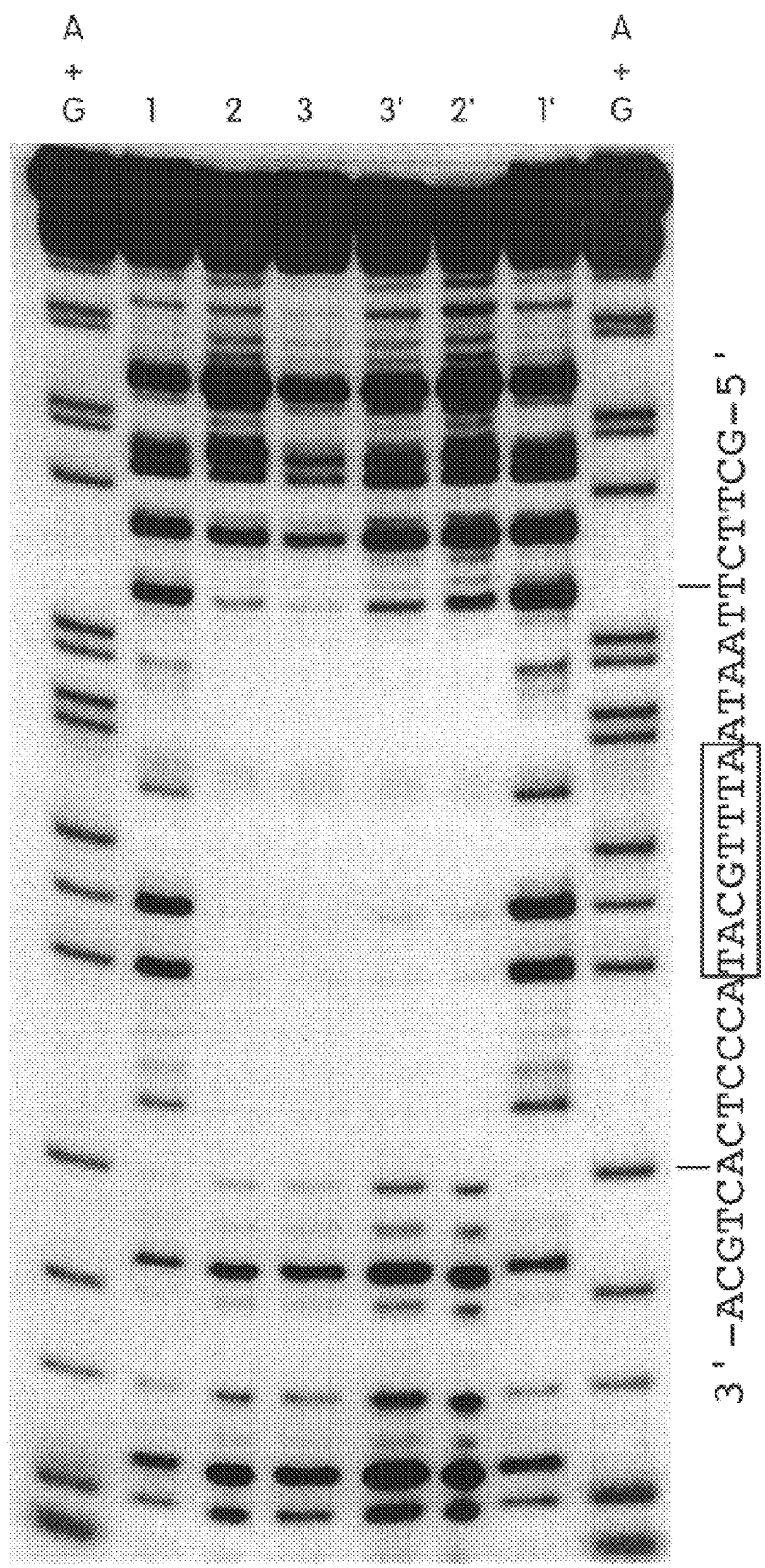
FIG. 3 shows the results of DNase I foot printing analysis of factor-DNA complexes.

3. DNase Footprinting of Factor-DNA Complexes. (FIG. 3)

The B cell nuclear extract was applied to a heparin-sepharose column equilibrated with 10 mM Hepes pH 7.9, 20% glycerol, 1 mM DTT, 1 mM EDTA, 5 mM MgCl$_2$ and 0.1 M KCl. The κ-promoter binding factor was eluted with a 0.25 M KCl step. Binding reactions with this fraction (30 μl) contained 2.5 mM MgCl$_2$, κ PvuII-SfaNI (~1 ηg, 100,000 cpm) and 4800 ηg poly(dI-dC)-poly(dI-dC) in addition to components detailed above. The coding strand of the κ promoter probe was 3' end-labeled (Eco RI site) with [α-$^{32}$P] dATP using the large fragment of E. coli DNA polymerase. Reaction 1 was digested with DNase I (5 μg/ml) for 2.5 min at room temperature in the absence of B cell nuclear protein. Reaction 2 was initially incubated with the heparin Sepharose fraction of the EW nuclear factor (14 μg protein) for 15 min at room temperature and then digested with DNase I as above. Each reaction was stopped with EDTA (5 mM) and the products separated by native polyacrylamide gel electrophoresis as detailed above. After autoradiography to visualize the various species, DNA was eluted from the free (reaction 1) and bound (B1 and B2, reaction 2) fragment bands by incubating gel slices in 0.5 M ammonium acetate (ph 7.5), 0.1% SDS and 1 mM EDTA with shaking at 37° C. overnight. The supernatants were extracted sequentially with phenol-chloroformisoamylalcohol (25:24:1 v/v) and chloroform-isoamylalcohol (24:1 v/v) and precipitated with 2 volumes of ethanol in the presence of carrier tRNA. After a reprecipitation step the products were analyzed by separation in a 10% polyacrylamide gel (20:1) in the presence of 8M urea followed by autoradiography at −70° C. with a screen. Lane 1 contains products of free fragment digestion from reaction 1. Lanes 2 and 3 contain digestion products eluted from bound bands B1 and B2, respectively, from reaction 1. Lanes 1', 2' and 3' corresponds to 1, 2 and 3, respectively, with the exception that the former set was digested with DNase .1 for 5 min. A-G chemical cleavage ladders of the K promoter probe were coelectrophoresed to map the binding domain. See Maxam, A. and Gilbert, W. Meth. Enzymol. 65, 499–525 (1980).

4. Binding of a Common Nuclear Factor to Three Ig Transcriptional Control Elements Nucleotide sequences of actual and putative binding sites, FIG. 4a. The V$_L$ binding site is defined by the DNase I protection assay (* indicates boundaries of the protected region). The V$_H$ and J$_H$-C$_U$ sequences are putative binding sites in the V$_{17.2.25}$ promoter and the mouse heavy chain enhancer, respectively. Numbers in brackets indicate start coordinated of octamer motif. Binding competitions. Binding assays (10 μl) were performed as detailed above using 1600 ng poly(dI-dC)-poly(dI-dC) and the heparin Sepharose fraction of the EW nuclear factor (1.5 μg protein). V$_L$ probe (about 0.1 ηg, 5000 cpm) lanes 1–3, 10, 11. V$_H$ probe (~0.2 ηg, 5000 cpm) lanes 4–6, 12—12. J$_H$-C$_μ$ probe (~0.2 ηg, 5000 cpm), lanes 7–9, 14, 15. Lanes 2, 5, 8 additionally contained 5 ng of a V$_L$ promoter oligomer (36 bp, spanning positions −81 to −44 of the MOPC-41 V$_K$ gene segment) whereas lanes 3, 6, 9 contained 50 ng of the same oligomer. Lanes 11, 13, 15 additionally contained 50 ηg of a J$_H$-C$_H$ oligomer (41 bp, spanning positions −1 to 40 of the heavy chain enhancer). Complementary single-stranded synthetic oligonucleotides were kindly made by Dr. Ronald Mertz, Genzentrum der Universitat Munchen and Dr. E. L. Winnacker, Institut fur Biochemie der Universitat Munchen. They were annealed prior to use as competition substrates in the binding assay.

Results

A radiolabeled SfaNI-SfaNI DNA fragment derived from the upstream region of the MOPC 41 κ light chain gene (FIG. 1a) was incubated with a nuclear extract of a human B cell line in the absence or-presence of two different competitor DNAs. The resulting complexes were resolved from the free fragment by electrophoresis through a low ionic strength, non-denaturing polyacrylamide gel and visualized by autoradiography (FIG. 1b). In the absence of competitor DNA all of the labeled fragment was retained at the top of the gel (lane 1) probably due to the binding of an excess of non sequence-specific proteins. With addition of increasing amounts of either poly(dI-dC)-poly(dI-dC) (lanes 2–6) or E. coli chromosomal DNA (lanes 7–11) as competitors, putative protein-DNA complexes which migrated more slowly than the free fragment were detected. The relative abundance of the major species of complex (B) as well as that of minor species was significantly greater in the presence of the alternating copolymer competitor DNA. Because substitution of the simple copolymer considerably increased the sensitivity of the assay, it was used in all subsequent binding analyses.

Figure 1C:
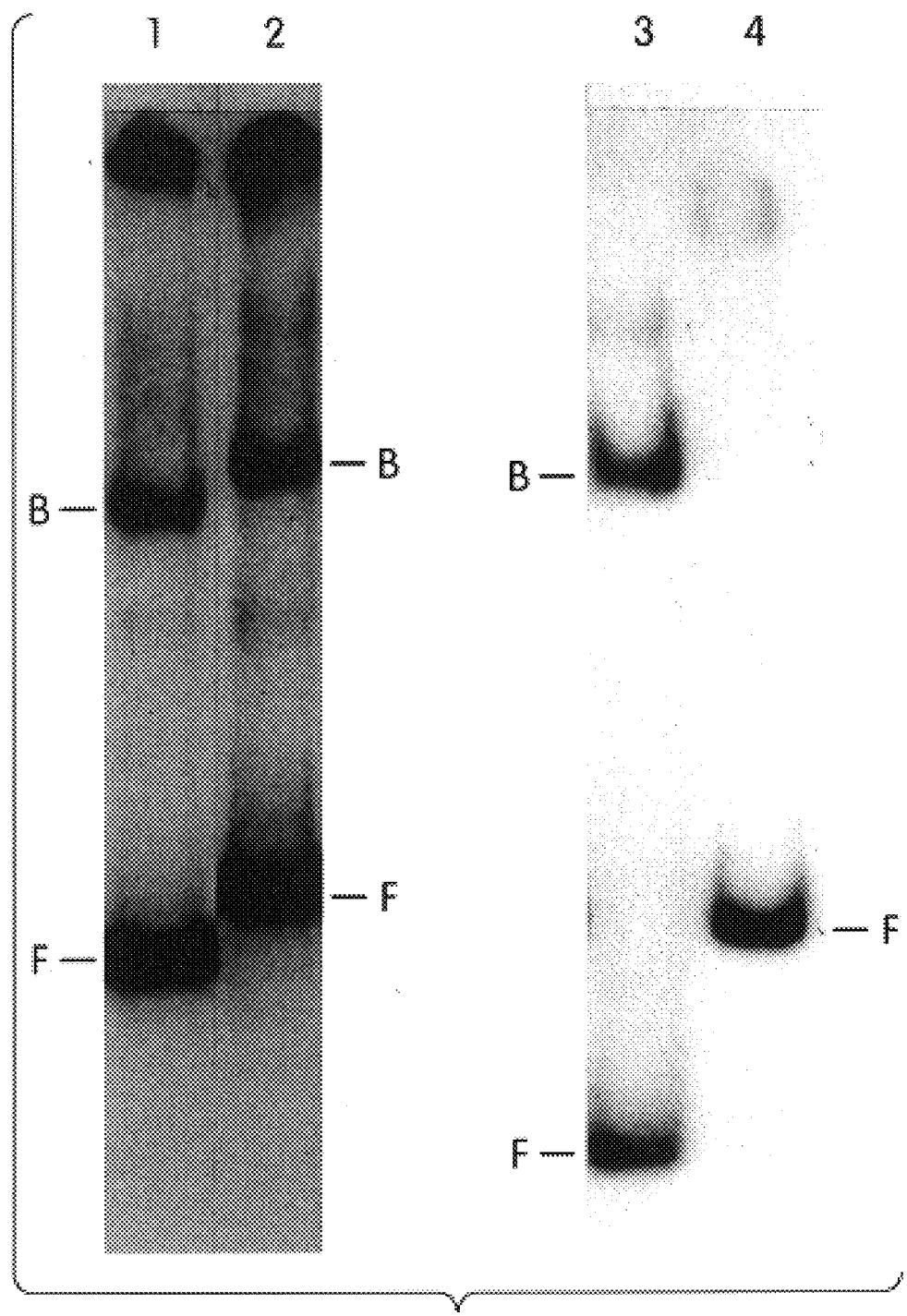
FIG. 1C is an autoradiograph of gel electrophoresis DNA binding assay with overlapping κ promoter fragments.

To test the sequence-specificity of the major species detected in the binding assay, a set of mutually overlapping Kappa promoter fragments (See FIG. 1a, SfaNI-SfaNI, PvuII-KpnI and PvuII-SfaNI) and a similar length fragment derived from the bacterial plasmid SP64 (EcoRI-PvuII) were individually assayed (FIG. 1c). Whereas the bacterial DNA fragment showed no appreciable binding (lane 4) all of the κ promoter fragments yielded major discrete complexes of similar mobilities (lanes 1–3). The mobilities of a series of complexes formed with different length fragment probes (75–300 bp) are approximately the same (data not shown). These data therefore suggested the binding of a specific nuclear factor within the region of overlap of the Kappa promoter fragments. This region includes the conserved octameric sequence but not the TATA element. Note that with the smallest 75 bp Kappa promoter fragment (lane 3) no appreciable label was retained at the top of the gel. Thus, as has been noted recently, the use of small probe fragments further enhances the sensitivity of detection of specific protein-DNA complexes.

The sensitivity gained by use of both the copolymer and a small fragment probe permitted the detection of two complexes, B1 and B2 (FIG. 2a, lane 1). The major species B1 corresponds to complex B in the earlier figure. The relative affinity of the factor(s) for κ promoter DNA was estimated by a competition assay (FIG. 2a). Whereas a control plasmid (pSP64), when added in the above incubation, failed to compete for binding in the concentration range tested (lanes 2–4), the recombinant plasmid (pSPIgV$_\kappa$) effectively reduced the formation of both species B1 and B2 in the same range (lanes 5–7). The latter plasmid was constructed by insertion of the upstream region of the Kappa promoter into pSP64. Assuming that the pSPIgV$_\kappa$ plasmid contains a single high affinity binding site these results suggest that the nuclear factor(s) responsible for B1 and B2 has at least a $10^4$-fold higher affinity for its cognate sequence than for heterologous plasmid DNA (see Methods section 2 above).

Figure 2B:
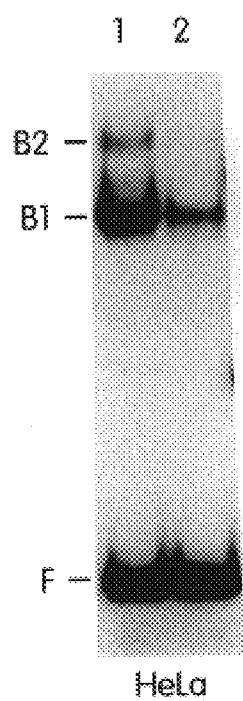

To determine if the factor(s) responsible for formation of B1 and B2 was specific to B lymphocytes, a nuclear extract derived from human HeLa cells was assayed for binding to the κ promoter probe (FIG. 2b). Both species B1 and B2 were generated at similar levels as that observed with B cell extracts, by the HeLa extract (lane 1). Furthermore, both were specifically competed by the pSPIgV$_\kappa$ plasmid (lane 2). Thus HeLa cells also contain a factor(s) which binds specifically to the κ promoter upstream region.

DNase I footprint analysis was used to delineate at a higher resolution the binding domain(s) of factor(s) present in complexes B1 and B2. To facilitate these studies, the binding factor(s) from B cells was partially purified by chromatography of nuclear extract protein on a heparin sepharose column. Most of the binding activity eluted in a 0.25 M KCl step fraction, giving a purification of approximately 5-fold (data not shown; see legend to FIG. 3). For footprint analysis, DNase I was added for a partial digestion after incubation of the partially purified factor(s) with the κ promoter probe B1 and B2 species were then resolved from free fragment by polyacrylamide gel electrophoresis. Bound DNA was eluted from both B1 and B2 bands and examined by denaturing polyacrylamide gel electrophoresis (FIG. 3, lanes 2, 3 and 2', 3'). DNase I digests of the κ promoter probe in the absence of B cell protein (lanes 1 and 1') and A+C chemical cleavage ladders were coelectrophoresed to map the binding domain. Factor(s) in the B1 complexes (lanes 2 and 2') appeared to protect a 19 nucleotide region on the coding strand. The 5' and 3' boundaries of the protected region map to positions −72 and −52, respectively, from the site of transcriptional initiation. The region of DNase I protection was centered about the conserved octanucleotide sequence ATTTGCAT suggesting its importance in the recognition of the Ig promoter by the nuclear factor. B2 complexes showed a virtually identical DNase I protection pattern as B1 complexes and therefore do not appear to involve additional DNA contacts (lanes 3 and 3'). The simplest interpretation of this observation is that the B2 complex is generated by dimerization through protein-protein interactions of the factor responsible for the B1 complex. Alternatively, the B2 complex could be formed either by the binding of another protein to the factor responsible for the B1 complex or by recognition of the same set of sequences by a distinct DNA binding protein.

Figures 4A, 4B:
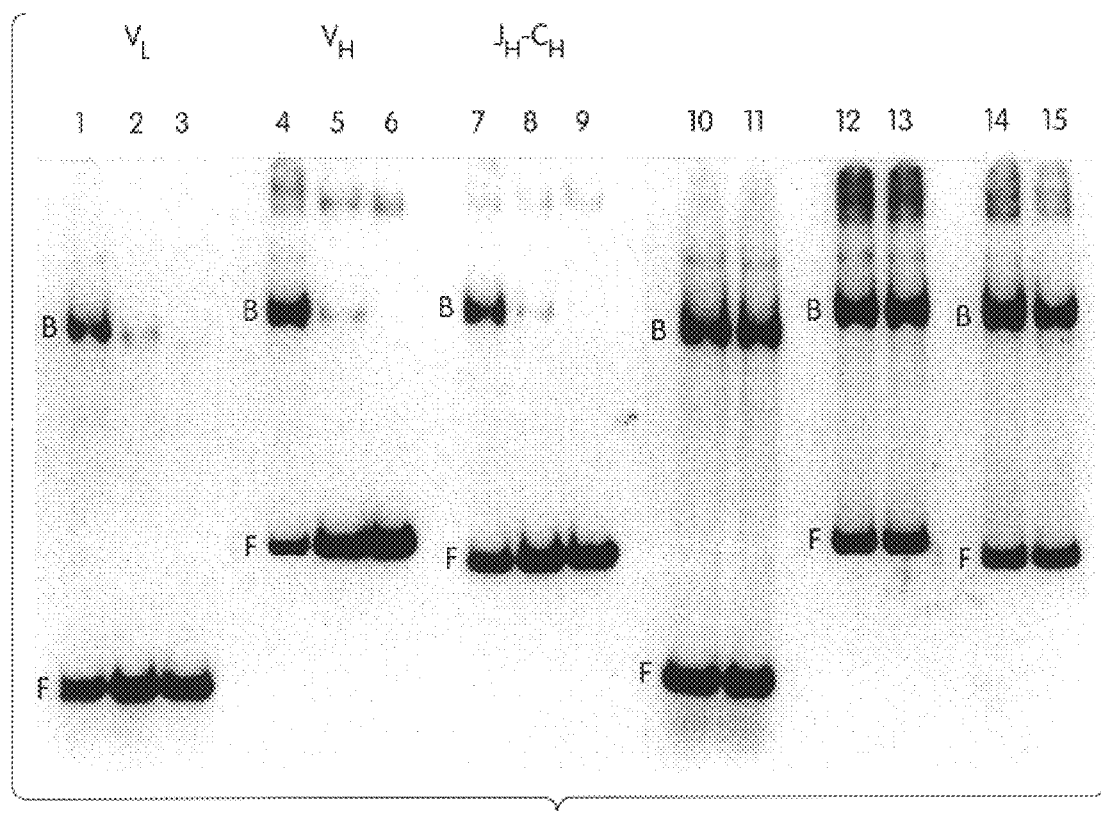
FIG. 4A shows the nucleotide sequences of actual and putative binding sites of IgNF-A.
FIG. 4B is an autoradiograph of binding assays with various DNA probes of three Ig transcriptional control elements.

Because the octamer sequence motif is present in both light and heavy chain gene promoters as well as in the enhancer elements of both mouse and human heavy chain genes, assays were performed for factor binding to fragments from a mouse heavy chain promoter (V$_H$) and the mouse heavy chain enhancer. The V$_H$ promoter fragment was derived from the 5' region of the V$_{17.2.25}$ gene and included nucleotides between positions −154 and +57 relative to the transcriptional start site. Grosscheal, R. and Baltimore, D. Cell 41 885–897 (1985). In this promoter the conserved octanucleotide spans positions −57 to −50 (FIG. 4a). The heavy chain enhancer fragment was derived from the germline J$_H$ C$_\mu$ region and spanned positions 81 to 251 within a 313 bp region implicated in enhancer function. Banerji, T. et al. Cell 33 729–740 (1983). The conserved octanucleotide is positioned between coordinates 166 to 173 in the above fragment (FIG. 4a). The B-cell heparin sepharose fraction (purified on the basis of binding to the Kappa promoter sequence, FIG. 4b, lane 1) evidenced binding to both the V$_H$ promoter fragment (lane 4) and to the enhancer fragment (lane 7). The mobilities of the complexes formed with the three fragments were very similar consistent with the binding of a common factor. Furthermore, binding to these fragments was specifically competed by a synthetic duplex 40-mer that spanned the octanucleotide motif of the MOPC 41 κ light chain gene promoter (lanes 1–9). An oligomer of equivalent size containing a sequence from a region of the mouse heavy chain enhancer lacking the octanucleotide motif (FIG. 4b) failed to compete for binding in the same concentration range (lanes 10–15). This competition analysis further strengthens the suggestion that a common nuclear factor (IgNF-A) binds to all three Ig transcriptional elements. As has been mentioned previously, these three transcriptional elements share an identical sequence motif ATTTGCAT (FIG. 4a). Thus, the binding of a common nuclear factor is almost certainly mediated by this motif.

Example 2

Dependency of in Vitro Transcription of Ig Genes on an Upstream Sequence

Methods

Figure 5A:
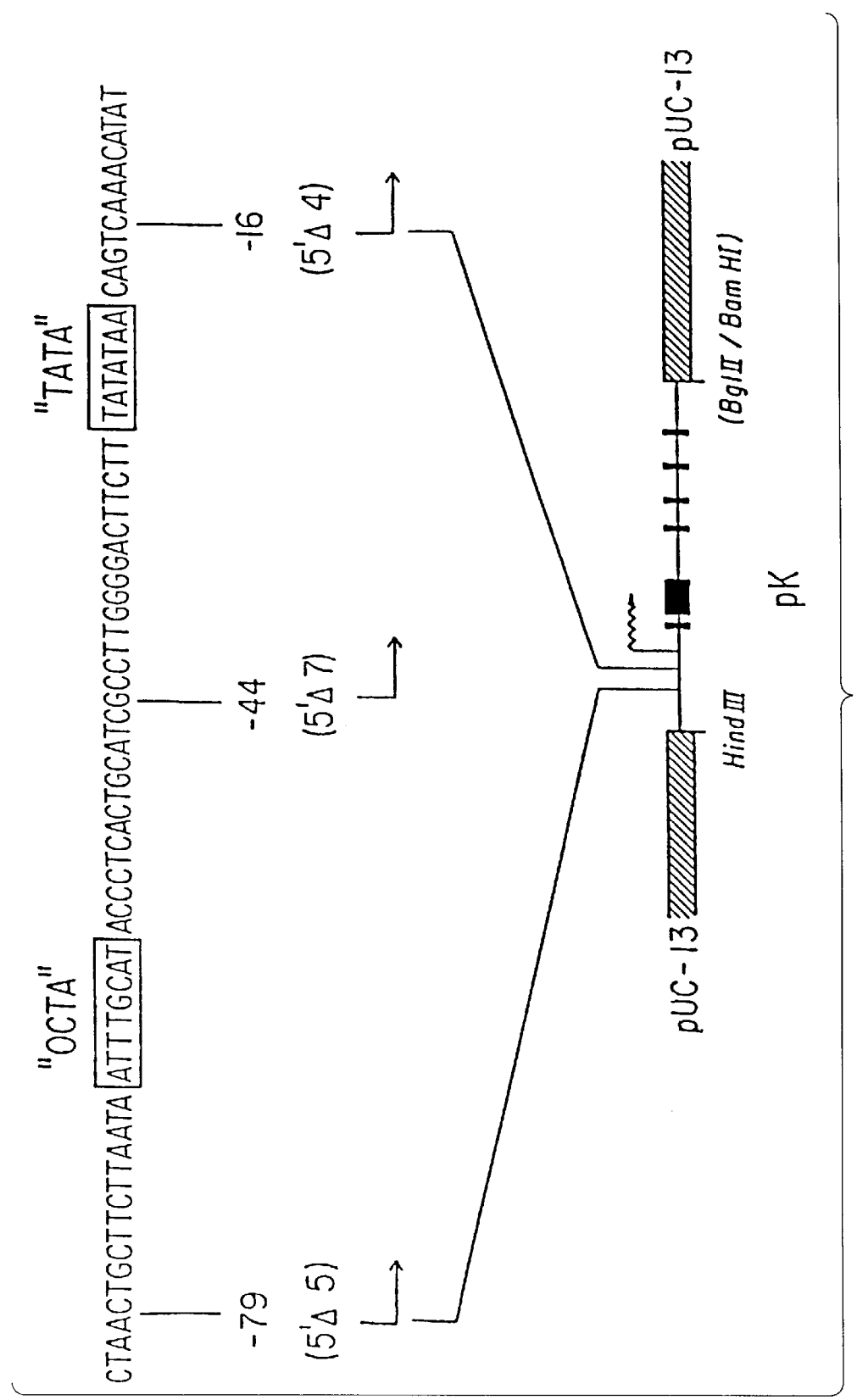
FIG. 5A shows the DNA sequence of the promoter region of MODC41.
Figure 5B:
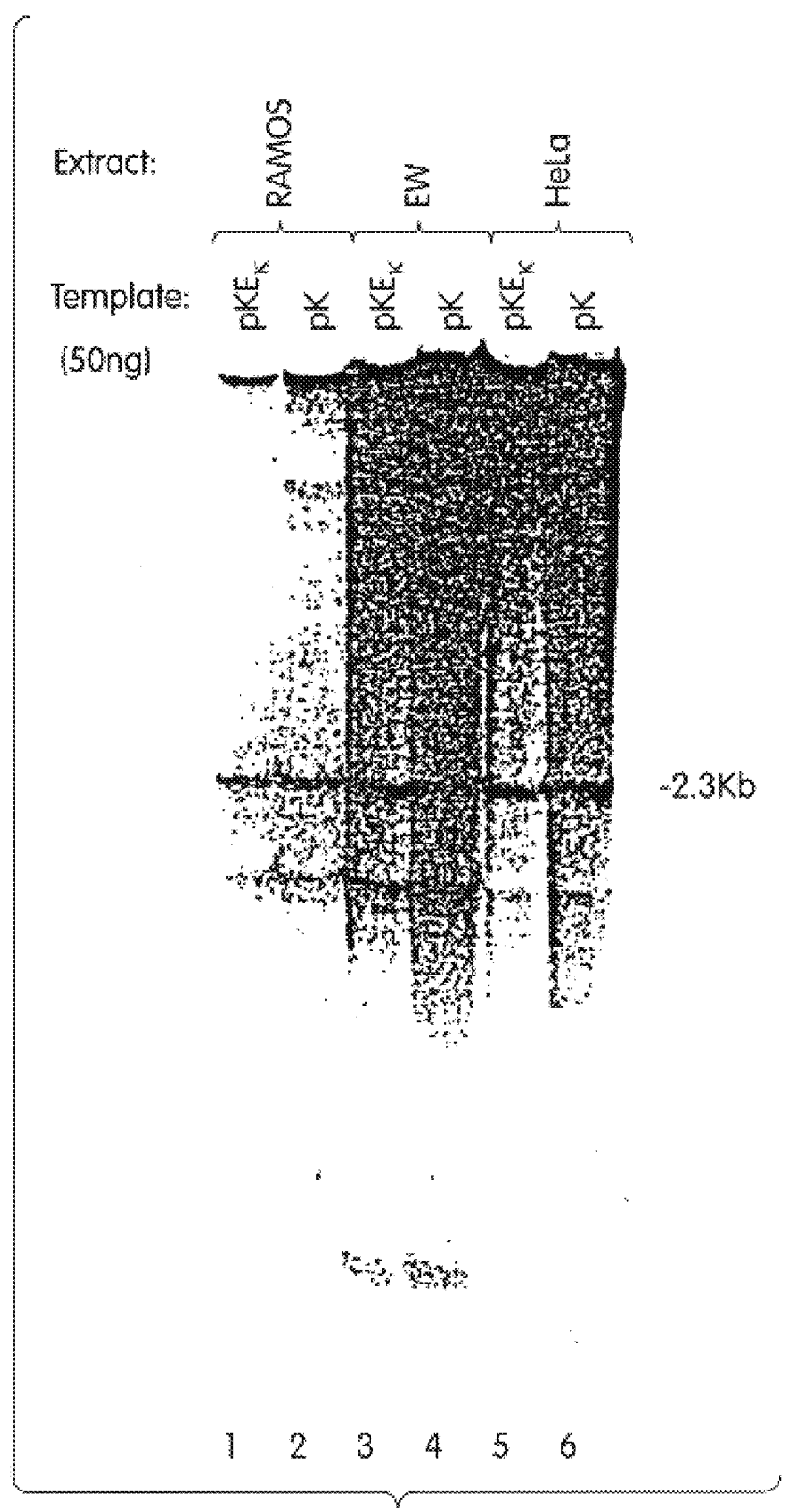
FIG. 5B shows an autoradiograph of RNA transcript generalized in whole cell extracts made from human B lymphoma cell lines RAMOS and EW and from HeLa cells from the indicated templates.

FIG. 5a: Templates. The deletions 5'Δ5 and 5'Δ7 have been described before. See Bergman Y. et al PNAS USA 81:7041 (1981). The highly conserved octanucleotide sequence which is found upstream of all sequenced heavy and light chain variable region genes is boxed (labelled "OCTA"). It is located approximately 30 base pairs upstream from the "TATA" box. The plasmids pκ and pΔκ were constructed by converting the 5'-ends of 5'Δ5 and 5'Δ7 into a Hind III site by means of synthetic linkers followed by cloning the fragment up to the Bgl II site in the J$_\kappa$-C$_\kappa$ major intron into Hind III, Bam HI digested pUC-13. pκE$_\kappa$ and pκE$_\kappa$ represent plasmids containing either the kappa enhancer of the heavy chain enhaner cloned into the unique Hind III site of pK. The segments used as the enhancers are an 800 bp Hind III-Mbo II fragment from the J$_\kappa$-C$_\kappa$ intron (Max, E. E. et al. (1981) J. Biol. Chem. 2565116) and a 700 bp Xba I-Eco RI fragment from the J$_H$-C$_\mu$ intron. Gillies, S. D. et al. Cell 33:717 (1983); Banjerji, J. et al. Cell 33:729 (1983). FIG. 5b; transcription in whole cell extracts made from the human B lymphoma cell lines RAMOS (lanes 1,2) and EW (lanes 3,4); transcription in a HeLa whole cell extract (from A Fire (lanes 5,6)). The expected 2.3 kb run off transcript is indicated.

The cell lines RAMOS and EW were grown in RPMI medium containing 10% inactivated fetal calf serum to a density of 5–8×10$^5$ cells per ml. Whole cell extracts were generated according to the procedure of Manley et al., PNAS USA 77:3855 (1980), and had a final protein concentration of approximately 18 mg/ml. Run off transcription reactions were carried out at 30° for 60' in a reaction volume of 20 μl. A typical reaction mix contained 9 ul (160 μg) of whole cell extract, 50 uM each of ATP, CTP and GTP, 0.5 uM UTP, 10 μCi of α-$^{32}$P UTP (NEG 007x, 7600 Ci/mM) 5 mM creatine phosphate, 0.3 mg/ml creatine phosphokinase (Sigma), 12 mM Hepes 7.9, 12% glycerol, 60 mM KC1, 5 mM MG$^{++}$, 1 mM EDTA, 0.6 mM DTT, linearized template (about 50 ηg) and poly (dI-dC)-poly(dI-dc) as a non-specific carrier (about 400 ηg). The reactions were terminated by adding 200 μl of stop buffer (7M urea, 100 mM LiCl, 0.5% SDS, 10 mM EDTA, 250 μg/ml tRNA, 10 mM Tris (pH 7.9), followed by two extractions with phenol: chloroform: isoamyl alcohol (1:1:0.05), one with chloroform and precipitation with ethanol. The RNA's were treated with glyoxal and analyzed by electrophoresis through a 1.4% agarose gel in 10 mM sodium phosphate (pH 6.8), 1 mM EDTA. See Manley et al. supra. The gel was then dried for autoradiography with an intensifying screen at −70° C.

Figure 6:
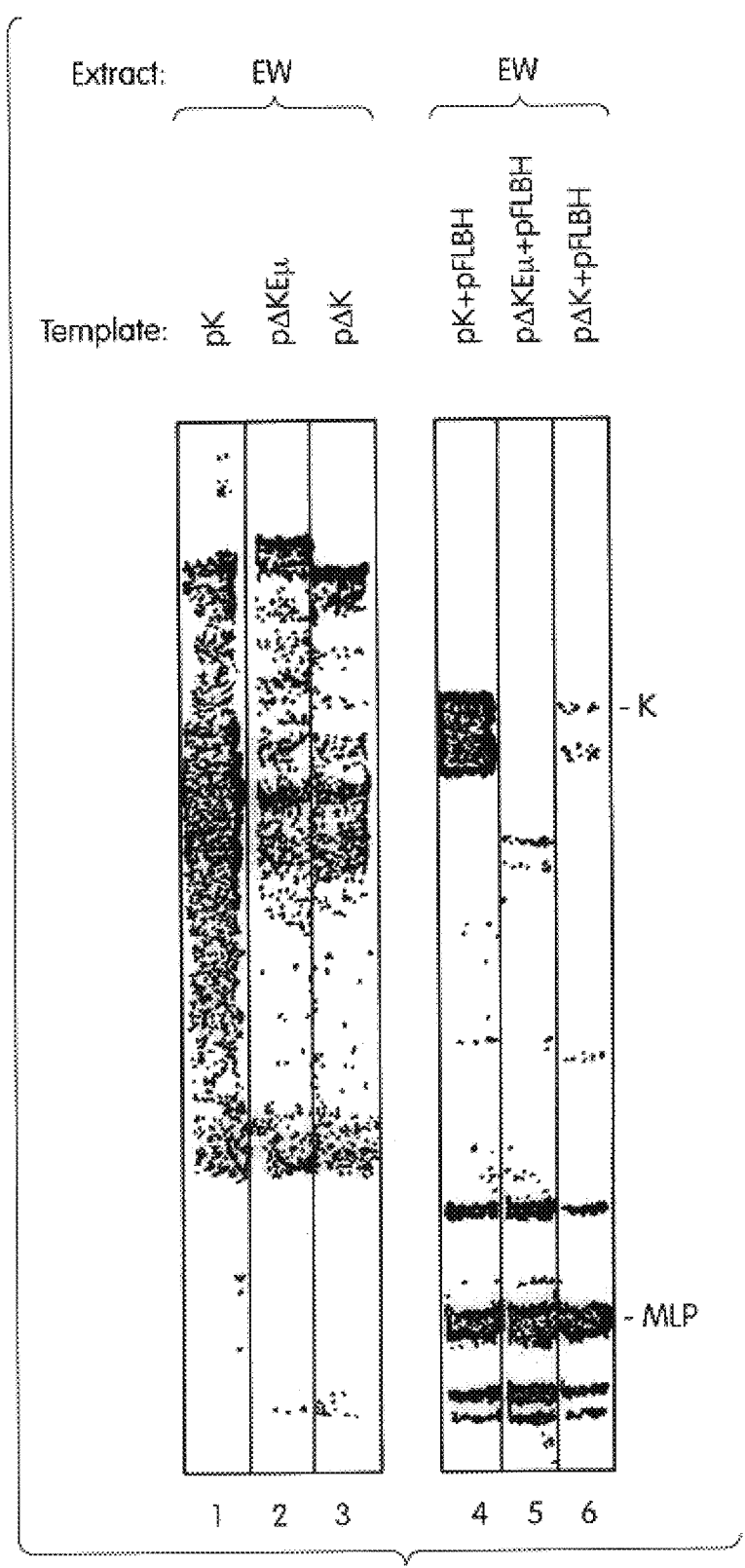
FIG. 6 shows an autoradiograph of RNA transcripts from templates containing an upstream deletion.

FIG. 6: Effect of the upstream deletion 5'Δ7 on in vitro transcription in B cell extracts utilizing a pre-incubation pulse chase protocol. Run off transcripts obtained utilizing templates containing either the wild type promoter (lane 1) or the truncated Kappa promoter (lanes 2,3). Lanes 4–6: In vitro transcription using closed circular templates containing the wild type promoter (lane 4) or the truncated κ promoter (lanes 5–6). In these reactions 50 ηg of a closed circular template containing the adenovirus major late promoter (MLP) was included as an internal control. The transcripts specific to the κ template or the adenovirus template are indicated as κ and MLP, respectively. For a template containing the major late promoter the plasmid pFLBH was used. The plasmid contains sequences from 14.7 to 17.0 map units of adenovirus inserted between the Bam HI and Hind III sites of pBR322 and was the kind gift of A. Fire and M. Samuels.

Either the linearized or the supercoiled template (50 ηg) was incubated in a volume of 20 μl with 9 μl (about 150 μg) of EW extract, 6% (wt/vol) polyethylene glycerol 20,000 and all other components described for FIG. 5b except the nucleotides for a period of 60 minutes at 30° C. Transcription was initiated by the addition of nucleotides and radioactive UTP to the following final concentrations: 60 uM each of ATP, CTP and GTP and 1 μM UTP and 10 μCi α-$^{32}$P UTP (NEG 007x, 600 Ci/mM). The initiating pulse was maintained for 10' at 30° followed by a 10' chase with a vast excess of non-radioactive nucleotides. Final concentrations during the chase were as follows: 330 μM ATP, CTP, GTP and 1 mM UTP. The reactions were quenched, worked up and the run off transcripts analyzed as described above. Mapping of the initiation site of the transcript was conducted as follows: Transcripts generated from closed circular templates were taken up in 20 μl of HE (50 mM Hepes, pH 0.7, 1 mM EDTA) and 10 μl was used for hybridization selection. A hybridization template complementary to the κ RNA was constructed by cloning the Pva II-Sau 3A fragment which contains the cap site of the MOPC41 gene (Queen and Baltimore, Cell 33:741 (1983)) into the M13 phage MP9. Single stranded phage DNA was prepared and purified by density gradient centrifugation through cesium chloride. MLP specific transcripts were detected using the M13 clone XH11 provided by A. Fire and M. Samuels. Hybridizations were done in a final volume of 15 μl in the presence of 750 mM NaCl and 100–200 ug of single stranded complementary DNA at 50° C. for 2 hrs. The reactions were then diluted with 200 μl of cold quench solution (0.2 M NaCl, 10 mM Hepes pH 7.5, 1 mM EDTA) and 2 U of ribonuclease T1 added. Digestion of single stranded RNA was allowed to proceed for 30' at 30° C. after which the reactions were extracted once with phenol chloroform isoamyl alcohol (1:1:0.05) and precipitated with carrier tRNA. The pellet was washed once with cold 70% ETOH, dried and resuspended in 80% v/v formamide, 50 mM Tris borate, pH 8.3 and 1 mM EDTA. The RNA was denatured at 95° C. for 3 min and then electrophoresed through a 6% polyacrylamide 8.3 M urea sequencing gel. The upper of 2 bands (κ) derived form the immunoglobulin promoter represent the correct start for κ transcription. The lower band is seen at variable intensities and probably does not represent a different cap site, as explained below.

Results

Whole cell extracts were made from two human Burkitt lymphoma lines, EW and RAMOS, by the procedure of Manley et al. supra. The templates used for in vitro transcription reactions are diagrammed in FIG. 5a. The template representing the wild type gene (pK) was derived from the MOPC41 κ gene and contained sequences from approximately 100 bp upstream from the transcription initiation site (end point 5'Δ5, FIG. 5a) to the Bgl II site in the major $J_κ$–$C_κ$ intron Max, E. E. J. Biol. Chem. 256:5116. This fragment retains the complete variable region which is rearranged to $J_κ$ 1, but not the κ enhancer which is further downstream of the Bgl II site. See, e.g., Queen and Stafford, Mol. Cell. Biol. 4:1042 (1984). This short 5' flank has been shown to be sufficient for accurate initiation and high level of transcription in a transient transfection assay. Bergman, Y. et al. PNAS USA 81:7041 (1984). Deletion analysis of the κ promoter showed previously that important regulatory sequences are present between nucleotides −79 and −44 because deletion 5'Δ7 completely abolished transcriptional competence of the gene while deletion 5'Δ5 had no effect. See Bergman et al. supra. The template representing an inactive promoter mutant (pΔκ) was constructed by engineering a Hind III site into the 5'-end of 5'Δ7 and cloning the segment of the gene up to the Bgl II site into pUC13 cut with Hind III and Bam HI.

To examine transcriptional activity in B cell extracts, a linear template truncated at the Sac I site in the polylinker was used and transcripts ending at this site (run off transcripts) were examined by electrophoretic separation. A run off transcript of 2.3 kb was evident when RAMOS, EW or HeLa cell extracts were used (FIG. 5b, lanes 2, 4 and 6). When a κ chain enhancer sequence was added to the construct, no effect was evident implying that transcription in these extracts is enhancer independent (FIG. 5b lanes 1, 3 and 5). (In EW and HeLa, the enhancer appears to cause a slight increase in the background radioactivity but not in the 2.3 kb band.) The band at 2.3 kb could be abolished by not adding the template or by transcribing in the presence of 0.5 μg/ml amanitin. Thus it represents a template-specific, RNA polymerase II transcript. The band just below 2.3 kb is not decreased by α-amanitin and presumably reflects end-labeling of endogenous 18S rRNA.

To assess whether initiation of transcription occurred at the natural cap site, a second assay was used. See Hansen, U. and P. A. Sharp (1983) *EMBO J* 2:2293. For this assay, the uniformly labeled RNA was hybridized to a single stranded DNA probe spanning the transcription initiation site (generated by cloning the Pvu II-Sau 3A fragment of the κ gene into phage M13). The resulting complex was digested with ribonuclease T1 and the ribonuclease-resistant RNA fragments were analyzed by electrophoresis through a 6% polyacrylamide gel with 8.3 M urea. Analysis of in vitro synthesized RNA by this method is shown in FIG. 6 (lane4). The upper band (labeled κ) represents the correct cap site. The band just below it was seen at variable intensities and probably does not represent a different cap site but rather arises from cleavage with ribonuclease T1 at the next G residue from the 3'-end of the protected region. (Examination of the sequence near the Sau 3A1 site shows that the second set of G residues on the RNA lies 19 bp upstream from the end of the region of homology with the single stranded DNA probe). Thus the extracts generated from B cells were capable of correctly initiating and transcribing the immunoglobulin promoter in vitro with approximately the same efficiency as a HeLa cell extract.

To analyze the effect of 5' flanking sequences in vitro, we examined the transcription of the deleted gene, pΔK. Because many regulatory effects act upon the rate of initiation of transcription, we chose to use a preincubation, pulse-chase protocol which measures the initiation rates. See Fire, A. et al. J. Biol. Chem. 259:2509 (1984). The template DNA was first preincubated with the extract to form a pre-initiation complex. Transcription was then initiated by the addition of nucleotides and radiolabeled UTP. The initiated transcripts were completed during a chase period with unlabelled nucleotides and analyzed by electrophoretic separation. Incorporated radioactivity in this assay is proportional to the number of correct initiations occurring during the pulse.

In FIG. 6, comparison of lanes 2 and 3 with lane 1 shows that the template pκ, which contains about 100 bp upstream of the initiation site, initiated approximately 10-fold more efficiently than did the deletion mutant, pκ. Again, the presence of the heavy chain enhancer placed at –44 bp to the truncated promoter did not alter the level of transcription. When closed circular templates were used, a similar effect of the promoter truncation was observed (FIG. 6, lanes 4–6). In these reactions a template containing the major late promoter of adenovirus was included as an internal control; the expected protected RNA fragment of 180 bp is labeled MLP. Comparison of lanes 5 and 6 with lane 4 shows that there was a 10-fold decrease in the efficiency of transcription from the mutant promoter, whereas the transcript of the major late promoter remained constant. The reason for the apparent decrease in the amount of transcription from the supercoiled template containing the heavy chain enhancer has not been further addressed. It is evident, however, that the dependence of transcription on an upstream sequence between –44 and –79 is observed whether the effect described above was specific to B cell extracts, the same templates were transcribed in the heterologous HeLa whole cell extract. A 4- to 5-fold decrease in transcription was seen with the deleted template when compared with the wild type template (data not shown). Thus, the effect of the deletion is at best, only modestly tissue-specific.

We have reported here the development of transcriptionally competent whole cell and nuclear extracts from two independent human B cell lymphomas. In such extracts, transcription from the promoter of the MOPC41 κ gene was correctly initiated and a promoter deletion significantly reduced the level of initiated RNA. In vitro, the effect of the deletion used here is several hundredfold when analyzed by a transient transfection assay. However, the effect observed in vitro is only about 10- to 15-fold. Although there are now several examples of upstream sequence requirements for in vitro transcriptions, See, e.g., Groschedl R. and Birsteil M. L. (1982) PNAS USA 79:297; Hen, R. et al. (1982) PNAS USA 79:7132, the effects have been smaller than the corresponding one in vivo. This is possibly due to the dominance of the TATA box and associated factors in determining the level of transcription in vitro Miyamoto, N. G. et al., Nucl. Acids Res. 12:8779 (1984).

Example 3

Discovery and Characterization of IgNF-B

The mobility shift gel electrophoresis assay was used to screen nuclear extracts from a variety of cell lines for octamer binding proteins. The band corresponding to IgNF-A was found in all extracts but a second band with distinct mobility from IgNF-A was found only in nuclear extracts from lymphoid cells. This lymphoid-specific octamer binding protein, termed IgNF-B, was found in nuclear extracts from all pre-B, mature B and myeloma cell lines tested and in nuclear extracts from some T cell lymphomas (see FIG. 7 and 8). IgNFB was not detected in nuclear extracts from the non-lymphoid cell lines, Hela, ψ2, Cos and Mel (see FIG. 8). IgNF-B was shown to be specific for the same octamer sequence as IgNF-A by competition experiments n which the IgNFB band was selectively competed by unlabelled DNA fragments sharing only the octamer sequence and not by DNA fragments lacking the octamer sequence.

The octamer sequence is found at approximately position –70 upstream of the transcription start site of all immunoglobulin (Ig) variable genes which is in the region that has been shown to control the lymphoid specificity of the Ig promoter. Thus, IgNF-B binds to the upstream octamer sequence in lymphoid cells and activate transcription.

Example 4

Factors Binding to μ-Enhancer: E Factor

The fully functional μ enhancer has been localized to a 700 bp XbaI EcoRI fragment from the major intron between $J_H$ and $C_\mu$. This fragment can be further sub-divided by cleaving at the PstI site to generate a 400 bp XbaI-PstI fragment (μ400) and a 300 bp PstI-EcoRI fragment (μ300). It has been shown by transient transfections that 30–50% of the tissue specific enhancer activity is retained in μ300, whereas there is no detectable activity of μ400. The gel binding assay was employed to investigate what protein factors may interact with the u-enhancer. Briefly, end-labelled DNA fragments were incubated with nuclear extracts made from tissue culture cells. After 20 min at room temperature the mixture was loaded on a low ionic strength polyacrylamide gel and electrophoresis carried out at 120V for 2 hrs. The gels were then dried for autoradiography. When the functional 300 bp (μ300) enhancer fragment was used in such an assay a DNA-protein complex was observed in extracts derived from the human B lymphoma cell line EW (FIG. 9b, lane 2). To show that this new band represented a specific complex binding reactions were carried out in the presence of varying amounts of non-radioactive competitor fragments (FIG. 9b, lanes 3–11). It is easily seen that when μ300 is added as the competitor fragment, the complex band is completely lost. In contrast, the adjacent u400 fragment (lanes 6,7,8) or a 450 bp fragment containing the κ light chain enhancer (lanes 9,10,11), cause only a minor effect even at the highest concentrations used. It is interesting to note that there appears to be a slight increase in the amount of specific complex in the presence of the κ enhancer fragment (compare lanes 9 and 2). As demonstrated below, both the μ and the κ enhancers interact with at least one common protein and this is not the factor being detected by binding the u300 fragment. The increase in the specific complex in the presence of the κ enhancer is probably due to the removal of factors common to both the enhancers from the reaction mix, thus leaving more of the labelled fragment available to bind to the μ specific factor being detected by it.

Figure 10A:
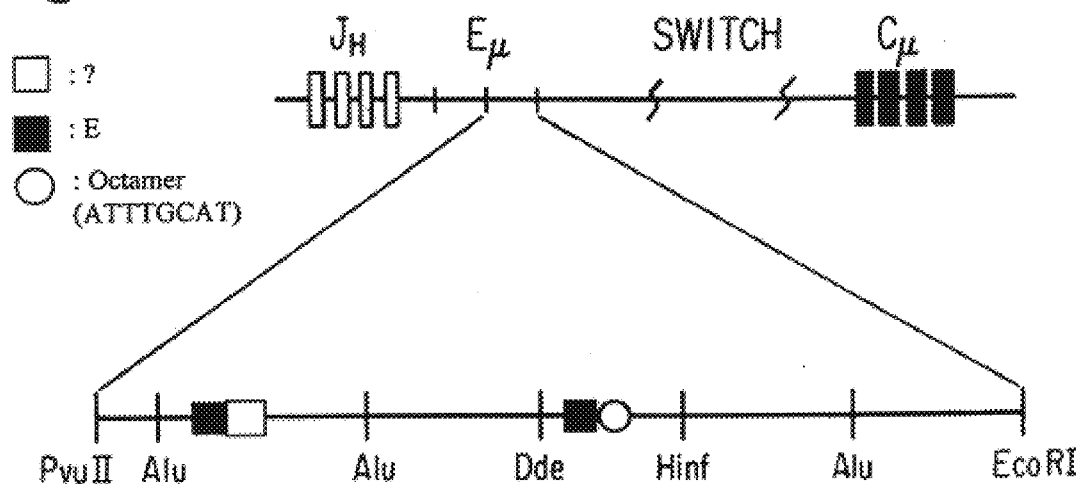
FIG. 10A shows a restriction map of the μ300 fragment.
Figure 10B:
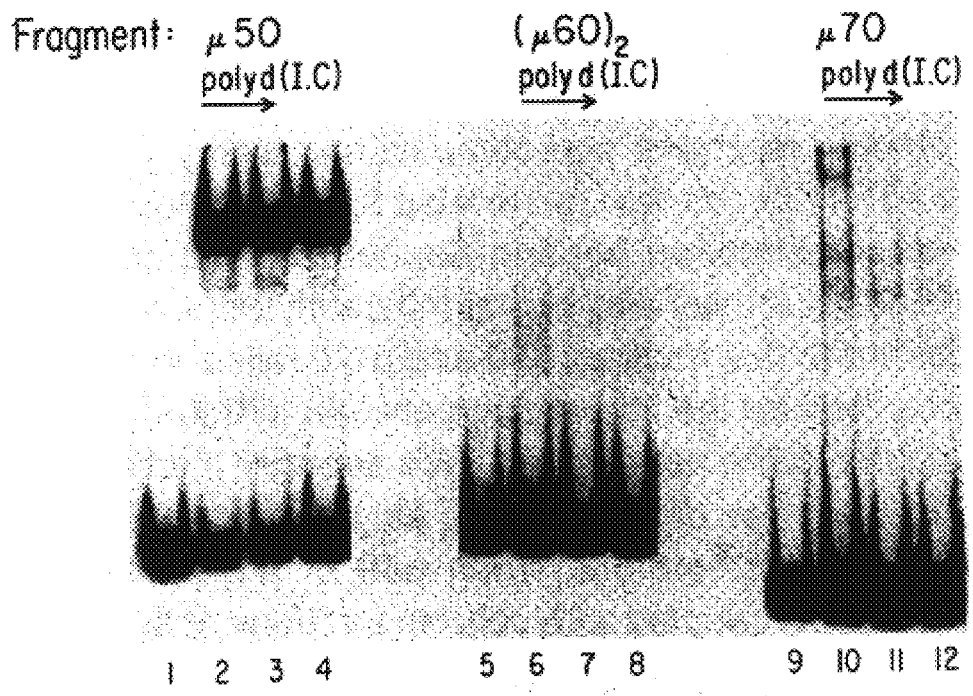
FIG. 10B shows complexes formed by various subfragments of μ300.

In order to be able to detect binding sites for less abundant proteins and also to more precisely define the complex detected with μ300, this fragment was further dissected. Each of the smaller fragments generated were analyzed for their ability to serve as binding sites for nuclear proteins. FIG. 10A shows a partial restriction map of the relevant region of the μ enhancer. μ300 was digested with AluI, HinfI and DdeI to generate a number of 50–70 bp fragments labelled μ50, μ(60)$_2$ (a mixture of AluI-DdeI and HinfI to AluI) and μ70 (AluI-AluI). Binding reactions were carried out with each of these fragments with nuclear extracts of EW lymphoma cells in the presence of increasing amounts of the non-specific competitor poly (dI-dC)-poly(dI-dC). The results are shown in FIG. 10B.

Fragment μ50 forms a major complex band (lanes 2,3,4) that is barely decreased even in the presence of 4 ug of poly(dI-dC)-poly(dI-dC) (lane 4). The mixture of the two 60 bp fragments does not give rise to a discrete complex band (lanes 6,7,8). Finally the μ70 fragment gave 2 faint, but discrete, nucleoprotein complex bands (lanes 10,11,12) of which the lower one is again barely affected by 3 ugm of non-specific carrier poly(dI-C)-(dI-C) (lane 12).

Figure 10C:
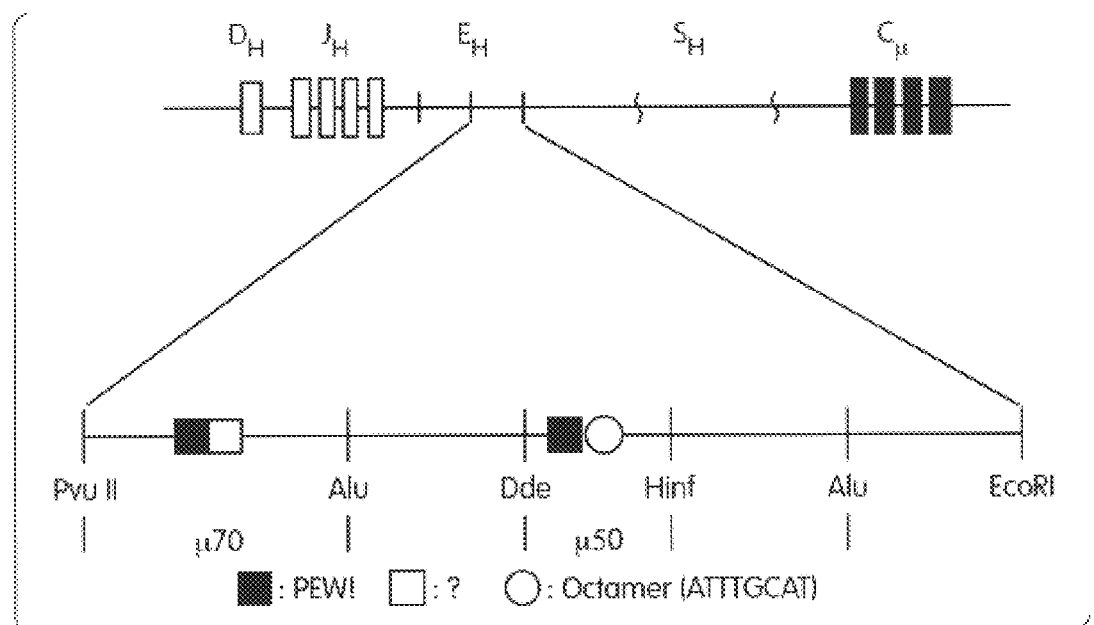
FIG. 10C is a restriction map of the relevant region.

Specificity of the complexes observed were shown by competition experiments using a variety of DNA fragments, FIG. 10C. Thus, the complex generated with μ50 is specifically competed away in the presence of μ300 (of which μ50 is a part), or a κ promoter fragment, but not by corresponding amounts of μ400 or a κ enhancer fragment, consistent with the complex being generated by the interaction of the previously described factor IgNF-A with its cognate sequence. (This factor recognizes a conserved octanucleotide, ATTTGCAT, found in the promoters of all sequenced immunoglobulin genes and within this subfragment of the heavy chain enhancer.)

Figure 10D:
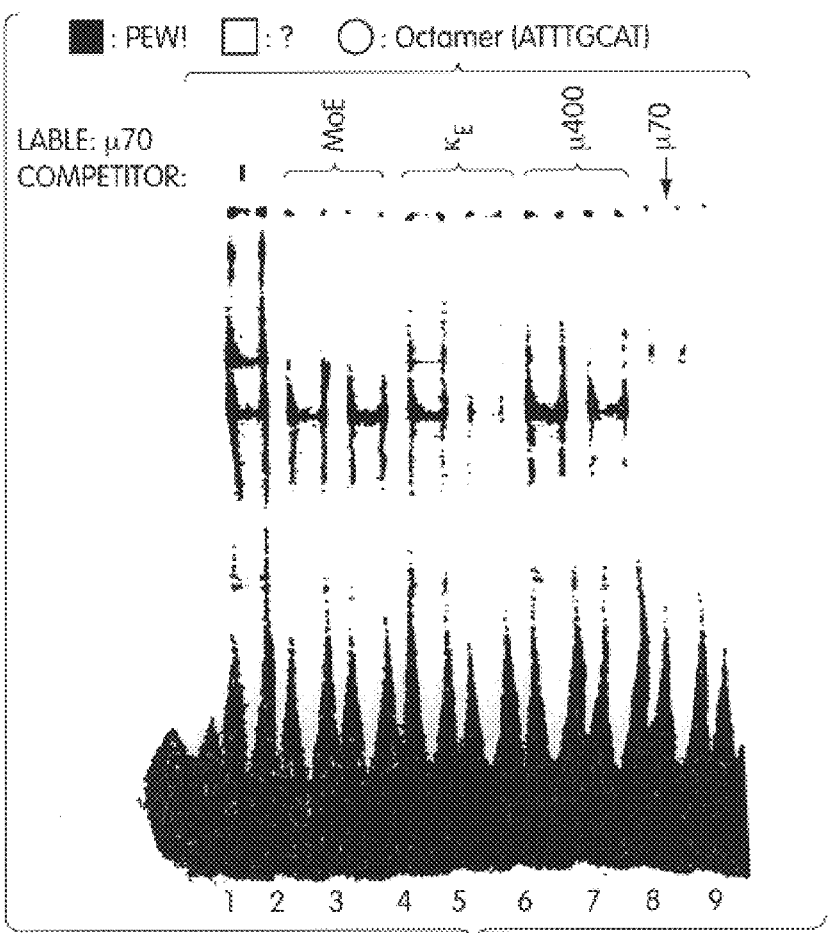
FIG. 10E and 10D show competition binding assays with the subfragment μ70.
Figure 10E:
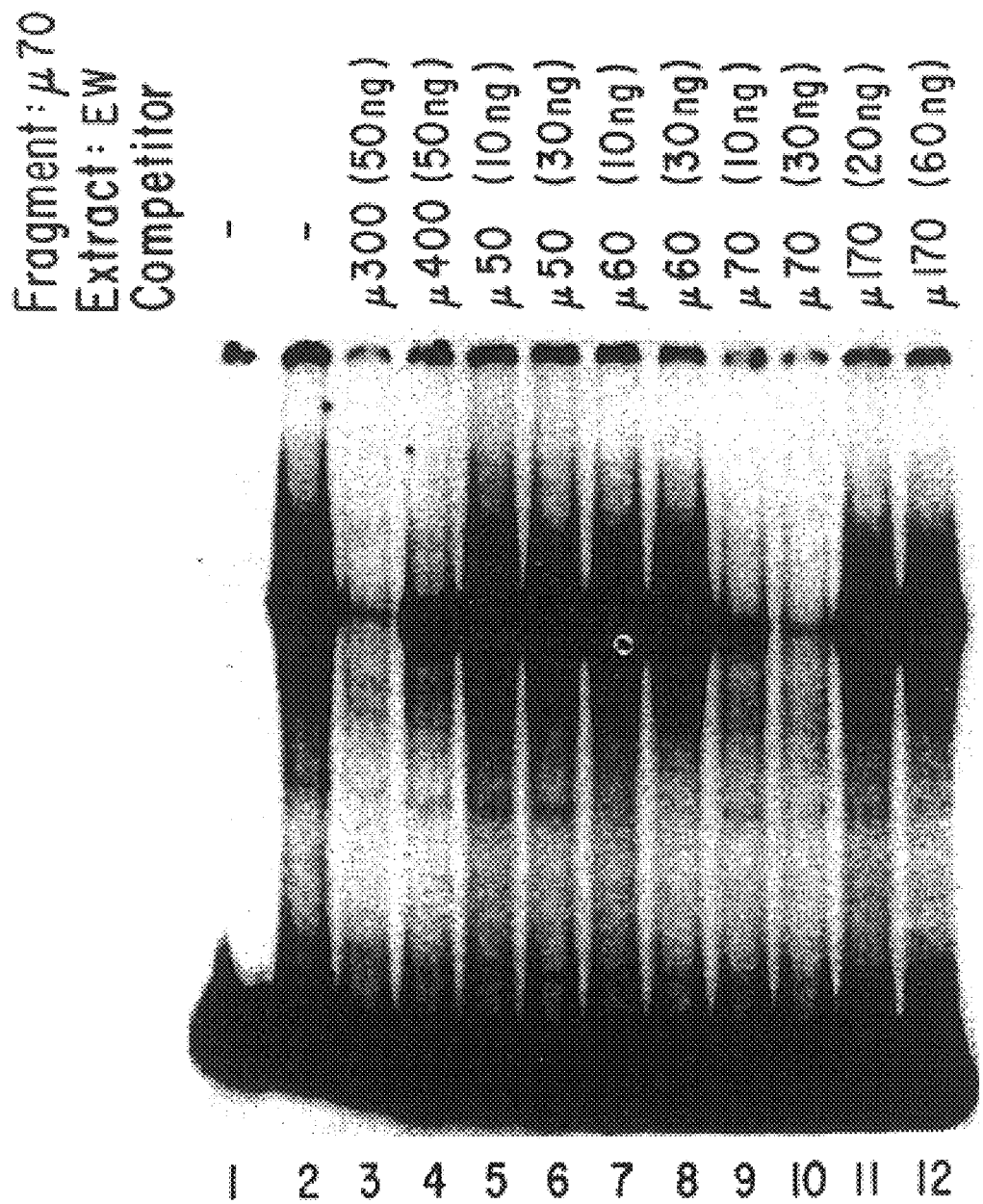

The complex observed with μ70 was specifically competed away by itself (lane 9) and to some extent with the κ enhancer (lanes 5,6 FIG. 10C) but not at all by either the Moloney murine leukemia virus enhancer (lanes 3,4) or by μ400 (lanes 7,8, FIG. 10D). Further competition analysis showed that this complex could not be competed away by either (μ60)$_2$ (FIG. 2D, lanes 7,8), μ50 (FIG. 2D, lanes 5,6) or μ170 (central AluI-AluI fragment) (FIG. 10D, lanes 11,12). The binding we have observed is therefore specific to this small fragment and was detected only upon further dissecting μ300 which separated the major observable interaction of IgNF-A with the enhancer sequence to another fragment (μ50).

Ephrussi et al. and Church et al. have used methylation protection experiments to define a set of G residues within the heavy chain enhancer that are specifically resistant to methylation by DMS in B cells. This result lead to the proposal that tissue-specific DNA binding proteins were responsible for this decreased accessibility of the reagent to DNA. The protection was observed in 4 clusters, the DNA sequences of which were sufficiently homologous to derive a consensus sequence for the binding site of a putative factor. All four postulated binding sites (E1–E4) are found within the 700 bp fragment; however μ300 retains only 2 complete binding domains (E3 and E4) for this factor and the octamer (0) sequence. The Alu-Alu fragment that shows that specific nucleoprotein complex described above contains the complete E3 domain and the factor we detect in vitro presumably is the same as that detected in vivo. Thus, it was unexpected that the HinfI-Dde fragment (μ50) containing E4 and 0 should not compete for binding to μ70 (FIG. 10D, lanes 5,6).

In case this was due to the fragment predominantly binding IgNF-A at the octamer site and thus making it unavailable as a competitor for μ70, binding reactions and competition assay were done for a fraction generated by chromatography of the crude extract over a heparin-sepharose column, that contained μ70 binding activity and was significantly depleted of IgNF-A. When μ50 or μ170 was endlabeled and incubated with the column fraction, no specific nucleoprotein complexes were seen upon electrophoretic analysis. Even in this fraction, μ50 and μ170 failed to compete successfully for the interaction between μ70 and its binding protein (data not shown), thus implying strongly that the binding site defined as E4 perhaps does not bind the same factor that binds at E3. Similarly, the E1 domain (isolated as a Hinf-PstI fragment) does not compete as effectively as μ70 itself for the binding of the factor to μ70.

To determine the location of the binding sites within individual fragments (μ70 and μ50), the technique of methylation interference was employed. End-labelled DNA fragments were partially methylated on guanines and adenines using dimethyl sulfate (DMS). Methylated DNA was then used for binding reactions with crude extracts and the complex was resolved from the free fragment by electrophoresis. Both complex and free fragment bands were then excised from the gel, and the DNA was recovered by electroelution. Piperidine cleavage of the recovered fragments was followed by electrophoresis through 12% polyacylamide urea sequencing gels. In principle, if any of methyl groups introduced by reaction with DMS interfere with the binding of a specific protein then that molecule of DNA will be selectively missing in the complex formed and subsequently the corresponding ladder. The method therefore allows identification of G residues making intimate contacts with the protein. [We have found that the use of DNaseI footprinting via the gel binding assay to be complicated in the case of some of these less abundant factors because of the short half lives of the complexes themselves. Thus, if a binding incubation is followed by partial DNaseI digestion, it is possible that in the course of time required to load the sample and have the complex enter the gel, DNA fragments that were in complex form may exchange with the larger amounts of free fragment in the binding reaction. Thus not leading to any distinction in the DNase patterns seen with wither the complex or the free DNA (e.g. the half life of the nucleoprotein complex in μ70 is less than 1 minute,)].

Figure 11A:
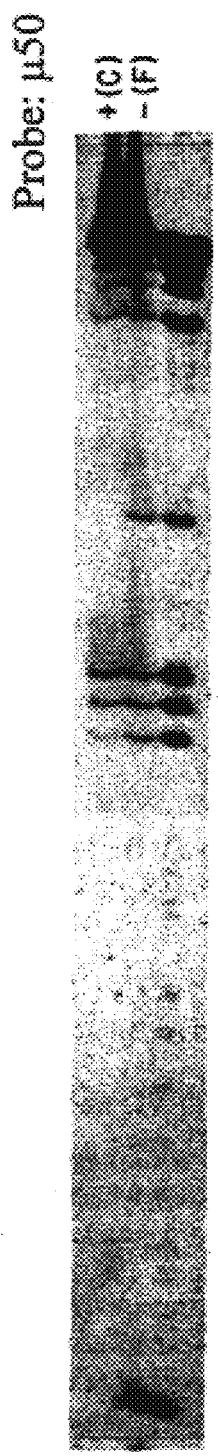
FIG. 11A and 11B show location of binding sites in μ50 and μ70 by the methylation interference technique.

The result of carrying out such an interference experiment using nuclear extracts and on the u50 DNA fragment shows that the complex observed arises via interaction of the IgNF-A protein at the conserved octameric sequence (FIG. 3A). The free fragment generates a characteristic G ladder (FIG. 11A), lane 2,3) and the complex form (lane 1) is specifically depleted in DNA molecules carrying a methyl group at the G residue indicated by the asterisk which lies in the middle of the conserved octamer. Presumably, modification at this residue seriously impedes the formation of a stable complex between the protein and its cognate sequence. This residue was also shown to be protected against methylation of DMS in vivo. Interestingly, however, none of the other G residues observed to be protected in vivo in this region of the μ enhancers appear to be affected in our in vitro interference experiment. Therefore, if these protections in vivo are due to the binding of a protein, this factor is different from IgNF-A or B and is not binding to fragment in vitro.

Figure 11B:
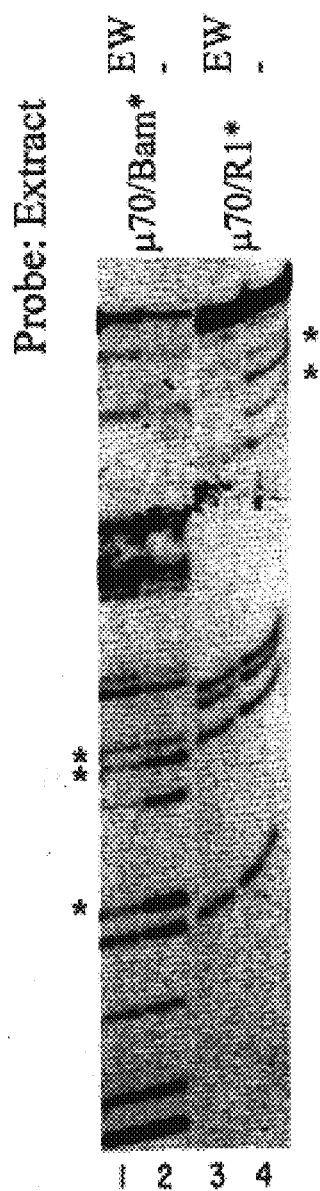
Figure 11C:
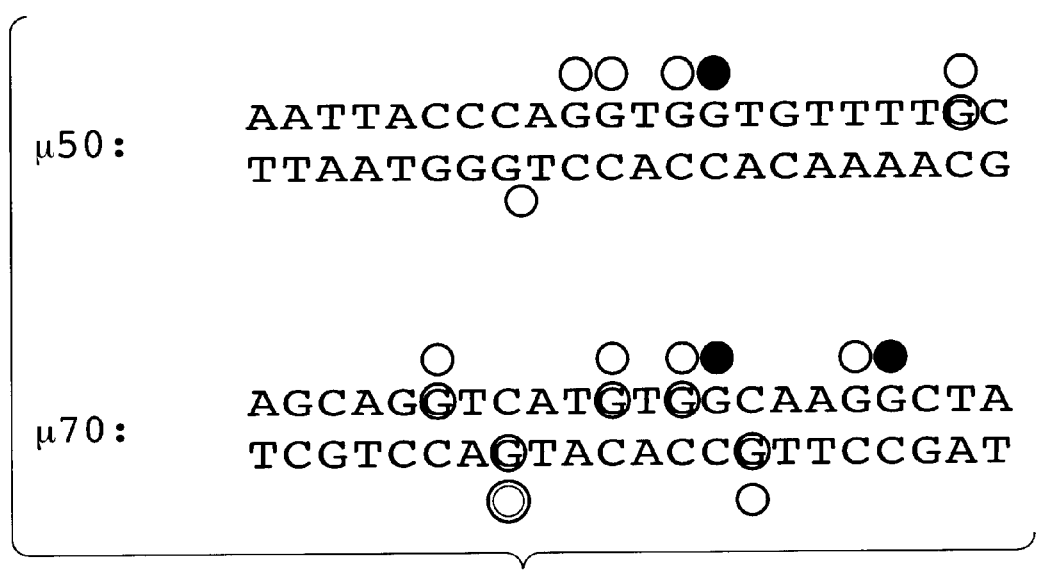
FIG. 11C provides a summary of these results.

On the μ70 fragment several G residues were identified as being important in forming intimate contacts with the binding protein (E) (FIG. 11B). On the coding strand bands the 3 G's are significantly reduced in intensity in the complex as compared to the free DNA fragment (FIG. 11B, compare lanes 1,2), and on the non-coding strand 2, G's are significantly affected (FIG. 11B, compare lanes 3 and 4).

Figure 12A:
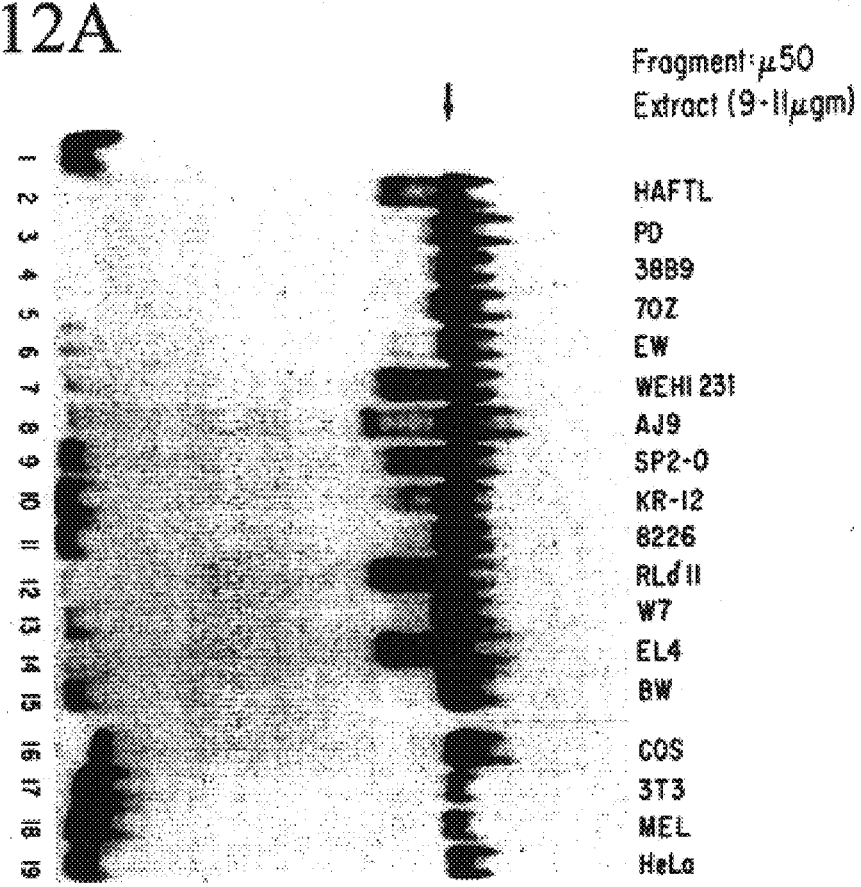
FIG. 12A and 12B show an autoradiograph of binding complexes formed with μ50 and μ70 in B-cell and non B-cell extracts.
Figure 12B:
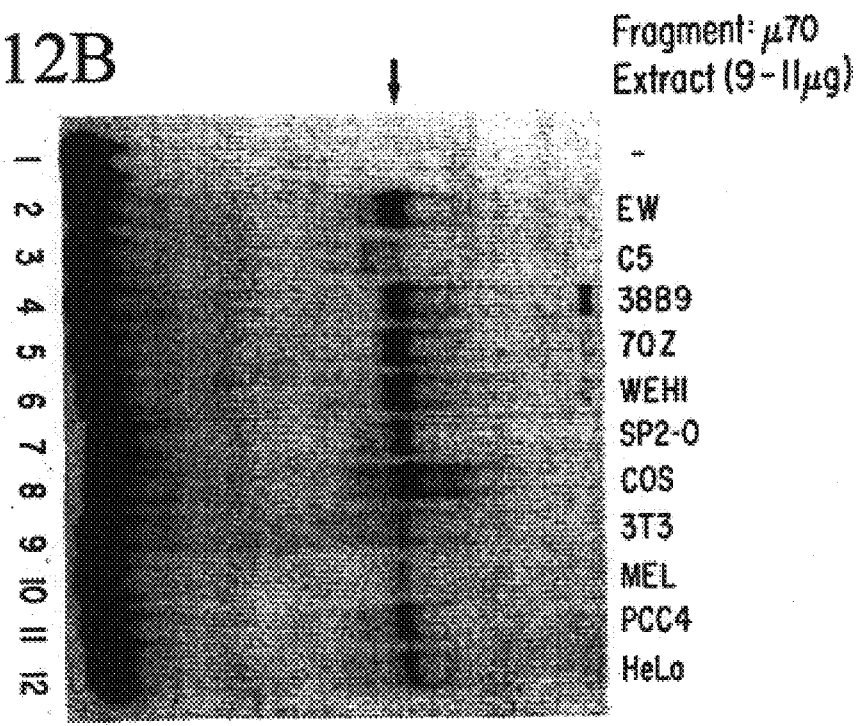

The results of both the in vivo DMS protection experiment and the in vitro methylation interference experiments are summarized in FIG. 3C. The open and closed circles above the sequence were the residues identified by Ephrussi et al. to be protected against methylation in vivo whereas the encircled G's are the ones identified by us in vitro. The pattern of protection and interference on the μ70 fragment over the consensus sequence is strikingly similar in vivo and in vitro, which indicated strongly that the protein identified here by means of the gel bind assay is the one that interacts with this sequence in vivo. Analogous to μ50, however, the second set of protections seen in this region in vivo was not observed in vitro. Tissue specificity of the factors detected: In order to determined whether the proteins identified are limited to expression only in B cells, a large number of extracts made from B cells and non-B cells were screened (FIG. 12). Complexes that co-migrate with the ones generated and characterized (by competition and methylation interference experiments) in the B cell line EW, were observed on both the fragments μ50 and μ70 (FIG. 12; μ70) in all the cell lines examined. Although the complex generated in each extract has not been further characterized, we interpret this data as indicating that both these factors are non-tissue specific. A second complex (NF-κB) was observed with the μ50 fragment that was restricted to B and T cells only.

A point to note is that although the amount of protein in each lane has been held constant at between 9 and 11 μg, the extent of complex generated was found to vary considerably from extract to extract. Thus, showing that quantitive estimations of the abundance of proteins in different cell lines using this assay is not very meaningful at this stage. (This is presumably due to subtle variations in the state of the cells and the extraction conditions for the different cell lines).

In summary, analysis of the functional 300 bp PstI-EcoRI fragment of the μ enhancer reveals that:
 (i) at least 2 different proteins bind within this DNA sequence. One protein (IgNF-A) interacts with an octamer sequence (ATTTGCAT) that is highly conserved upstream of all heavy and light chain variable region genes and is also found in the u enhancer. The second protein interacts with a sequence shown by Ephrussi and Church to be protected in a tissue specific manner against methylation by DMS in whole cells;
 (ii) both factors can be detected in nuclear extracts from a variety of cell lines and are therefore not B-cell specific;
 (iii) both E1 and E4 sequences hardly compete for the binding of the factor to μ70 (which corresponds to E3), thus implying that these sequences do not interact with the same factor, although the sequence homology amongst the sites would have lead one to expect that they should.

Example 5

Identification of Factors Binding to Kappa-light Chain Enhancer

An enhancer element has also been identified in the major intron of the κ light chain gene. Picard and Schaffner showed that the enhancement activity can be localized to a ~500 bp AluI-AluI fragment and Queen and Stafford have further refined the 5' and 3' boundaries so that the enhancer may be considered restricted to 275 base pairs within the larger fragment. We have dissected this region into a number of smaller fragments and assayed each of these by means of the gel binding assay for the location of protein binding sites.

A restriction map of the relevant region of the κ enhancer is shown in FIG. 13a. The black boxes represent sequences identified by Church et al. to be homologous to the putative protein binding domains detected in the μ enhancer in vivo.

Figure 13B:
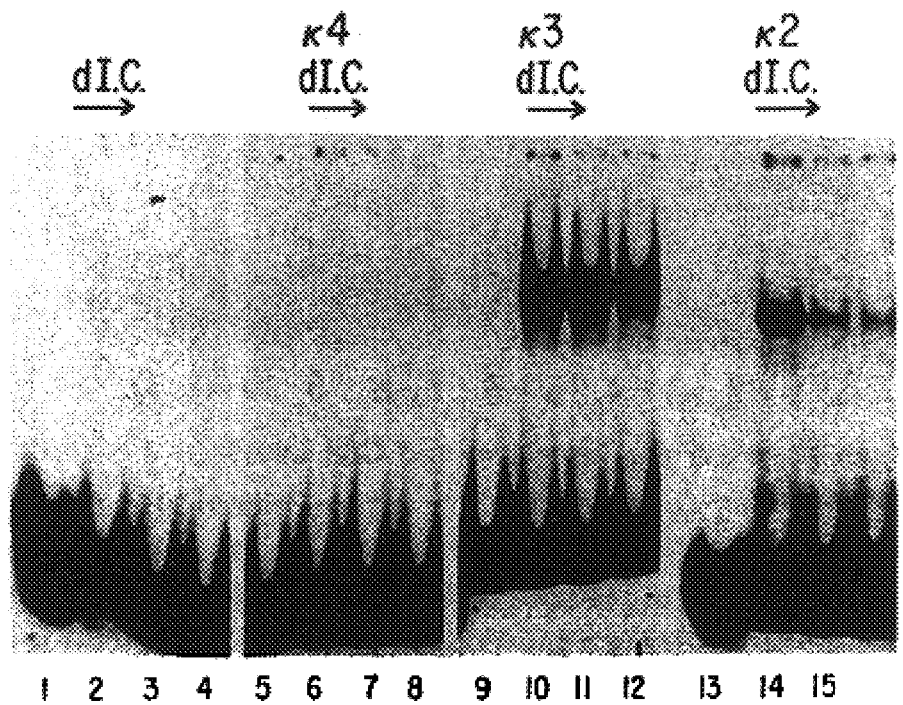
FIG. 13B shows an autoradiograph of binding assays with κ-enhancer fragments.

Fragments generated by cutting with Dde and HaeIII (κ1, κ2, κ3, κ4 and κ5; FIG. 13a) were assayed for binding in the presence of increasing amounts of poly(dI-dC)-(dI-dc) as a non-specific carrier, κ4 and κ5 appeared to be obviously negative (FIG. 13b, lanes 1–8) while κ3 and κ2 appeared to be positive (FIG. 13b, lanes 10–12 and 14–16). Preliminary results show that the internal fragment does not contain any specific binding sites either. The nucleoprotein complex bands generated with 0.5–1 ηg of radiolabelled probe could be detected even in the presence of 3 μg of the carrier (lanes 12, 16, FIG. 13b).

Figure 13C:
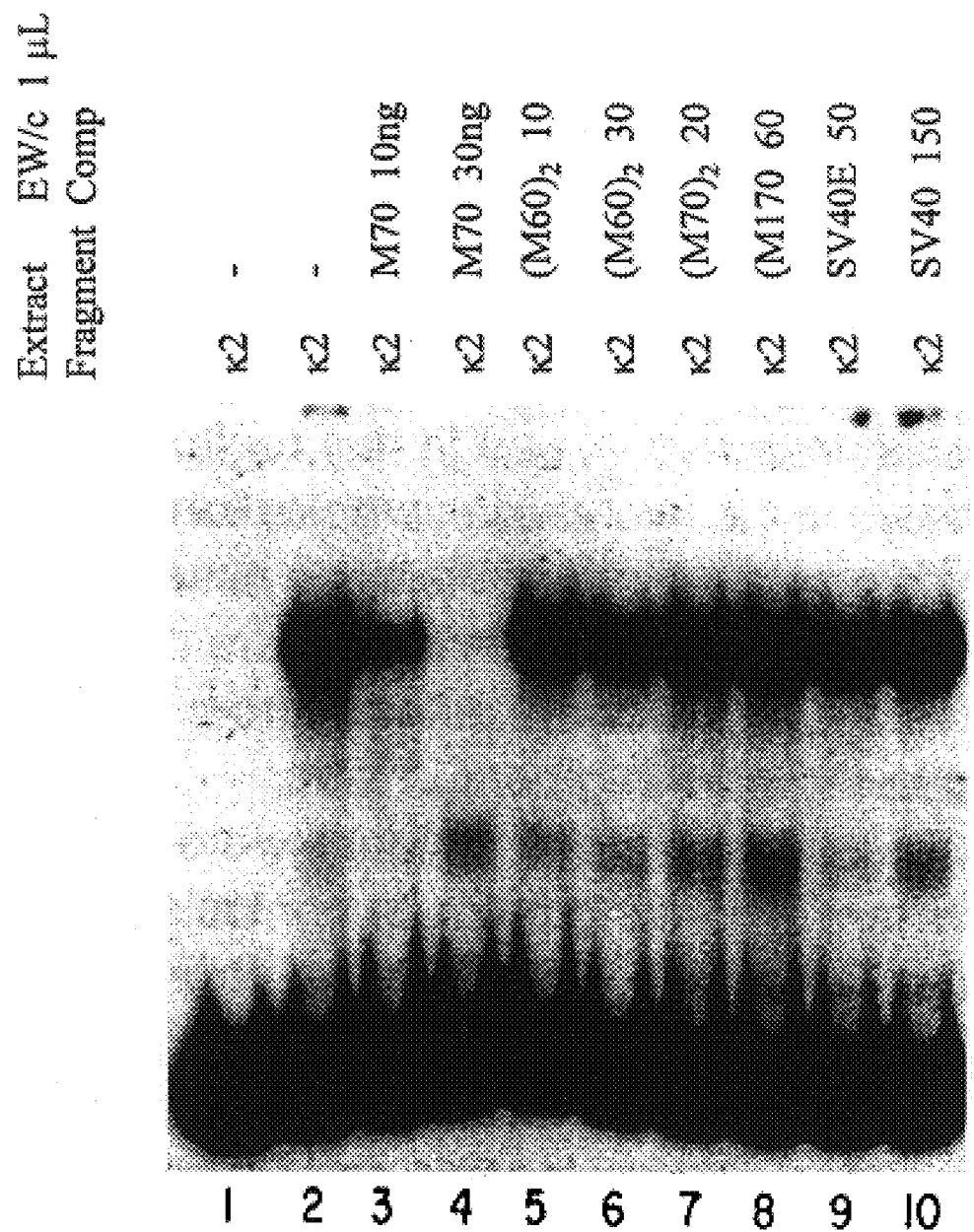
FIGS. 13C and 13D show an autoradiograph of competition assays with κ-enhancer fragments.
Figure 13D:
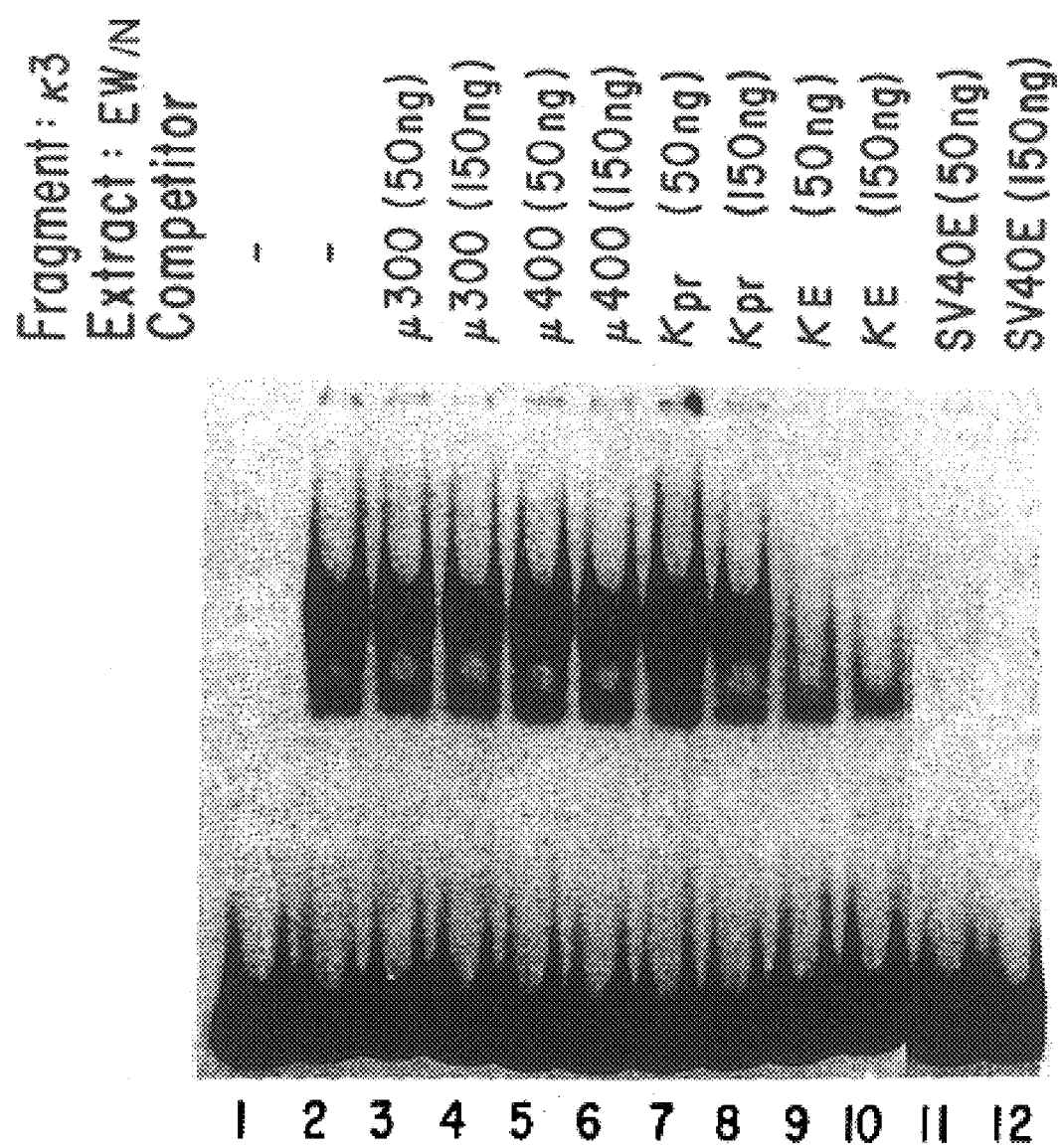

To show that the bands detected represented a specific interaction between a protein and DNA, we carried out competition experiments (FIG. 13c and 13d). The competition pattern for κ2 was strikingly similar to what had been earlier observed with the μ70 fragment; relatively large amounts of u400, the Moloney leukemia virus enhancer, the SV40 enhancer or the κ promoter (containing the conserved octa) to κ2 did not compete for binding, although u300 and the κ enhancer did. Since κ2 contains a putative E box identified by sequence comparison (as does μ70) we competed its binding with smaller fragments from μ300 (FIG. 5C). The complex is specifically competed away by the addition of unlabelled μ70 during the incubation (compare lanes 3 and 4 with lane 2), but not by μ60 (lanes 5,6), μ170 (lanes 7,8) or the SV40 enhancer (lanes 9,10). Further, the protein that binds to this sequence co-fractionates with the μ70 binding activity through two sequential chromatographic steps (Heparin agarose and DEAE Sepharose). Thus, we conclude that the same sequence specific protein binds to both the fragments μ70 and κ2 and that there is at least one common protein interacting with both the μ and the κ enhancers.

The κ3 complex (indicated by the arrowhead, FIG. 13d) failed to be competed away by μ300 (compare lanes 3 and 4 with lane 2), μ400 (compare lanes 5 and 6 with lane 2) as a κ promoter containing fragment (compare lanes 7 and 8 with lane 2). However, the complex was specifically competed away with both the complete κ enhancer (lanes 9,10) and the SV40 enhancer (lanes 11,12). The band below the major κ3 complex was seen at variable intensities in different experiments and failed to compete even with the complete κ enhancer in this experiment and has not been further investigated at this stage. The observation that the SV40 enhancer specifically competes for binding of this factor is not altogether surprising, since this fragment and the SV40 enhancer share an identical stretch of 11 nucleotides.

Figure 14:
FIG. 14 shows location of NK-κB binding by methylation interference experiments.

The binding site of this factor on the κ3 fragment was localized by methylation interference experiments. In two different extracts, methylation at three of a stretch of 4 residues within this sequence completely abolished binding (FIG. 14, compare lane 1 [complex] and 2 [free]; and lanes 3 [complex] and 4 [free]). This stretch of G's forms a part of the conserved region (GGGGACTTTCC) between the SV40 enhancer and κ3. Thus, the binding site was localized towards one end of the κ3 fragment. The results also served to explain the specific competition observed earlier with the SV40 Enhancer. Interestingly, deletion mapping of the κ enhancer shows that sequences within the κ3 fragment are extremely important for enhancer function.

Figure 15A:
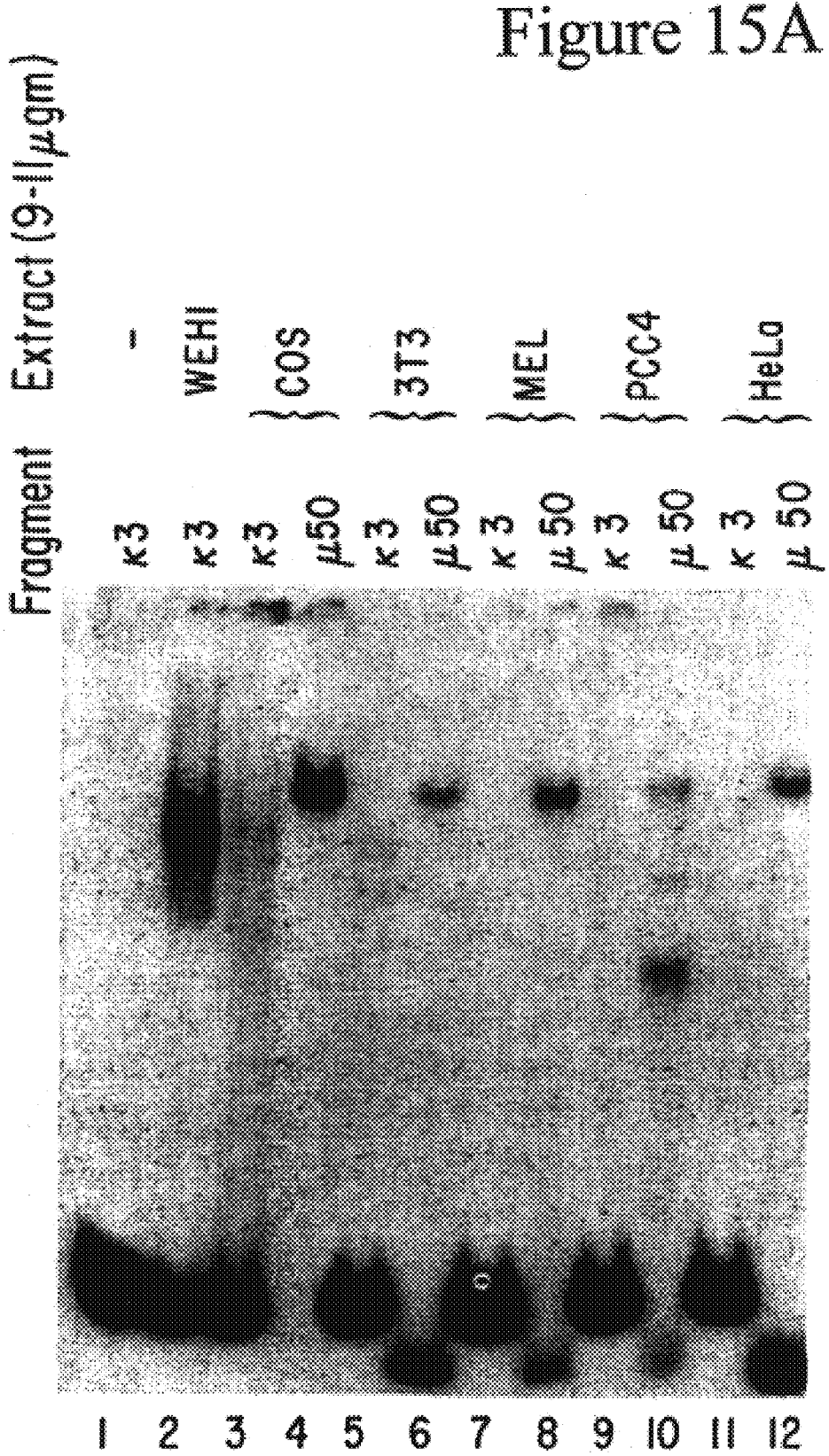
FIG. 15A shows binding analysis of NK-κB in various lymphoid and non-lymphoid cells.

The tissue range of this factor was examined by carrying out binding analysis with κ3 in extracts from a variety of cell lines. Nucleoprotein complex formation κ3 was detected in a mouse B cell line (FIG. 15a, lane 2), but not in 5 other non-B cell lines (FIG. 15a, odd numbered lanes from 5–11). Even numbered lanes show that the ubiquitous factor detected by $\mu$50 is present in all these cell lines and served as a positive control for the experiment. The factor κ3 therefore appears to be restricted to expression to B lymphoid cells.

Figure 15B:
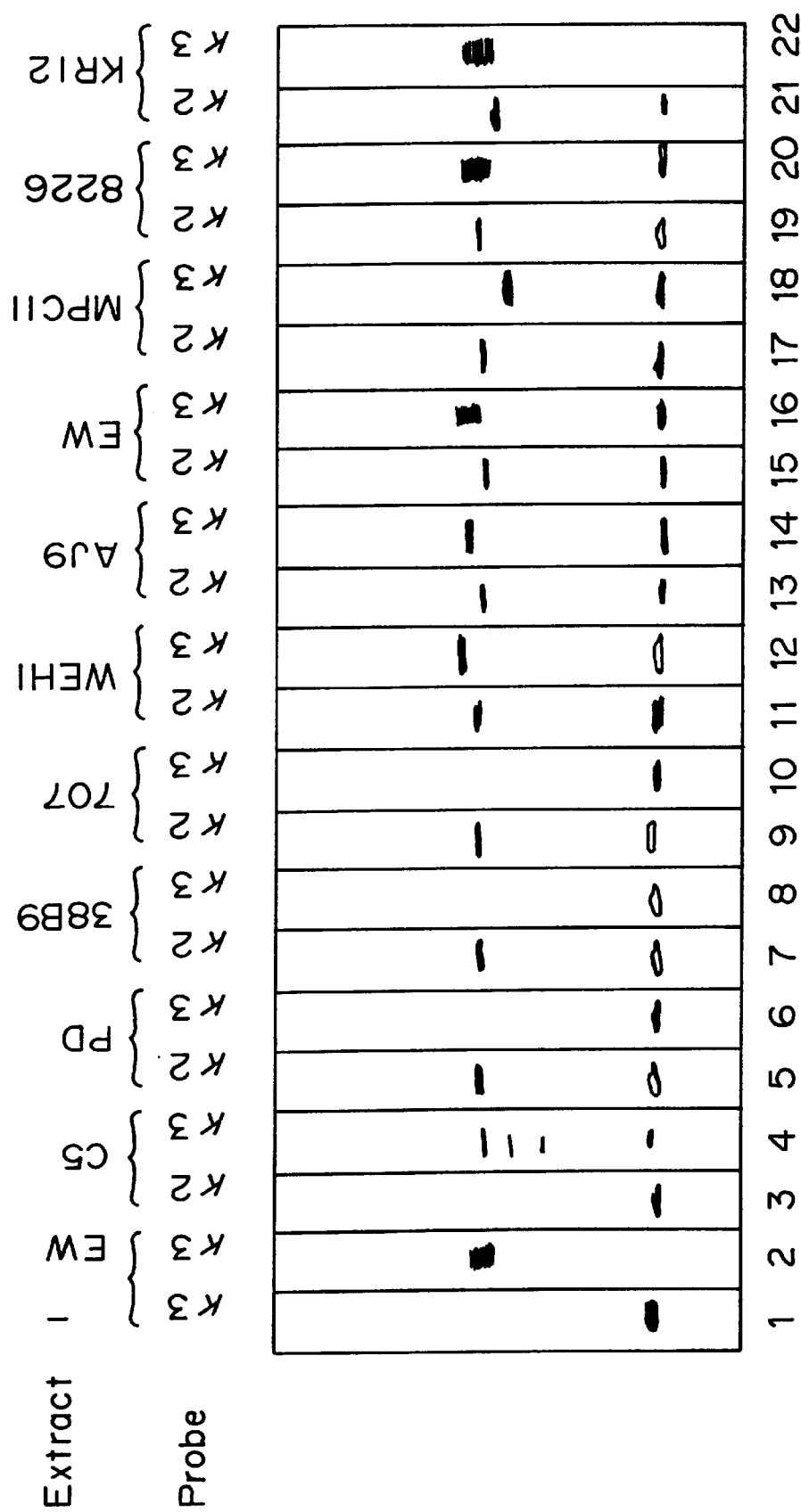
FIG. 15B shows the binding analysis of NK-κB in cells at various stages of B-cell differentiation.

We then examined extracts made from cells at various stages of B cell differentiation (FIG. 15B). Interestingly κ3 binding protein can be detected in the Abelson murine leukemia virus transformed pre-B cell line PD, in two mouse B cell lines (WEH1231 and AJ9, FIG. 15B, lanes 12,14), one human B cell line (EW, FIG. 15B, lane 16) mouse myeloma line (MPC22, FIG. 15B, lane 18) and 2 human myelomas (KR12 and 8226, FIG. 15B, lanes 20,22). However, it does not appear to be present in a pre-preB cell line (C5, FIG. 15B, lane 4) and in mouse pre-B cell lines (HATFL, 38B9, 70Z, FIG. 15B, lanes 6,8,10). Thus, this factor appears to be not only tissue-specific, i.e., limited to cells of the B lymphoid lineage, but also stage-specific within that lineage. In the series of extracts examined, the presence of this factor bears a striking correlation with κ expression.

The results with the Kappa enhancer can be summarized follows: Dissection of the κ enhancer enabled detection of two distinct binding proteins with this DNA. One of these proteins appears to be ubiquitous and interacts with the u heavy chain enhancer as well. The second protein appears to be highly expressed in a stage-specific manner within the B cell lineage and can be detected only in those cell lines where the endogenous κ gene is active. There does not appear to be a binding site for this factor in the heavy chain enhancer, although there is one in the SV40 enhancer. Examples 6 and 7 describe cloning of two transcriptional factors: NF-κB and IgNFB.

Example 6

Cloning of Putative NF-κB

Experimental Procedures
λgt11-EBNA-1 Recombinant

A HinfI-AhaII DNA fragment of the EBV genome (coordinates 107,946–109,843), that contains the EBNA-1 open reading frame, was subcloned using BamHI linkers into the BamHI site of pUC13 (pUCEBNA-1). The λgt11-EBNA-1 recombinant was constructed by inserting the 600 bp SamI-BamHI fragment of pUCEBNA-1 (EBV coordinates 109,298-109,893) into the EcoRI site of λgt11 using an EcoRI linker (GGAATTCC). A phage recombinant containing the EBNA-1 insert in the sense orientation was isolated by immunoscreening with EBNA-1 antibodies (see below). In this recombinant, the carboxy-terminal region of EBNA-1 (191 amino acids) is fused in frame to the carboxy-terminus of β-galactosidase.
λgt11 cDNA Expression Library The human B cells (RPMI 4265) cDNA library constructed in the expression vector λgt11 was purchased from Clontech Laboratories, Inc. The library contains approximately 9×10$^5$ independent clones and has an average insert size of 1.2 kb.

E. Coli Strains

The standard pair of λgt11 host strains, Y1090 and Y1098, were employed. The former was used to screen λgt11 recombinants and the latter to generate λlysogens for the analysis of β-gal fusion proteins.
Plasmids The plasmid pUCoriP1 was constructed by subcloning the EcoRI-NcoI fragment from the oriP region of the EBV genome into the SmaI site of pUC13. This fragment contains 20 high affinity binding sites for EBNA-1. pUCoriP2 was derived from pUCoriP1 by subcloning of an oriP fragment (EcoRI-BstXI) of the latter into the SmaI site of pUC13. pUCoriP2 contains 11 high affinity binding sites for EBNA-1. pUCORIλ2 was made by insertion of a synthetic binding site for the bacteriophase λO protein (AAATCCCCTAAAACGAGGGATAAA) into the SmaI site of pUC13. The complementary oligonucleotides were a gift of R. MacMacken. pUCMHCI and pUCmhcI were constructed by insertion of the following oligonucleotides:
GATCCGGCTGGGGATTCCCCATCT GATCCGGCT-
   GcGGATTCCCaATCT
GCCGACCCCTAAGGGGTAGACTAG GCCGACgC-
   CTAAGGGtTAGACTAG
into the BamHI site of pUC13. The wild type sequence is a binding site for H2TF1 and NF-κB. pUCOCTA is a similarly constructed pUC18 derivative that contains a synthetic recognition site (ATGCAAAT) for the mammalian octamer binding protein(s). The plasmids p190H2KCAT (−190 to +5) and p138H2KCAT (−138 to +5) contain 5'-deletions of the H-2K$^b$ gene promoter fused to the coding sequence for chloramphenicol acetyl transferase. All plasmid DNAs were purified by an alkaline lysis protocol followed by two bandings in CsCl-EtBr gradients.
Binding Site Probes Competitor DNAs The MHC, mhc1, ori and OCTA probes were generated by digesting the corresponding pUC plasmids with EcoRI and HindIII. The resulting products were end-labeled with [α-$^{32}$P]dATP using the large fragment of E. coli DNA polymerase I. dCTP, dGTP and dTTP were included in these reactions so as to fill in the ends of the restriction fragments. The labeled fragments were separated by native polyacrylamide gel electrophoresis. The binding site fragments (60–75 bp) were eluted from the gel and purified by ELUTIP™ (Schleicher and Schuell) chromatography. Using high specific activity [α-$^{32}$P]dATP (5000 Ci/mmol), typical labelings yielded DNA probes with specific activities of 2–4×10$^7$ cpm/pmol.

To generate the oriP probe, pUCoriP2 was digested with EcoRI and HindIII, and the oriP fragment (~400 bp) isolated by low melt agarose gel electrophoresis. This DNA fragment was then digested with HpaII and the products labeled as detailed above. The smaller of the two HpaII fragments (~90 bp) was isolated for use as the oriP probe. The MHCg probe was prepared by digesting p190H2KCAT with XhoI was labeling as before. The labeled DNA was then digested with HincII and the 90 bp probe fragment purified as before. This probe contains sequence from −190 to −100 of the upstream region of the H–2K$^b$ gene.

The Δ6MHCg (−190 to +270) and Δ11MHCg (−138 to +270) competitor DNAs were prepared by digesting the plasmids, p190H2KCAT and p138H2KCAT, with XhoI and EcoRI. The H2KCAT fragments were isolated by low melt agarose gel electrophoresis.

RESULTS

Specific Detection of a λ Recombinant Expressing EBNA-1

Figures 16, 17:
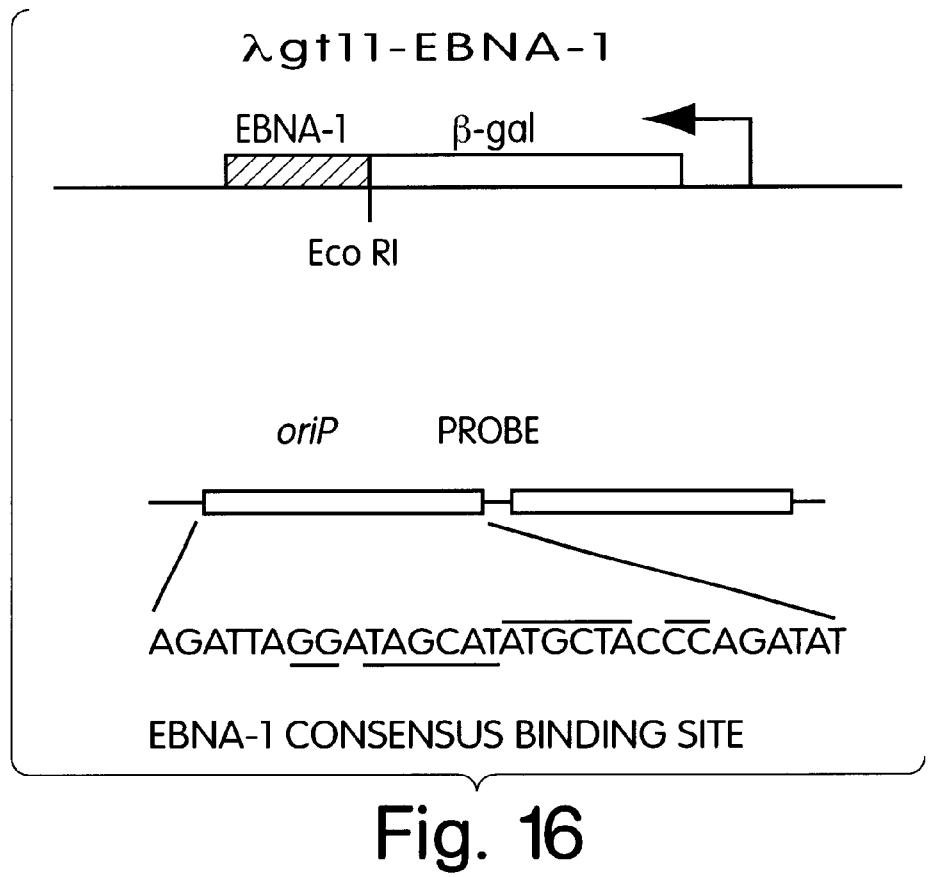
FIG. 16 shows the λgt11-EBNA-1 (λEB) recombinant and the oriP probe.
FIG. 17 shows the sequence of the DNA probe used to screen for an H2TF1 and NF-κB expression.

A model system was used to test the notion that a recombinant clone encoding a sequence-specific DNA binding protein could be specifically detected with a recognition site probe. The Epstein-Barr virus nuclear antigen (EBNA-1) was selected as the model protein. EBNA-1 is required for maintenance of the EBV genome as an autonomously replicating plasmid in human cell lines. It is also a transactivator of viral gene expression. The carboxy-terminal region of EBNA-1 (191 amino acids) has been expressed in E. coli as a fusion protein and shown to encode a sequence-specific DNA binding domain. The fusion protein binds to multiple high affinity sites at three different loci in the EBV genome. Two of these loci consitute a cis-acting element required for maintenance of the plasmid state (oriP). In the λgt11-EBNA-1 (λEB) recombinant the carboxy-terminal region of ENBA-1 was fused in frame to the carboxy-terminus of β-galactosidase (FIG. 16). A lysogen harboring the λEB phage conditionally expressed a βgal-EBNA-1 fusion protein of expected size (approximately M.W. 145,000) that accumulated to a level of about 1%. The DNA binding activity of the fusion protein was assayed with a segment of oriP DNA that contained two high affinity sites for EBNA-1 (FIG. 16). Extracts of λgt11 and λEB-lysogens were incubated with labeled oriP DNA and the products resolved by native polyacrylamide gel electrophoresis. With the λEB extract, a distinct set of protein-DNA complexes was observed. The formation of these complexes was specifically competed by an excess of plasmid DNA containing EBNA-1 binding sites. Thus, the β-gal-ENBA-1 fusion protein has the expected sequence-specific DNA binding activity.

To establish conditions for detection of EB plaques with probes of oriP DNA, protein replica filters were generated from platings of the phage. These filters were screened with a variety of protocols using oriP or control DNAs. Under a defined set of conditions (see Experimental Procedures), λEB plaques can be specifically detected using radiolabeled oriP DNA. The control probe (ori) contains a high affinity binding site for the bacteriophage λO protein. The specific array of spots generated by the oriP probe corresponded to plaques on the master plate as well as to spots that reacted with antiserum to β-gal on the replica filter. Furthermore, in a similar experiment the oriP probe did not detect control λgt11 plaques. From a series of such experiments the following conclusions were drawn; (i) the specific detection of λEB plaques requires a DNA probe with at least one binding site for EBNA-1 (a duplex 30-mer with a consensus binding site sequence gave a signal comparable to a probe containing two or more binding sites), (ii) DNA probes longer than 150 bp yield higher non-specific signals, (iii) the addition of an excess of non-specific competitor DNA [poly(dI-dC)-poly(dI-dC)] to the binding solution reduces the non-specific signal, and (iv) both specific and non-specific interactions of the DNA probe with proteins on the replica filter are reversible. In view of this latter point and the fact that non-specific interactions typically have much shorter half-lives than the specific interactions, sequence-specific binding proteins can be detected after a suitable wash time.

Given the ability to specifically detect λEB plaques with oriP DNA, reconstruction experiments were carried out to test the sensitivity of the screen. In these experiments the λEB phage was mixed with an excess of control λgt11 recombinants. Relica filters generated from such mixed platings were screened initially with oriP DNA and subsequently with antibodies to EBNA-1. In an experiment where approximately 5,000 phage were plated, with λEB being present at a frequency of $10^{-2}$, a identical number of positives (approximately 50) were detected with both oriP DNA and antibody probes. In fact, the two patterns are superimposable. Furthermore the signal to noise ratio of the DNA binding site probe was better than that of the antibody probe. Thus it is possible to screen for the λEB phage with an oriP DNA probe.

Screening for Mammalian Clones Encoding Sequence-Specific DNA Binding Proteins

A λgt11 library of cDNAs prepared with mRNA from human B cells was screened using the conditions developed with λEB. The DNA probe used in the screen contained a regulatory element from a mouse MHC class I gene (H-2K$^b$. FIG. 17). This sequence (MHC) was synthesized and cloned into the pUC polylinker. The mammalian transcriptional regulatory factors H2TF1 and NF-κB bind with high affinity to this MHC element. In a screen of $2.5 \times 10^5$ recombinants, two positive phage, designated λh3 and λh4, were isolated. In an autoradiogram of a filter from the primary screen, a positive spot resulted in the isolation of λh3. Partially purified λh3 and λh4 phage were challenged with other DNA probes to determine if their detection was specific for the MHC probe. λh3 and λh4 were not detected by the ori probe. These phage were also not detected by labeled pUC polylinker DNA or by a related probe (OCTA) containing a recognition site for the immunoglobulin octamer binding protein(s). A mutant MHC binding site probe (mhcl FIG. 17) was used to more stringently test the sequence-specificity of the presumptive fusion proteins. The mhcl probe did not detect either λh3 or λh4 plaques. These data strongly suggested that the two phage express proteins that bind specifically to the MHC element.

Characterization of the DNA Binding Proteins Encoded by λh3 and λh4

Direct evidence that the β-gal fusion proteins encoded by λh3 and λh4 are responsible for the sequence-specific DNA binding activities was obtained by screening Western blots with DNA and antibody probes. Lysogens of λgt11, λh3 and λh4 were isolated and induced to generate high levels of their respective β-gal proteins. Western blots of proteins from induced lysogens were prepared and the immobilized proteins were briefly denatured with 6M guanidine and then allowed to renature (see Experimental Procedures above). This treatment increased the recovery of active molecules. Two equivalent transfers were initially probed with either the MHC element or the OCTA control DNA. A set of four bands specific to the MHC probe and the λh3, λh4 tracks was observed. The two largest species of this set are labeled P1 and P2. The same transfers were then probed with antibodies to β-gal. A pair of novel fusion protein bands was observed with each of the two recombinant lysogens. These bands corresponded to the species P1 and P2 detected with the MHC probe. This shows that λh3 and λh4 encode β-gal fusion proteins which bind specifically to the MHC element DNA. The two phage may be identical since they encode the same size fusion proteins. P1 (approximate m.w. 160,000) probably represents the full length fusion protein whereas P2 is a presumptive proteolytic cleavage product. Since the β-gal portion of this fusion polypeptide has a molecular weight of approximately 120,000, the cDNA encoded portion must have a molecular weight of 40,000.

A gel electrophoresis DNA binding assay was used to confirm the sequence specificity of the λh3 and λh4 fusion proteins as well as to better define their recognition properties. Extracts derived from the λgt11, λh3 and λh4 lysogens were assayed, with the MHC probe. A novel DNA binding activity was detected specifically in extracts of the λh3 and λh4 lysogens. This activity was IPTG inducible indicating that it was a product of the lacZ fusion gene. A competition assay indicated that the activity represented a sequence-specific DNA binding protein. Two 5' deletion mutants of the H–2K$^b$ genomic sequence was used as competitor DNAs. The segment 6MHCg extends to 190 nucleotides upstream of the transcription start site and contains the MHC sequence element. The segment Δ11MHCg, on the other hand, only contains 138 nucleotides of sequences upstream of the initiation site and therefore lacks the MHC element. Increasing amounts of Δ6MHCg specifically competed for the binding of the λh3 fusion protein to the MHC element oligonucleotide probe while the control Δ11MHCg did not compete. It should be noted that the sequences flanking the MHC element in the probe used for the initial screening, the cloned oligonucleotide, are totally difference from the sequences flanking the same element in the genomic probe, Δ6MHCg. Therefore, the fusion protein appears to exclusively recognize the common MHC element. This was confirmed by a direct DNA binding assay with a genomic sequence probe (MHCg) containing the MHC element. Both the oligonucleotide (MHC) and genomic (MHCg) probes gave rise to similarly migrating complexes. Furthermore, a double base substitution mutant (mhc1, FIG. 17) abolished recognition by the fusion protein. The mutant sequence contains a transverion in each half of the symmetric MHC element. These changes destroy the symmetry of the element and abolish binding by either H2TF1 or NF-κB.

The immunoglobulin κ chain gene enhancer contains a binding site ( EN) for NF-κB. This site is related in sequence to the MHC element but is recognized by H2TF1 with a 10 to 20 fold lower affinity (FIG. 17). A mutant κ enhancer (κEN) has been characterized both in vivo and in vitro. This mutant sequence has no B cell specific enhancer activity and is not bound by NF-κB. The mutant contains clustered base substitutions and an insertion of a base pair in one of the two symmetric half sites (FIG. 17). The binding of the λh3 fusion protein to the wild type κ-element and the mutant version was tested. The κEN probe generated a complex with a mobility similar to those obtained with the MHC probes. No specific complex was formed with the mutant κ-enhancer DNA. Experiments in which the MHC and κ-enhancer binding sites were tested for competition with binding of the MHC probe showed that the fusion protein bind with 2–5 fold higher affinity to the MHC site (data not shown). The κEN site differs, in part, from the MHC site by the substitution of two adenine residues for guanine residues. As discussed below, these guanine residues are probably contacted by the fusion.

The contacts of the fusion protein with the MHC element were probed chemically by modification of the DNA with dimethylsulfate. After partial methylation at purine residues, the modified probe was used in the gel electrophoresis DNA binding assay. Free (F) and bound (B) probe DNA was recovered, subjected to chemical cleavage at methylated interference experiment. On both the coding and non-coding strands strong interference was detected when any of central guanine residues of each putative half site was modified at the N-7 position in the major groove. Weaker interference was observed when the external guanine residue in either putative half site was similarly modified. Thus the fusion protein appears to symmetrically contact the MHC element in a manner similar to both H2TF1 and NF-κB.

Hybridization Analysis with the cDNA Segment of the Recombinant Phage

The recombinant phage λh3 and λh4 contain cross-hybridizing and equivalent size (approximately 1 b) cDNA segments. The inserts also have indistinguishable restriction maps and therefore appear to be identical. Southern blot hybridization confirmed that these cDNA segments are homologous to sequences in the human genome. The patterns of hybridization to restriction digests of genomic DNAs of various human cell lines are identical. Furthermore, the fact that restriction digests with Bam HI (no site in cDNA) and Pst I (on site in cDNA) both generate two prominent bands suggests that the cDNAs are derived from a single copy gene. A similarly simple hybridization pattern is observed on probing the mouse and rat genomes.

The expression of the human gene was analyzed by Northern blot hybridization. A single, large transcript (approximately 10 kb) was observed with polyA(+) RNA from both B (X50-7) and non-B human cells (HeLa). This transcript is moderately abundant in both cell types. Since the cDNA library was constructed by oligo dT priming, we were probably fortunate to obtain the coding region for the DNA binding domain within the 1 kb segments of the recombinant phage. However, this only illustrates the power of the screening strategy for the isolation of clones encoding sequence-specific DNA binding domains.

Discussion

A novel strategy is disclosed for the molecular cloning of genes encoding sequence-specific DNA binding proteins. This strategy can be used to isolate genes specifying mammalian transcription regulatory proteins. An important step in this approach is the detection of bacterial clones synthesizing significant levels of a sequence-specific DNA binding protein by screening with a labeled DNA binding site probe. This approach is similar to that previously developed for the isolation of genes by screening recombinant libraries with antibodies specific for a given protein. In fact, the phage expression vector, λgt11, developed previously for immunological screening can be in this approach.

The feasibility of the strategy was established by the specific detection of a phage recombinant, λEB, encoding a β-gal-EBNA-1 fusion polypeptide with oriP DNA. Conditions have also been developed for the selective detection of E. coli colonies expressing high levels of EBNA-1 or the bacteriophage λO protein with their respective binding site DNAs. In these cases, a plasmid expression vector was employed. Using the conditions developed with λEB, we have screened phage cDNA libraries with three difference DNA probes. Screening with a probe containing the H2TF1 site in the MHC class I gene H-2K$^b$ led to the isolation of two identical clones that specify a putative transcription regulatory protein (properties discussed below). In similar screens with two other DNA probes, positive recombinant phage were also isolated at a frequency of approximately 1/100,000. However, the DNA binding proteins encoded by these phage do not appear to recognize specific sequence elements but rather to bind sequence nonspecifically to either single strand or double strand DNA. Although detection of these types of clones represented a troublesome background in this study their isolation suggests that recombinants encoding different types of DNA binding proteins can be detected by such functional screens of expression libraries. In future screens for recombinants encoding site-specific DNA binding proteins, the detection of these other types of clones might be selectively suppressed by inclusion of a non-specific competitor DNA that is structurally more similar to the probe than poly(dI-dC)-poly(dI-dC).

The prospects for the isolation of other cDNAs encoding sequence-specific binding protein by this strategy can be assessed by examining the three assumptions on which it is based: (i) functional expression of the DNA binding domain of the desired protein in E. coli, (ii) a strong and selective interaction of the binding domain and its recognition site, and (iii) high level expression of the DNA binding domain. A number of eukaryotic sequence-specific DNA binding proteins have been functionally expressed in E. coli. These include the proteins GAL4, GCN4 and MAT 2 of yeast, ftz of Drosophila, TFIIIA of Xenopus, E2 of the bovine papilloma virus and EBNA-1 of the Epstein Barr Virus. In most cases, the functional DNA binding domain is contained within a short tract of amino acids. Thus, it is reasonable to expect the functional expression in E. coli of the sequence-specific DNA binding domain of most eukaryotic regulatory proteins. The equilibrium association constants of site-specific DNA binding proteins range over many orders of magnitude ($10^7$–$0^{12}$ M). The following analysis suggests that successful screening may be restricted to proteins with relatively high binding constants. If a regulatory protein has an association constant of $10^{10}$ M, then under the screening conditions (the DNA probe is in excess and at a concentration of (~$10^{10}$ M) approximately half of the active molecules on the filter will have DNA bound. Since the filters are subsequently washed for 30 minutes, the fraction of protein-DNA complexes that remain will be determined by their dissociation rate constant. Assuming a diffusion limited association rate constant of $10^7$ $M^{-1}$ $S^{-1}$, the dissociation rate constant will be $10^{-3}$ $S^{-1}$. Such a protein-DNA complex will have a half life of approximately 15 minutes. Thus only a quarter of the protein-DNA complexes will survive the 30 minute wash. For a binding constant of $10^9$ M, only about a tenth of the active protein molecules will have DNA bound and much of this signal will be lost, since the half-life of these complexes is approximately 1.5 minutes. Isolation of recombinants encoding proteins with binding constants of $10^9$ or lower may be possible given that the binding of probe to less than 1% of the total fusion protein within a plaque can be detected. The sensitivity of the current methodology for low affinity proteins could be significantly enhanced by covalent stabilization of protein-DNA complexes. This might be accomplished by procedures such as UV-irradiation of pre-formed complexes. Since the binding constants of regulatory proteins are dependent on ionic strength, temperature and pH, these factors might also be manipulated to enhance detection.

The successful detection of λEB and λh3 recombinants with DNA binding site probes required high level expression of their fusion proteins. In both cases, the fusion proteins accumulate, after induction, to a level of about 1% of total cellular protein. This level of recombinant protein expression is typical of λgt11 as well as other E. coli vectors. The strategy of cloning a gene on the basis of specific detection of its functional recombinant product in E. coli has considered potential. Indeed, while our work was in progress, this approach was used by other to isolate clones encoding a peptide acetyltransferase and a calmodulin-binding protein. Direct screening of clones encoding recombinant protein products has also been used to isolate ras GTP-binding mutants.

The λh3 recombinant expresses a β-gal fusion protein that recognizes related transcription control elements in the enhancers of the MHC class I and immunoglobulin κ-chain genes (see FIG. 17 for sequences). This protein also binds a similar element in the SV40 enhancer 72 bp repeat. Furthermore, there are two putative binding sites in the long terminal repeat (LRT) of the HIV genome (FIG. 17). One of these is identical to the site in the SV40 enhancer and therefore should be recognized by the fusion protein. The existence of a clone such as λh3 was anticipated since it had previously been shown that a common factor, NF-κB, binds to the three related elements in the enhancer, the SV40 72 bp repeat an the HIV-LTR. Interestingly, these three binding sites are more closely related to one another than they are to the MHC site (FIG. 17). The former set can be viewed as variants of the MHC site which exhibits perfect two-fold symmetry. It should be noted that the pUC polylinker contains the sequence, CGGGGA, which is a variant of one of the symmetric halves (TGGGGA) of the MHC element. The fusion protein does not bind with detectably affinity to the pUC polylinker. Thus, a high affinity interacter appears to require both symmetric halves.

Even though the above control elements represent quite similar sequences, they function in very different regulatory capacities. The MHC element is a component of an enhancer that functions in a variety of cell types that express MHC class I genes. The κ-element, on the other hand, is a component of a cell-type specific enhancer that functions only in B cells. The activity of this enhancer is induced in pre-B cells upon their differentiation into mature B lymphocytes. Such differentiation, in vitro, is accompanied by transcriptional activation of the chain gene. The κ-element appears to dictate the B cell specificity of the κ-enhancer. The different modes of functioning of the MHC and κ-elements are correlated with the properties of their corresponding recognition factors, H2TF1 and NF-κB. H2TF1 activity is detected in a variety of differentiated cell types and this protein appears to stimulate MHC class I gene transcription approximately 10-fold. On the other hand, NF-κB activity is detected only a mature B cells. In addition, this activity is induced during differentiation of pre-B cells to mature lymphocytes. Finally, NF-κB activity is also induced by phorbol ester treatment of non-B cell lines (HeLa, Jurkat). In the case of Jurkat cells, a T4$^+$ human T cell line, NF-κB appears to stimulate the transcriptional activity of the HIV-LTR. It should be noted that induction of NF-κB in non-B cells does not require new protein synthesis. Thus the protein for NF-κB must exist in cells before induction and the activated by a post-translational modification.

The DNA binding properties of the fusion protein encoded by the recombinant λh3 overlap those of H2TF1 or NF-κB. Mutants of the MHC and κ-elements that are not recognized by H2TF1 or NF-κB are also not bound by the fusion protein. The recombinant protein binds the MHC element DNA with 2–5 fold higher affinity than the κ-element. In this regard, the fusion protein has relative affinities intermediate between those of H2TF1 and NF-κB. H2TF1 binds the MHC element with 10- to 20-fold higher affinity than the κ-element while NF-κB recognizes both elements with roughly equivalent affinity. This intermediate relationship is also observed in the comparison of the methylation interference patterns of the three DNA binding activities. Methylation of any of the central six guanine residues in the MHC site strongly interfers with the binding of all three activities. Methylation at either of the two external guanines partially interferes with recognition by the fusion protein. In contrast, H2TF1 binding is strongly suppressed upon methylation of either of these residues while NF-κB binding shows little perturbation upon this modification. This analysis of the three DNA binding activities is limited by the use of cell extracts and not purified proteins. Furthermore, the properties of a recombinant protein may be different from those of its native counterpart. Thus, it is not possible to be definitively relate the protein encoded by λh3 to either H2TF1 or NF-κB.

Antibodies raised against the λh3 fusion protein will be useful in clarifying its structural relationship with H2TF1 and NF-κB. A definitive relationship will emerge from a comparison of the deduced amino acid sequence of the cDNA and the protein sequences of H2TF1 and NF-κB. It should be noted that in terms of protein expression, both H2TF1 and NF-κB are present in a wide variety of mammalian cells. Furthermore, the DNA binding specificities of these two factors are remarkably similar. These facts as well as the observations that the cDNA in λh3 hybridizes to a single copy gene and to a single mRNA in both B and non-B cells suggest that all three binding activities may be products of the same gene. This hypothesis would imply that H2TF1 and NF-κB represent alternative modifications of a common protein.

Example 7

Cloning of the IgNFB Gene

Methods

DNA Sequencing

DNA sequencing was performed on double stranded plasmid DNA templates according to the Sanger dideoxynucleotide protocol as modified by United States Biochemical for use with bacteriophage T7 DNA polymerase (Sequenase). The entire sequence was confirmed by sequencing the opposite strand and in the GC-rich regions by sequencing according to Maxam and Gilbert (*Methods Enzymol.,* 65: 449–560, (1980).

Plasmid Constructions cDNA's were subcloned from λgt11 to pGEM4 (Promega), and these plasmids were used for DNA sequence analysis and in vitro transcription. Plasmid pBS-ATG was kindly provided by H. Singh and K. LeClair and was constructed by ligating a 27 bp long oligonucleotide containing an ATG codon surrounded by the appropriate boxes for efficient initiation, TGCACACCATGGCCATCGATATCGATC, into the Pstl site of pBS-/+Bluescropt plasmid (Stratagene). The expression vector pBS-ATG-oct-2 depicted in FIG. 19A was designed for transcription and translation in vitro and was constructed by cleaving pBS-ATG with SmaI and ligating the blunt-ended EcoRI 1.2 kb cDNA fragment from plasmid 3-1 (position 655 to 1710 in FIG. 18A).

In Vitro Transcription/Translation

In vitro transcription and translation reactoins were performed as recommended by the manufacturer (Promega).

DNA Binding Assay

The EcoRI/HindIII 50 bp fragment containing the wild type octanucleotide sequence ATGCAAAT in the BamHI site of pUC18 polylinker was $^{32}$P-labeled (50,000 cpm/ng) and 1 ng DNA probe was incubated with 1 µl of the reacted/unreacted reticulocyte lysate. The bindign reactions were incubated at room temperature for 30 min. and contained 10 mM Tris HCl pH7.5, 50 mM NaCl, 1 mM DTT, 1 mM EDTA pH8, 5% glycerol, 25 µl/ml sonicated denatured calf thymus DNA in 2.5 µl/ml sonicated native calf thymus DNA as nonspecific competitors. The complexes were resolved by electrophoresis in 4% polyacrylamide gel (acrylamide: bisacrylamide weight ratio of 20:1), containing as buffer 25 mM Tris HCl pH8.5, 190 mM glycine, 1 mM EDTA buffer as previouly described (Singh et al., Nature 319: 154–158 (1986)).

Purification of NF-A2

NF-A2 was purified to >90% homogeneity from nuclear extracts derived from the human Burkett's lymphoma cell line, BJAB. Purification was accomplished by sequential fractionation on Zetachrom QAE discs (Cuno Inc.), heparin sepharose (Pharmacia), ssDNA cellulose (Pharmacia), and on a DNA affinity column which contained an immobilized double straded (ds) segment containing the octanucleotide sequence. In vitro translated, $^{35}$S-methionine-labeled, oct-2 protein was purified by chromatography on dsDNA cellulose followed by affinity chromatography on the octanucleotide DNA affinity column.

Tryptic Digestions of NF-A1 and oct-2 Protein

Tryptic digests were performed at room temperature in a buffer consisting of 20 mM Hepes,KOH, pH 7.9, 20% glycerol, 0.5 M KCl, 0.2 mM EDTA, 0.5 MM DTT. Aliquots of purified NF-A2 (~250 ng) or of affinity purified oct-2 protein (90,000 cpm) were incubated with varying amounts of trypsin (affinity incubated with varying amounts of trypsin (affinity purified trypsin was a gift of Dan Doering). After 60 minutes, reactions were terminated by the addition of 2.5 volumes of SDS-PAGE sample buffer and were boiled for 5 minutes. The tryptic digestes were resolved on 10% polyacrylamide gels. Tryptic fragments of NF-A2 were visualized by silver-staining. Tryptic fragments of $^{35}$S-methionine labeled oct-2 protein were visualized by autoradiography after treatment of the gel with En$^3$hance (Dupont).

To clone the gene encoding the lymphoid-specific octamer binding protein, IgNF-B (NF-A2), a randomly primed, non-size selected cDNA library in λgt11 was constructed using cytoplasmic poly (A)-containing mRNA from a human B cell lymphoma cell line, BJAB. We had previously observed that this cell line contained a particularly large amount of NF-A2 when 28 lymphoid cell lines were surveyed. By randomly priming the cDNA synthesis we expected to obtain recombinant phage encoding the octamer motif binding domain even if that domain was encoded by the 5' end of a long mRNA. The randomly primed cDNA library in λgt11 was generated by standard methods (Gubler, U. and Hoffman, B. J., Genes 25:263–269 (1983)). Random hexamers (Pharmacia) were used to prime the first strand cDNA synthesis. The unamplified library contained 500,000 recombinants. This library was screened by the method described above using a radiolabelled DNA probe consisting of four copies, in direct orientation, of a 26 bp oligonucleotide derived from the Vk41 promoter. The probe was constructed by cloning four copies of the oligonucleotide in direct orientation into the BamH1 site of the pUC polylinker and radiolabelling the 112 bp Sma1-Xba1 fragment. The library was screened with the tetramer probe (at 1×10$^6$ cpm/ml) as described above for the cloning of NF-κB with the following modification. Previous screens using poly(dI-dC)-poly(dI-dC) as the nonspecific competitor DNA yielded recombinant phage encoding single stranded DNA binding proteins. The signal from these phage but not phage encoding sequence-specific DNA binding proteins could be efficiently competed with denatured calf thymas DNA (5 µg/ml) and therefore this nonspecific competitor was substituted for poly(dI-dC)-poly(dI-dC) in all subsequent screens.

From a primary screen of 450,000 phage plaques, three plaques were isolated which bound this tetramer probe. Two of these phage, phage 3 and phage 5, were found to give plaques that bound specifically to the tetramer probe in that they did not bind DNA probes which lacked the octamer motif. These two phage bound probes containing one copy of the κ promoter octamer motif with a much lower affinity than they bound the tetramer probe. Even when four-fold more monomer probe was used then tetramer probe, the tetramer probe still gave a greater signal suggesting that the better binding of the tetramer probe was not merely a result of increasing the molar concentration of binding sites in the screen. Certainly in the case of phage 5, which showed dramatically better binding to the tetramer probe, it seems most likely that the tetramer probe was able to bind simultaneously to multiple phage fusion proteins on the filter. This multipoint attachment would be expected to dramatically decrease the dissociation rate and thus, increase the avidity of the interaction. Genes encoding DNA binding proteins with relatively low binding affinities could be cloned by screening λgt11 expression libraries with such multimer probes.

The specificity of the DNA binding proteins encoded by the recombinant phage was investigated by preparing extracts of induced phage lysogens. Lysogen extracts from both phages bound to the tetramer probe in a mobility shift assay whereas lysogen extracts from non-recombinant λgt11 showed no binding to this probe. Only the phage 3 extract bound strongly to the κ promoter probe. Because the inserts of phage 3 and phage 5 (1.2 kb and 0.45 kb in size, respectively) were found to cross-hybridize by Southern blotting analysis, phage 3 was chosen for further analysis.

Phage 3 encoded an octamer binding protein as demonstrated by a competition mobility shift assay in which the lysogen extract was bound to the κ promoter probe in the presence of competing unlabelled DNA fragments containing either the wild type or mutant octamer motifs. Phage lysogen extracts were prepared as described above for NK-κB cloning. The extracts were assayed in a mobility shift assay as described above using the octamer-containing PvuII-EcoR1 fragment from pSPIgVk as the radiolabelled probe. Binding reactions were carried out in the absence or presence of 24 ηg of cold competitor DNA containing no octamer motif, the wild type octamer motif or mutant octamer motifs as described.

The wild type octamer motif competed efficiently for binding but the octamer motifs containing point mutations either did not compete or competed less well than the wild type motif. In fact, the two mutants which showed slight competition for the binding of the lysogen protein, TCATTT CCAT and ATATTGCAT, were the only mutants which somewhat competed the binding of NF-A1 and NF-A2 in a WEHI 231 nuclear extract.

The phage-encoded octamer binding protein was further compared to NF-A1 and NF-A2 using a methylation interference footprinting assay. Methylation interference was performed as described using the non-coding strand of the octamer-containing PvuII-EcoR1 fragment of pSPIgVk as radiolabelled probes. The probes were partially methylated and used in preparative mobility shift DNA binding assays. DNA present in the bound bands (NF-A1 and NF-A2 bands from a nuclear extract from the BJAB cell line (or phage 3 lysogen extract bound band or free bands) was isolated, cleaved at the modified purine residues and subjected to denaturing polyacrylamide gel electrophoresis. The footprint obtained using the lysogen extract was centered over the octamer motif and was very similar to the footprints of NF-A1 and NF-A2 from a BJAB nuclear extract and from a WEHI 231 nuclear extract (see above). Minor differences were seen between the footprints of the lysogen and nuclear extract proteins which could reflect changes in affinity and/or specificty of DNA binding as a result of fusion of the insert-encoded octamer binding protein with β-galactosidase. Alternatively, the phage insert could encode an octamer binding protein distinct from NF-A1 and NF-A2.

The phage-encoded β-galactosidase fusion protein was directly shown to be the octamer binding protein in the phage lysogen extracts. Phage lysogen extracts were subjected to SDS polyacrylamide gel electrophoresis and transferred to nitrocellulose filters. After a denaturation/renaturation procedure (Celenza, J. L. and Carlson, M. *Science* 233:1175–1180 (1986)), the filters were probed with either the radiolabelled octamer-containing tetramer probe (OCTA) or a non-specific DNA probe (pUC). The OCTA probe specifically bound to the β-galactosidase fusion proteins of phage 3 and phage 5 to a much greater extent than the pUC probe, thus formally showing that the octamer binding activity was encoded by the phage inserts. The apparent molecular weights of the largest fusion proteins of phage 3 and phage 5 lysogens are consistent with the entire phage inserts contributing coding sequences to the fusion proteins. Prototeolysis was presumed to account for the heterogeneity in apparent molecular weight of the fusion proteins.

The insert of phage 3, which defines what we term the OCT-2 gene, was used in a Southern blot analysis to probe human and mouse genomic DNA digested with several restriction enzymes. Restriction enzyme digested genomic DNA was electrophoresed through a 1% agarose gel and transferred to Zetabind (CUNO Laboratory, Inc.) by standard techniques (Maniatis, T., Frisch, E. F. and Sambrook, J. Molecular Cloning. A Laboratory Manual. Cold Spring Harbor Laboratory Press, NY. (1982)). The phage 3 insert was radiolabelled by randomly primed synthesis using hexanucleotides (Pharmacia). Following standard prehybridization high-stringency hybridization (Maniatis, supra.) with the OCT-2 probe the filters were washed with 0.2×SSC, 0.1% SDS or 2×SSC, 0.1% SDS.

One or two bands were observed in each restriction enzyme digest which is consistent with OCT-2 being a single genetic locus. No rearrangements or amplifications of the gene were observed in a survey of 8 lymphoid and non-lymphoid cells lines including BJAB. The strength of the signal on the mouse Southern blot at high stringency suggested that the gene is highly conserved between human and mouse.

The oct-2 cDNA segment (1.2 kb) of phage 3 was used to identify additional overlapping recombiants in the same library. One of these phage (pass-3) contained a 1.8 kb DNA insert. Sequence analysis of the cDNA segment in the original λgt11 phage (3-1) revealed a long open reading frame (ORF) which was ended with multiple nonsense codons at its 3' terminus. Sequence analysis of the pass-3 segment yielded an identical sequence through the open reading frame but an abrupt transition to a novel sequence occurred at the C-terminue (FIG. 18B; see below). The N terminus of the open reading frame in both of these cDNA segments was not represented in the cDNA inserts. Additional recombinats from the λgt11 library were identified by screening with a probe from the N0terminal portion of the pass-3 segment. This resulted in the isolation of a 0.75 kb cDNA segment (pass-5.5) whose sequence extended the N-terminal portion o the previously identified open readign frame. In this cDNA segment, a nonsense codon is found 36 pb upstream of the first AUG in the open frame. The sequence context of this AUG conforms well to that expected for an initiation codon (Kozak, Cell 44: 283–292 (1986)). Two other AUG codons occur at positions 6 and 13 in the reading frame. Each of these also has an excellent context for initiation. The N terminus of the protein has been arbitrarily assigned to the 5'-most AUG codon. The cDNA sequence extends 66 bases 5' from this position but the total length of the 5' untranslated region has not been determined.

The sequences of pass-5.5, pass-3 and 3-1 were combined to form an open reading frame encoding a protein of 466 amino acids in length as shown in FIG. 46 amino acids in length as shown in FIG. 18. FIG. 18 shows the amino-acid sequence of oct-2 protein depicted in plain capital letters.

cDNA-clone pass-5.5 spans from position 1 (5' end) to position 750 (3' end). cDNA clone pass-3 5' end and 3' end are respectively at position 92 in FIG. 18a and 1847 in FIG. 18b. cDNA clone 3-1 starts at position 650 and ends at position 1710. The nucleotide sequence shown in panel A was reconstructed by merging the DNA sequences from clone pass-5.5 from position 1 to 100, from clone pass-3 from 100 to 660 and from clone 3-1 from position 660–1710. Extensive nucleotide sequence overlaps were available to allow unequivocal merges. Sequence of protein encoded by the long overlappingopen reading frame (LORF, 277aa) is shown in italic letters. Wavy arrows delimit the glutamine (Q)-rich, glutamic and aspartic (E/D)-rich and glycine (G)-rich regions, respectively. Solid arrows delimt the helix-turn-helix motif. Boxed leucine (L) residues are spaced exactly by seven residues. Vertical arrow indicates the position where the nucleotide sequence diverges with that shown in panel B. Stars indicate stop codons.

FIG. 18b shows the nucleotide sequence of the 3' terminus and redicted amino acid sequence of the C-terminus derived from clone pass-3. The code is the same as in A and the vertical arrow denote sthe divergence point.

Figure 18C:
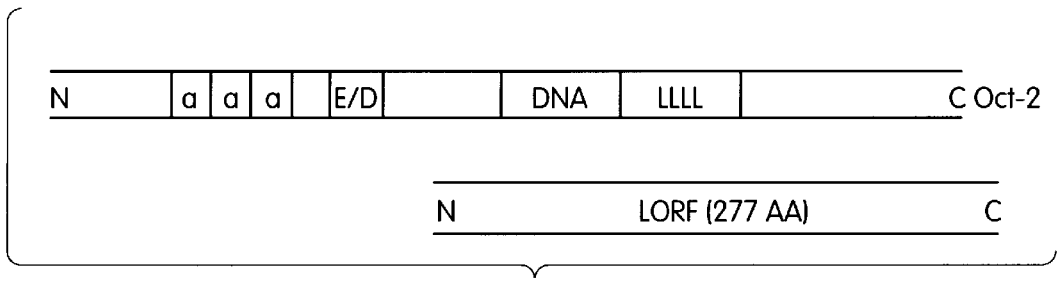
FIG. 18C is a schematic representation of the amino acid sequence deduced from oct-2 gene derived cDNA.

FIG. 18c is a schematic representation of the amino acid sequence deduced from oct-2 gene derived cDNA. The code is as in panel A. The DNA binding domain is depicted as DNA and the region containing the four regularly spaced L residues is boxed-in. LORF stands for long open reading frame, N stands for N-terminus and C for COOH-terminus.

Data presented below suggests that this ORF encodes one form of NF-A2 (oct-2). The amino acid sequence of oct-2 has several interesting features (FIG. 18C). It contains three glutamine (Q) rich blocks (ranging from 50% of Q content) in the N-terminal part of the polypeptide, beginning at nucleotide positions 376, 448 and 502, and a comparably acidic region [aspartic (E) or glutamic (D) amino acids] between positions 648 and 678. Clusters of Q resideus as well as E or D amino acids have been described previously in many transcription factors. Such acidic regions in other factors have been shown to be important in activation of transcription (Gill and Ptashne, Cell 51: 121–126 1987; Hope et al., Nature 333: 635–640 (1988)).

The region of oct-2 responsible for sequence-specific DNA binding, depicted "DNA", is discussed below. Downstream of this position is a series of four leucine residues separated by exactly seven amino acids (position 1227 to 1293 in FIG. 18A). A similar configuration of leucine residues in the transcription factor C/EBP has been suggested to form an amphipathic α-helical structure where the leucine residues are arranged along one side of the helix. Two such helices are throught to interact by a "leucine zipper" mechanism generating a dimeric protein (Handschultz et al., Science 240: 1759–1764 (1988); Landschultz et al., Genes & Development 2: 786–800 (1988)).

Consistent with this sugestion, no helix disrupting proline residue is present in oct-2 in the 22 amino acid tract defined by the four leucines. However, unlike the first example of a leucine zipper", protein C/EBP, the potential α-helical region in oct-2 does not possess a high density of paried charged residues which could stabilize the structure. Also, unlike the C/EBP protein, which binds DNA specifically as a homodimer probably by pairing through the "leucine zipper", the oct-2 protein appears to specifically bind DNA as a monomer. It is interesting to speculate that the "leucine zipper" region of oct-2 might be important for interaction with other proteins as there is no obvious reason to restrict the binding of such a structure to self-recognition.

Searches for sequence similarities in the GenBank library revealed that a region of the oct-2 protein from position 952 to 1135 was distantly related to a family of proteins containing homeoboxes. The 60-residue homeobox domain is highly conserved among 16 examples in different Drosophila genes (Gehering, Science 236: 1245–1252 (1987)). This level of conservation extends to homeobox sequences found in vertebrates and worms. Among this total family, nine of the 60 residues are invariant. The oct-2 protein only contains six of these nine residues and four of these six sites are clustered in the sub-region of the homeobox thought to be related to the helix-turn-helix structure (see FIG. 20). As shown in FIG. 20A, a 60 amino acid region of oct-2 contains 30% identity with the prototype homeobox sequence in the Antennapedia (Antp) protein.

FIG. 20 shows the amino acid sequence alignment of the DNA binding domain of oct-2 factor with homeoboxes from Antp. (Schneuwly et al., EMBO J. 5: 733–739 (1986), cut (Blochlinger, Nature 333:629–635 (1988), en (Poole et al., Cell 40: 37–43 (1985), proteins (boxed-in amino acid sequences from the S. cerevisae proteins Matal (Miller, EMBO J. #: 1061–1065 (1984), Matα2 (Astell et al., Cell 53: 339–340 (1988) and C. elegans protein mec-3 (Way and Chalfie, Cell 54: 5–16 (1988). THe nine invariant residues in canonical homeobox sequences Atnp, cut, and en are listed below the boxed-in amino acid sequences and shown in bold print if present in the amino acid sequences. The stars indicate the hydrophobic amino acids that are critical for the protein to maintain the helix-turn-helix structure (Pabo and Sauer, 1984). Solid arrows delimit the helix-turn-helix domain.

That the homeobox specifies a sequence-specific DNA binding domain is most strongly argued by its homology with the DNA binding domain of the yeast mating regulatory protein, MATα (Astell et al., Cell 27: 15–23 (1981); Scott and Weiner, Proc. Natl. Acad. Sci. USA 81: 4115–4119 (1984)), which also has homology through this. subregion of the homeobox but does not conserve the other invariant of the homeobox. The homologous regions in these proteins can be folded into a helix-turn-helix-structure similar to that first identified in the structural analysis of phage λ repressor (for a review see Pabo and Sauer, Ann. Rev. Biochem. 53: 293–321 (1984)). A prediction of the most probable secondary structure of oct-2 also revealed a helix-turn-helix structure between the residues of isoleucine (position 1041) and cysteine (position 1090). Thus, by analogy, we propose that this region of oct-2 specifies the sequence-specified binding of the protein.

As mentioned above, sequences at the 3' end of the pass-3 recombinant abruptly diverged from that of recombinant 3-1 at the position (1463) of its termination codon (see vertical arrow in FIG. 18B). The substituted sequences in the second recombinant, pass-3, extended the reading frame of the oct-2 realted protein by an additional 16 amino acids. To rule out a possible artifactual sequence generated by the insertion of fragment during construction of the cDNA library, total polyA(+) RNA from the BJAB cell line was analyzed by Northern blot with a DNA fragment from the novel 3' terminal portion of the pass-3 cDNA. This specific probe hydribized only to the two fastest migrating mRNAs of the total family of six mRNAs which were detected by hybridization with the total 3-1 cDNA. A similar specific probe was excised from the 3' terminus of the 3-1 cDNA. In contracts, this probe only hybridized to the two slowest migrating mRNAs in the total family of six. This suggests that the two cDNA segments correspond to different populations of oct-2 mRNAs.

The proteins encoded by the two cDNAs should only differ at their C terminus by 16 amino acids or approximately 1.5 kD. In vitro transcription/translation of subfragments of the 3-1 and pass-3 recombinants was used to confirm this prediction. Fragments representing the 3' portions of 3-1 and pass-3 were subcloned into the expression plasmid PBS-ATG. The resulting plasmid DNAs were transcribed with bacteriophage T7 RNApolymerase and were subsequently translated in a reticulocyte system. The resulting polypeptides migrated with the mobilities of the anticipated molecular weights 34 kD and 32.4 kD. the polypeptide from the pass-3 cDNA was 1.6 kD larger than that from the 3-1 cDNA. Both polypeptides specifically bound a probe containing the octanucleotide sequence, producing a readily detectable DNA-protein complex in the gel mobility assay. This suggests that the oct-2 gene is expressed as a family of polypeptides in B-cells.

The potential significance of these additional 16 amino acids is unclear. These two cDNAs almost certainly differ by alternative splicing patterns of RNA transcribed from the oct-2 gene. Furthermore, it is likely that the oct-2 gene encodes a more diverse set of mRNAs than those partially defined by these two cDNAs. Six different length mRNAs are produced at significant levels in mature B cells. The relative amounts of these mRNAs vary between pre-B, B and plasma cell lines (Staudt et al., Science 241: 577–580 (1988)). This population could reflect variations in sites of initiation of transcription and of polyadenylation as well as further differences in splicing patterns.

The expression of the OCT-2 gene was assessed by Northern blot analysis of mRNA from 13 lymphoid and non-lymphoid cell lines and was found to be predominantly restricted to lymphoid cells. Poly(A)-containing mRNA (3 μg, or 20 μg) or total mRNA (30 μg) was analyzed from the following cell lines. 1. NIH 3T3: mouse fibroblast; 2. 38B9: mouse pre-B cell line; 3. WEHI 231: mouse mature B cell line; 4. A431: human epidermal cell line; 5. U1242: human glioma cell line; 6. RB27: human retinoblastoma cell line; 7. Jurkat: human T cell line; 8. Namalwa: human mature B cell line; 9. BJAB: human mature B cell line (poly(A)-containing mRNA); 10. BJAB (total mRNA); 11. Hut78: human T cell line; 12. HeLa: human cervical carcinoma cell line; 13. EL4: mouse T cell line. mRNA was electrophoresed through a formaldehyde-containing 1.3% agarose gel and transferred to a nitrocellulose filter by standard techniques (Maniatis, supra.). Following prehybridization, the filter was hybridized at high stringency with radio-labelled OCT-2 probe (above). The filter was washed in 0.2×SSC, 0.1% SDS at 68° C. and autoradiographed with an intensifying screen at −70° C. for 24 hrs. The filter was stripped by washing in 50% formamide, 10 mM Tris (pH 7.4), 1 mM EDTA at 68° C. for 1 hr. and rehybridized with a radiolabelled rat alpha tubulin cDNA probe (Lemischka, I. R., Farmer, S., Racaniello, V. R. and Sharp, P. A., *J. Mol. Biol.* 151:101–120 (1981)) to control for the amount of mRNA loaded.

All five B lymphoma cell lines, including pre-B and mature B cell lines, and one of three T lymphoma cell lines expressed a family of 6 transcripts. Of the five non-lymphoid cell lines tested, only a glioma cell line, U1242( ), showed detectable expression of this gene. Even at low stringency we were unable to detect a transcript present in all cell lines which might correspond to NF-A1. The various transcripts, estimated to be 7.2 kb, 5.8 kb, 5.4 kb, 3.7 kb, 3.1 kb and 1.2 kb long, were expressed in somewhat varying amounts relative to each other in the positive cell lines. Whether these transcripts represent alternative mRNA splicing or highly specific mRNA degradation remains to be determined. In this regard, it is interesting that highly purified preparations of NF-A2 consist of three or more major polypeptides with distinct molecular weights which could be the products of the family of transcripts that we have observed.

Previously, we and others (See above and Gerster, T. et al. *EMBO J.* 6:1323–1330 (1987); Landolfi et al., *Nature* 323:548–51 (1986)) showed that the octamer binding protein NF-A2 varied considerably in expression among lymphoid cell lines. We therefore investigated the relationship between levels of expression of the OCT-2 gene and levels of NF-A2 as judged by mobility shift analysis. BJAB, the cell line which expressed the largest amount of transcript showed the largest amount of NF-A2. Nuclear extracts from the pre-B cell lines, 38B9 and 70Z, showed very little NF-A2 and, correspondingly, expressed very little transcript (more poly(A)-containing mRNA from these two cell lines was loaded to see a readily detectable signal). Of the three T lymphoma cell lines tested, Jurkat, HUT78 and EL4, EL4 was the only line that showed large amounts of NF-A2. Although NF-A2 was previously believed to be expressed only in lymphoid cells we found that nuclear extracts from the glioma cell line that expressed the OCT-2 gene contained an octamer binding protein which comigrated with NF-A2 in the mobility shift assay. Nuclear extracts from two glioma cell lines which were negative for OCT-2 expression did not contain NF-A2. We have at present no explanation for this apparent non-lymphoid expression of NF-A2 and the cloned octamer binding protein gene. Previously, we had shown that NF-A2 but not NF-A1 was inducible in pre-B cells by treatment of the cells with bacterial lipopolysaccharide (LPS) and that this induction required new protein synthesis. Therefore, we prepared poly(A)-containing mRNA from the pre-B cell line 70Z/3 before and after LPS treatment and observed that LPS increased the expression of the OCT-2 gene. Thus, in every instance, the expression of the OCT-2 gene correlated with the presence of NF-A2 and is thus a good candidate for the gene which encodes NF-A2.

Further evidence that the oct-2 gene encodes NF-A2 was discovered when the NF-A2 factor was purified from nuclear extracts of BJAB cells by conventional chromatography followed by multiple passages over an affinity column containing immobilized oligomers of the octanucleotide sequence. The purified NF-A2 consisted of three bands, as resolved by gel electrophoresis: a major band and two minor bands with deduced molecular weights of 61 kD and 58 kD, and 63 kD, respectively. A cDNA (pass-3) for the oct-2 gene was inserted into the polylinker of the pGEM (Promega) expression vector. Translation of RNA transcribed from the SP6 promoter-pass-3 cDNA construct yielded a major polypeptide from the purified sample of NF-A2.

The nobility of a DNA-protein complex in the gel assay is primarily determined by the molecular weight of the protein. Complexes were generated with the affinity purified NF-A2 and the products of translational in vitro of RNA from the oct-2 cDNA. These complexes co-migrated during electrophoresis in a native gel, again suggesting that the oct-2 cDNA encodes the major form of the NF-A2 factor.

The affinity purified NF-A2 protein and the polypeptide translated in vitro from the oct-2 cDNA were also compared by partial tryptic digestion. Samples from different digestion times of NF-A2 were resolved by denaturing gel electrophoresis and detected by staining with silver. The mobility of these partial fragments was compared with those observed after a parallel analysis of $^{35}$S-methionine labelled polypeptide from transcription/translation of the pass-3 cDNA in vitro. The two samples generated a similar set of digestion fragments, again suggesting that NF-A2 is encoded by the oct-2 cDNA.

Figure 19:
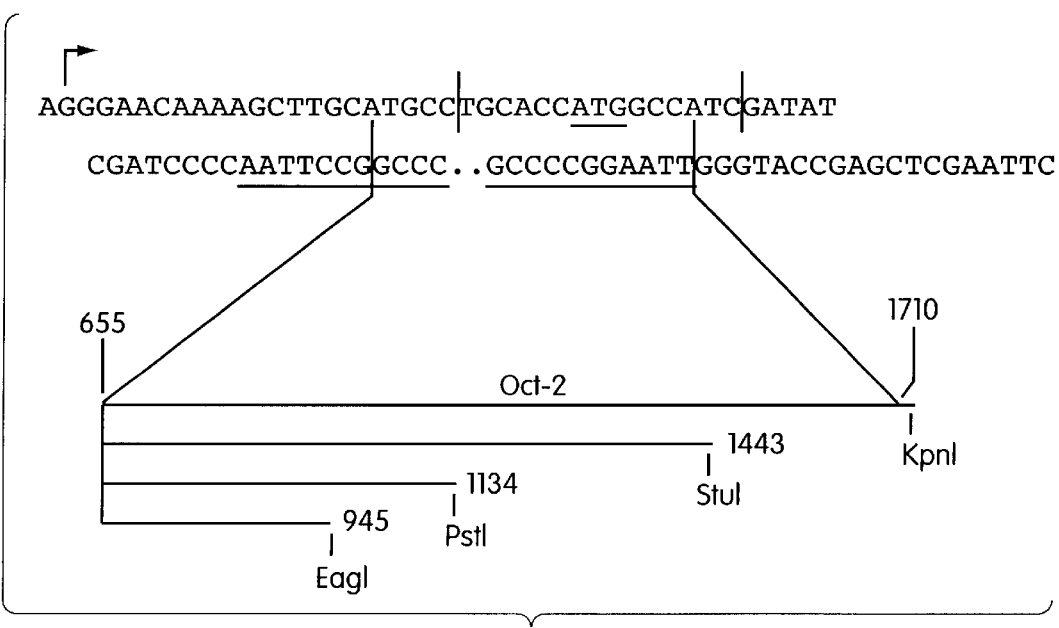
FIG. 19 is a schematic representation of expression plasmid pBS-ATG-oct-2.

Protein sequence comparisons suggested that the DNA binding domain of oct-2 was specified by a domain (positions 952–1135) that was distantly related to both the helix-turn-helix structure of bacterial repressors and the homeobox-proteins. To directly test this analogy a fragment of the cDNA encompassing this region (655 to 1710) was inserted into the expression vector pBS-ATG so that RNA could be transcribed from the truncated templates by bacteriophage T7 RNA polymerase as indicated in FIG. 19A. The polypeptides translated in vitro from these RNAs were tested for specific DNA binding by addition of the total translation mix to the DNA-protein gel assay. Polypeptides produced from RNAs terminating at positions 1710 (Kpnl), 1443 (Stul), and 1134 (Pstl) specifically bound the octa-nucleotide containing probe, while the polypeptide translated from RNA terminating at the 945 (Eagl) site did not specifically bind. The region containing the helix-turn-helix portion of oct-2 is deleted in the latter protein. Since the truncated polypeptide encoded by RNA from the latter template was efficiently translated in the reticulocyte reaction, this suggests that the specific binding of the oct-2-protein requires the helix-turn-helix structure.

Two distinct but similarly migrating protein-DNA complexes were detected in the sample generated by translation of RNA from the Stul cleaved template. Faint slower migrating complex comigrated with the complex generated with templates cleaved by Kpnl. The presence of the two complexes in the Stul-sample is due to a partial digestion of the plasmid DNA. The slower migrating complex is probably produced by protein terminated at the stop codon TAA located at position 1465. The faster migrating complex probably results from molecules terminated at the Stul site. This interpretation was supported by the resolution of two $^{35}$S-labeled polypeptides during gel electrophoresis of the Stul sample and confirms the position of the termination codon of oct-2.

Many sequence-specific binding proteins have an oligomeric structure. For example, bacterial repressor proteins typically bind sites with two-fold rotational symmetry by forming a similarly symmetric dimer (Ptashne, Cell Press and Blackwell Scientific Publications, (1986)). It should be noted that the binding site sequence of the oct-2 protein is not symmetric but oligomeric proteins could bind to non-symmetric sites. Other examples of oligomerization of sequence-specific bindingprotiens are the GCN4 protein of yeast (Hope and Struhl, EMBO J. 6: 2781–2784, (1987)) and the C/EBP protein of mammals. In the latter case, an α-helical region with an amphipathic character reflected in the spacing of four leucine residues by exactly seven residues is thought to be responsible for dimer formation (Landschultz et al., Science 240: 1759–1764 (1988); Landschultz et al., Genes & Development 2: 786–800 (1988)). A convenient assay for detection of dimerization of sequence-specific bindignproteins is to co-translate RNAs encoding two different size forms of the protein and test whether protein-DNA complexes with novel mobilities are generated (Hope and Struhl, EMBO J. 6: 2781–2784 (1987). If only monomers bind to the probe, the sample containing the co-translated polypeptides will generated only the complexes detected when either RNA is assayed singularly. This was the case with combinations of different length RNAs transcribed from the oct-2 cDNA segment. Specifically, cotranslation of RNAs from templates cleaved at Stul (1443) and Pstl (1134) did not generate novel bands in the gel mobility assay. Thus, on the basis of this negative evidence, we suggest that a single molecule of the oct-2 protein is present in the resolved DNA-protein complexes and that it does not require dimerization for binding to DNA.

Anti-sera raised in rabbits against a bacterial fusion protein containing oct-2 encoded sequence (prepared employing the vestor pRIT2T (Pharmacia)) recognized the native oct-2 protein in metabolically labeled ($^{35}$S-methionine) human B cells.

The molecular cloning of a lymphoid-restricted octamer binding protein gene demonstrates that higher eukaryotes have adopted a strategy of genetic diversification of transcriptional regulatory proteins which bind a common regulatory motif. The ubiquitous and lymphoid-specific octamer binding proteins have indistinguishable DNA binding sites, yet appear to have distinct functional properties (Staudt, L. M. et al, Nature 323:640–643 (1986)). Structure-function analysis of cloned yeast transcription factors (Petkovich, M. et al., Cell 330:444–450 (1987); Giguere, V. et al., Nature 330:625–629 (1987)) and steroid receptor related transcription regulatory activity of a transcription factor often reside in discrete protein domains that can be experimentally interchanged. The present findings suggest that similar diversification of function among proteins which bind the octamer motif has occurred during evolution. The octamer motif has been shown to be necessary and sufficient for lymphoid-specific promoter activity (Fletcher, C. et al., Cell 51:773–781 (1987)) and NF-A2 has been shown to function as a transcription factor using octamer containing templates in vitro (Scheidereit, C. et al., Cell 51:783–793 (1987)). A further understanding of the lymphoid-specific activity of immunoglobulin promoters may now come from an understanding of the mechanisms underlying the lymphoid-specific expression of the OCT-2 gene.

Example 8

Induction of NF-KB in Cells in which it is not Constitutively Present

The following work demonstrates that NF-KB is inducible in cells other than B (lymphoid) cells. As described below, it has now been shown that NF-KB is inducible in pre-B cells and in non-lymphoid cells. In particular, the following work demonstrates that: 1) NF-kB factor can be induced by the mitogen lipopolysaccharide (LPS) in two cell lines representing a pre-B stage of B cell differentiation; 2) induction of this factor involves a post-translational modification of a pre-existing protein because the induction takes place even in the presence of translational inhibitors like cycloheximide and anisomycin; 3) these translational inhibitors by themselves can at least partially induce NF-kB and synergize with LPS to produce a superinduction; 4) an active phorbol ester like PMA can induce NF-kB by itself, and the time-course of this activation is more rapid than that with LPS alone; and 5) it is also possible to induce this factor in cell lines other than those having a pre-B phenotype by means of an appropriate stimulus (e.g., in the human T cell line, Jurkat, by PHA and/or PMA or in HeLa cells with PMA). Thus, B cells and plasma cells appear to support constitutive presence of this factor whereas in other cell types it can be induced transiently by an appropriate stimulus.

Experimental Procedures

Cell lines and Extracts: 70Z/3 and PD cells were grown in RPMI 1640 medium supplemented with 10% inactivated fetal calf serum, 50 μM β-mercaptoethanol and penicillin and streptomycin sulfate (pen-strep) antibiotics. LPS (GIBCO) stimulation was carried out with 10–15 μg/ml. For experiments using protein synthesis inhibitors and LPS, cell cultures were treated with inhibitors approximately 20 min prior to addition of LPS. Cycloheximide (Sigma) was used to 10 μg/mo which causes greater than 95% inhibition of protein synthesis in 70Z/3 cells (Wall, R., et al., Proc. Natl.

Acad. Sci. USA 83:295–298, (1986). Anisomycin (Sigma) was used at 10 which causes approximately 99% inhibition of protein synthesis in HeLa cells (Grollman, A. P., J. Biol. Chem. 242:3226–3233, 1967). Phorbol ester activation of 70Z/3 cells was carried out using the active ester phorbol 12-myristate-13-acetate (PMA) or the inactive ester phorbol 12,13-didecanoate at a concentration of 25 ng/ml for the times indicated in the text. All treatments were carried out at cell densities varying between $5 \times 10^5$–$10^6$ cells/ml. Jurkat cells were grown in RPMI 1640 medium with 10% inactivated fetal calf serum and pen-strep antibiotics. Phytohemmagglutinin (PHA) treatment was done at 5 $\mu$g/ml and PMA treatment at 50 $\mu$/ml. HeLa cells were grown in MEM medium with 5% horse serum and pen-strep antibiotics. Phorbol ester (PMA treatment was at 50 $\mu$g/ml with cell density varying between $7 \times 10^5$–$10^6$ cells/ml.

Nuclear extracts were generated essentially according to the protocol of Dignam, J. D. et al., Nucl. Acids Res. 11:1475–1489 (1983) and protein concentration were determined using a Bradford assay with serum albumin standards.

Gel Binding Analysis: Gel binding analyses were carried out as described earlier using a radioactive DdeI to HaeIII fragment (k3) derived from the enhancer (Sen and Baltimore, 1986). Levels of NF-KB induced by various stimuli were normalized to total protein present in the extracts. Further, analysis with a different fragment that contains a binding site for the ubiquitous factor NF-A, shows that this nuclear protein remains at approximately constant levels in all of the extracts reported here. Thus, the modulation of NF-KB activity is not a reflection of variability of nuclear factors in general under these conditions. For competition experiments, the specific and non-specific competitors DNA's were included in the mixture (in amounts shown in FIG. 24C) prior to addition of the protein. The competitor fragments $\mu$300, $\mu$400, KE and SV40E which have been described earlier (Sen and Balitmore, 1986) were isolated from low melting point agarose gels and quantitated by spotting onto ethidium bromide-containing agarose plates.

NF-KB can be Induced in Pre-B Cell Lines with Bacterial Lipopolysaccharide

To examine whether NF-KB might be inducible in 70Z/3 cells, cells were stimulated with LPS for 20 hr and nuclear extracts derived from these cells were assayed for the presence of NF-KB using the electrophoretic mobility shift assay described previously. Singh, H. et al., Nature, 319:154–158 (1986). U.S. patent application Ser. No. 817, 441, To assay for NF-KB, a DNA fragment containing its binding site (K3 fragment; Sen and Baltimore, supra,) was end-labelled and incubated with extracts derived from either unstimulated 70Z/3 (11 s (FIG. 21A, lanes 2,3) or LPS-stimulated 70Z/3 cells (FIG. 21A, lanes 4,5) in the presence of increasing amounts of the carrier poly d(IC). Binding reactions were carried out for 15–30 minutes at room temperature in a final volume of 15 $\mu$l containing 9 $\mu$g of total protein 3.5 $\mu$g (lanes 2,4) or 4.5 $\mu$g (lanes 3,5) of nonspecific carrier DNA poly d(IC) and 0.2–0.5 $\mu$g of probe. Reaction products were fractionated by electrophoresis through low ionic strength polyacrylamide gels and visualized by autoradiography. Lane 1: free DNA fragments; lane 6: nucleoprotein complex generated by interaction of NF KB with the fragment 3 in a nuclear extract derived from the B cell line WEHI 231.

Figure 21A:
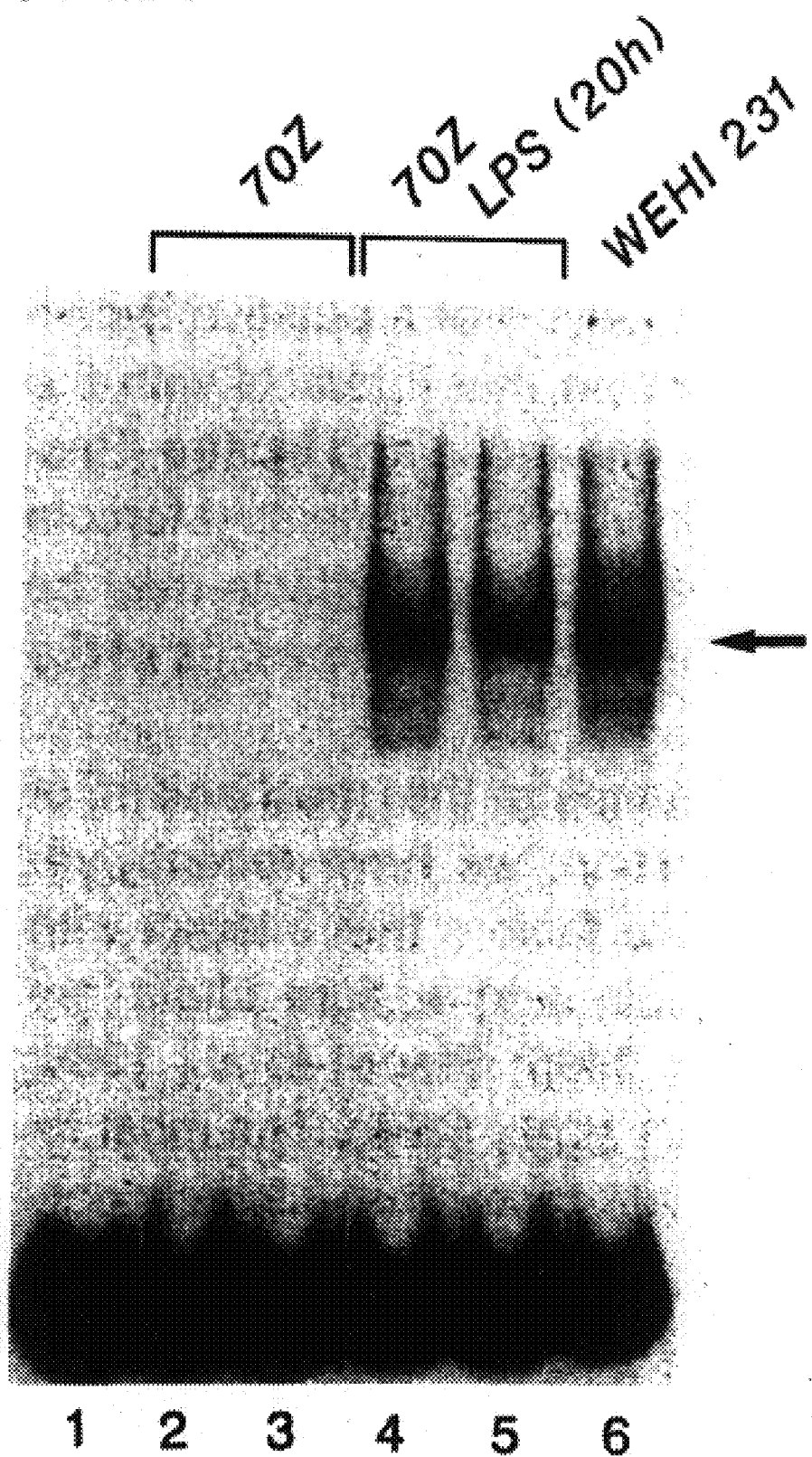
FIGS. 21A–21B show the electrophoretic mobility shift analysis of (A) extracts derived from 10Z/3 cells before and after simulation with bacterial lipopolysaccharide (LPS) and (B) extracts derived from PD, an Abelson murine leukemia virus transformed pre-B cell line before and after stimulation with LPS.
Figure 21B:
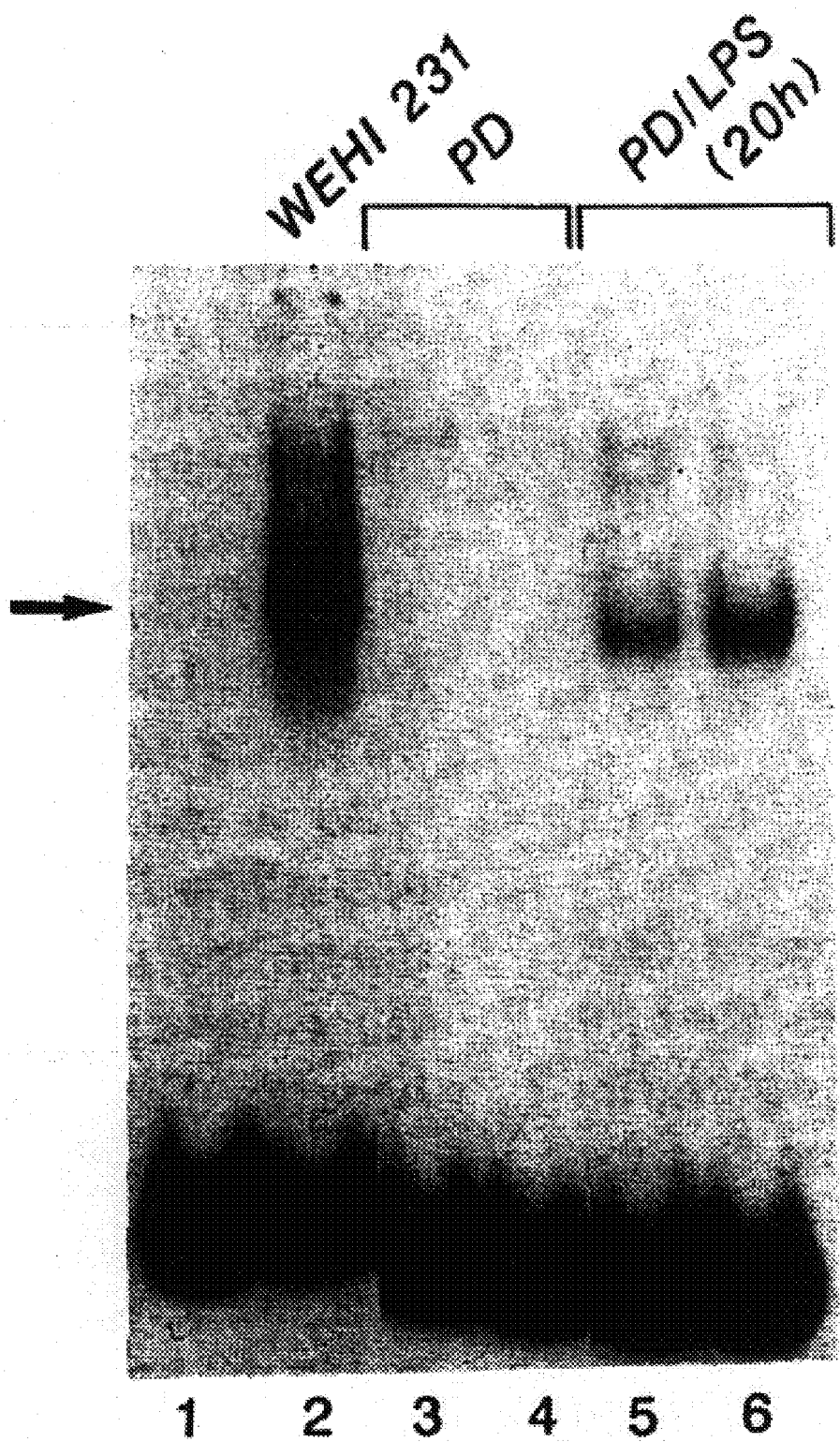

Unstimulated 70Z/3 cell extracts lacked a major band evident with B cell extracts (FIG. 21A, lane 6; arrow). This nucleoprotein complex band was induced in the 70Z/3 cells after LPS treatment for 20 hr. The band was not competed away even with 4.5 ugm of poly d(IC) (lane 5). This induction phenomenon was not restricted to the 70Z/3 cell line; another pre-B cell line, PD (Lewis S., et al., Cell 30:807–816 (1982)), was weakly positive for the factor prior to induction (FIG. 21B, lane 3; Sen and Baltimore, 1986) but was strongly induced by LPS (FIG. 21B lanes 5,6). A number of other minor bands could be seen in the binding assay, some of which were inducible and others not. The major inducible band comigrated with the major band produced by B cell and plasma cell extracts (typified by WEHI 231 extracts in FIG. 21A, lane 6 and FIG. 21B, lane 2). We have earlier characterized this band by competition experiments and localized the binding site of the factor by methylation interference experiments defining the band as one produced by interaction of the NF-KB factor with the B site within the enhancer (a site containing the sequence GGGGACTTTCC). Thus two pre-B cell lines, one with a rearranged K gene (70Z/3) and the other in the process of undergoing rearrangement (PD), are clearly inducible by LPS for NF-KB activity.

Induction of NF-KB by LPS does not Require Protein Synthesis

Recently it has been reported that induction of transcription in 70Z/3 does not require new protein synthesis. Nelson, K. J. et al., Proc. Nat. Acad. Sci. USA 82:5305–5309 (1985). Thus, induction of gene expression was evident in cells pretreated (10 min) with the translation inhibitors cycloheximide or anisomysin followed by stimulation with LPS. Further, Wall et al. reported that expression could be induced in the presence of cycloheximide alone which led them to argue in favor of a labile repressor blocking the activation of genes in this cell line. See Wall, R. et al. Proc. Nat. Acad. Sci. USA 83:295–298 (1986). To determine if these characteristics of transcriptional activation were paralleled by changes in the levels of NF-KB, we analyzed extracts derived from 70Z/3 cells which had been treated either with LPS alone, or with a translation inhibitor alone or with both together. To be able to make direct correlations with the published reports concerning the effects of translational inhibitors on expression in pre-B cells, we examined a 4 hr time point in these experiments, although maximal stimulation of expression by LPS takes 14–20 hr. Binding reactions were carried out as detailed in FIG. 21A legend and contained 2.5, 3.5 or 4.5 $\mu$g poly dIG) with each set of extracts. End-labelled K3 fragment was the proble lane 1) and was incubated with 9–11 $\mu$g or protein from extracts derived from: untreated 70Z/3 cells (lanes 2,3,4), 70Z/3 cells treated for 4 hr with 10 $\mu$g/ml of LPS (lanes 5,6,7), 70Z/3 cells treated for 4 hr with 10 $\mu$g/ml of LPS and 10 $\mu$g/ml cycloheximide (lanes 8,9,10); 70Z/3 cells treated with 10 $\mu$g/ml of cyclheximide alone (lanes 11,12,13) and WEHI 231 cells (lane 14). The characteristic nucleoprotein complex is indicated by the arrow. In accord with the transcriptional analyses, uninduced 70Z/3 cells were negative for NF-KB (FIG. 22A, lanes 2–4), and treatment with either LPS alone (FIG. 22A, lanes 5–7) or with cycloheximide alone (FIG. 22A, lanes 11–13) for 4 hrs induced the factor. Unexpectedly, stimulation of 70Z/3 with LPS in the presence of cycloheximide for 4 hr gave a superinduction of NF-KB (FIG. 22A, lanes 8–10), increasing it to a level above that seen after a 20 hr induction.

Figure 22A:
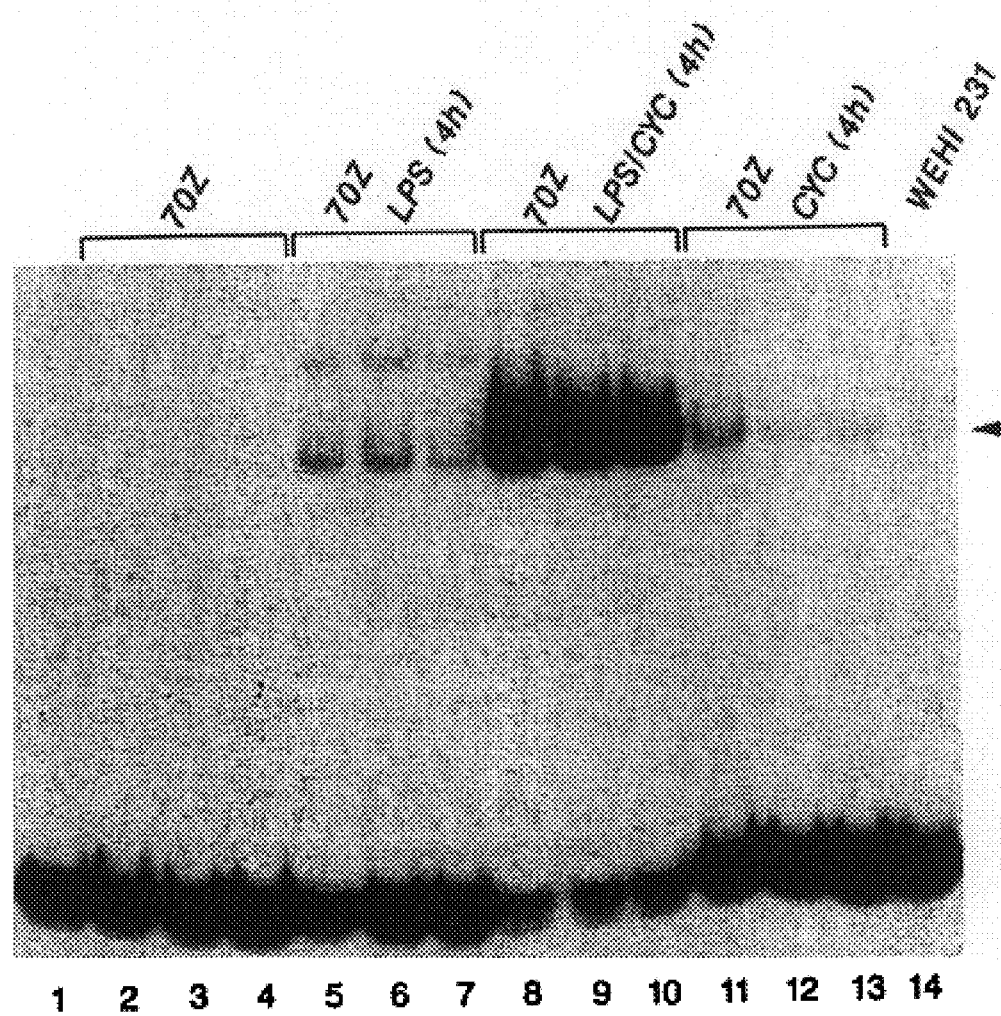
FIGS. 22A–22B show the effect (A) of cycloheximide on LPS stimulation of 70Z/3 cells and (B) of anisomycin on LPS stimulation of 70Z/3 cells.
Figure 22B:
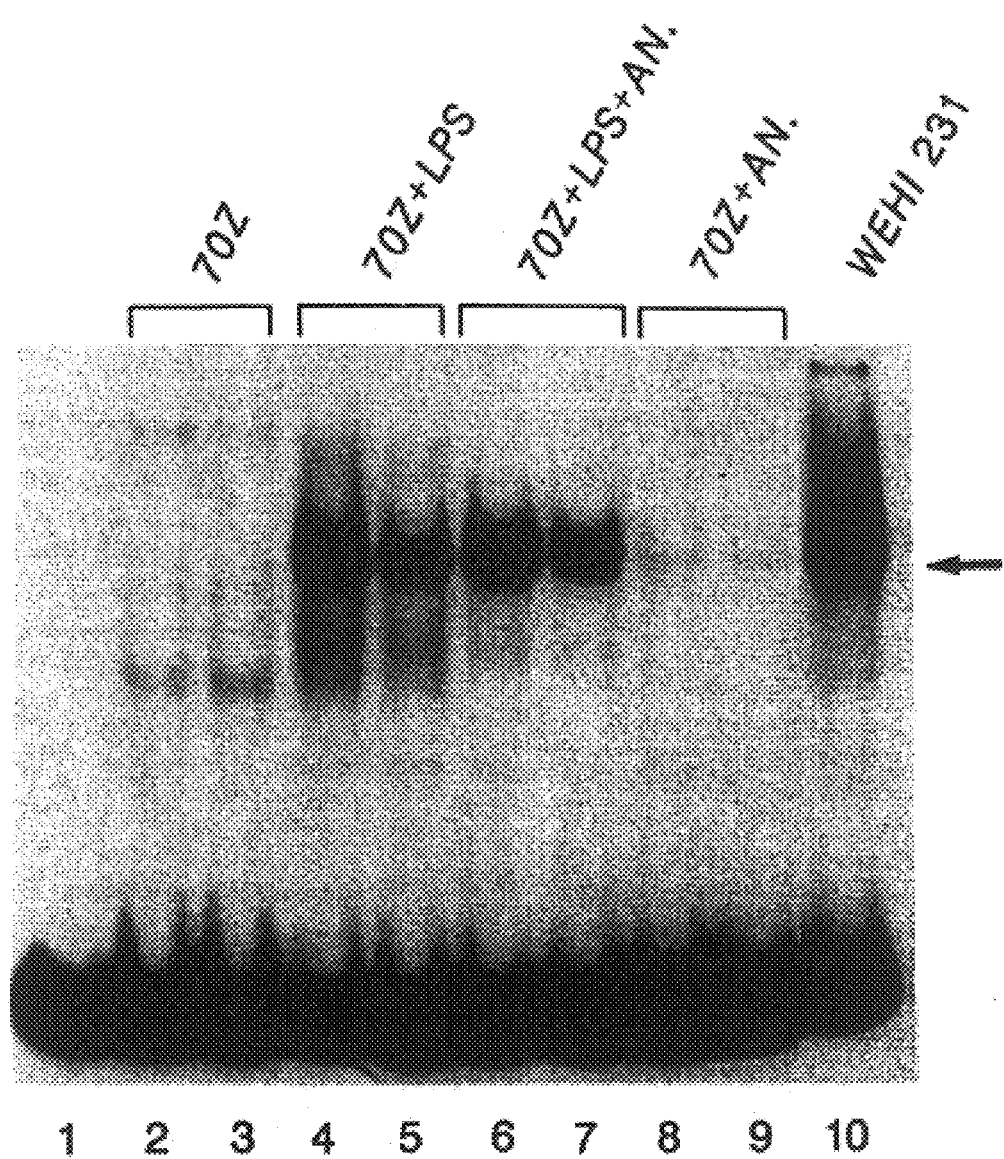

Qualitatively, the same result was observed when anisomycin was used as a translation inhibitor (FIG. 22B). Binding reactions were as detailed in FIG. 21A legend using 2.5 and 3.5 $\mu$g of poly d(IC) and protein from untreated 70Z/3 cells (lanes 2,3); 70Z/3 cells after induction with LPS alone (lanes 4,5); 70Z/3 cells with LPS induction in the presence of anisomycin (lanes 6,7); 70Z/3 cells treated with anisomycin by itself (lanes 8,9) and the B cell WEHI 231 as a positive control (lane 10). The characteristic nucleoprotein complex is indicated by the arrow. Thus, the presence of anisomycin (10 uM) during a 4 hr stimulation with LPS gave a superinduction of NF-KB (FIG. 22B, lanes 6,7) relative to either LPS alone (FIG. 22B, lanes 4,5) or anisomycin alone (FIG. 22B lanes 8–9). Once again, prior to LPS treatment there was no detectable NF-KB activity in 70Z/3 (FIG. 22B lanes 2,3). Although treatment of 70Z/3 with cycloheximide alone or with LPS alone gave approximately equivalent amounts of NF-KB (FIG. 22A compare lanes 5–7 with lanes 11–13), the level of NF-KB induced with anisomycin alone appeared to be much less (FIG. 22B, compare lanes 8,9 with lanes 4,5). This is probably due to drug toxicity because, even after a short exposure to anisomycin, the cells looked quite unhealthy. Presumably this also accounts for lesser degree of superinduction seen with LPS and anisomycin. Thus the enhancer binding factor NF-KB appears to be inducible in 70Z/3 cells in the absence of protein synthesis. Further, it appears to be inducible by either of 2 different translation inhibitors alone and is superinduced when the cells are stimulated with LPS and the inhibitor.

Phorbol Ester can Induce NF-KB in 70Z/3

Figure 23A:
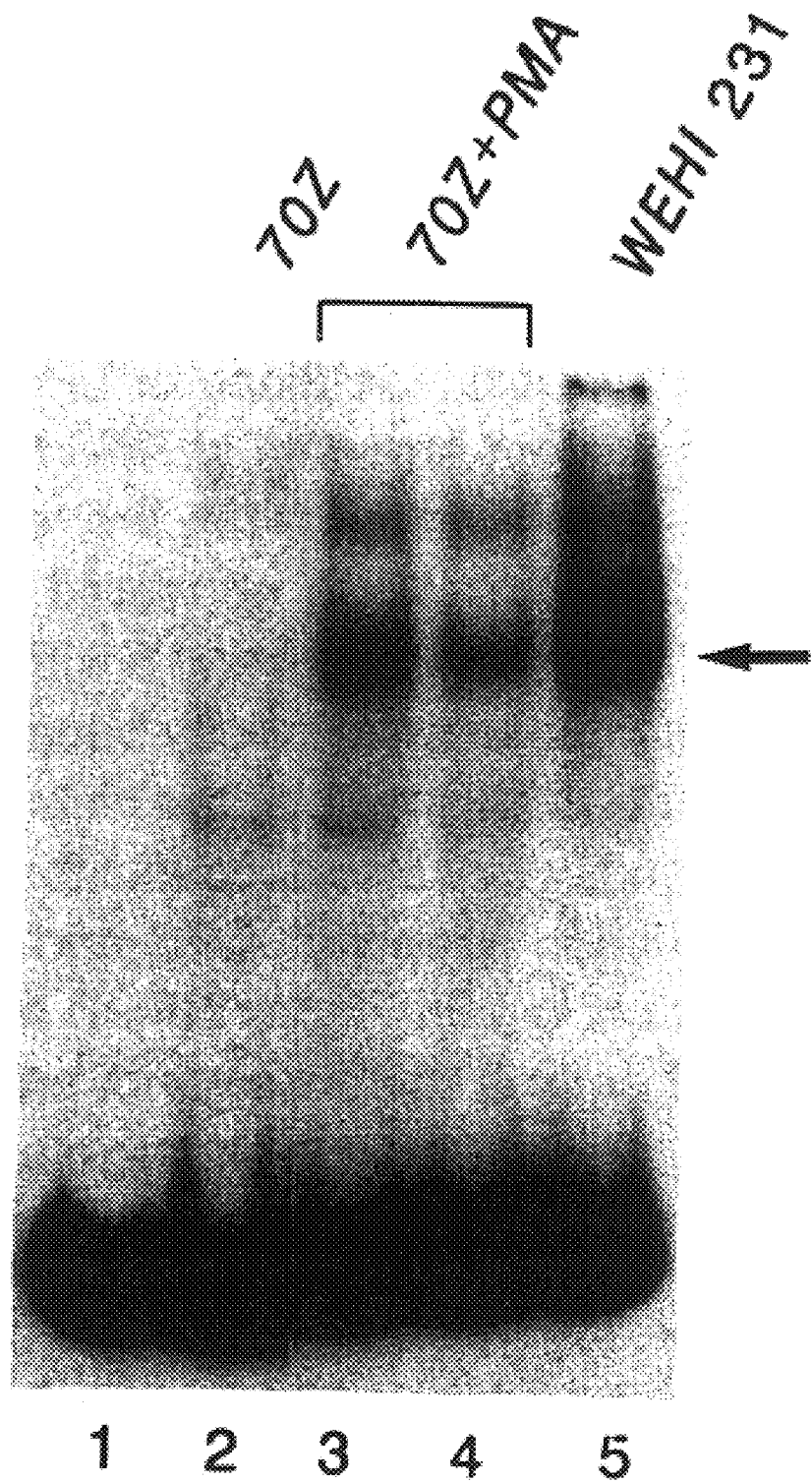
FIGS. 23A–23B show the effect of phorbol 12-myristate-13-acetate (PMA) on NF-B in 70Z/3 cells.

The tumor promoting phorbol ester, phorbol 12-myristate-13-acetate (PMA), has been shown to induce surface immunoglobulin in 70Z/3, presumably via activation of K transcription and transport of complete immunoglobulin to the cell surface (Rosoff P. M. et al., *J. Biol. Chem.* 259:7056–7060 1984; Rosoff, P. M. and Cantley, L. C., *J. Biol. Chem.* 260 9209–9215, (1985). To determine if this activation is reflected in an increase of NF-KB, we analyzed extracts derived from 70Z/3 cells after a 4 hr stimulation with PMA at 50 ng/ml. Binding reactions using K3 as a problem (lane 1) were carried out as detailed in FIG. 21A legend with protein from untreated 70Z/3 cells (lane 2) or 70Z/3 cells that had been treated with PMA at 50 ng/ml for 4 hr (lanes 3,4). Lane 5 is the positive control for NF-KB in extracts from WEHI 231. There was a striking induction of NF-KB activity in these extracts (FIG. 23A, compare lanes 3,4 with lane 2). Thus an active phorbol ester by itself is capable of inducing NF-B activity in 70Z/3 cells, implicating protein kinase C as a possible intermediate in the post-translational modification reaction that produces NF-B in these cells [(Bell, R. M. *Cell* 45:631–632 (1986); Nishizuka, Y. *Nature* 308:693–697, (1984)]. An inactive phorbol ester (phorbol 12, 13 didecanoate) did not cause induction of NF-KB under similar conditions (data not shown).

Time Course of Activation of NF-B by LPS and PMA are Different

Figure 23B:
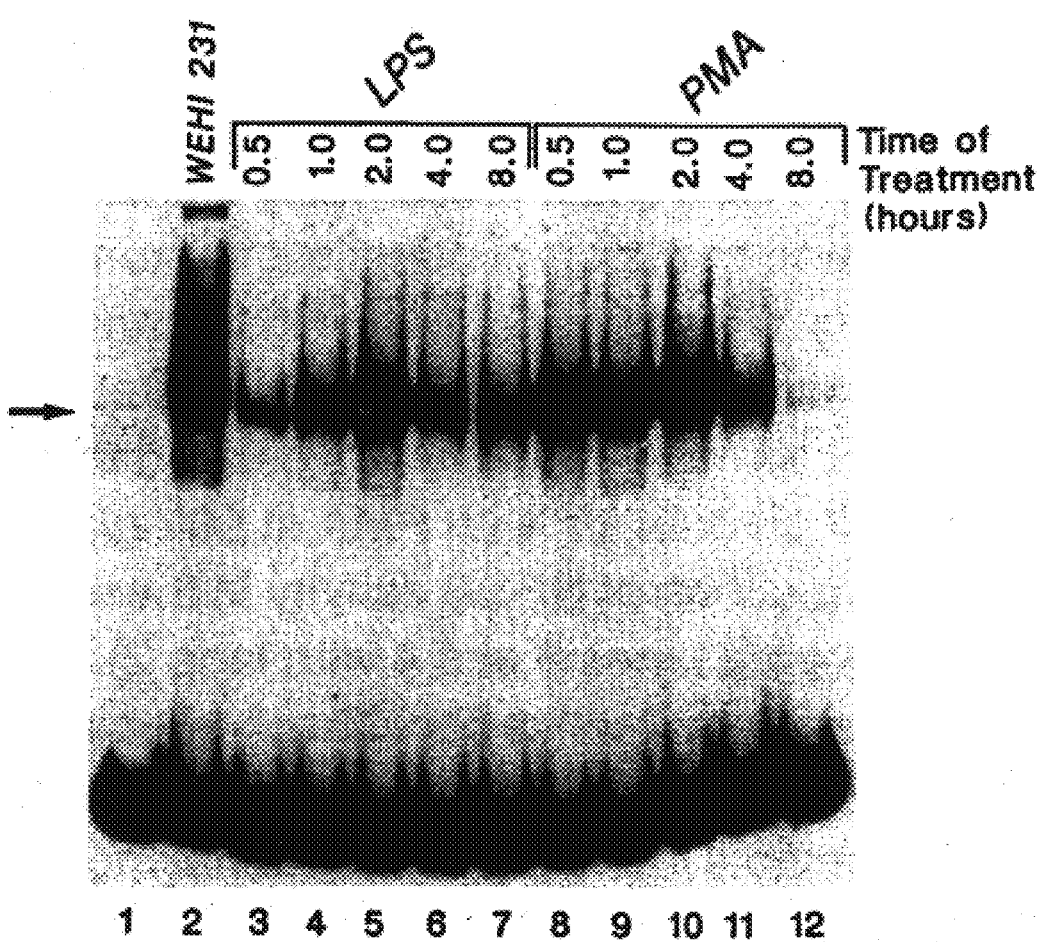

LPS-mediated stimulation of surface Ig expression of mRNA accumulation reaches a maximum after at least one cell cycle, i.e., in 14–18 hr. Recent work has shown that LPS stimulation of RNA synthesis, as measured by nuclear run on assays [Nelson, K. J., et al., *Proc. Natl. Acad. Sci USA* 82:5305–5309 (1985); Wall et al. supra, (1986)] can be seen as early as 4 hr after stimulation and that the DNAse I hypersensitive site associated with the enhancer can be detected as early as 1 hr post-stimulation. To examine the time-course of NF-KB induction, we generated 70Z/3 cell extracts after stimulation either by LPS or PMA for varying lengths of time. Analysis for NF-KB activity using the binding assay showed that the time course of activation of NF-KB by these two agents was quite different (FIG. 23B). Binding reactions were carried out with extracts derived from 70Z/3 cells that had been treated with LPS at 10 $\mu$g/ml (lanes 3–7) or PMA at 25 ng/ml (lanes 8–12) for various lengths of time as shown above each lane in the figure. Lane 2 is a positive control for NF-KB in WEHI 231 extracts. With LPS alone, a nucleoprotein complex band reflecting the presence of NF-KB increased until 2 hr post-stimulation after which a slight decrease occurred and then the level remained constant. By contrast, in PMA-stimulated cells, NF-KB was detected at maximal levels within 0.5 hr after stimulation, remained at this level for 2–3 hours and then began to drop off rapidly, such that by 8 hr it was barely detectable. Because prolonged exposure of cells to phorbol esters is known to result in desensitization of endogenous protein kinase C (Rodriquez-Pena, A. and Rozengurt, E., *Biochem Biophys. Res. Comm.* 120:1053–1009, 1984; *EMBO J,* 5:77–83 1986), a possible explanation for the rapid decline of NF-KB may be that its maintenance as a binding factor requires continuous activity of protein kinase C. A similar phenomenon has been described recently by Blemis and Erikson where S6 kinase activity assayed by phosphorylation of S6 protein) first rises and then falls during prolonged exposure to PMA. See Blemis, J. and Erikson, R. L. *Proc. Natl. Acad. Sci. USA* 83:1733–1737 (1986). Although it has been reported that LPS may directly activate protein kinase C (Wightman, P. D. and Raetz, C. R. H., *J. Biol. Chem.* 259:10048–10052, 1984) the different kinetics of induction of NF-KB by LPS and PMA implies that these activators feed into a common pathway through distinguishable sites of activation.

Non Pre-B Cell Lines can also Be Activated to Produce NF-KB

In our previous analysis we have shown that NF-KB is present only in cell lines representing the B cell or plasma cell stages of B lymphoid differentiation, but was undetectable in a variety of non B cells, pre-B cells and T cells (Sen and Baltimore, 1986). However, as shown above, this factor may be induced to high levels in pre-B cells upon stimulation with LPS. To check if this inducibility was restricted to cells having a pre-B pheno-type only or was a general characteristic of the other constitutively negative cell lines we have taken representative examples of cell types (T cells and non lymphoid cells) and examined then for induction of NF-KB after appropriate stimulation.

Figure 24A:
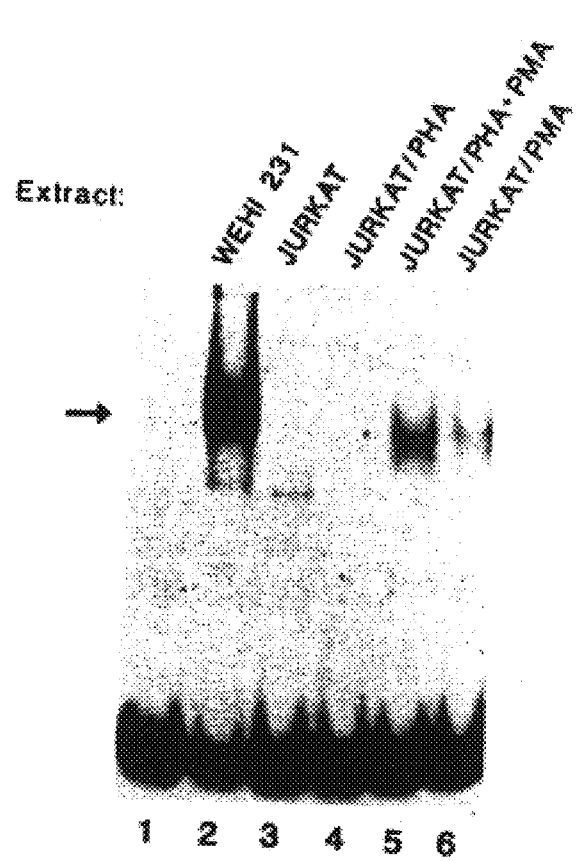
FIGS. 24A–24C shows the induction of NFKB in a human lymphoma and in HeLa cells.

The human T leukemia cell line, Jurkat, can be stimulated to produce interleukin-2 (IL-2) by the combined influence of phytohemagglutinin (PHA) and phorbol ester (PMA) (Gillis, S. and Watson, J., *J. Exp. Med.,* 152:1709–1719, 1980; Weiss et al., *J. Immunol.* 133:123–128, 1984). Nuclear extracts were prepared from Jurkat cells that had been stimulated with either PHA alone or PMA alone or both together and analyzed for the presence of NF-KB (FIG. 24A). The human T lymphoma Jurkat was stimulated with phytohemagglutinin (PHA) and phorbol 12-myristate-13-acetate (PMA) individually or together for 20 hr. Nuclear extracts made after treatment were analyzed by the mobility shift assay using K-3 fragment as the labelled probe. Binding reactions typically contained 6 g of protein, 2.5–3.5 g of poly d(IC) and 0.3–0.5 ng of end-labelled DNA probe. Lane 1: no protein added; lane 2: WEHI 231 extract (positive control); lane 3: extract from uninduced Jurkat cells: lane 4: Jurkat cells stimulated with PHA alone; lane 5: Jurkat cells stimulated with pHA and PMA; Lane 6: Jurkat cells stimulated with PMA alone. The arrow shows the position of the expected nucleoprotein complex generated by interaction of NF-KB with K-3 fragment. As originally observed, extracts derived from uninduced Jurkat cells were negative for NF-KB activity (FIG. 24A, lane 3). However, extracts made from Jurkat cells which had been stimulated either with PHA or PMA contained detectable levels of NF-KB (FIG. 24A, lanes 4,6) and the extracts from the co-stimulated cells showed higher levels of the factor (FIG. 24A, lane 5). Thus a factor with the properties of NF-KB can be induced in a T cell lines after appropriate activation.

Figure 24B:
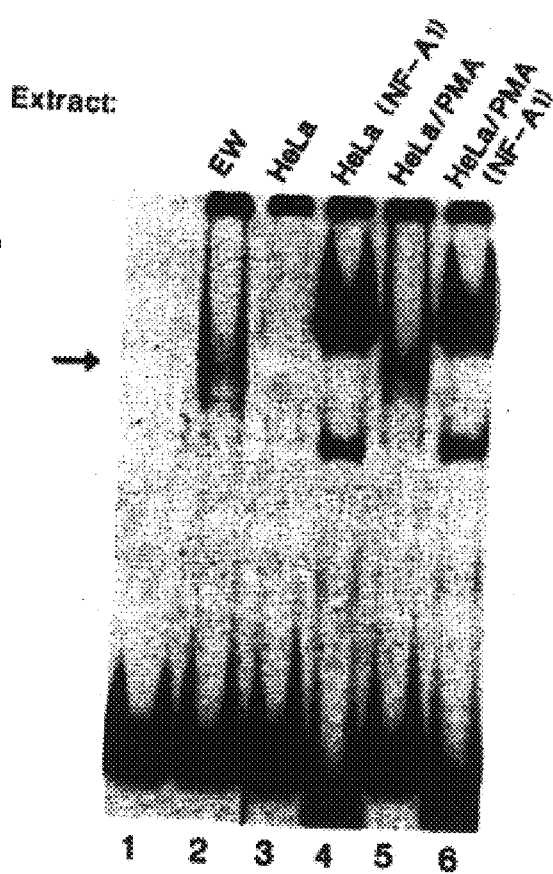

As an example of a non-lymphoid line we used the human HeLa cell lines which is constitutively negative for NF-KB (Sen and Baltimore, 1986). These cells were induced with PMA for 2 hr and extracts derived from treated and untreated cells were analyzed for NF-KB activity (FIG. 24B). HeLa cells were treated with PMA (50 ng/ml) for 2 hrs. and the extracts derived thereafter were analyzed for induction of NF-KB. Binding reactions contained 15–18 µg of protein, 3.5 µg of poly d(IC) and 0.3–0.5 µg of end-labelled DNA probe. Lane 1: 3 fragment/no protein added; lane 2: 3 fragment incubated with extracts derived from the human B lymphoma EW; lane 3: K3 fragment incubated with uninduced HeLa cell nuclear extract; lane 4: p50 fragment (derived from the µ-heavy chain enhancer and containing a copy of the conserved octamer sequence ATTTGCAT) incubated with uninduced HeLa cell extracts; lane 5: K3 fragment incubated with induced HeLa cell extracts. The untreated HeLa extract (FIG. 24B, lane 3) did not show a nucleoprotein complex which comigrated with the complex generated in B cell extracts. However treatment with PMA induced a factor that generated the characteristic DNA-protein complex produced by NF-KB (FIG. 24B, lane 5). As a control, both the uninduced and induced extracts showed equivalent levels of the ubiquitous NF-A1 DNA binding protein when analyzed using a probe containing the sequence ATTTGCAT (FIG. 24B, lanes 4,6; Singh, H. et al., Nature 319:154–158, 1986). Therefore treatment of HeLa cells with PMA induces a factor that can form a nucleoprotein complex with the K3 fragment.

Figure 24C:
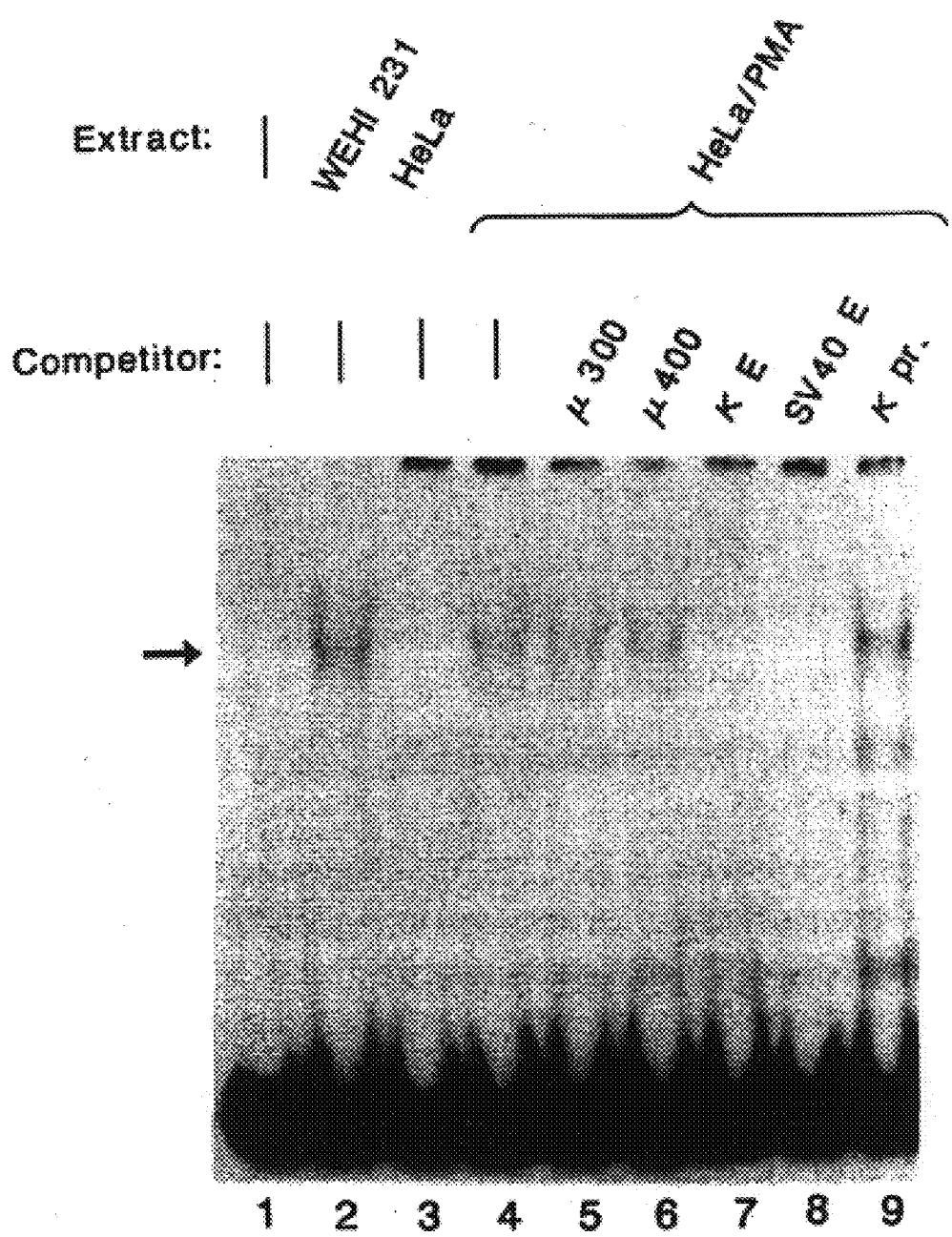

To further characterize the DNA-protein complex formed in the PMA-treated HeLa cell extracts, we carried out competition experiments. Binding reactions were carried out using end-labelled K3 fragment, 3.5 µg of poly d(IC) and 15–18 µg of nuclear extract in the present of 50 ng of unlabelled competitor DNA derived from various immunoglobulin and viral regulatory sequences (lanes 5–9). The complex generated in PMA-induced HeLa cell extracts (FIG. 24C, lane 4) was specifically competed away by the inclusion of 50 ng of unlabelled DNA in the binding reaction containing either the enhanced (FIG. 24C, lane 7) or the SV40 enhanced (FIG. 24c, lane 8) but was unaffected by two DNA fragments that together span the K enhancer (FIG. 24C, lane 5,6), or by a 250 bp fragment containing the K promoter (FIG. 24C, lane 9). This pattern of competition exactly parallels the pattern observed earlier using the K3 fragment in binding experiments with B cell derived extracts (Sen and Baltimore, 1986). These results further strengthen the conclusion that the NF-KB factor can be induced in non-lymphoid cells as well as lymphoid cells following appropriate stimulation.

Example 9

Figure 26A:
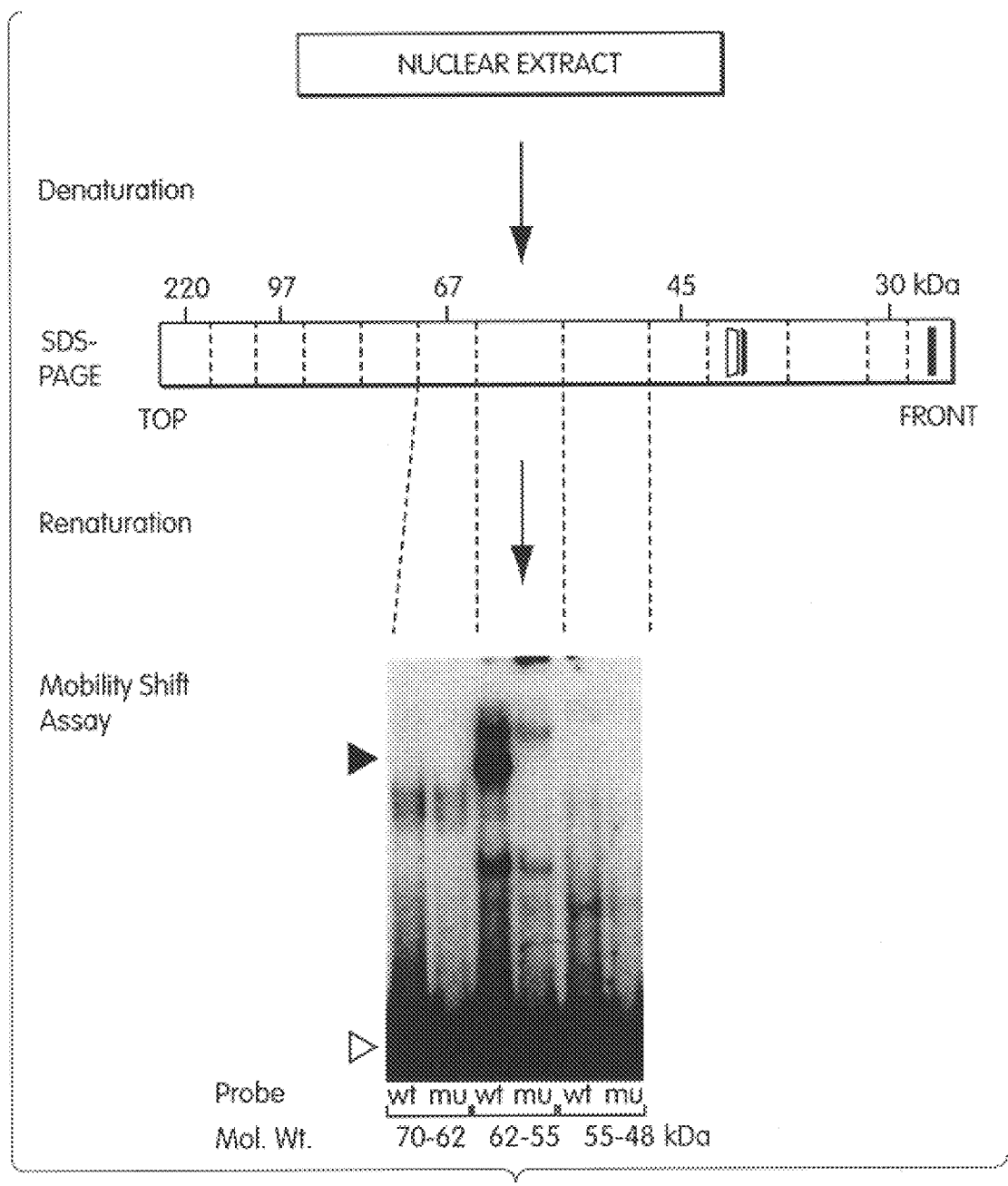
FIGS. 26A–26B are a characterization of the NF-kB protein.
Figure 26B:
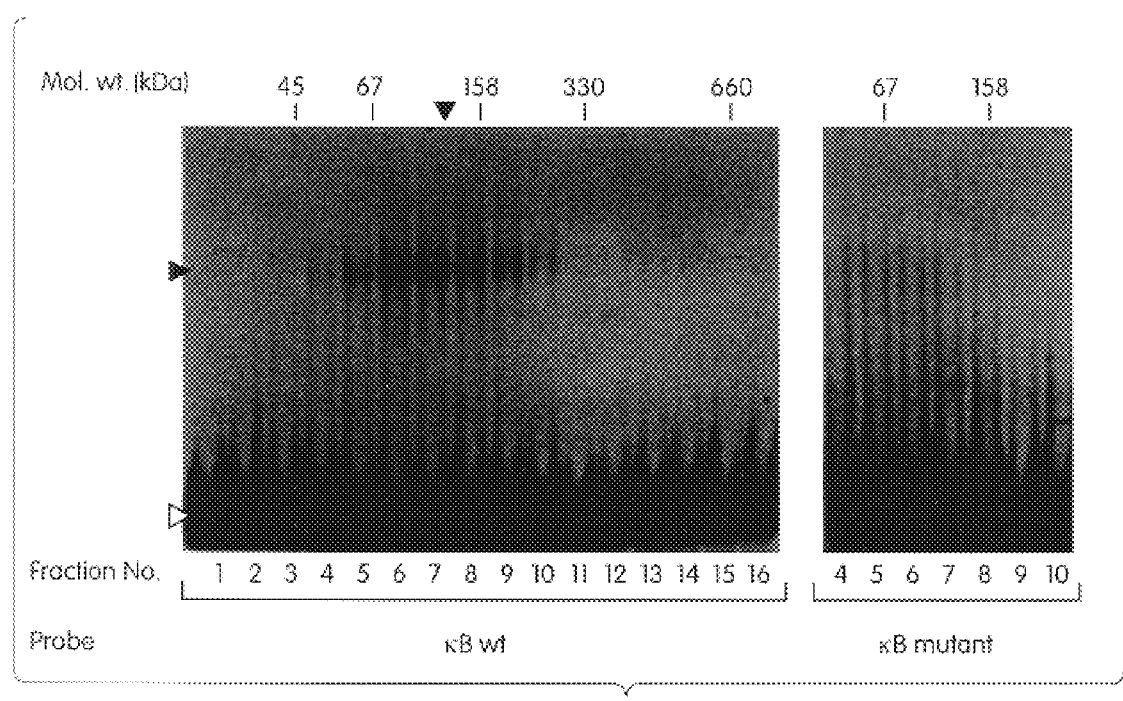

Characterization of the NF-kB Protein and Electrophoretic Mobility Shift Analysis of Subcellular Fractions of 70Z/3 Cells Characterization of the NF-kB protein Mouse NF-kB is a polypeptide with a molecular weight around 60 kDa. This has been determined by a DNA-binding renaturation experiment using eluates from different molecular weight fractions of a reducing SDS-gel (FIG. 26A). The size of the native NF-kB protein was determined in the following manner: Nuclear extract from TPA-stimulated cells was subjected to ultracentrifugation on a continuous glycerol gradient. The fractions were assayed for DNA-binding activity of NF-kB by electrophoretic mobility shift assays (FIG. 26B). NF-kB activity was found highest between the co-sedimented bovine serum albumin (67 kDa) and IgG (158 kDa) standards (FIG. 26B, lanes 6 to 8). The specificity of binding was shown by the absence of a complex when a DNA probe with a mutation in the NF-kB binding sequence was used to assay the fractions (FIG. 26B, right lanes 4 to 10). Lenardo, M. et al., Science, 236:1573–1577 (1987). Little NF-KB activity was contained in the fractions where a 60 kDa protein would be expected to sediment (FIG. 26B, lanes 4 and 5). If the sedimentation of NF-kB is not highly abnormal, the results from the glycerol gradient centrifugation suggest that NF-kB is associated with another protein of approximately the same size. Presumably NF-kB forms a homodimer because the protein-DNA complex formed in native gels using whole nuclear extract is of the same mobility as the complex formed with renatured NF-kB protein from a single spot of a two-dimensional gel.

70Z/3 cell cultures were incubated in the absence (Co) and presence of phorbol ester (TPA), followed by subcellular fractionation of cells. In the DNA-binding reactions, 8.8 ug of protein of nuclear extracts (N), cytosolic fractions (C), and post-nuclear membrane fractions (P) in 4 ul buffer D(+) were used. The end-labeled DNA-fragments were incubated in the presence of 3.2 ug poly(d[I-C]) with the subcellular fractions in a final volume of 20 ul for 15 to 30 minutes followed by separation of protein-DNA complexes and unbound DNA on native 4% polyacrylamide gels. Fluorograms of native gels are shown. To detect kB-specific DNA-binding activity a DdeI-HaeIII wild type fragment of the kappa light chain enhancer (kB wt; lanes 1–6) was used. Sen, R. and D. Baltimore, Cell, 46:705–716 (1986). kB-unspecific activities binding to the kappa enhancer fragment were detected using a fragment mutated in NF-kB binding site that was otherwise identical to the wild type fragment (lanes 7–12). Lenardo, M. et al., Science, 236:1573–1577 (1987). NF-uE3-binding activity and octamer binding protein activity were assayed with a HaeIII-DdeI kappa enhancer fragment (uE3; lanes 13–18) and a PvuII-EcoRI kappa heavy chain promoter fragment (OCTA; lanes 19–24), respectively. Sen, R. and D. Baltimore, Cell, 46:705–716 (1986); Singh, H. et al., Nature, 319:154–158 (1986,). Specific protein-DNA complexes are indicated by filled arrowheads and the positions of unbound DNA-fragments by open arrowheads.

Example 10

Renaturation of NF-kB

70Z/3 cells were grown in spinner cultures with RPMI 1640 medium supplemented with 10% newborn calf serum and 50 uM 2-mercaptoethanol. HeLa cells were also grown in spinner cultures with MEM medium supplemented with 10% horse serum. Cell cultures were treated with 25 ng/ml 12-O-tetradecanoylphorbol 13-acetate (TPA; Sigma) for 30 minutes at cell densities between $7 \times 10^5$ and $2 \times 10^6$/ml.

Subcellular Fractionation

Cells were collected by centrifugation for 10 minutes at 150×g. Cell pellets were resuspended in ice-cold phosphate-buffered saline and collected again by centrifugation. All following steps were carried out at 4° C.. Washed cells were resuspended in four packed cell volumes of a hypotonic lysis buffer (buffer A; Dignam, J. P. et al., *Nucleic Acid Research*, 11:1475–1489 (1983)). After 20 minutes, cells were homogenized by 15 (HeLa) or 20 strokes (70Z/3 cells) with a loose fitting Dounce homogenizer. Nuclei were collected by centrifugation for 6 minutes at 4300×g, resuspended in five volumes of buffer A and washed once by centrifugation. Proteins were extracted from washed nuclei by high salt, followed by centrifugation of the nuclear extracts and dialysis against buffer D as described. Dignam, J. P. et al., *Nucleic Acids Research*, 11:1475–1489 (1983). One percent NP-40 (v/v) was added to the dialyzed nuclear extracts. The postnuclear supernatant was centrifuged for 6 minutes at 4300×g and the resulting supernatant ultracentrifuged for 1 hour at 150,000×g. The pellet after ultracentrifugation containing postnuclear membranes was dissolved in buffer D containing 1% (v/v) NP-40 (referred to as buffer D(+)). Insoluble material was removed by centrifugation for 10 minutes in a Microfuge. The supernatant after ultracentrifugation (referred to as cytosolic fraction) was adjusted to buffer D(+) conditions by the addition of stock solutions. Fractions were stored at −70° C.

Protein concentrations were determined by an assay using bicinchoninic acid. Smith, P. K. et al., *Anals of Biochemistry*, 150:76–85 (1985). The ratio of the total protein recovered during a fractionation experiment in nuclear extracts, cytosolic fractions and postnuclear membrane fractions was 2:4:1 for 70Z/3 cells and 1:10:1.5 for HeLa cells. These ratios were used to adjust the fractions to protein concentrations reflecting equal cell-equivalents of subcellular fractions.

Electrophoretic Mobility Shift Assays and Treatments with Dissociating Agents

DNA-binding reactions were carried out as described above. The DNA-binding reaction mixture contained poly (d[I-C]) (Pharmacia), 3000–6000 cpm of [$^{32}$P]end-labeled DNA-fragments and a buffer composed of 10 mM Tris-HCl, pH 7.5, 50 mM NaCl, 1 mM dithiothreitol (DTT), 1 mM EDTA and 5% glycerol. Binding reactions and subsequent analysis on native 4% polyacrylamide gels were performed at room temperature as described. Sen, R. and D. Baltimore, *Cell*, 46:705–716 (1986). Subcellular fractions were treated with formamide (DNA grade; American Bioanalytical) prior to the addition of the DNA-binding reaction mixture. Sodium desoxycholate (Fisher Scientific Company) was added after the DNA-binding reaction.

Renaturation of NF-kB

Protein in the subcellular fractions was precipitated at −20° C. by the addition of four volumes of acetone. Pellets were dissolved in SDS-sample buffer containing 3.3% 2-mercaptoethanol and boiled for 5 minutes. Laemmli, U. K., *Nature.*, 227:680–685 (1970). After SDS-polyacrylamide gel electrophoresis, gel pieces from different molecular weight regions were cut out, ground, and proteins eluted overnight at 4 ° C. in 500 ul of a buffer containing 50 mM Tris-HCl, pH 7.9, 0.1% SDS, 0.1 mg/ml bovine serum albumin, 1 mM DTT, 0.2 mM EDTA, 0.1 mM phenylmethylsulfonyl fluoride (PMSF) and 2.5% glycerol. After centrifugation for 2 minutes in a Microfuge, the supernatant was removed and recentrifuged for 10 minutes to remove gel debris.

To 200 ul of the supernatant four volumes of acetone were added and proteins were allowed to precipitate for 2 hours at −20° C. The precipitate was collected by centrifugation for 10 minutes in a Microfuge, washed once with 1 ml methanol at −20° C. and dried for 30 minutes in the inverted tube. The dried pellet was dissolved in 2.5 ul of a saturated solution of urea (ultrapure; American Bioanalytical) and dilued with 125 ul of a buffer containing 20 mM Tris-HCl, pH 7.6, 10 mM KCl, 2 mM DTT and 10 uM PMSF. Renaturation was allowed for a minimum of 18 hours at 4° C. kB-specific DNA-binding activity was detectable in mobility shift assays for at least 48 hours after storage of renatured fractions at 4° C. without appreciable loss of activity.

Example 11

Subcellular Localization of the NF-kB Precursor

Because NF-kB is a DNA-binding protein, it is expected to reside in the nucleus. This is certainly true for NF-kB of phorbol ester-treated cells and mature B-cells where the activity is detectable in nuclear extracts. It is however not mandatory for a precursor of NF-kB especially, in view of the fact that the precursor is activated by protein kinase C, a cytosolic protein that is associated in its active state with the plasma membrane.

Figure 27A:
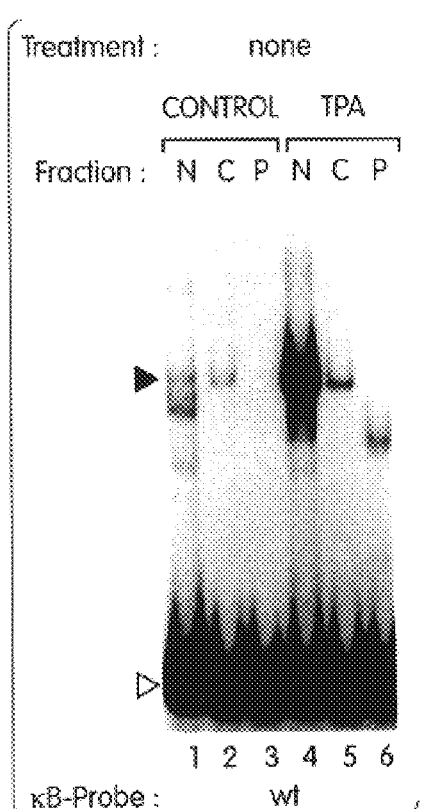
FIGS 27A–27C represent detection of a cytosolic precursor of NF-kB.

The precursor of NF-kB was analyzed by an investigation of subcellular fractions of unstimulated pre-B cells for the presence of NF-kB activity, using electrophoretic mobility shift assays (FIG. 27A). Little DNA-binding activity was detected in the subcellular fractions, indicating that the precursor must exist in a form of low affinity for its cognate DNA (FIG. 27A, lanes 1 to 3). In fractions from TPA-stimulated cells, the newly activated NF-kB was almost exclusively contained in the nuclear extract (FIG. 27A, lanes 4 to 6).

Figure 27B:
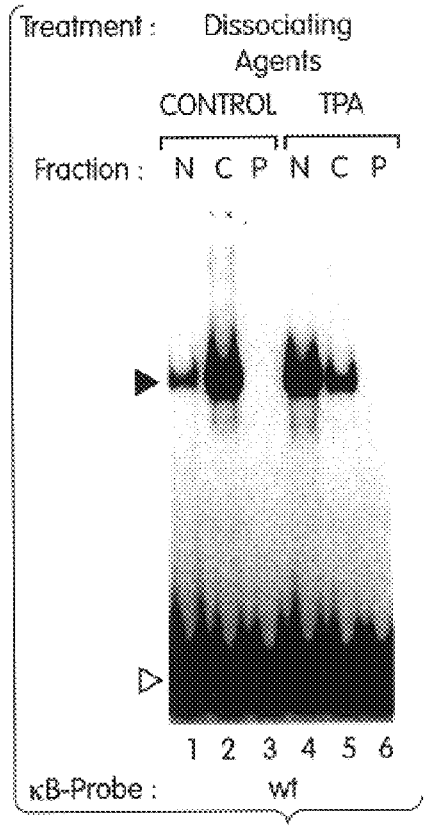
Figure 27C:
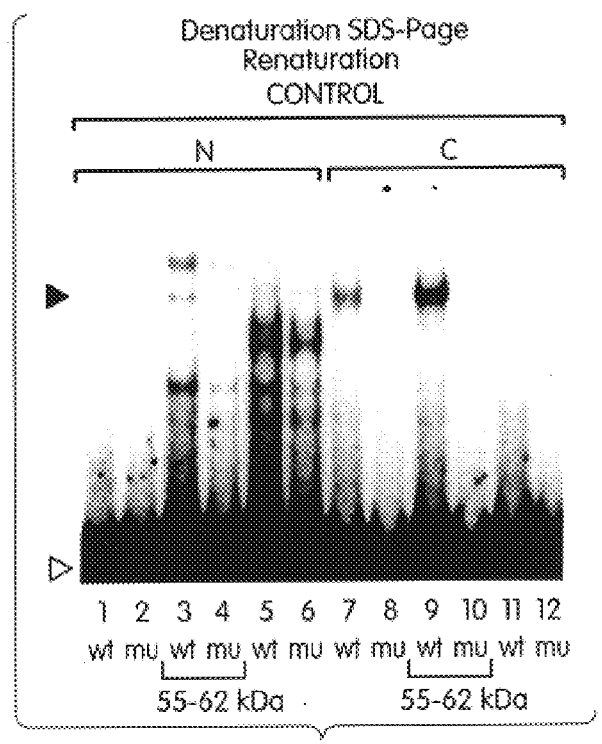

In an attempt to activate the DNA-binding activity of the NF-kB precursor, the various subcellular fractions were treated with agents known to gently dissociate protein-protein interactions. Low concentrations of desoxycholate, formamide or a combination of both included in the mobility shift assay mixture led to the activation of an NF-kB-specific DNA-binding activity (FIG. 27B). The fraction containing the bulk of the in vitro activatable NF-kB precursor was the cytosol (FIG. 27B, lanes 1 to 3). When fractions from TPA-stimulated cells were subjected to the same treatment, the amount of precursor in the cytosolic fraction was found strongly reduced, apparently because of redistribution of activated NF-kB into the nuclear extract fraction (FIG. 27B, lanes 4 and 5). In both control and TPA-stimulated cells, the amount of total cellular NF-kB activity revealed after treatment with dissociating agents was equal, suggesting a complete conversion of the NF-kB precursor into active NF-kB. Cytosolic fractions from HeLa cells and from calf spleen also contained NF-kB precursor which could be demonstrated after activation with dissociating agents. These observations strongly suggest that NF-kB is localized as an inactive precursor in the cytosol. Activation of protein kinase C by phorbol ester then would result in two events: induction of DNA-binding activity and nuclear translocation of NF-kB.

Figure 28:
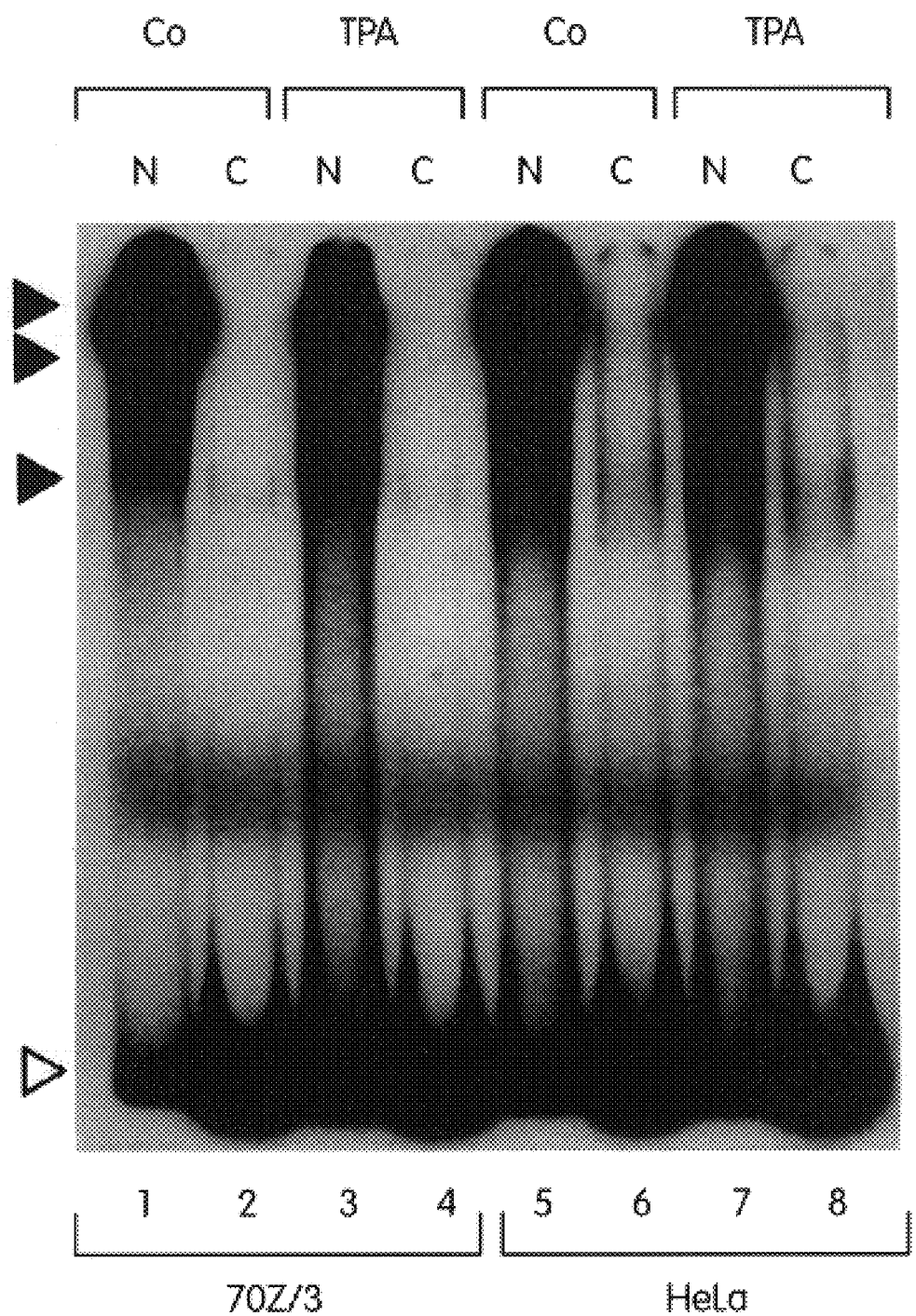
FIG. 28 represents analysis of subcellular fractions for DNA-binding activity of the TPA-inducible transcription factor AP-1. Equal cell-equivalents of nuclear extracts (N) and cytosolic fractions (C) from 70Z/3 and HeLa cells were used in mobility shift assays. AP-1 specific DNA-binding activity was detected using an end-labeled EcoRI-HindIII fragment from the yeast HIS 4 promoter containing three binding sites for GCN4 recognized by mammalian AP-1. The three protein-DNA complexes seen on shorter exposures of the fluorogram are indicated by filled arrowheads and the position of unbound DNA-fragment by an open arrowhead.

Using subcellular fractions from HeLa cells, another TPA-inducible transcription factor, AP-1, was tested to determine whether it also exhibits activation and subcellular redistribution upon TPA-stimulation. As detected by mobility shift assays, AP-1 from nuclear extracts did not show an increase in DNA-binding activity after TPA-stimulation nor were there significant amounts of AP-1 activity present in the cytosolic fractions from control and stimulated cells (FIG. 28). This showed that the mechanism by which the transcription factor activity of NF-kB is induced is fundamentally different from that of AP-1 although the initial signal—activation of protein kinase C by phorbol ester—is the same.

Example 12

Investigation of the DOC-dependence of Cytosolic NF-kB

Cytosol from unstimulated 70Z/3 pre-B cells in buffer A (Dignam, J. P. et al., *Nucl. Acids. Res.*, 11:1475 (1983); Baeuerle, P. A. and D. Baltimore, *Cell*, 53:211 (1988)) was adjusted to a final concentration of 50 mM NaCl, 20 mM (HEPES) (pH 7.9), 1.5 mM EDTA, 5% glycerol and 0.2% NP-40. Cytosolic protein (45 mg) was mixed to a final volume of 4 ml with 0.6% DOC, 0.75 g calf thymus (wet weight) DNA-cellulose [Sigma; equilibrated in buffer G: 10 mM Tris-HCl (pH 7.5), 5 mM NaCl, 1 mM EDTA, 1 mM dithiothreitol (DTT), 5% glycerol, 0.2% DOC, 0.2% NP-40, and 0.5 mM phenylmethyl sulfonylfluoride (PMSF)] and 1.2% NP-40. The suspension was incubated in a mini column for 1 hour at room temperature on a rotary shaker. The flow-through fraction was used for gel filtration. DNA-cellulose was washed with buffer G and eluted with a NaCl step gradient in buffer G. Equal proportions of fractions were assayed by EMSA (Sen, R. and D. Baltimore, *Cell*, 46:705 (1986); Baeuerle, P. A. and D. Baltimore, *Cell*, 53:211 (1988)) at a final concentration of 1.2% NP-40 in the presence of either 0.03% DOC (non dissociating condition) or 0.6% DOC (dissociating condition) and with 10 µg of bovine serum albumin (BSA) as carrier. Results of this investigation are represented in FIG. 34 and described above.

Example 13

Characterization of IkB and its Complex with NF-kB

The flow-through fraction from the DNA-cellulose column (1.55 mg of protein in 250 µl described in Example 4) was subjected to a G-200 Sephadex column (280 by 7 mm) with a flow rate of 0.15 ml/min in buffer G at room temperature. A mix of size markers (dextran blue; immunoglobulin G, 158 kDa, BSA, 67 kDa, ovalbumin, 45 kDa, myoglobin, 17 kDa; Biorad) was run separately on the column prior to sample runs. Markers were detected in fractions by their color and using SDS-polyacrylamide gel electrophoresis (SDS-PAGE) followed by Coomassie Blue staining.

To detect inhibiting activity, portions of fractions (5 µl; in buffer G) were mixed with 1 µl of nuclear extracts [in buffer D(+)] and 0.5 µl 10% NP-40. Dignam, J. P. et al., *Nucl. Acids Res.*, 11:1475 (1983). After 30 minutes at room temperature, the reaction volume was brought to 20 µl by the addition of a DNA binding reaction mixture containing 3.2 µg of poly(dI-dC) (Pharmacia), 5 to 20 fmoles of $^{32}$P-end labeled k enhancer fragment, 75 mM NaCl, 15 mM Tris-HCl (pH 7.5), 1.5 mM EDTA, 1.5 mM DTT, 7.5% glycerol, 0.3% NP-40 and 20 µg BSA. After a 20-minute DNA binding reaction, samples were analyzed by EMSA.

Gel filtration fractions containing IkB (25 µg of protein) were incubated for 1 hour at room temperature in buffer G without any addition or with 2 µg of TPCK-treated trypsin (Sigma), 8 µg of BPTI (Sigma), or with 2 µg of trypsin that had been incubated with 8 µg of BPTI. Tryptic digestion was stopped by a 10-minute incubation with 8 µg of BPTI and samples analyzed as described above.

Nuclear extract from TPA-stimulated 70Z/3 cells and cytosol from untreated cells (both 220 µg of protein) were sedimented through 5 ml of a continuous 10 to 30% glycerol gradient in buffer D(+) and 150,000 g (SW 50.1 rotor; Beckman) for 20 hours at 4° C. Cosedimented size markers were detected in fractions by SDS-PAGE and Coomassie Blue staining. Portions of glycerol gradient fractions (4 µl) were analyzed by EMSA with 10 µg of BSA as carrier and 0.5 µg of poly(dI-dC). NF-kB precursor was activated by treating 4 µl of fractions with 1.5 µl of formamide before the DNA binding reaction mixture was added.

Example 14

Demonstration of the Presence of the NF-kB—IkB Complex in Enucleated Cells

HeLa cells were grown in Eagle's Minimum Essential Medium supplemented with 10% horse serum, penicillin (50 I.U./ml) and streptomycin (50 µg/ml) (referred to as MEM-medium) on discs (1.8 cm in diameter) cut from cell culture plastic ware. For enucleation, discs were placed upside down into centrifuge tubes filled with 10 ml of MEM-medium of 37° C. containing cytochalasin B (10 µg/ml) and held for the same time in the incubator. To estimate the enucleation efficiency, enucleated cells on one disc were fixed with formaldehyde (3.7%) in phosphate-buffered saline (PBS) for 20 minutes, stained for 4 minutes with 4',6-diamidino-2-phenylindole (DAPI, 1 µg/ml; Sigma) in PBS, and washed in PBS. Fluorescence microscopy under UV light and phase contrast microscopy were performed with a Zeiss Photomicroscope III. Control and enucleated cells were allowed to recover in cytochalasin B-free MEM-medium for 30 minutes before a 2-hour incubation in the absence or presence of TPA (50 ng/ml). Cells were then washed in ice-cold PBS, scraped off the discs in 100 µl of a buffer containing 20 mM HEPES (pH 7.9), 0.35M NaCl, 20% glycerol, 1% NP-40, 1 mM MgCl$_2$, 1 mM DTT, 0.5 mM EDTA, 0.1 mM EGTA, 1% aprotinin (Sigma) and 1 mM PMSF. After lysis and extraction for 10 minutes on ice, particulate material was removed by centrifugation (Microfuge) for 15 minutes at 4° C. and the resulting supernatants were analyzed by EMSA.

Example 15

Demonstration of the Role of NF-KB as Mediator in Regulation of a Gene in Non-Lymphoid Cells The following demonstrates that NF-κB has the role of mediator in cytokine gene regulation (in this case, positive regulation of β-IFN gene expression). NF-κB has been shown to interact with a virus-inducible element (PRDII) in the β-IFN gene and to be highly induced by either virus infection or treatment of cells with double-standard RNA.

A. Experimental Procedure

Cell Culture and Transfection

Mouse L929 fibroblasts were maintained in MEM medium (Gibco) with 5% serum (Gibco). Jurkat (human T lymphocytes), Namalwa (human Burkitt lymphoma), S194 (mouse myeloma), and 70Z/3 (mouse pre-B lymphocyte) cells were grown in RPMI 1640 medium supplemented with 10% fetal calf serum (Life Science) and 50 µM β-mercaptoethanol. Sendai virus (SPAFAS) or poly(rI:rC) (Pharmacia) inductions were either 6 hours in length for protein extracts (Zinn et al., *Cell*, 34:865–879 (1983)) or 12 hours for transfections. Phorbol myristate acetate (Sigma) and phytohemagglutinin (PHA) induction was carried out as described by Sen, R. and D. Baltimore (*Cell*, 47:921–928 (1986)).

Transient transfections of L929 cells were performed according to Kuhl et al., *Cell,* 50:1057–1069 (1987); and for S194 cells, according to Pierce et al., *Proc. Natl. Acad. Sci. USA,* 85:1482–1486 (1988). A β-galactosidse (β-gal) expression plasmid (Edlund et al., *Science,* 230:912–916 (1985)) was co-transfected to monitor the transfection efficiency. CAT assays were described by Gorman et al., *Mol. Cell. Biol.,* 2:1044–1051 (1982), and the amount of protein assayed was normalized to a constant amount of β-gal activity. An et al., *Mol. Cell. Biol.,* 2:1628–1632 (1982).

Plasmid Constructions

The plasmids p-41βCAT (-41β), p-41PII4r (-41β(P)$_4$), and p-41PII2r (-41β(P)$_2$) were constructed as follows: in Fan, C. M. and T. Maniatis, *EMBO J.,* in press (1989). The nucleotide sequence of the PRDII×2 (PRDII$_2$) is 5'-GATCTGTGGGAAATTCCGTGGGAAATTCCGGATC-3'. The construction of Δ56 (c-fosCAT), Δ56(B)$_2$ (J16), and Δ56(B⁻) (J32) were described by Pierce et al., *Proc. Natl. Acad. Sci. USA,* 85:1482–1486 (1988). The κB oligonucleotides were: Wild-type: 5'-TCGACAGAGGGGACTTTCCGAGAGGCTCGA-3' and mutant: 5'-TCGACAGAATTCACTTTCCAGGAGGCTCGA-3'. The IRE was isolated as a BglII-BamHI fragment (Goodbourn et al., *Cell,* 45:601–610 (1986)) and cloned into pSP73. Mutant PRDII sites were described in Goodbourn, S. and T. Maniatis, *Proc. Natl. Acad. Sci. USA,* 85:1447–1451 (1988).

Preparation of Subcellular Protein Fractions and Mobility Shift Electrophoresis

Buffers A, C and D are those described by Dignam et al., *Nucl. Acids Res.,* 11:1475–1489 (1983). Frozen pellets containing from $1 \times 10^6$ to $1 \times 10^7$ cells were thawed in the presence of an equal volume of buffer A. The suspension was mixed using 10 strokes of a Dounce homogenizer and the nuclei were pelleted for 20 minutes at 4° in a microcentrifuge. The supernatant, termed cytosol, was ultracentrifuged for 1 hour at 100,000×g and adjusted to 20% glycerol, 10 mM HEPES, pH 7.9, 1 mM EDTA, and 0.1 M KCl. The nuclei were extracted with 2 volumes of the buffer C for 20 minutes and the nuclear extract was cleared by centrifugation and dialyzed against buffer D. To minimize proteolysis, all buffers included 0.5 mM PMSF, 0.3 μg/ml leupeptin, and 0.3 μg/ml antipain and buffers A and C included 0.3 TIU/ml aprotinin, 0.5 mg/ml benzamidine, 0.1 μg/ml chymostatin, and 0.7 μg/ml pepstatin.

Binding assays were carried out as described in Lenardo et al., *Science,* 236:1573–1577 (1987) and Lenardo et al., *Proc. Natl. Acad. Sci. USA,* 85:8825–8829 (1988). Assay samples of 20 μl contained nuclear extract incubated with 0.25 ng $^{32}$P-labeled DNA fragment (5,000 CPM), 10 mM Tris:Cl, pH 7.5, 1 mM dithiothreitol, 1 mM EDTA, 0.5 mM MgCl$_2$, 3 mM GTP (omitted in experiments varying amounts of added GTP), 2 μg poly(dI-dC), and 5% glycerol for 20 minutes at room temperature. Cytosol was activated in vitro using 0.8% sodium deoxycholate followed by addition of the binding mixture including 0.75% NP-40. Methylation interference assays were performed using the procedure of Gilman et al., *Mol. Cell. Biol.,* 6:4305–4316 (1986).

RNA Analysis

RNA preparation and Northern blot analysis were carried out as previously described by Zinn et al., *Cell,* 34, 865–879 (1983).

B. Results

NF-κB binds specifically to PRDII

Figure 39:
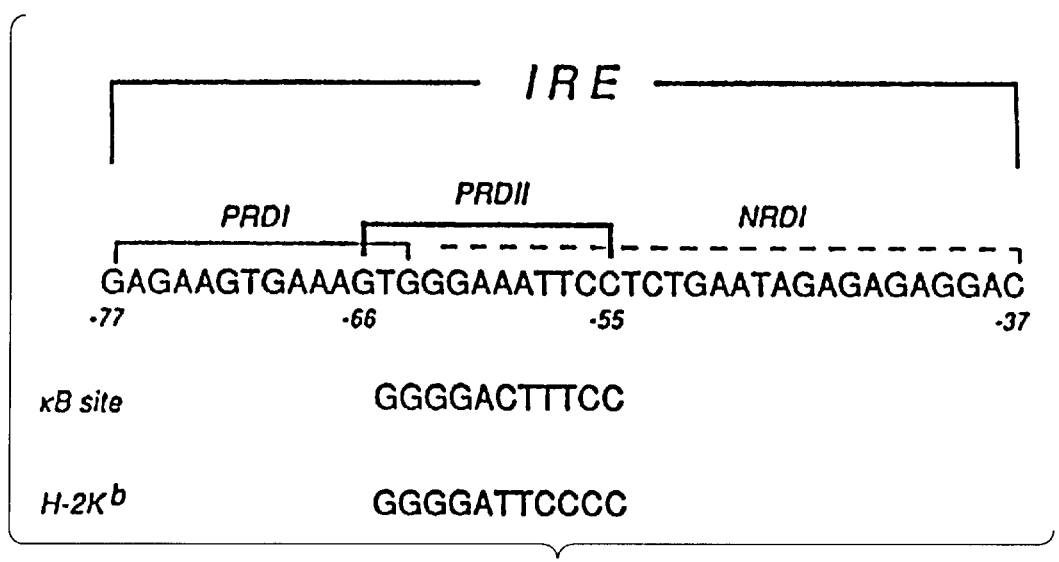
FIG. 39 is a diagram showing the location of positive regulatory domain II (PRDII) within the interferon gene regulatory element (IRE) and a comparison of the nucleotide sequences of the PRDII site, κB site, and the H2TF1 site.

The protein encoded by the PRDII-BF1 cDNA binds to the PRDII site and to the H2-K$^b$ and κB binding sites (FIG. 39, Singh et al., *Cell,* 52:415–423 (1988); Fan and Maniatis, unpublished). Thus, the ability of NF-κB to bind to PRDII and to the κB site was compared, using an electrophoretic mobility shift assay. Fried, M. and Crothers, D. M., *Nucleic Acid Res.,* 9:6505–6525 (1981). NF-κB is present in the human T lymphocytic line Jurkat in an inactive form, but its binding is inducible by phorbol myristate acetate (PMA) and phytohemagglutinin (PHA). Sen, R. and D. Baltimore, *Cell,* 47:921–928 (1986); and Nabel, G. and D. Baltimore, *Nature,* 326:711–713 (1987). The entire interferon gene regulatory element (IRE) or an oligonucleotide comprised of two copies of the PRDII sequences (PRDII$_2$ or (P)$_2$) was used. A complex with PMA/PHA-induced Jurkat nuclear extracts that migrated identically to that formed with the κB site was detected. It was assumed that the additional slower migrating complex observed with the PRDII$_2$ oligonucleotide corresponds to DNA molecules in which both of the PRDII sites are bound to protein. Specific κB complexes were undetectable in extracts from unstimulated Jurkat cells.

To determine whether the same protein binds to PRDII and κB, competition experiments were carried out. Increasing amounts of unlabeled κB oligonucleotide inhibited complex formation with either the IRE or the κB site. The ability of PRDII and κB to compete for NF-κB binding was also reciprocal; an unlabeled fragment prevented complex formation with either labeled fragment. Quantitatively, both sites competed equally for NF-κB. Furthermore, the IRE and the κB sites both formed an identical complex using cytosol from unstimulated Jurkat cells after treatment with the detergent deoxycholate. This observation is in agreement with the finding that NF-κB binding activity can be unmasked in cytosolic extracts by deoxycholate. Baeuerle, P. and D. Baltimore, *Cell,* 53:211–217 (1988).

A number of single base mutations in PRDII decrease the level of virus induction of the β-IFN gene. Goodbourn, S. and T. Maniatis, *Proc. Natl. Acad. Sci. USA,* 85:1447–1451 (1988). Therefore, these mutations were examined to assess whether they also affect in vitro binding to NF-κB. Four point mutations that impair inducibility of the β-IFN gene were shown to reduce binding of NF-κB. (64G→A, 62G→A, 60A→G and 56C→T). A single point mutation that has no effect on inducibility allows specific NF-κB binding (65T→C). Taken together, these results strongly suggest the NF-κB plays a direct role in β-IFN gene regulation.

The in Vivo Activities of PRDIII and the κB Site are Indistinguishable

Figure 41A:
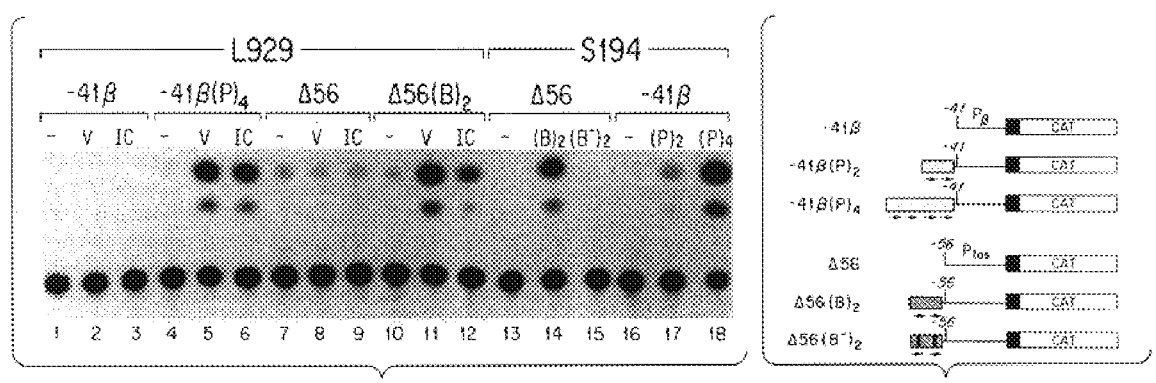
FIGS. 41A–41B demonstrate the functional interchangeability of PRDII and NF-κB in vivo.
Figure 41B:
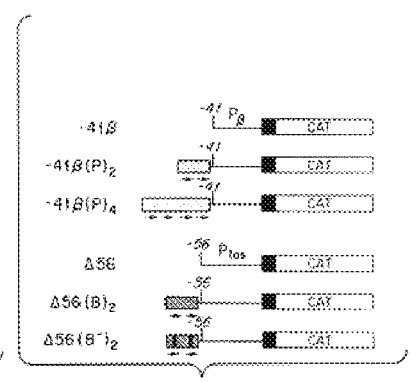
Figure 42A:
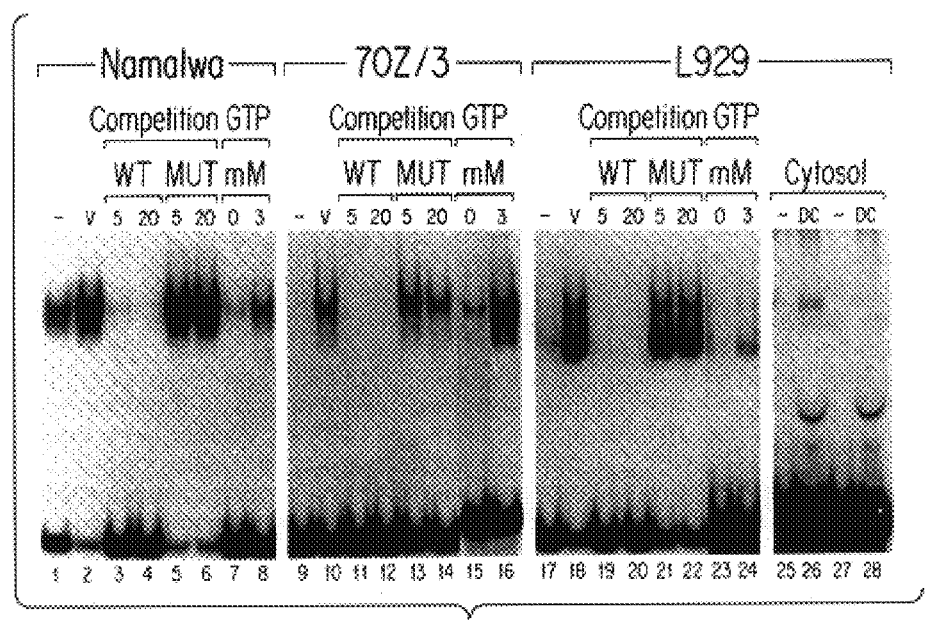
FIGS. 42A–42C demonstrate that virus infection activates binding of NF-κB and gene expression in B lymphocytes and fibroblasts.
Figure 42B:
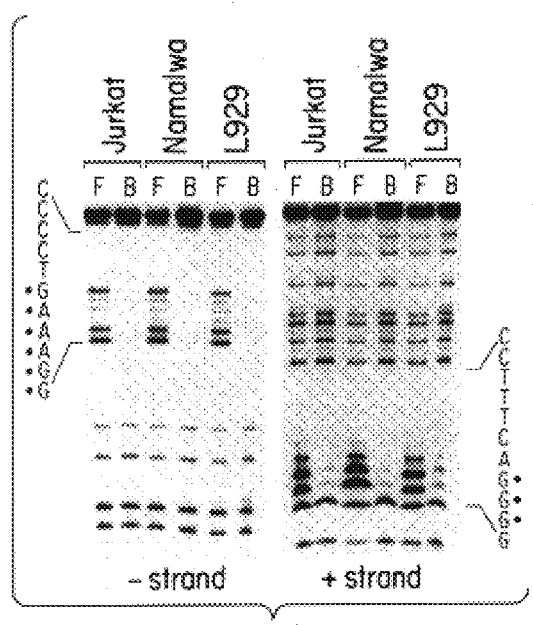
Figure 42C:
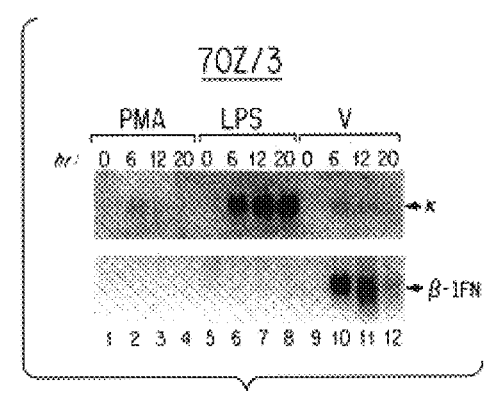

To determine whether the PRDII and κB sites function similarly in vivo, we compared their transcriptional activities were compared, using chloramphenicol acetyltransferase gene (CAT) reporter plasmids in virus-induced mouse L929 fibroblasts and in S194 mouse myeloma cells. The structures of the reporter genes are illustrated in FIG. 41B. The -41 β-globin/CAT gene was not expressed in L929 cells before or after induction by inactivated Sendai virus or poly(rI:rC) (FIG. 41A, lanes 1–3). However, the reporter gene linked to four copies of PRDII (-41β(P)$_4$) was highly inducible (FIG. 41A, lanes 4–6). Remarkably, two tandemly-repeated κB sites also conferred virus and poly (rI:rC) inducibility on a c-fos promoter/CAT fusion gene in L929 cells (FIG. 41A, compare lanes 7–9 to 10–12). Mutations in the κB site that eliminated binding of NF-κB also abolished virus inducibility. Thus, in L929 cells, the same inducible factor may interact with PRDII and the κB site to stimulate transcription.

Figure 40A:
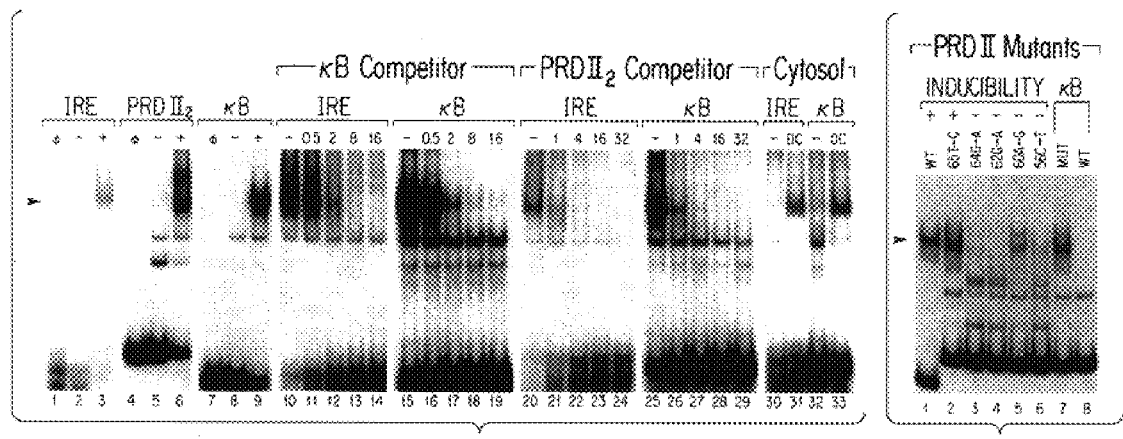
FIGS. 40A–40B show the results of assays demonstrating that NF-κB binds to PRDII in vitro.
Figure 40B:
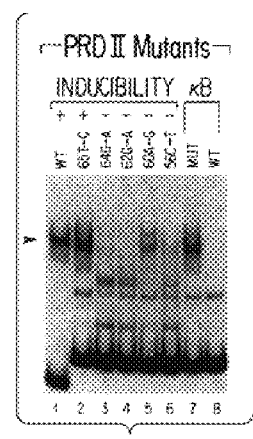

The B-cell specific activities of PRDII and the κB site were compared by transfecting the reporter enes into S194 mouse myeloma cells. As previously demonstrated, wild-type, but not mutant, κB sites were highly active in mature B-cells which constitutively express NF-κB (FIG. 40A, lanes 13–15; Pierce et al., *Proc. Natl. Acad. Sci. USA*, 85:1482–1486 (1988)). Significantly, multiple PRDII elements were also highly active in S194 cells (lanes 16–18). These results further suggest that the same factor, NF-κB, interacts productively with PRDII and the κB site.

Virus Induction Stimulates NF-κB Binding in Lymphoid and Non-lymphoid Cells

The ability of PRDII to bind NF-κB suggested that virus infection might activate NF-κB. Therefore, nuclear extracts prepared from cells before and after virus induction were analyzed. NF-κB binding activity was virus-inducible in Namalwa human mature B lymphocytes, 70Z/3 murine pre-B lymphocytes, and murine L929 fibroblasts. Virus Induction of NF-κB in Namalwa cells was unexpected because these cells display significant constitutive NF-κB binding activity in the nucleus. Thus, only a fraction of the NF-κB in Namalwa cells is in the active state, and the remaining molecules can be activated by virus. Virus-induced complexes in all three cell types appeared to contain NF-κB because they could be eliminated by competition with wild-type (WT) but not mutant (MUT) κB sites. Moreover, complex formation could be stimulated by GTP, a biochemical property of NF-κB. Lenardo et al., *Proc. Natl. Acad. Sci. USA*, 85:8825–8829 (1988). The NF-κB complex was also induced by poly(rI:rC) in 70Z/3 cells, but the effect was less dramatic.

Additional evidence that the virus-induced complexes contain NF-κB was provided by comparisons of the methylation interference patterns of the virus-induced complexes from Namalwa and L929 cells with the PMA/PHA-induced complex in Jurkat cells. All of the interference patterns were identical and exhibited the close base contacts that are distinctive of the interaction between NF-κB and its cognate binding site in the κ enhancer. Sen, R. and D. Baltimore, *Cell*, 46:705–716 (1986); and Baldwin, A. S. and P. A. Sharp, *Mol. Cell. Biol.*, 7:305–313 (1988). Finally, the level of NF-κB revealed by deoxycholate in the cytosol of L929 cells was diminished after virus induction. Therefore, like phorbol ester treatment, virus infection apparently releases NF-κB from an active cytosolic form and allows translocation to the nucleus. Baeuerle, P. and D. Baltimore, *Cell*, 53:211–217 (1988).

Endogenous β-IFN and Ig Kappa Gene Expression are Activated by Virus in Pre-B Lymphocytes As shown above, virus infection dramatically increased the levels of nuclear NF-κB and induced reporter genes containing PRDII or κB sites. Therefore, the ability of virus to induce the transcription of an endogenous κ gene was also assessed. The pre-B cell line 70Z/3, which produces cytoplasmic Ig μ heavy chains, but not light chains, was used for this purpose. Paige et al., *J. Immunol.*, 121:641–647 (1978). The κ gene in 70Z/3 cells is functionally rearranged and can be transcriptionally induced by lipopolysaccharide (LPS) and phorbol myristate acetate (PMA), conditions which powerfully induce NF-κB. Nelson et al., *Nucl. Acids Res.*, 12: 1911–1923 (1984); Rosoff and Cantley, *J. Biol. Chem.*, 259:7056–7060 (1985); and Sen, R. and D. Baltimore, *Cell*, 47:921–928 (1986). As expected, treatment of 70Z/3 cells with phorbol esters or, more strikingly, with LPS resulted in the activation of the endogenous κ gene. Surprisingly, virus infection also induced κ gene expression to a level comparable to that observed with PMA induction. Under the same conditions, endogenous β-IFN mRNA was induced by virus, but not by PMA or LPS. Thus, NF-κB is necessary and sufficient for expression of the endogenous κ gene in 70Z/3 cells, but not for the β-IFN gene. These results indicate the virus-induced complex has all the in vitro binding properties and in vivo transcriptional properties of NF-κB.

EQUIVALENTS

Those skilled in the art will recognize or be able to ascertain, using no more than routine experimentation, many equivalents of the specific embodiments of the invention described therein. Such equivalents are intended to be encompassed by the following claims.

What is claimed is:

1. A method for inhibiting expression, in a eukaryotic cell, of a gene whose transcription is regulated by NF-κKB, the method comprising reducing NF-κKB activity in the cell such that expression of said gene is inhibited.

2. A method for selectively inhibiting expression, in a eukaryotic cell, of genes whose transcription is regulated by NF-κB, the method comprising reducing NF-κB activity in the cell such that expression of said genes is inhibited.

3. A method for reducing the level of expression of a viral gene whose transcription is regulated by NF-κB in a eukaryotic cell, the method comprising reducing NF-κB activity in the cell such that expression of said viral gene is reduced.

4. The method of claim 3, wherein the viral gene is a cytomegalovirus (CMV), human immunodeficiency virus (HIV) or simian virus 40 (SV40) gene.

5. A method for reducing the level of expression of a cytokine gene whose transcription is regulated by NF-κB in a eukaryotic cell comprising reducing NF-κB activity in the cell such that expression of said cytokine gene is reduced.

6. A method for diminishing induced NF-κB-mediated intracellular signaling comprising reducing NF-κB activity in cells such that NF-κB-mediated intracellular signaling is diminished.

7. A method for modifying effects of external influences on a eukaryotic cell, which external influences induce NF-κB-mediated intracellular signaling, the method comprising altering NF-κB activity in the cells such that NF-κB-mediated effects of external influences are modified.

8. The method of claim 7, wherein NF-κB activity in the cell is reduced.

9. A method for reducing, in eukaryotic cells, the level of expression of genes which are activated by extracellular influences which induce NF-κB-mediated intracellular signaling, the method comprising reducing NF-κB activity in the cells such that expression of said genes is reduced.

10. A method for reducing the effects of bacterial infection on mammalian cells comprising reducing NF-κB activity in mammalian cells so as to reduce bacterial lipopolysaccharide-induced gene expression in the mammalian cells.

11. A method for reducing the effects of viral infection on mammalian cells comprising reducing NF-κB activity in mammalian cells so as to reduce virus-mediated gene expression in the mammalian cells.

12. A method for reducing the effects of bacterial infection on mammalian immune cells comprising reducing NF-κB activity in mammalian immune cells so as to reduce bacterial lipopolysaccharide-mediated stimulation of the immune cells.

13. A method for reducing the effects of bacterial lipopolysaccharide on mammalian cells comprising reducing NF-κB activity in the cells so as to reduce bacterial lipopolysaccharide-induced gene expression in the cells.

14. A method for reducing bacterial lipopolysaccharide-induced expression of cytokines in mammalian cells, which method comprises reducing NF-κB activity in the cells so as to reduce bacterial lipopolysaccharide-induced expression of said cytokines in the cells.

15. A method for reducing bacterial lipopolysaccharide-induced expression of Tumor Necrosis Factor-α in mammalian cells, which method comprises reducing NF-κB activity in the cells so as to reduce bacterial lipopolysaccharide-induced expression of Tumor Necrosis Factor-α in the cells.

16. A method for reducing bacterial lipopolysaccharide-mediated stimulation of immune cells, which method comprises reducing NF-κB activity in the cells so as to reduce bacterial lipopolysaccharide-mediated stimulation of the immune cells.

17. A method for reducing bacterial-induced NF-κB signaling in cells, which method comprises reducing NF-κB activity in the cells so as to reduce bacterial-induced NF-κB signaling in the cells.

18. A method for reducing Interleukin-1 or Tumor Necrosis Factor-α activity in mammalian cells comprising reducing NF-κB activity in the cells so as to reduce intracellular signaling caused by Interleukin-1 or Tumor Necrosis Factor-α in the cells.

19. A method for reducing bacterial lipopolysaccharide-induced nuclear translocation of NF-κB in eukaryotic cells comprising inhibiting one or more of: (a) modification of an IκB protein which reduces binding to NF-κB, (b) degradation of an IκB protein, or (c) dissociation of NF-κB-IκB complexes so as to reduce nuclear translocation of NF-κB in the cells.

20. The method of claim 1 wherein NF-κB activity is reduced by decreasing the level of NF-κB not bound in an NF-κB:IκB complex.

21. The method of claim 1 wherein NF-κB activity is reduced by inhibiting the passage of NF-κB into the nucleus of cells.

22. The method of claim 1, wherein NF-κB activity is reduced by inhibiting modification of an IκB protein, which modification otherwise reduces IκB binding to NF-κB.

23. The method of claim 1, wherein NF-κB activity is reduced by inhibiting degradation of an IκB protein.

24. The method of claim 1, wherein NF-κB activity is reduced by inhibiting dissociation of NF-κB:IκB complexes.

25. The method of claim 1 wherein reducing NF-κB activity comprises reducing binding of NF-κB to NF-κB recognition sites on genes which are transcriptionally regulated by NF-κB.

26. The method of claim 1, carried out on mammalian cells.

27. The method of claim 1, carried out on human cells.

28. The method of claim 26 or 27, carried out on immune cells.

29. The-method of claim 26 or 27 carried out on lymphoid cells.

30. The method of claim 26 or 27, carried out on liver cells.

31. The method of claim 2 wherein NF-κB activity is reduced by decreasing the level of NF-κB not bound in an NF-κB:IκB complex.

32. The method of claim 2 wherein NF-κB activity is reduced by inhibiting the passage of NF-κB into the nucleus of cells.

33. The method of claim 2, wherein NF-κB activity is reduced by inhibiting modification of an I-κB protein, which modification otherwise reduces IκB binding to NF-κB.

34. The method of claim 2, wherein NF-κB activity is reduced by inhibiting degradation of an IκB protein.

35. The method of claim 2, wherein NF-κB activity is reduced by inhibiting dissociation of NF-κB:IκB complexes.

36. The method of claim 2 wherein reducing NF-κB activity comprises reducing binding of NF-κB to NF-κB recognition sites on genes which are transcriptionally regulated by NF-κB.

37. The method of claim 2, carried out on mammalian cells.

38. The method of claim 2, carried out on human cells.

39. The method of claim 37 or 38, carried out on immune cells.

40. The method of claim 37 or 38, carried out on lymphoid cells.

41. The method of claim 37 or 38, carried out on liver cells.

42. The method of claim 3 wherein NF-κB activity is reduced by decreasing the level of NF-κB not bound in an NF-κB:IκB complex.

43. The method of claim 3 wherein NF-κB activity is reduced by inhibiting the passage of NF-κB into the nucleus of cells.

44. The method of claim 3, wherein NF-κB activity is reduced by inhibiting modification of an I-κB protein, which modification otherwise reduces IκB binding to NF-κB.

45. The method of claim 3, wherein NF-κB activity is reduced by inhibiting degradation of an IκB protein.

46. The method of claim 3, wherein NF-κB activity is reduced by inhibiting dissociation of NF-κB:IκB complexes.

47. The method of claim 3 wherein reducing NF-κB activity comprises reducing binding of NF-κB to NF-κB recognition sites on genes which are transcriptionally regulated by NF-κB.

48. The method of claim 3, carried out on mammalian cells.

49. The method of claim 3, carried out on human cells.

50. The method of claim 48 or 49, carried out on immune cells.

51. The method of claim 48 or 49, carried out on lymphoid cells.

52. The method of claim 48 or 49, carried out on liver cells.

53. The method of claim 5 wherein NF-κB activity is reduced by decreasing the level of NF-κB not bound in an NF-κB:IκB complex.

54. The method of claim 5 wherein NF-κB activity is reduced by inhibiting the passage of NF-κB into the nucleus of cells.

55. The method of claim 5, wherein NF-κB activity is reduced by inhibiting modification of an IκB protein, which modification otherwise reduces IκB binding to NF-κB.

56. The method of claim 5, wherein NF-κB activity is reduced by inhibiting degradation of an IκB protein.

57. The method of claim 5, wherein NF-κB activity is reduced by inhibiting dissociation of NF-κB:IκB complexes.

58. The method of claim 5 wherein reducing NF-κB activity comprises reducing binding of NF-κB to NF-κB recognition sites on genes which are transcriptionally regulated by NF-κB.

59. The method of claim 5, carried out on mammalian cells.

60. The method of claim 5, carried out on human cells.

61. The method of claim 59 or 60, carried out on immune cells.

62. The method of claim 59 or 60, carried out on lymphoid cells.

63. The method of claim 59 or 60, carried out on liver cells.

64. The method of claim 6 wherein NF-κB activity is reduced by decreasing the level of NF-κB not bound in an NF-κB:IκB complex.

65. The method of claim 6 wherein NF-κB activity is reduced by inhibiting the passage of NF-κB into the nucleus of cells.

66. The method of claim 6, wherein NF-κB activity is reduced by inhibiting modification of an IκB protein, which modification otherwise reduces IκB binding to NF-κB.

67. The method of claim 6, wherein NF-κB activity is reduced by inhibiting degradation of an IκB protein.

68. The method of claim 6, wherein NF-κB activity is reduced by inhibiting dissociation of NF-κB:IκB complexes.

69. The method of claim 6 wherein reducing NF-κB activity comprises reducing binding of NF-κB to NF-κB recognition sites on genes which are transcriptionally regulated by NF-κB.

70. The method of claim 6, carried out on mammalian cells.

71. The method of claim 6, carried out on human cells.

72. The method of claim 70 or 71, carried out on immune cells.

73. The method of claim 70 or 71, carried out on lymphoid cells.

74. The method of claim 70 or 71, carried out on liver cells.

75. The method of claim 8 wherein NF-κB activity is reduced by decreasing the level of NF-κB not bound in an NF-κB:IκB complex.

76. The method of claim 8 wherein NF-κKB activity is reduced by inhibiting the passage of NF-κB into the nucleus of cells.

77. The method of claim 8, wherein NF-κB activity is reduced by inhibiting modification of an IκB protein, which modification otherwise reduces IκB binding to NF-κB.

78. The method of claim 8, wherein NF-κB activity is reduced by inhibiting degradation of an IκB protein.

79. The method of claim 8, wherein NF-κB activity is reduced by inhibiting dissociation of NF-κB:IκB complexes.

80. The method of claim 8 wherein reducing NF-κB activity comprises reducing binding of NF-κB to NF-κB recognition sites on genes which are transcriptionally regulated by NF-κB.

81. The method of claim 7, carried out on mammalian cells.

82. The method of claim 8, carried out on mammalian cells.

83. The method of claim 7, carried out on human cells.

84. The method of claim 8, carried out on human cells.

85. The method of any of claims 81–84, carried out on immune cells.

86. The method of any of claims 81–84, carried out on lymphoid cells.

87. The method of any of claims 81–84, carried out on liver cells.

88. The method of claim 9 wherein NF-κB activity is reduced by decreasing the level of NF-κB not bound in an NF-κB:IκB complex.

89. The method of claim 9 wherein NF-κB activity is reduced by inhibiting the passage of NF-κB into the nucleus of cells.

90. The method of claim 9, wherein NF-κB activity is reduced by inhibiting modification of an IκB protein, which modification otherwise reduces IκB binding to NF-κB.

91. The method of claim 9, wherein NF-κB activity is reduced by inhibiting degradation of an IκB protein.

92. The method of claim 9, wherein NF-κB activity is reduced by inhibiting dissociation of NF-κB:IκB complexes.

93. The method of claim 9 wherein reducing NF-κB activity comprises reducing binding of NF-κB to NF-κB recognition sites on genes which are transcriptionally regulated by NF-κB.

94. The method of claim 9, carried out on mammalian cells.

95. The method of claim 9, carried out on human cells.

96. The method of claim 94 or 95, carried out on immune cells.

97. The method of claim 94 or 95, carried out on lymphoid cells.

98. The method of claim 94 or 95, carried out on liver cells.

99. The method of claim 10 wherein NF-κB activity is reduced by decreasing the level of NF-κB not bound in an NF-κB:IκB complex.

100. The method of claim 10 wherein NF-κB activity is reduced by inhibiting the passage of NF-κB into the nucleus of cells.

101. The method of claim 10, wherein NF-κB activity is reduced by inhibiting modification of an IκB protein, which modification otherwise reduces IκB binding to NF-κB.

102. The method of claim 10, wherein NF-κB activity is reduced by inhibiting degradation of an IκB protein.

103. The method of claim 10, wherein NF-κB activity is reduced by inhibiting dissociation of NF-κB:IκB complexes.

104. The method of claim 10 wherein reducing NF-κB activity comprises reducing binding of NF-κB to NF-κB recognition sites on genes which are transcriptionally regulated by NF-κB.

105. The method of claim 10, carried out on human cells.

106. The method of claim 11, carried out on immune cells.

107. The method of claim 11, carried out on lymphoid cells.

108. The method of claim 11, carried out on liver cells.

109. The method of claim 11 wherein NF-κB activity is reduced by decreasing the level of NF-κB not bound in an NF-κB:IκB complex.

110. The method of claim 11 wherein NF-κB activity is reduced by inhibiting the passage of NF-κB into the nucleus of cells.

111. The method of claim 11, wherein NF-κB activity is reduced by inhibiting modification of an IκB protein, which modification otherwise reduces IκB binding to NF-κB.

112. The method of claim 11, wherein NF-κB activity is reduced by inhibiting degradation of an IκB protein.

113. The method of claim 11, wherein NF-κB activity is reduced by inhibiting dissociation of NF-κB:IκB complexes.

114. The method of claim 11 wherein reducing NF-κB activity comprises reducing binding of NF-κB to NF-κB recognition sites on genes which are transcriptionally regulated by NF-κB.

115. The method of claim 11, carried out on human cells.

116. The method of claim 11 or 115, carried out on immune cells.

117. The method of claim 11 or 115, carried out on lymphoid cells.

118. The method of claim 11 or 115, carried out on liver cells.

119. The method of claim 12 wherein NF-κB activity is reduced by decreasing the level of NF-κB not bound in an NF-κB:IκB complex.

120. The method of claim 12 wherein NF-κB activity is reduced by inhibiting the passage of NF-κB into the nucleus of cells.

121. The method of claim 12, wherein NF-κB activity is reduced by inhibiting modification of an IκB protein, which modification otherwise reduces IκB binding to NF-κB.

122. The method of claim 12, wherein NF-κB activity is reduced by inhibiting degradation of an IκB protein.

123. The method of claim 12, wherein NF-κB activity is reduced by inhibiting dissociation of NF-κB:IκB complexes.

124. The method of claim 12 wherein reducing NF-κB activity comprises reducing binding of NF-κB to NF-κB recognition sites on genes which are transcriptionally regulated by NF-κB.

125. The method of claim 12, carried out on human immune cells.

126. The method of claim 12, carried out on lymphoid cells.

127. The method of claim 125, carried out on lymphoid cells.

128. The method of claim 13 wherein NF-κB activity is reduced by decreasing the level of NF-κB not bound in an NF-κB:IκB complex.

129. The method of claim 13 wherein NF-κB activity is reduced by inhibiting the passage of NF-κB into the nucleus of cells.

130. The method of claim 13, wherein NF-κB activity is reduced by inhibiting modification of an IκB protein, which modification otherwise reduces IκB binding to NF-κB.

131. the method of claim 13, wherein NF-κB activity is reduced by inhibiting degradation of an IκB protein.

132. The method of claim 13, wherein NF-κB activity is reduced by inhibiting dissociation of NF-κB:IκB complexes.

133. The method of claim 13 wherein reducing NF-κB activity comprises reducing binding of NF-κB to NF-κB recognition sites on genes which are transcriptionally regulated by NF-κB.

134. The method of claim 13, carried out on human cells.

135. The method of claim 13, carried out on immune cells.

136. The method of claim 134, carried out on immune cells.

137. The method of claim 13 or 134, carried out on lymphoid cells.

138. The method of claim 13 or 134, carried out on liver cells.

139. The method of claim 14 wherein NF-κB activity is reduced by decreasing the level of NF-κB not bound in an NF-κB:IκB complex.

140. The method of claim 14 wherein NF-κB activity is reduced by inhibiting the passage of NF-κB into the nucleus of cells.

141. The method of claim 14, wherein NF-κB activity is reduced by inhibiting modification of an IκB protein, which modification otherwise reduces IκB binding to NF-κB.

142. The method of claim 14, wherein NF-κB activity is reduced by inhibiting degradation of an IκB protein.

143. The method of claim 14, wherein NF-κB activity is reduced by inhibiting dissociation of NF-κB:IκB complexes.

144. The method of claim 14 wherein reducing NF-κB activity comprises reducing binding of NF-κB to NF-κB recognition sites on genes which are transcriptionally regulated by NF-κB.

145. The method of claim 14, carried out on human cells.

146. The method of claim 14 or 145, carried out on immune cells.

147. The method of claim 14 or 145, carried out on lymphoid cells.

148. The method of claim 14 or 145, carried out on liver cells.

149. The method of claim 15 wherein NF-κB activity is reduced by decreasing the level of NF-κB not bound in an NF-κB:IκB complex.

150. The method of claim 15 wherein NF-κB activity is reduced by inhibiting the passage of NF-κB into the nucleus of cells.

151. The method of claim 15, wherein NF-κB activity is reduced by inhibiting modification of an IκB protein, which modification otherwise reduces IκB binding to NF-κB.

152. The method of claim 15, wherein NF-κB activity is reduced by inhibiting degradation of an IκB protein.

153. The method of claim 15, wherein NF-κB activity is reduced by inhibiting dissociation of NF-κB:IκB complexes.

154. The method of claim 15 wherein reducing NF-κB activity comprises reducing binding of NF-κB to NF-κB recognition sites on genes which are transcriptionally regulated by NF-κB.

155. The method of claim 15, carried out on human cells.

156. The method of claim 15 of 155, carried out on immune cells.

157. The method of claim 15 or 155, carried out on lymphoid cells.

158. The method of claim 15 or 155, carried out on liver cells.

159. The method of claim 16 wherein NF-κB activity is reduced by decreasing the level of NF-κB not bound in an NF-κB:IκB complex.

160. The method of claim 16 wherein NF-κB activity is reduced by inhibiting the passage of NF-κB into the nucleus of cells.

161. The method of claim 16, wherein NF-κB activity is reduced by inhibiting modification of an IκB protein, which modification otherwise reduces IκB binding to NF-κB.

162. The method of claim 16, wherein NF-κB activity is reduced by inhibiting degradation of an IκB protein.

163. The method of claim 16, wherein NF-κB activity is reduced by inhibiting dissociation of NF-κB:IκB complexes.

164. The method of claim 16 wherein reducing NF-κB activity comprises reducing binding of NF-κB to NF-κB recognition sites on genes which are transcriptionally regulated by NF-κB.

165. The method of claim 16, carried out on human cells.

166. The method of claim 16 or 165, carried out on lymphoid cells.

167. The method of claim 17 wherein NF-κB activity is reduced by decreasing the level of NF-κB not bound in an NF-κB:IκB complex.

168. The method of claim 17 wherein NF-κB activity is reduced by inhibiting the passage of NF-κB into the nucleus of cells.

169. The method of claim 17, wherein NF-κB activity is reduced by inhibiting modification of an IκB protein, which modification otherwise reduces IκB binding to NF-κB.

170. The method of claim 17, wherein NF-κB activity is reduced by inhibiting degradation of an IκB protein.

171. The method of claim 17, wherein NF-κB activity is reduced by inhibiting dissociation of NF-κB:IκB complexes.

172. The method of claim 17 wherein reducing NF-κB activity comprises reducing binding of NF-κB to NF-κB recognition sites on genes which are transcriptionally regulated by NF-κB.

173. The method of claim 17, carried out on human cells.

174. The method of claim 17 or 173, carried out on immune cells.

175. The method of claim 17 or 173, carried out on lymphoid cells.

176. The method of claim 17 or 173, carried out on liver cells.

177. The method of claim 18 wherein NF-κB activity is reduced by decreasing the level of NF-κB not bound in an NF-κB:IκB complex.

178. The method of claim 18 wherein NF-κB activity is reduced by inhibiting the passage of NF-κB into the nucleus of cells.

179. The method of claim 18, wherein NF-κB activity is reduced by inhibiting modification of an IκB protein, which modification otherwise reduces IκB binding to NF-κB.

180. The method of claim 18, wherein NF-κB activity is reduced by inhibiting degradation of an IκB protein.

181. The method of claim 18, wherein NF-κB activity is reduced by inhibiting dissociation of NF-κB:IκB complexes.

182. The method of claim 18 wherein reducing NF-κB activity comprises reducing binding of NF-κB to NF-κB recognition sites on genes which are transcriptionally regulated by NF-κB.

183. The method of claim 18, carried out on human cells.

184. The method of claim 18 or 183, carried out on immune cells.

185. The method of claim 18 or 183, carried out on lymphoid cells.

186. The method of claim 18 or 183, carried out on liver cells.

187. The method of claim 19, carried out on mammalian cells.

188. The method of claim 19, carried out on human cells.

189. The method of claim 187 or 188, carried out on immune cells.

190. The method of claim 187 or 188, carried out on lymphoid cells.

191. The method of claim 193 or 194, carried out on liver cells.

192. The method of claim 4 wherein NF-κB activity is reduced by decreasing the level of NF-κB not bound in an NF-κB:IκB complex.

193. The method of claim 4 wherein NF-κB activity is reduced by inhibiting the passage of NF-κB into the nucleus of cells.

194. The method of claim 4, wherein NF-κB activity is reduced by inhibiting modification of an IκB protein, which modification otherwise reduces IκB binding to NF-κB.

195. The method of claim 4, wherein NF-κB activity is reduced by inhibiting degradation of an IκB protein.

196. The method of claim 4, wherein NF-κB activity is reduced by inhibiting dissociation of NF-κB:IκB complexes.

197. The method of claim 4 wherein reducing NF-κB activity comprises reducing binding of NF-κB to NF-κB recognition sites on genes which are transcriptionally regulated by NF-κB.

198. The method of claim 4, carried out on mammalian cells.

199. The method of claim 4, carried out on human cells.

200. The method of claim 198 or 199, carried out on immune cells.

201. The method of claim 198 or 199, carried out on lymphoid cells.

202. The method of claim 198 or 199, carried out on liver cells.

203. A method of inhibiting expression, in a mammalian cell, of a gene whose transcriptional activity is activated by binding of NF-κB to said gene, comprising introducing a nucleic acid decoy molecule into the cell in an amount sufficient to inhibit expression of the gene, which decoy includes a NF-κB binding site that binds to NF-κB.

\* \* \* \* \*

(12) EX PARTE REEXAMINATION CERTIFICATE (8241st)
United States Patent
Baltimore et al.

(10) Number: US 6,410,516 C1
(45) Certificate Issued: May 17, 2011

(54) NUCLEAR FACTORS ASSOCIATED WITH TRANSCRIPTIONAL REGULATION

(75) Inventors: David Baltimore, New York, NY (US); Ranjan Sen, Cambridge, MA (US); Phillip A. Sharp, Newton, MA (US); Harinder Singh, Chicago, IL (US); Louis Staudt, Silver Springs, MD (US); Jonathan H. Lebowitz, Zionsville, IN (US); Albert S. Baldwin, Jr., Chapel Hill, NC (US); Roger G. Clerc, Binningen (CH); Lynn M. Corcoran, Port Melbourne (AU); Patrick A. Baeuerle, Eichenau (DE); Michael J. Lenardo, Potomac, MD (US); Chen-Ming Fan, San Francisco, MA (US); Thomas P. Maniatis, Belmont, MA (US)

(73) Assignee: Whitehead Institute for Biomedical Research, Cambridge, MA (US)

Reexamination Request:
No. 90/007,503, Apr. 4, 2005
No. 90/007,828, Dec. 2, 2005

Reexamination Certificate for:
Patent No.: 6,410,516
Issued: Jun. 25, 2002
Appl. No.: 08/464,364
Filed: Jun. 5, 1995

Related U.S. Application Data

(60) Division of application No. 08/418,266, filed on Apr. 6, 1995, now Pat. No. 5,804,374, which is a continuation of application No. 07/791,898, filed on Nov. 13, 1991, now abandoned, which is a continuation-in-part of application No. 07/341,436, filed on Apr. 21, 1989, now abandoned, and a continuation-in-part of application No. 07/318,901, filed on Mar. 3, 1989, now abandoned, and a continuation-in-part of application No. 07/280,173, filed on Dec. 5, 1988, now abandoned, and a continuation-in-part of application No. 07/162,680, filed on Mar. 1, 1988, now abandoned, and a continuation-in-part of application No. 07/155,207, filed on Feb. 12, 1988, now abandoned, which is a continuation-in-part of application No. 06/946,365, filed on Dec. 24, 1986, now abandoned, and a continuation-in-part of application No. 06/817,441, filed on Jan. 9, 1986, now abandoned.

(51) Int. Cl.
| | |
|---|---|
| *C07K 14/005* | (2006.01) |
| *C07K 14/435* | (2006.01) |
| *C07K 14/16* | (2006.01) |
| *C07K 14/47* | (2006.01) |
| *C12Q 1/68* | (2006.01) |
| *C12N 15/85* | (2006.01) |
| *G01N 33/68* | (2006.01) |

(52) U.S. Cl. .................. 514/44 R; 435/325; 435/366; 435/370; 435/372; 435/372.2; 435/372.3; 435/455; 435/6

(58) Field of Classification Search ............ None
See application file for complete search history.

(56) References Cited

U.S. PATENT DOCUMENTS

| | | | |
|---|---|---|---|
| 4,418,068 A | 11/1983 | Jones | |
| 4,684,623 A | 8/1987 | Larrick et al. | |
| 4,775,624 A | 10/1988 | Bang et al. | |
| 5,009,889 A | 4/1991 | Taylor, Jr. et al. | |
| 5,393,763 A | 2/1995 | Black et al. | |
| 5,439,923 A | 8/1995 | Cullinan | |
| 5,439,931 A | 8/1995 | Sales | |
| 5,441,966 A | 8/1995 | Dodge | |
| 5,446,053 A | 8/1995 | Keohane | |
| 5,451,589 A | 9/1995 | Dodge | |
| 5,451,590 A | 9/1995 | Dodge | |
| 5,457,117 A | 10/1995 | Black et al. | |
| 5,461,064 A | 10/1995 | Cullinan | |
| 5,462,949 A | 10/1995 | Jones et al. | |
| 5,500,365 A | 3/1996 | Fischhoff et al. | |
| 5,534,526 A | 7/1996 | Cullinan | |
| 5,574,048 A | 11/1996 | Cullinan | |
| 5,593,987 A | 1/1997 | Cullinan et al. | |
| 5,596,004 A | 1/1997 | Dodge | |
| 5,625,136 A | 4/1997 | Koziel et al. | |
| 5,658,803 A | 8/1997 | Kuo | |
| 5,698,419 A | 12/1997 | Wolpe et al. | |
| 5,804,374 A | 9/1998 | Baltimore et al. | |
| 5,811,120 A | 9/1998 | Gibson et al. | |
| 5,939,421 A | 8/1999 | Palanki et al. | |
| 5,972,383 A | 10/1999 | Gibson et al. | |
| 6,060,310 A | 5/2000 | Cho-Chung | |
| 6,150,090 A | 11/2000 | Baltimore et al. | |
| 6,410,516 B1 | 6/2002 | Baltimore et al. | |
| 6,417,198 B1 | 7/2002 | Bryant et al. | |
| 6,489,296 B1 | 12/2002 | Grinnell et al. | |
| 6,545,027 B1 | 4/2003 | Berg et al. | |
| 6,841,371 B2 | 1/2005 | Gerlitz et al. | |
| 7,791,898 B2 | 9/2010 | Peytavy et al. | |
| 2003/0073632 A1 | 4/2003 | Ciaccia et al. | |
| 2007/0207943 A1 | 9/2007 | Ebner et al. | |

FOREIGN PATENT DOCUMENTS

| | | |
|---|---|---|
| WO | 8907614 | 8/1989 |
| WO | 9220795 | 11/1992 |

OTHER PUBLICATIONS

Paine et al. J. Virology 1995, 69(7) :4572–4576.*

Yamamoto et al., Inflamm. Bowel Dis. 11(6) (Jun. 2005) pp. 589–596.*

*Ariad Pharmaceuticals* v. *Dudas*, Civil Action No. 1:06cv679 (U.S. Dist. Ct.: Eastern District of Va: Alexandria): Memorandum of Points and Authorities In Support of Motion To Dismiss Or In the Alternative For Summary Judgement and Opposition to Plaintiff's Motion For Summary Judgement: pp. 1–30.*

Harant et al. Eur. J. Biochem. vol. 250, pp. 63–71 (1997).*

(Continued)

*Primary Examiner*—Evelyn Huang

(57) ABSTRACT

Constitutive and tissue-specific protein factors which bind to transcriptional regulatory elements of Ig genes (promoter and enhancer) are described. The factors were identified and isolated by an improved assay for protein-DNA binding. Genes encoding factors which positively regulate transcription can be isolated and employed to enhance transcription of Ig genes. In particular, NF-κB, the gene encoding NF-κB, IκB and the gene encoding IκB and uses therefor.

OTHER PUBLICATIONS

Stephen G. Kunin, Mark Nagumo, Brian Stanton, Linda S. Therkom, and Stephen Walsh, Reach–Through Claims in the Age of Biotechnology, 51 AM. U.L. REV. 609–638 (2002).*
Roman–Blas M.D. et al., Osteoarthritis and Cartilage, 14 (2006) pp. 839–848.*
Frantz et al. Embo J. 13 (1994) pp. 861–870.*
Meyer et al., FEBS Lett 413 (1997) pp. 354–358.*
Bielinska et al. Science 250 :997 (1990).*
Tanaka et al. Nucleic Acids Res. 22:3069 (1994).*
Eck et al. Mol. Cell. Biol. 6530 (1993).*
Staal et al. Proc Nat'l Acad Sci 87 :9943 (Dec. 1990).*
Schreck et al. J. Exp. Med. 175:1181 (May 1992).*
Baldwin and Sharp, Proc. Nat'l Acad Sci 85:723 (Feb. 1988).*
Schorpp et al. J. Mol. Biol. 202:307 (1988).*
Li et al. Mol. Cell. Biol. 8:432 (1988).*
Hai et al. Cell 54 :1043 (1988).*
Chu et al. Nucleic Acids Res. 15:1311–1326 (1987).*
Molecular Biology of THE CELL, 2nd Ed. (1989) p. 423.*
Griffith et al. Cardiovasc. Surg. 99:952–957 (Dec. 1984).*
Hölschermann et al., Circulation 96:4232–4238 (Dec. 1997).*
Decision issued Apr. 3, 2009 in the concurrent litigation captioned *ARIAD Pharmaceuticals, Inc., et al.* v. *Eli Lilly and Company*, U.S. Court of Appeals for the Federal Circuit.
U.S. Appl. No. 06/817,441, filed Jan. 9, 1986.
U.S. Appl. No. 06/946,365, filed Dec. 24, 1986.
U.S. Appl. No. 07/155,207, filed Feb. 12, 1988.
U.S. Appl. No. 07/162,680, filed Mar. 1, 1988.
U.S. Appl. No. 07/280,173, filed Dec. 5, 1988.
U.S. Appl. No. 07/318,901, filed Mar. 3, 1989.
U.S. Appl. No. 07/341,436, filed Apr. 21, 1989.
U.S. Appl. No. 07/791,898, filed Nov. 13, 1991.
U.S. Appl. No. 08/418,266, filed Apr. 6, 1995.
U.S. Appl. No. 08/463,397, filed Jun. 5, 1995.
U.S. Appl. No. 08/464,364, filed Jun. 5, 1995.
U.S. Appl. No. 08/959,160, filed Oct. 28, 1997.
Decision issued Mar. 22, 2010 in the concurrent litigation captioned *ARIAD Pharmaceuticals, Inc., et al.* v. *Eli Lilly and Company*, U.S. Court of Appeals for the Federal Circuit.
Order issued Aug. 21, 2009 in the concurrent litigation captioned *ARIAD Pharmaceuticals, Inc., et al.* v. *Eli Lilly and Company*, U.S. Court of Appeals for the Federal Circuit.
Decision issued Jun. 1, 2009 in the concurrent litigation captioned *Amgen, Inc., et al.* v. *ARIAD Pharmaceuticals, Inc., et al.*, U.S. Court of Appeals for the Federal Circuit.
Feb. 1, 2006 Second Declaration of Jeffrey Ravetch M.D., Ph.D., Document 201, filed Feb. 3, 2006, in Civil Case 02 CV 11280.
Feb. 3, 2006 Concise Statement of Material Facts As to Which There Is A Genuine Issue In Support of Plaintiff's Opposition to Lilly's Motion For Summary Judgment of Invalidity Under 35 U.S.C. §102, Document 202, filed Feb. 3 2006, In Civil Case 02 CV 11280 RWZ.
Feb. 3, 2006 Declaration of Vladimir V. Drozdoff In Support of Plantiffs' Opposition to Defendant Eli Lilly & Co.'s Motion For Summary Judgment of Invalidity Under 35 U.S.C. section 102 and Related Documents, Document 203, filed Feb. 3, 2006, in Civil Case 02 CV 11280 RWZ.

Feb. 3, 2006 Declaration of Vladimir V. Drozdoff in Support of Plaintiffs' Opposition to Defendant Eli Lilly & Co.'s Motion For Summary Judgment of Invalidity Under 35 U.S.C. Section 101 and 112, First Paragraph , Document 200, filed Feb. 3, 2006, in Civil Case 02 CV 11280 RWZ.
Feb. 3, 2006 Plaintiffs' Opposition to Defendant Eli Lilly & Co.'s Motion For Summary Judgment of Invalidity Under 35 U.S.C.
§§101 and 112, First Paragraph filed under seal, Document 198–1, filed Feb. 3, 2006, in Civil Case 02 CV 11280 RWZ.
Feb. 4, 2006 Plaintiffs' Memorandum In Opposition To Defendant Eli Lilly & Co.'s Motion For Summary Judgment of Invalidity Under 35 U.S.C. Section 102 filed under seal, Document 201–1, filed Feb. 3, 2006, in Civil Case 02 CV 11280 RWZ.
Feb. 24, 2006 Declaration of Leslie A. McDonell in Support of Defendant Eli Lilly and Company's Reply Memorandum In Support of Its Motion For Summary Judgment of Invalidity Under 35 U.S.C. §102, Document 214–1, filed Feb. 24, 2006, in Civil Case 02 CV 11280 RWZ.
Feb. 24, 2006 Declaration of Leslie A. McDonell in Support of Defendant Eli Lilly and Company's Reply Memorandum In Support of Its Motion For Summary Judgment of Invalidity Under 35 U.S.C. §§101 and 112, First Paragraph, Document 211, filed Feb. 24, 2006, in Civil Case 02 CV 11280 RWZ.
Feb. 24, 2006 Motion For Leave To File Reply Memorandum In Support Of Defendant Eli Lilly and Company's Motion For Summary Judgment Of Invalidity Under 35 U.S.C. §§Φand 112, First Paragraph, Document 210–1, filed Feb. 24, 2006, in Civil Case 02 CV 11280 RWZ.
Feb. 24, 2006 Reply Memorandum In Support of Defendant's Motion For Summary Judgment of Invalidity Under 35 U.S.C. §102, Document 213–2, Filed Feb. 24, 2006, in Civil Case 02 CV 11280 RWZ.
Feb. 24, 2006 Reply Memorandum In Support of Defendant's Motion for Summary Judgment of Invalidity Under 35 U.S.C. §§101 and 112, First Paragraph, Document 210–2, filed Feb. 24, 2006, in Civil Case 02 CV 11280 RWZ.
Mar. 3, 2006 Plaintiffs' Opposition To Defendant Eli Lilly & Co.'s Motion For Leave To File A Reply Brief In Support of its Summary Judgment of Invalidity Under 35 U.S.C. Section 102 including Exhibit 1, Document 218, filed Mar. 3, 2006, in Civil Case 02 CV 11280 RWZ.
Mar. 3, 2006 Concise Statement Of Material Facts As To Which There Is A Genuine Issue In Support of Plaintiffs Opposition to Defendant Eli Lilly & Company's Motion for Summary Judgment of Invalidity Under 35 U.S.C. §§101 and 112, First Paragraph, Document 199, filed Feb. 3, 2006, in Civil Case 02 CV 11280 RWZ.
Mar. 3, 2006 Plaintiffs Opposition to Defendant Eli Lilly & Company's Motion For Leave To File Reply Memorandum In Support Of Eli Lilly and Company's Motion for Summary judgment of Invalidity under 35 U.S.C. §§101 and 112, First Paragraph, Document 217, filed Mar. 3, 2006, in Civil Case 02 CV 11280 RWZ.
Undated Declaration of Stavros Manolagas, M.D. Ph.D. in Reexamination Control No. 90/007,503, Document 201, filed Feb. 3, 2006, in Civil Case 02 CV 11280 RWZ.
Claims from U.S. Serial No. 07/341,438, filed Apr. 21, 1989 in Civil Case 02 CV 11280 RWZ.
Dec. 30, 1996 Office Action in U.S. Appl. No. 08/464,364, Document 198, filed Feb. 3, 2006 in Civil Case 02 CV 11280 RWZ.

Oct. 15, 1997 Office Action in U.S. Appl. No. 08/464,364, Document 198, filed Feb. 3, 2006 in Civil Case 02 CV 11280 RWZ.
Jun. 10, 1998 Amendment and Response in U.S. Appl. No. 08/464,364, Document 198, filed Feb. 3, 2006, in Civil Case 02 CV 11280 RWZ.
Jul. 14, 1998 Office Action in U.S. Appl. No. 08/464,364, Document 198, filed Feb. 3, 2006, ADL 0000542–0000566, Document 198, filed Feb. 3, 2006 in Civil Case 02 CV 11280 RWZ.
Jan. 14, 1999 Response and Amendment in U.S. Appl. No. 08/464,364, ADL 0000570–0000588, Document 198, filed Feb. 3, 2006 in Civil Case 02 CV 11280 RWZ.
Mar. 11, 1999 Office Action in U.S. Appl. No. 08/464,364 ADL 0000611–0000621, Document 198, filed Feb. 3, 2006 in Civil Case 02 CV 11280 RWZ.
Sep. 14, 1999 Declaration Under 37 C.F.R. §1.132 by David Baltimore including Exhibits A–J, ADL 0000625–0000696, Document 198–5 filed Feb. 3, 2006 in Civil Case 02 CV 11280 RWZ.
Nov. 19, 1999 Office Action in U.S. Appl. No. 08/484,364, ADL 0000708–0000716, Document 198, filed Feb. 3, 2006 in Civil Case 02 CV 11280 RWZ.
May 30, 2000 Response and Amendment to Nov. 29, 1999 Office Action in U.S. Appl. No. 08/464,364, Document 214–2, filed Feb. 24, 2006 in Civil Case 02 CV 11280 RWZ.
May 30, 2000 Response and Amendment in U.S. Appl. No. 08/464,364, ADL 0000722–0004732, Document 198, filed Feb. 3, 2006 in Civil Case 02 CV 11280 RWZ.
Aug. 11, 2000 Office Action in U.S. Appl. No. 08/464,364, ADL 0000822–0000833, Document 198–4, filed Feb. 3, 2006 in Civil Case 02 CV 11280 RWZ.
Feb. 12, 2001 Response and Amendment in U.S. Appl. No. 08/464,364, ADL 0000843–0000853, Document 201, filed Feb. 3, 2006 in Civil Case 02 CV 11280 RWZ.
Feb. 12, 2001 Response and Amendment in U.S. Appl. No. 08/464,364, ADL 0000843–0000853, Document 198, filed Feb. 3, 2006 in Civil Case 02 CV 11280 RWZ.
Sep. 12, 2001 Response and Amendment in U.S. Appl. No. 08/464,364, ADL 0000874–0000921, Document 201, filed Feb. 3, 2006 in Civil Case 02 CV 11280 RWZ.
Sep. 12, 2001 Response and Amendment in U.S. Appl. No. 08/464,364, ADL 0000874–0000888, Document 198, filed Feb. 3, 2006 in Civil Case 02 CV 11280 RWZ.
Oct. 4, 2001 Examiner's Amendment in U.S. Appl. No. 08/464,364, ADL 0000924–0000953, Document 198–8, filed Feb. 3, 2006 in Civil Case 02 CV 11280 RWZ.
Bressler et al., Journal of Virology (1993) 67:288–293, Document 198, filed Feb. 3, 2006 in Civil Case 02 CV 11280 RWZ.
Cohen, J., Nature (2002) 420:885–891, Document 201, filed Feb. 3, 2006 in Civil Case 02 CV 11280 RWZ.
Davis et al., Science (1991) 253:1268–1271, Document 198, Feb. 3, 2006 in Civil Case 02 CV 11280 RWZ.
Dofferhoff et al., Scand. J. Infect. (1991) 23:739–754, Document 201, filed Feb. 3, 2006 in Civil Case 02 CV 11280 RWZ.
Epstein, F.H., The New England Journal of Medicine (1997) 336:1066–1071, Document 198, filed Feb. 3, 2006 in Civil Case 02 CV 11280 RWZ.
Evans and Pollack, The Journal of Infectious Diseases (1993) 167:1336–43, Document 201, filed Feb. 3, 2006 in Civil Case 02 CV 11280 RWZ.

Galdiero et al., Microbiology (2001) 147:2697–2704, Document 201, filed Feb. 3, 2006, in Civil Case 02 CV 11280 RWZ.
Haskill, et al., Cell (1991) 65:1281–12889, Document 198, filed Feb. 3, 2006 in Civil Case 02 CV 11280 RWZ.
Hoffman et al., Science (2002) 298:1241–1245, Document 198, filed Feb. 3, 2006 in Civil Case 02 CV 11280 RWZ.
Hurley et al., Antimicrobial Agents and Chemotheraphy (1991) 35:2388–2394, Document 201, filed Feb. 3, 2006 in Civil Case 02 CV 11280 RWZ.
Leeson and Morrison, Shock (1994) 2:235–245, Document 201, filed Feb. 3, 2006 in Civil Case 02 CV 11280 RWZ.
Lepper et al., Intensive Care Med. (2002) 28:824–833, Document 201, filed Feb. 3, 2006 in Civil Case 02 CV 11280 RWZ.
Logeat et al., The EMBO Journal (1991) 10:1827–1832, Document 198, filed Feb. 3, 2006 in Civil Case 02 CV 11280 RWZ.
Mustafa et al., The Journal of Infectious Diseases (1989) 160:891–895. Document 201, filed Feb. 3, 2006 in Civil Case 02 CV 11280 RWZ.
Nitsche et al., Arch Surg. (1996) 131:192–199, Document 201, filed Feb. 3, 2006 in Civil Case 02 CV 11280 RWZ.
Physicians' Desk Reference 24$^{th}$ ed. 1970, pgs. Cover, title page, Generic and Chemical Index Section 3, p. 305, 307, 309, 312, 326–328, Product Information 638–639, 809, 880–881, 1167, 1210–1211, 1309–1310, 1323, 1379–1380, Document 201, filed Feb. 3, 2006 in Civil Case 02 CV 11280 RWZ.
Shenep and Mogan, The Journal of Infectious Diseases (1984) 150:380–388, Document 201, filed Feb. 3, 2006 in Civil Case 02 CV 11280 RWZ.
(2004) Surgeon General's Report including the following: Abbreviations and Acronyms; Acknowledgments ix–xxvi; Appendix A; Appendix B; Appendix C; Chapter 1: key Messages; Chapter 2: Key Messages: Chapter 3 Diseases of Bone; Chapter 4; Key Messages; Chapter 5: Key Messages; Chapter 6: Key Messages; Chapter 7: Key Messages; Chapter 8: Key Messages; Chapter 9: Key Messages; Chapter 10: Key Messages; Chapter 11: Key Messages; Chapter 12: Key Messages; Chapter 13: A Vision for the future: a framework for action to promote bone health; United States Department of Health & Human Services (2004); Index; Message from Tommy G. Thompson; Part Five; Part Four; Part One; Part Six; Part Three; Part Two; Preface; Bone Health and Osteoporosis A Report of the Surgeon General in Civil Case 02 CV 11280 RWZ.
Taber's Cyclopedic Medical Dictionary 16$^{th}$ Ed. (1989), pp. 1120, Document 198–9, filed Feb. 3, 2006 in Civil Case 02 CV 11280 RWZ.
Ting and Endy, Science (2002) 298:1189–1190, Document 198, filed Feb. 3, 2006 in Civil Case 02 CV 11280 RWZ.
Xigris drotrecogin alfa (activated) 2002–2004, EX 0579 0001–EX0579 0049 in Civil Case 02 CV 11280 RWZ.
Trial Transcript—Apr. 27, 2006 Jury Trial Day 13, First Session pp. 1–86, in Civil Case 02 CV 11280 RWZ.
Trial Transcript—Apr. 27, 2006 Jury Trial Day 13, Second Session pp. 88–141, in Civil Case 02 CV 11280 RWZ.
Nov. 24, 2003 unsigned Defendant Eli Lilly and Company's Opening Claim Construction Brief, Document 198–3, filed Feb. 3, 2006, in Civil Case 02 CV 11280 RWZ.
Dec. 22, 2003 Supplemental Declaration of Dr. Thomas D. Gilmore, Document 201, filed Feb. 3, 2006, in Civil Case 02 CV 11280 RWZ.

Feb. 24, 2004 Motion For Leave To File Reply Memorandum In Support Of Defendant Eli Lilly And Company's Motion For Summary Judgment Of Invalidity Under 35 U.S.C. §102, Document 213–1, filed Feb. 24, 2006, in Civil Case 02 CV 11280 RWZ.

Mar. 3, 2004 Memorandum of Decision And Order, Document 201, filed Feb. 3, 2006, in Civil Case 02 CV 11280 RWZ.

Mar. 3, 2004 Memorandum of Decision and Order, Document 198, filed Feb. 3, 2006, in Civil Case 02 CV 11280 RWZ.

Aug. 23, 2004 Videotaped Deposition of Dr. David Baltimore, pp. 1–4, and 85–87 in Civil Case 02 CV 11280 RWZ.

Sep. 7, 2005 Expert Report of Peter Barnes, Ph.D. in Civil Case 02 CV 11280 RWZ.

Sep. 9, 2005 Expert Report of Dr. Laurie H. Glimcher in Civil Case 02 CV 11280 RWZ.

Sep. 9, 2005 Expert Report of Dr. Laurie H. Glimcher, pages cover, 9, 14–15, and 32 in Civil Case 02 CV 11280 RWZ.

Sep. 9, 2005 Expert Report of David Latchman, DSc., Ph.D.., pp. Cover, 5 and 11, in Civil Case 02 CV 11280 RWZ.

Oct. 3, 2005 Eli Lilly and Company's Fifth Supplemental Responses To Plaintiff's First Set of Interrogatories (Nos. 1–5), pp. 1–6, in Civi Case 02 Cv 11280 RWZ.

Oct. 20, 2005 Expert Report of Jeffrey V. Ravetch, M.D., Ph.D., pp. 1–43 with Certificate of Service, in Civil Case 02 CV 11280 RWZ.

Oct. 20, 2005 Expert Report of Jeffrey V. Ravetch, M.D., Ph.D., pp. Cover, 14–15, and 36, Document 198–10, filed Dec. 3, 2006, in Civil Case 02 CV 11280 RWZ.

Oct. 21, 2005 Expert Report of Dr. Stephen Prescott, pp. Cover, 52–53 and 60, Document 198–11, filed Feb. 3, 2006, in Civil Case 02 CV 11280 RWZ.

Oct. 21, 2005 Rule 26(A)(2) Rebuttal Report Of Thomas R. Kadesch, Ph.D. in Civil Case 02 CV 11280 RWZ.

Oct. 21, 2005 Rule 26(A) (2) Rebuttal Report of Thomas R. Kadesch, Ph.D., Document 198, filed Feb. 3, 2006, in Civil Case 02 CV 11280 RWZ.

Oct. 21, 2005 Rule 26(a) (2) Rebuttal Report of George R. Stark, Ph.D., Document 198, filed Feb. 3, 2006, in Civil Case 02 CV 11280 RWZ.

Oct. 28, 2005 Rule (26)(A) (2) Rebuttal Report of Michael Sofocleous, pp. Cover, 22 and 33, in Civil Case 02 CV 11280 RWZ.

Nov. 10, 2005 Eli Lilly and Company's Sixth Supplemental Reponses To Plaintiffs' First Set of Interrogatories (Nos. 1–5), pp. 1–6, in Civil Case 02 CV 11280 RWZ.

Nov. 11, 2005 Reply Expert Report of Dr. Jeffrey Ravetch, pp. 1–11, in Civil Case 02 CV 11280 RWZ.

Nov. 11, 2005 Reply Expert Report of Dr. Laurie H. Glimcher, pp. 1–13, in Civil Case 02 CV 11280 RWZ.

Nov. 11, 2005 Reply Expert Report of David Latchman, DSc., Ph.D., Document 198, filed Feb. 3, 2006, pp. 1–58, in Civil Case 02 CV 11280 RWZ.

Nov. 21, 2005 Plaintiffs' Supplemental Responses To Eli Lilly & Co.'s First, Second, Third, and Fourth Sets of Interrogatories (Nos. 2, 3, 6–8), in Civil Case 02 CV 11280 RWZ.

Dec. 9, 2005 Deposition of Dr. George Stark, Document 198, filed Feb. 3, 2006, pp. 1–5, 128–129, 134–135, 147–148 and 277, Document 198, filed Feb. 3, 2006, in Civil Case 02 CV 11280 RWZ.

Dec. 13, 2005 Confidential Deposition of Peter Barnes pp. 1, 111–125 and 133–136, in Civil Case 02 CV 11280 RWZ.

Dec. 13, 2005 Confidential Deposition of Peter Barnes, pp. 1–2, 48–49, 181–182, in Civil Case 02 CV 11280 RWZ.

Dec. 14, 2005 Deposition of David Latchman, pp. 1–3, 64–65, 174 & 275, Document 198, filed Feb. 3, 2006, in Civil Case 02 CV 11280 RWZ.

Dec. 20, 2005 Videotaped Deposition of Thomas R. Kadesch, pp. 1–4, 138, 196, 269, 297–299, 307–308 and 332, Document 198, filed Feb. 3, 2006, in Civil Case 02 CV 11280 RWZ.

Dec. 22, 2005 Videotaped and Oral Deposition of Stavros, C. Manolagas, pp. 1–3, and 208–209, Document 198, filed Feb. 3, 2006 in Civil Case 02 CV 11280 RWZ.

Dec. 23, 2005 Declaration of Lawrence R. Robins In Support Of Defendant Eli Lilly and Company's Motion For Summary Judgment of Invalidity Under 35 U.S.C. §102 including Exhibits 1–13 in Civil Case 02 CV 11280 RWZ.

Dec. 23, 2005 Declaration of Lawrence R. Robins In Support of Defendant Eli Lilly and Company's Motion For Summary Judgment of Invalidity Under 35 U.S.C. §§101 and 112, First Paragraph, including Exhibits A–N in Civil Case 02 CV 11280 RWZ.

Dec. 23, 2005 Defendant Eli Lilly and Company's Motion For Summary Judgment of Invalidity Under 35 U.S.C. §§ 101 and 112, First Paragraph in Civil Case 02 CV 11280 RWZ.

Dec. 23, 2005 Defendant Eli Lilly and Company's Memorandum In Support of its Motion For Summary Judgment of Invalidity Under 35 U.S.C. §102 in Civil Case 02 CV 11280 RWZ.

Dec. 23, 2005 Defendant Eli Lilly and Company's Motion For Summary Judgment of Invalidity Under 35 U.S.C. §102 in Civil Case 02 CV 11280 RWZ.

Dec. 23, 2005 Defendant Eli Lilly and Company's Rule 56.1 Statement In Support of Its Motion For Summary Judgment of Invalidity Under 35 U.S.C. §102 in Civil Case 02 CV 11280 RWZ.

Dec. 23, 2005 Memorandum In Support of Defendant Eli Lilly And Company's Motion For Summary Judgment of Invalidity Under 35 U.S.C. §§101 and 112, First Paragraph filed under seal pursuant to parties' stipulated protective order in Civil Case 02 CV 11280 RWZ.

Dec. 23, 2005 Defendant's Rule 56.1 Statement In Support of Its Motion for Summary Judgment of Invalidity Under 35 U.S.C. §§101 and 112, First Paragraph in Civil Case 02 CV 11280 RWZ.

Jan. 17, 2006 Eli Lilly and Company's Renewed Motion To Stay This Litigation Pending Reexamination of the '516 Patent–In Suit in Civil Case 02 CV 11280 RWZ.

Jan. 17, 2006 Memorandum In Support of Eli Lilly and Company's Renewed Motion To Stay This Litigation Pending Reexamination of the '516 Patent–In Suit including Exhibits A–T in Civil Case 02 CV 11280 RWZ.

Jan. 31, 2006 Declaration of Peter Barlett Bressler, M.D., Document 198, filed Feb. 3, 2006 in Civil Case 02 CV 11280 RWZ.

Jan. 31, 2006 Plaintiffs' Memorandum In Opposition To Eli Lilly and Company's Renewed Motion To Stay This Litigation Pending Reexamination Of the '516 Patent–In Suit including Exhibits 1–7 and 8A–8I, Document 194, filed Jan. 31, 2006, in Civil Case 02 CV 11280 RWZ.

Feb. 1, 2006 First Declaration of Jeffrey V. Ravetch, MD, Ph.D., Document 198, filed Feb. 3, 2006, in Civil Case 02 CV 11280 RWZ.

Hämäläinen, M. et al., "Calcineurin Inhibitors, Cyclosporin A and Tacrolimus Inhibit Expression of Inudcible Nitric Oxide Synthase In Colon Epithelial And Macrophase Cell Lines", European Journal of Pharmacology (2002) 448:239–244.

Han, C.W. et al., "Glucocorticoid–Mediated Repression of Inflammatory Cytokine Production In Fibroblast–like Rheumatoid Synoviocytes Is Independent of Nuclear Factor–κB Activation Induced By Tumor Necrosis Factor α", Rheumatology (2001) 40:267–273.

Ho, S. et al., "The Mechanism of Action of Cyclosporin A and FK506", Clinical Immunology and Immunopathology (1996) 80:S40–S45.

Hofmann, T.G., "The Promoter Context Determines Mutual Repression or Synergism Between NF–κB and the Glucocorticoid Receptor", Biol. Chem. (2002) 383:1947–1951.

Hogan P. Et al., "Transcriptional Regulation by Calcium, Calcineurin, and NFAT", Genes & Development (2003) 17:2205–2232.

Hölschermann, H. et al., "Cyclosporin A Inhibits Monocyte Tissue Factor Activation in Cardiac Transplant Recipients", Circulation (1997) 96:4232–4238.

Hölschermann, H. et al., "Opposite Regulation of Tissue Factor Expression by Calcineurin in Monocytes and Endothelial Cells", The Journal of Immunology (2001) 166:7112–7120.

Horwitz, B. et al., "Failure of Lymphopoiesis After Adoptive Transfer of NF–κB–Deficient Fetal Liver Cells", Immunity (1997) 6:765–772.

Ito, C.Y. et al., "Three NF–κB Sites in the IχB–α Promoter Are Required for Induction of Gene Expression by TNFα", Nucleic Acids Research (1994) 22:3787–3792.

Janssen–Heininger, et al., "Recent Advances Towards Understanding Redox Mechanisms In the Activation of Nuclear Factor κB", Free Radical Biology & Medicine (2000) 28:1317–1327.

Keller, A.D., "Indentification of an Inducible Factor That Binds To A Positive Regulatory Element of The Human B–Interferon Gene", Proc. Natl. Acad. Sci. USA (1988) 85:3309–3313.

Kerr, L.D. et al., "The Rel–Associated pp40 Protein Prevents DNA Binding of Rel and NF–κB: Relationship With IκBβ and Regulation by Phosphorylation", Genes & Development (1991) 5:1464–1476.

Kim, Hyoung–Pyo, "The Basis For TCR–Mediated Regulation of the IL–2 receptor α Chain Gene: Role of Widely Separated Regulatory Elements", The EMBO Journal (2002) 21:3051–3059.

Kinoshita, S. et al., "The T Cell Activation Factor NF–ATc Positively Regulates HIV–1 Replication and Gene Expression in T Cells", Immunity (1997) 6:235–244.

Kopp, E., "Inihibition of NF–κB by Sodium Salicylate and Aspirin", Science, (1994) 265:956–959.

Krönke, M. et al., "Cyclosporin A Inhibits T–cell Growth Factor Gene Expression At the Level of mRNA Transcription", Proc. Natl. Acad. Sci. USA (1984) 81:5214–5218.

Lenardo, M.J. et al., "Protein–Binding Sites In Ig Gene Enhancers Determine Transcriptional Activity and Inducibility", Science (1987) 236:1573–1577.

Lenardo, M.J. et al., "The Involvement of NF–κB in α—Interfereron Gene Regulation Reveals Its Role as Widely Inducible Mediator of Signal Transduction", Cell (1989) 57:287–294.

Lenardo, M.J., "NF–κB–a Paradigm For Inducible and Tissue–Specific Gene Control", Draft Mar. 28, 1989.

Liou, Hsiou–Chi, "Regulation of the NF–χB/rel Transcription Factor And IxB Inhibitor System", Current Opinion in Cell Biology (1993) 5:477–487.

Locksley, R. et al., "The TNF and TNF Receptor Superfamilies: Integrating Mammalian Biology", Cell (2001) 104:467–501.

LyB, G. et al., "The Anti–Inflammatory Sesquiterpene Lactone Helenalin Inihibits the Transcription Factor NF–κB by Directly Targeting p. 65", The Journal of Biological Chemistry (1998) 273:33508–33516.

Matsuda, S., "Mechanisms of Action of Cyclosporine", Immunopharmacology (2000) 47:119–125.

Mauxion, F., "Alteration of a Single Nucleotide Allows Efficient Binding of H2TF1/KBF1 To The Immunoglobulin K Enhancer B Motif", Molecular & Cellular Biology (1989) 9:3548–3552.

Mauxion, F.et al., "Comparison of Constitutive and Inducible Transcriptional Enhancement Mediated by κB–related Sequences: Modulation of Activity in B Cells by Human T–Cell Leukemia Virus Type I tax Gene", Proc. Natl. Acad. Sci. USA (1991) 88:2141–2145.

McCaffrey, P.G. et al., "Cyclosporin A Sensitivity Of The NF–χB Site of the IL2Rα Promoter In Untransformed Murine T Cells", Nucleic Acids Research (1994) 22:2134–2142.

Mukaida, N. et al., "Novel Mechanism of Glucocorticoid–Mediated Gene Repression", The Journal of Biological Chemistry (1994) 969:13289–13295.

Nabel, G., "An Inducible Transcription Factor Activates Expression of Human Immonodeficiency Virus In T Cells", Nature, (1987) 326:711–713.

Nagpal, S., "Vitamin D Analogs: Mechanism of Action and Therapeutic Applications", Current Medicinal Chemistry (2001) 8:1661–1679.

Nelsen, B., "Regulation of Immunoglobulin Gene Transcription", International Review of Cytology, (1992) 133:121–149.

Nelsen, B., "The NF–κB–Binding Site Mediates Phorbol Ester–Inducible Transcription in Nonlymphoid Cells", Molecular & Cellular Biology (1988) 8;3526–3531.

Park, Su–Kil, et al., "Dexamethasone Regulates AP–1 to Repress TNF–α Induced MCP–1 Production in Human Glomerular Endothelial Cells", Nephrology Dial. Transplant. (2004) 19:312–319.

Pendurthi, U.R. et al., "Resveratrol, a Polyphenolic Compound Found in Wine, Inhibits Tissue Factor Expression In Vascular Cells A Possible Mechanism for the Cardiovascular Benefits Associated with Moderate Consumption of Wine", Arterioscler Thromb Vasc Biol. (1999) 19:419–426.

Perez–G, M. et al., "Aspirin and Salicylates Inihibit the IL–4–and IL–13–Induced Activation of STAT6[1]", The Journal of Immunology (2002) 168:1428–1434.

Pruett, S.B. et al., "Characterization of Glucocorticoid Receptor Translocation, Cytoplasmic IκB, Nuclear NfκB, and Activation of NfκB in T Lymphocytes Exposed To Stress–Inducible Concentrations of Corticosterone In Vivo", International Immunopharmacology (2003) 3:1–16.

Ray, A., "Physical Association And Functional Antagonism Between The p65 Subunit of Transcription Factor NF–κB and The Glucocorticoid Recetor", Proc. Natl. Acad. Sci. USA (1994) 91:752–756.

Rengarajan, J. et al., "Interferon Regulatory Factor 4 (IRF4) Interacts with NFATc2 to Modulate Interleukin 4 Gene Expression", J. Exp. Med. (2002) 195:1003–1012.

Rupec, R.A. et al., "Structural Analysis, Expression, and Chromosomal Localization of the Mouse ikba Gene", Immunogenetics (1999) 49:395–403.

Ryu, Y.S. et al., "Acetaminophen Inhibits iNOS Gene Expression in RAW 264.7 Macrophages: Differential Regulation of NF–κB by Acetaminophen and Salicylates", Biochemical and Biophysical Research Communications (2002) 272:758–764.

Sadikot, R. T. et al., "High–Dose Dexamethasone Accentuates Nuclear Factor–κB Activation in Endotoxin–Treated Mice", Am. J. Respir. Crit. Care Med. (2001) 164:873–878.

Scheinman, R. et al., "Characterization of Mechanisms Involved In Transrepression of NF–κB by Activated Glucocorticoid Receptors", Molecular and Cellular Biology (1995) 15:943–953.

Figure 7:
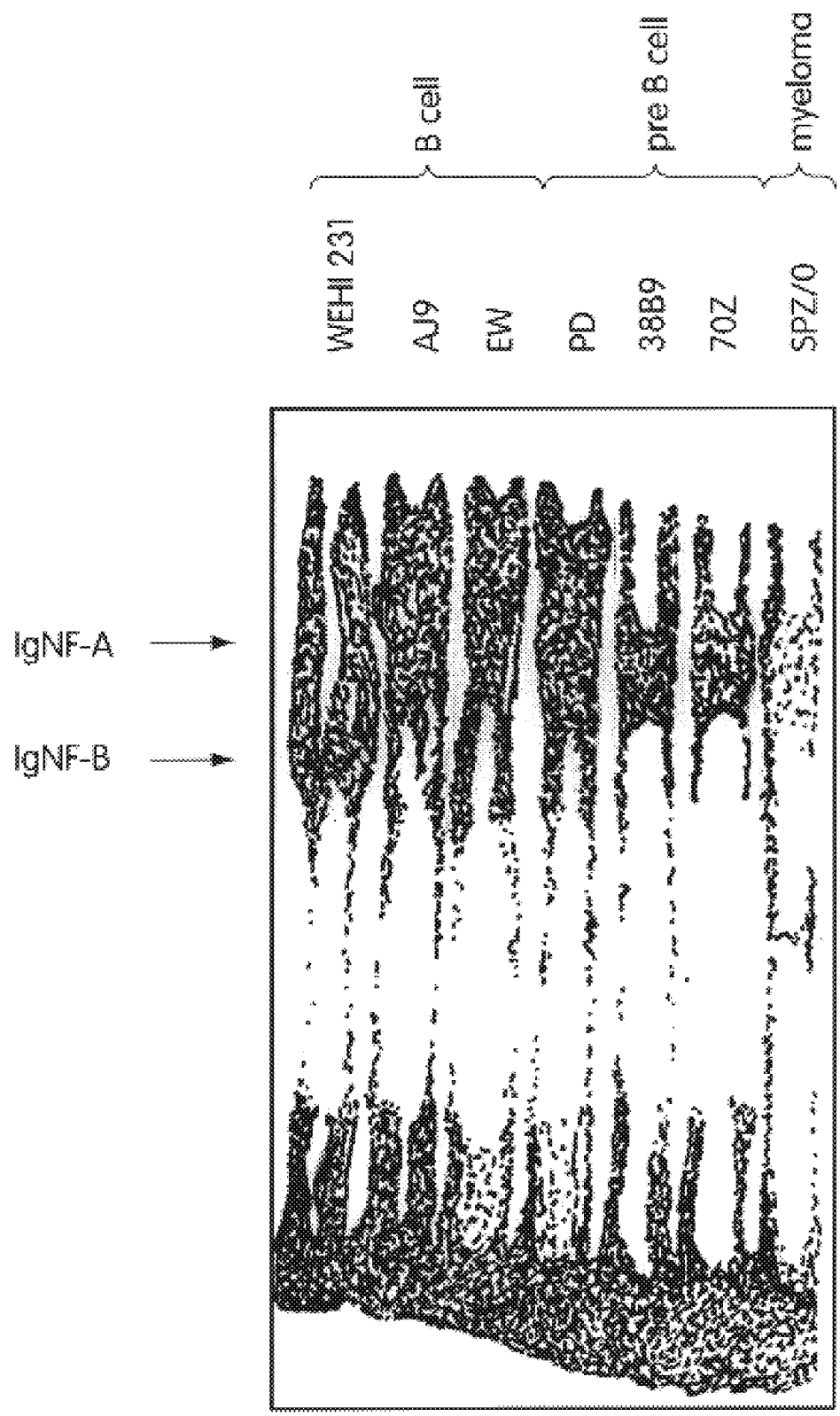
FIG. 7 is a radioautograph of the binding of B cell nuclear extract to the MOPC-41 κ promoter region showing the IgNF-A and IgNF-B complexes.

Fig. 7 and Fig. 8 of Scheinman, et al., "Characterization of Mechanisms Involved In Transrepression of NF–κB by Activated Glucocorticoid Receptors", Molecular and Cellular Biology (1995) 15:949–950.

Scheinman, R.I. et al., "Role of Transcriptional Activation of IκBα in Mediation of Immunosuppression by Glucocorticoids", Science (1995) 270:283–286

Schmitz, M.I. et al., "Proteins Controlling The Nuclear uptake of NF–κB, Rel and Dorsal", Trends in Cell Biology (1991) 1:130–137.

Schreck, R. and Baeuerle, P., "A Role for Oxygen Radicals As Second Messengers", Trends In Cell Biology, Forum (1991) 1:39–42.

Schreiber, S.L., "The Mechanism of Action of Cyclosporin A and FK506" Immunology Today (1992) 13:136–142.

Sen, R., "Inducibility of κ Immunoglobulin Enhancer–Binding Protein NF–κB by a PostTranslational Mechanism", Cell (1986) 47:921–928.

Sen, R., "Multiple Nuclear Factors Interact With The Immunoglobulin Enhancer Sequences", Cell (1986) 46:705–716.

Sica, A. et al., "Interaction of NF–κB and NFAT With the Interferon–65 Promoter", The Journal of Biological Chemistry (1997) 272:30412–30420.

Staal, F.J.T. et al., "Intracellular Thiols Regulate Activation of Nuclear Factor κB and Transcription of Human Immunodeficiency Virus", Proc. Natl. Acad. Sci. USA (1990) 87:9943–9947.

Stark, L.A. et al., "Aspirin–Induced Activation of the NF–κB Signaling Pathway: A Novel Mechanism For Aspirin–Mediated Apoptosis in Colon Cancer Cells[1]", The FASEB Journal (2001) 15:1273–1275.

Takeuchi, A. et al., "Nuclear Factor of Activated T Cells (NFAT) As a Molecular Target For 1α, 25–Dihydroxyvitamin $D_3$–Mediated Effects", The Journal of Immunology (1998) 160:209–218.

Ting, J. Pan–Yun, "Regulation of MHC Expression", Current Opinion in Immunology (1993) 5:8–16.

Traber, K.E. et al., "Anti–Rheumatic Compound Aurothioglucose Inhibits Tumor Necrosis Factor–α–Induced HIV–1 Replication in Latently Infected OM10.1 and Ach2 Cells", International Immunology (1999) 11:143–150.

Wadsworth, T.L., "Effects of the Wine Polyphenolics Quercetin and Resveratrol on Pro–Inflammatory Cytokine Expression in RAW 264.7 Macrophages", Biochemical Pharmacology (1999) 57:941–949.

Wahl, C. et al., "Sulfasalazine: A Potent and Specific Inhibitor of Nuclear Factor Kappa B", J. Clin. Invest. (1998) 101:1163–1174.

Wang, W. et al., "A NF–αB/c–myc–Dependent Survival Pathway Is Targeted by Corticosteriods In Immature Thymocytes[1]", The Journal of Immunology (1999) 162:314–322.

Wang, W.et al., "Pentoxifylline Inhibits Ig α Gene Transcription And Rearrangements in Pre–B Cells[1]", The Journal of Immunology (1998) 160:1789–1795.

Weissmann, G. et al., "Non–Prostaglandin Effects of Aspirin III and Salicylate: Inhibition of Integrin–Dependent Human Neutrophil Aggregation And κB (P105)—Knockout Mice", Eicosanoids and Other Bioactive Lipids in Cancer, Inflammation, and Radiation Injury 5 (2002) pp. 571–577.

Yamamoto, Y. , "Therapeutic Potential of Inhibition of the NFκB Pathway In The Treatment of Inflammation and Cancer", The Journal of Clinical Investigation (2001) 107:135–142.

Yamamoto, Y. et al., "Sulindac Inhibits Activation of the NF–κB Pathway", The Journal of Biological Chemistry (1999) 274:27307–27314.

Yan, F., "Aminosalicylic Acid Inhibits IκB Kinase α Phosphorylation of IκBαin Mouse Intestinal Epithelial Cells", The Journal of Biological Chemistry (1999) 274:36631–36635.

Yin, Min–Jean et al., "The Anti–Inflammatory Agents Aspirin And Salicylate Inhibit The Activity of IκB Kinase–β", Nature (1998) 396:77–80.

Zabel, U., "Purified Human IκB Can Rapidly Dissociate the Complex of the NF–κB Transcription Factor With Its Cognate DNA", Cell (1990) 81:255–265.

Zinn, K. et al., "Identification of Two Distinct Regulatory Regions Adjacent to the Human β–Interferon Gene", Cell (1983) 34:865–879.

Jun. 25, 2002 Complaint, 02 CV 11280 RWZ.

Aug. 18, 2002 Declaration of Michael Karin (20 pgs), including Tabs 1–24, 02 CV 11280 RWZ.

Aug. 19, 2002 Defendants Eli Lilly & Company Memorandum In Support Of Its Combined Motion To Dismiss Under Red.R.Civ.P. 12(b) (6) and Motion for Summary Judgment of Invalidity Under 35 USC Section 102 and 112, including Exhibits A–D, 02 CV 11280 RWZ.

Oct. 14, 2002 Declaration of Charles A. Dinarello, M.D. including Tabs A–D, 02 CV 11280 RWZ.

Oct. 15, 2002 Declaration of Laurie H. Glimcher, M.D. including Tabs A–F, 02 CV 11280 RWZ.

Oct. 16, 2002 Declaration of Brendan F. Boyce, M.B. Ch.B. including Tabs A–D, 02 CV 11280 RWZ.

Oct. 16, 2002 Declaration of Dr. Thomas D. Gilmore including Exhibits A–C and D1–D24, 02 CV 11280 RWZ.

Oct. 17, 2002 Plaintiffs Opposition to Defendants Eli Lilly & Com.'s Combined Motion to Dismiss Pursuant to Fed. R.Civ.P. 12(b) (6) and Motion for Summary Judgment Under 35 ESC Sections 102 and 112 including Tabs A–M, 02 CV 11280 RWZ.

Nov. 18, 2002 Defendants's Eli Lilly & Company Reply In Support of Its Conbimed Motion to Dismiss Under Fed.R.Civ.R.12(b) (6) And Motion For Summary Judgment of Invalidity Under 35 USC Sections 102 & 112, 02 CV 11280 RWZ.

Nov. 21, 2002 Hearing for Summary Judgment, Computer–Aided Transcript, 02 CV 11280 RWZ.

May 12, 2003 Memo of Decision & Order, 02 CV 11280 RWZ.
May 27, 2003 Eli Lilly and Company's Answer To Plaintiffs Complalint And Counter Claims, 02 CV 11280 RWZ.
Jun. 19, 2003 Plaintiffs' Answer to Defendants Eli Lilly & Company's Answer and Counterclaims, 02 CV 11280 RWZ with letter from Anne Marie Longobacco of Bromberg & Sunstein LLP.
Nov. 3, 2003 Tutorial Hearing, 02 CV 11280.
Nov. 3, 2003 Evidentiary Hearing before Honorable Rya W. Zobel, 02 CV 11280 RWZ.
Nov. 24, 2003 Plaintiffs Opening Brief on Claim Construction, 02 CV 11280 RWZ.
Nov. 24, 2003 Declaration of Laurie H. Glimcher, M.D.
Nov. 24, 2003 Declaration of Vladimir V. Drozdoff in Support of Plaintiffs Opening Brief on Claim Construction, including Tabs 1–22, 02 CV 11280 RWZ.
Nov. 24, 2003 Declaration of Dr. Thomas D. Gilmore, 02 CV 11280 RWZ.
Nov. 24, 2003 Defendants Eli Lilly & Company Opening Claim Construction Brief (not signed), 02 CV 11280 RWZ, including Exhibits to Eli Lilly's Opening Claim Construction Brief, inc. Exhibits A–H and I & J, 02 CV 11280 RWZ.
Dec. 22, 2003 Plaintiffs Opposition Brief in Claim Construction, 02 CV 11280 RWZ.
Dec. 22, 2003 Declaration of Vladimir V. Drozdoff in Support of Plaintiffs Opposition Brief on Claim Construction, including Tabs 1–18, 02 CV 11280 RWZ.
Dec. 22, 2003 Supplemental Declaration of Dr. Thomas D. Gilmore, 02 CV 11280 RWZ.
Dec. 22, 2003 Defendants Eli Lilly & Company's Opposition Claim Construction Brief, 02 CV 11280 RWZ.
Jan. 9, 2004 Supplemental Declaration of Dr. Thomas D. Gilmore, 02 CV 11280 RWZ.
Jan. 13, 2004 Markman Transcript Hearing before the Honorable Rya W. Zobel, U.S District Judge, 02 CV 11280 RWZ.
Jan. 13, 2004 Markman Hearing by Plaintiff, 02 CV 11280 RWZ.
Jan. 13, 2004 Markman Hearing, A Scientific Turorial by Eli Lilly & Comp. Paul H. Berghoff.
Mar. 3, 2004 Memorandum of Decision & Order re: Claim Construction, 02 CV 11280 RWZ.
Mar. 23, 2004 Subpoena in a Civil Case 02 CV 11280 RWZ Albert S. Baldwin, Jr., Ph.D.
Dec. 15, 2004 Plaintiffs Ariad Pharm., Inc. et al. Responses to Eli Lilly & Com.'s First Set of Requests For Admission (Nos. 1–25), 02 CV 11280 RWZ.
Jun. 7, 2004 Hearing before Honorable Rya W. Zobel, without Jury.
Aug. 23, 2004 Defendant's Exhibit 45—Asserted Claims Against EVISTA.
Jun. 6, 2005 Order Concerning Discovery & Stay of Proceedings, 02 CV 11280 RWZ.
May 7, 2004 Subpoena in a Civil Case 02 CV 11280 RWZ Chen–Ming Fan Ph.D.
May 7, 2004 Subpoena in a Civil Case 02 CV 11280 RWZ David Baltimore, Ph.D.
May 7, 2004 Subpoena in a Civil Case 02 CV 11280 RWZ Harinder Singh Ph.D.
May 7, 2004 Subpoena in a Civil Case 02 CV 11280 RWZ Jonathan H. LeBowitz, Ph.D.
May 7, 2004 Subpoena in a Civil Case 02 CV 11280 RWZ Michael J. Lenardo M.D.

May 12, 2004 Subpoena in a Civil Case 02 CV 11280 RWZ Ranjan Sen Ph.D.
Declaration for U.S. Appl. No. 07/791,898, filed Nov. 13, 1991 signed by LeBowitz on Feb. 12, 1992.
Declaration of David Baltimore Under Rule 1.132 & In re Brana dated Feb. 2001, in U.S. Appl. No. 08/464,364.
Feb. 11, 1983 Grant Application by Maniatis, Thomas Peter, NIH IEN Grant Proposal 1983–1988.
Feb. 23, 1986 Grant Application by Maniatis, Thomas Peter, NIH AI20642 Interferon 1986–1991 Competing continuation Years 04–08.
Apr. 20, 1988 NIH–IFN Award Letter 1986–87, 1987–88.
Jan. 9, 1991 NIH/IFN Award Letter 1991–91.
May 6, 1992 IDS filed in U.S. Appl. No. 07/791,898.
M. Grieve, Garlic, Botancal.com [online], [retrieved on Aug. 16, 2002], from the Internet <URL:http://www.botancial.com/botanical/mgmh/g/garlic06.html>.
The Glorious Tea, the origins of tea [online], [retrieved on Aug. 16, 2002], retrieved from Internet: <URL:http://www.tea.co.uk.tGloriousT/index.htm>.
Curcuma longa Common Name: Tumeric, Nutrisana.com [online], [retrieved on Aug. 16, 2002], retrieved from the Internet: <URL:http:www.nutrisana.com/html/Monograph–Curcuma.html<.
Bayer, Questions and Facts, [online], [retrieved on–unknown].
Bottero et al. (2006) "NF–κB and the regulation of hematopoiesis," *Cell Death and Differentiation*, 13: 785–797.
Doucas et al. (2000) "Cytoplasmic catalytic subunit of protein kinase A mediates cross–repression by NF–κB and the glucocorticoid receptor," *PNAS*, 97(22): 11893–11898.
Withoff, S. et al. "Regulating the Master Regulator NF–κB: From Natural Strategies to Rationally Designed Superdrugs." in: Ghosh, S., *Handbook of Transcription Factor NF–kappaB* (Boca Raton, FL, CRC Press, 2007), pp. 195–211.
Berry et al., (2002) 1α, 25–Dihydroxyvitamin $D_3$ Stimulates Phyophorylation of IκBα and Synergizes with TPA to Induce Nuclear Translocation of NFκB during Monocytic Differentiation of NB4 Leukemia Cells, Experimental Cell Research, 272:176–184.
Lepper et al., (2002) "Clinical implications of antibiotic–induced endotoxin release in septic shock," Intensive Care Med, 28:824–833.
Jan. 14, 1999 Response and Amendment in U.S. Appl. No. 08/464,364, ADL 0000570–0000588, Document 198, filed Feb. 3, 2006 in Civil Case 02 CV 11280 RWZ.
Mar. 11, 1999 Office Action in U.S. Appl. No. 08/464,364 ADL 0000611–0000621, Document 198, filed Feb. 3, 2006 in Civil Case 02 CV 11280 RWZ.
Sep. 14, 1999 Declaration Under 37 C.F.R. §1.132 by David Baltimore including Exhibits A–J, ADL 0000625–0000696, Document 198–5, filed Feb. 3, 2006 in Civil Case 02 CV 11280 RWZ.
Nov. 19, 1999 Office Action in U.S.Appl. No. 08/484,364, ADL 0000708–0000716, Document 198, filed Feb. 3, 2006 in Civil Case 02 CV 11280 RWZ.
May 30, 2000 Response and Amendment to Nov. 29, 1999 Office Action in U.S. Appl. No. 08/464,364, Document 214–2, filed Feb. 24, 2006 in Civil Case 02 CV 11280 RWZ.
May 30, 2000 Response and Amendment in U.S. Appl. No. 08/464,364, ADl 0000722–0000732, Document 198, filed Feb. 3, 2006 in Civil Case 02 CV 11280 RWZ.

Aug. 11, 2000 Office Action in U.S. Appl. No. 08/464,364, ADL 0000822–0000833, Document 198–4, filed Feb. 3, 2006 in Civil Case 02 CV 11280 RWZ.

Feb. 12, 2001 Response adn Amendment in U.S. Appl. No. 08/464,364, ADL 0000843–0000853, Document 201 filed Feb. 3, 2006 in Civil Case 02 CV 11280 RWZ.

Feb. 12, 2001 Response and Amendment in U.S. Appl. No. 08/464,364 ADL 0000843–000853, Document 198, filed Feb. 3, 2006 in Civil Case 02 CV 11280 RWZ.

Sep. 12, 2001 Response and Amendment in U.S. Appl. No. 08/464,364, ADL 0000874–0000921, Document 201, filed Feb. 3, 2006 in Civil Case 02 CV 11280 RWZ.

Sep. 12, 2001 Response and Amendment in U.S.Appl. No. 08/464,364, ADL 0000874–0000888, Document 198, filed Feb. 3, 2006 in Civil Case 02 CV 11280 RWZ.

Oct. 4, 2001 Examiners Amendment in U.S. Appl. No. 08/464,364, ADL 0000924–0000953, Document 198–8, filed Feb. 3, 2006 in Civil Case 02 CV 11280 RWZ.

Alroy, I. et al., "Transcriptional Repression of the Interleukin–2 Gene By Vitamin D3: Direct Inhibition of NFATp/AP–1 Complex Formation by a Nuclear Hormone Receptor", Molecular and Cellular Biology (1995) 15:5789–5799.

Aoki, N., "Patenting Biological Pathways", Boston Globe (2002) p. 1 and 3.

Auphan, N. et al., "Immunosuppression by Glucocorticoids: Inhibition of NF–κB Activity Through Induction of IκB Synthesis", Science (1995) 270:286–290.

Baeuerle, P., "Activation of DNA–Binding Activity In An Apparently Cytoplasmic Precursor of the NF–κB Transcription Factor", Cell, (1988) 53:211–217.

Baeuerle, P., "NF–κB: Ten Years After", Cell, (1996) 87:13–20.

Baeuerle, P.A. "NF–κB as a Frequent Target For Immunosuppresive and Anti–Inflammatory Molecules", Advances in Immunology (1997) 55:111–137.

Baeuerle, P.A. et al., "Phorbol–ester–induced Activation Of the NF–κB Transcriptional Factor Involves Dissociation of an Apparently Cytoplasmic NF–κB/Inhibitor Complex", Cold Spring Harbor Symposia on Quantitative Biology (1988) vol. LIII pp. 789–798.

Baeuerle, P.A., "IκB: A Specific Inhibitor of the NF–κB Transcription Factor", Science (1988) 242:540–546.

Baeuerle, P.A., "The Inducible Transcription Activator NF–κB: Regulation by Distinct Protein Subunits", Biochimica Biophysica. Acta. (1991) 1072:63–80.

Baldwin Jr., A.S., "The NF–κB and IκB Proteins: New Discoveries and Insights", Annu. Rev. Immunol. (1996) 14:649–81.

Baldwin Jr., A.S., "The Transcription Factor NF–κB and Human Disease", The Journal of Clinical Investigation (2001) 103:3–5.

Baldwin, A.S., "Binding Of a Nuclear Factor to a Regulatory Sequence in the Promoter of the Mouse H–2K$^b$ Class I Major Histocompatibility Gene", Molecular & Cellular Biology (1987) 7:305–313.

Baldwin, A.S., "Two Transcription Factors, NF–κB and H2TF1, Interact With a Single Regulatory Sequence In the Class I major Histocompatibility Complex Promoter", Proc. Natl. sci. USA, (1988) 85:723–727.

Baltimore, D., "Gene Therapy: Intracellular Immunization", Nature (1988) 335:395–396.

Banerji, S. et al., "The Immunosuppressant FK–506 Specifically Inhibits Mitogen–Induced Activation of the Interleukin–2 Promoter and the Isolated Enhancer Elements NFIL–2A and NF–AT1", Molecular and Cellular Biology (1991) 11:4074–4087.

Beg, A.A. et al., "Tumor Necrosis Factor and Interleukin–1 Lead to Phosphorylation and Loss of IκBα: a Mechanism for NF–κB Activation", Molecular and Cellular Biology (1993) 13:3301–3310.

Beg, A.A. et al., "Embryonic Lethality and Liver Degeneration In Mice Lacking The RelA Component of NF–κB", Nature (1995) 376:167–170.

Bergmann, M. et al., "Glucocorticoid Inhibition of Granulocyte Macrophage–Colony–Stimulating Factor From T Cells Is Independent of Control by Nuclear Factor–κB and Conserved Lymphokine Element O", American Journal of Respiratory Cell and Molecular Biology (2004) 30:555–563.

Bergmann, M. et al., "Nuclear Factor–κB Does Not Mediate The Inhibitory Effects of Dexamethasone On Granulocyte–Macrophage Colony–Stimulating Factor Expression", Immunology (2004) 111:430–434.

Beutler, B. et al., "Control of Cachectin (Tumor Necrosis Factor) Synthesis: Mechanisms of Endotoxin Resistence", Science (1986) 232:977–980.

Blanar, M.A. et al., "A Gamma–Interferon–Induced Factor That Binds the Interfereon Response Sequence Of the MHC Class I Gene, H–2K$^b$", The EMBO Journal (1989) 8:1139–1144.

Blanco–Colio, L.M. et al., "Red Wine Intake Prevents Nuclear Factor–κB Activation In Peripheral Blood Mononuclear Cells of Healthy Volunteers During Postprandial Lipemia", Circulation (2000) 102:1020–1026.

Bochkov, V.N. et al., "Oxidized Phospholipids Stimulate Tissue Factor Expression In Human Endothelial Cells Via Activation of ERK/EGR–1 and Ca++/NFAT", Blood (2002) 99:199–206.

Brostjan, C. et al., "Glucocorticoid–Mediated Represion of NfκB Activity in Endothelial Cells Does Not Involve Induction of IκBα Synthesis", The Journal of Biological Chemistry (1996) 271:19612–19616.

Caldenhoven, E. et al., "Negative Cross–Talk Between RelA and the Glucocorticoid Receptor: A Possible Mechanism for the Antiinflammatory Action of Glucocorticoids", Mol. ENDO (1995) 9:401–412.

Callejas, N.A. et al., "Absence of Nuclear Factor κB Inhibition by NSAIDs in Hepatocytes", Hepatology (2002) 35:341–348.

Castrillo, A. et al., "Inhibition of I?B Kinase and IκB Phosphorylation by 15–Deoxy–$\Delta^{12,14}$—Prostaglandin $J_2$ in Activated Murine Macrophages", Molecular And Cellular Biology (2000) 20:1692–1698.

Cenci, S. et al., "Estrogen Deficiency Induces Bone Loss By Enhancing T–Cell Production of TNF–α", The Journal of Clinical Investigation (2000) 106:1229–1237.

Cogswell, P.C. et al., "Promoter Of The Human NF–κB p50/p105 Gene Regulation by NF–κB Subunits and by c–REL1", The Journal of Immunology (1993) 150:2794–2804.

Collart, M.A. et al., "Modulations of Functional Activity In Differentiated Macrophages Are Accompanied By Early And Transient Increase or Decrease In c–FOS Gene Transcription", The Journal of Immunology (1987) 139:949–955.

Collart, M.A., "Regulation of Tumor Necrosis Factor Alpha Transcription in Macrophages: Involvement of Four κB–Like Motifs and of Constitutive and Inducible Forms of NF–κB", Molecular & Cellular Biology (1990) 10:1498–1506.

Cross, S.L. et al., "Functionally Distinct NF–κB Binding Sites In the Immunoglobulin κ and IL–2 Receptor α Chain Genes", Science (1989) 244:466–469.

DeBosscher, K. et al., "Glucocorticoid–Mediated Repression of Nuclear Factor–κB–Dependent Transcription Involves Direct Interference With Transactivation", Proc. Natl. Acad. Sci. USA (1997) 94:13504–13509.

Din, FVN, "Evidence For Colorectal Cancer Cell Specificity Of Aspirin Effects On NfκB Signalling and Apoptosis", British Journal of Cancer (2004) 91:381–388.

Fan, Chen–Ming, "A DNA–Binding Protein Containing Two Widely Seperated Zinc Finger Motifs That Recognize The Same DNA Sequence", Genes & Development (1990) 4:29–42.

Fan, Chen–Ming, "Generation of p50 Subunit of NF–κB by Processing of p105 Through an ATP–Dependent Pathway", Nature (1991) 354:395–398. Fan, Chen–Ming, "Two Different Virus–Inducible Elements Are Required For Human β–Interferon Gene Regulation", The EMBO Journal (1989) 8:101–110.

Fan, Chen–Ming, "Two Different Virus–Inducible Elements Are Required For Human β–Interferon Gene Regulation", The EMBO Journal (1989) 8:101–110.

Frantz, B. et al., "Calcineurin Acts In Synergy With PMA To Inactivate IχB/MAD3 an Inhibitor of NF–χB", the EMBO Journal (1994) 13:881–870.

Giffin, M.J. et al., "Structure of NFAT1 Bound As A Dimer To The HIV–1 LTR κB Element", Nature Structural Biology (2003) 10:800–806.

Goldfeld, A.E., "Coordinate Viral Induction Of Tumor Necrosis Factor α and Interfereon β In Human B cells and Moncytes", Proc. Natl. Acad. Sci. USA (1989) 86:1490–1494.

Goldfeld, A.E., "Human Tumor Necrosis Factor α Gene Regulation By Virus and Lipopolysaccharide", Proc. Natl. Acad. Sci. USA (1990) 87:9769–9773.

Goodman & Gilman's The Pharmacological Basis of Therapeutics, Ninth Edition, Chapter 27, R.R. Donnelley and Sons Co., (1996) p. 625–631 including Table A–II–1 p. 1780 and p. 1712.

Goodman & Gilman's The Pharmacological Basis of Therapeutics, Ninth Edition, Chapter 27, R.R. Donnelley and Sons Co., (1996) p. 633–635 including p. 1783.

Grilli, M. et al., "NF–κB and Rel: Participants In A Multiform Transcriptional Regulatory System", International Review of Cytology (1993) 143:1–62.

Grilli, M. et al., "Tumor Necrosis Factor α Mediates A T Cell Receptor–Independent Induction Of The Gene Regulatory Factor NF–κB In T Lymphocytes", Molecular Immunology (1993) 30:1287–1294.

Sep. 9, 2005 Expert Report of Stavros C. Manolagas, M.D., Ph.D. [DDX324].

Declaration of Stavros Manolagas, M.D. Ph.D. [DDX325].

Adams and Teegarden, J. Nutr., (2004), 134:2948–2952 [DDX326].

Berry, et al., Experimental Cell Research (2002), 272:176–184 [DDX327].

Alroy, et al., Molecular and Cellular Biology, (1995), 15:5789–5799 [DDX328].

Nagpal et al., Currnet Medicinal Chemistry (2001), 8:1661–1679 [DDX329].

Takeuchi et al., The Journal of Immunology, (1998), 160:209–218 [DDX330].

Blanco–Colio et al., Circulation, (2000), 102:1020–1026 [DDX331].

Blanco–Colio et al., Manuscript [DDX332].

Sep. 9, 2005 Expert Report of Dr. Jesus Egido [DDX333].

Nov. 11, 2005 Reply Expert Report–Dr. Jesus Egido [DDX334].

Schmidt et al., Journal of Virology, (1990), 64:4037–40441 [DDX335].

Brini et al., Eur. Cytokine Net., (1990), 1:131–139 [DDX336].

Emmel et al., Science (1989), 246:1617–1620 [DDX337].

Yin et al., Nature, (1998), 396:77–80 [DDX337].

Baeuerle and Baichwal, Advances in Immunology, (1997), 65:111–137 [DDX339].

Sep. 7, 2005 Expert Report of Peter Barnes, Ph.D. [DDX340].

Jun. 8, 2005 Order Granting/Denying Request for Ex Parte Reexamination [DDX341].

Nov. 30, 2005 Condensed Deposition of Jeffrey V. Ravetch in Civil Case 02 CV 11280 RWZ including deposition Exhibits 1–11 attached with this Third Supplemental Information Disclosure Statement, namely.

Curriculum vitae of Jeffrey V. Ravetch [342 Nov. 30, 2005]; Oct. 21, 2005 Expert Report of Jeffrey V. Ravetch, M.D., Ph.D. [343 Nov. 30, 2005]. Mar. 3, 2004 Memorandum of Decision And Order [345 Nov. 30, 2005].

Mar. 3, 2004 Memorandum of Decision And Order [345 Nov. 30, 2005].

Kopp and Gosh, Science, (1994), 265:956–959 [347 Nov. 30, 2005].

Kinoshita et al., Immunity, (1997), 6:235–244 [348 Nov. 30, 2005].

Yan and Polk, The Journal of Biological Chemistry, (1999), 274:36631–36636 [349 Nov. 30, 2005].

Bantel et al., The American Journal of Gastroenterology, (2000), 95:3452–3457 [350 Nov. 30, 2005].

Kaltschmidt et al., Biol. Chem. (1995), 376:9–16 [351 Nov. 30, 2005].

Hölschermann, et al., Circulation, (1997), 96:4232–4238 [352 Nov. 30, 2005].

Palombella et al., Proc. Natl. Acad. Sci. USA (1998), 95:15671–15676 [353 Nov. 30, 2005].

U.S. Patent No. 5,939,421, issued Aug. 17, 1999, Palanki et al. [354 Nov. 30, 2005].

Dec. 9, 2005 Condensed Deposition of George Stark in Civil Case 02 CV 11280 RWZ including deposition Exhibits 1–20 attached with this Third Supplemental Information Disclosure Statement, namely: Curriculum vitae of George R. Stark, Ph.D. [DDX 356 Dec. 9, 2005].

Oct. 21, 2005 Rule 26(A) (2) Rebuttal Report Of George R. Stark, Ph.D. [DDX357 Dec. 9, 2005].

Sep. 9, 2005 Expert Report of David Latchman, DSc., Ph.D. [DDX358 Dec. 9, 2005].

Nov. 11, 2005 Reply Expert Report Of David Latchman, DSc., Ph.D. [DDX359 Dec. 9, 2005].

Sep. 9, 2005 Expert Report of Peter Barnes, Ph.D. [DDX360 Dec. 9, 2005].

File History of U.S. Appl. No. 07/341,436:Filed Apr. 21, 1989 [DDX370 Dec. 9, 2005].

Horuk, R., Journal of Immunological Methods, (1989), 119:255–258 [DDX371 Dec. 9, 2005].
Scott and Smith, Science, (1990), 249:386–390 [DDX372 Dec. 9, 2005].
File History of U.S. Appl. No. 07/280,173, filed Dec. 5, 1988 [DDX373 Dec. 9, 2005].
Khaled et al., Clinical Immunology and Immunopathology, (1998), 56:170–179 [DDX374 Dec. 9, 2005].
Tomita et al., J. Hypertens, (1998), 16:993–1000 [DDX375 Dec. 9, 2005].
Du et al., Molecular Brain Research (2005), 136:177–188 [DDX376 Dec. 9, 2005].
Davis, et al., Science, (1991), 253:1268–1271 [DDX377 Dec. 9, 2005].
Liou and Baltimore, Current Opinion in Cell Biology, (1993), 5:477–487 [DDX378 Dec. 9, 2005].
Siebenlist et al., Annul. Rev. Cell Biol. (1994), 10:405–455 [DDX379 Dec. 9, 2005].
Castrillo et al., Molecular and Cellular Biology, (2000), 20:1692–1698 [DDX380 Dec. 9, 2005].
Yan and Polk, The Journal of Biological Chemistry, (1999), 274:36631–3636 [DDX381].
Declaration of David Baltimore under Rule 1.132 and In re Brana [DDX382 Dec. 9, 2005].
Mar. 3, 2004 Memorandum of Decision And Order [DDX383 Dec. 9, 2005].
Dec. 12, 2005 Condensed Deposition of Jesus Egido in Civil Case 02 CV 11280 RWZ including deposition Exhibits 1–8 attached with this Third Supplemental Information Disclosure Statement, namely.
Pasaje de los Aucianos, 24, 28034 Madrid [Egido 1 Dec. 12, 2005].
Abbreviated Curriculum Vitae of Jesus Egido MD [Egido 2 Dec. 12, 2005].
Sep. 9, 2005 Expert Report–Dr. Jesus Egido [Egido 3 Dec. 12, 2005].
Binder of references for J. Edigo which includes: St. Leger et al., The Lancet, (1979), 1017–1020.
Manna et al., The Journal of Immunology (2000), 164:6509–6519.
Holmes–McNary and Baldwin Jr., Cancer Research (2000), 60:3477–3483.
Blanco–Colio, Circulation., (2000), 102:1020–1026.
Department of Health & Human Services Public Health Service, <hhttp://www.nal.usda.gov/fnic/Dietary/dietdor.htm>.
Gaziano et al., The New England Journal of Medicine, (1993), 329:1829–1834.
Dell'Agli, Cardiovascular Research, (2004), 63:593–602.
Bellido et al., Am. J. Clin. Nutr. (2004), 80:1487–1491.
Ritchie, M.E., Circulation. (1998), 98:1707–1713.
Ghanim et al., Circulation, (2004) 110:1564–1571.
Hofman et al., Diabetologia (1999), 42:222–232.
Hofman et al., Diabetes Care, (1998), 21:1310–1316.
Martin–Ventura et al., Stroke (2004), 35:458–463.
Tsang et al., British Journal of Nutrition, (2005), 94:170–181.
Tsang et al., Br. J. Nutr. (2005), 2pgs.
Baldwin Jr., A. S., The Journal of Clinical Investigation, (2001), 107:3–6.
Deo et al., Journal of the American College of Cardiology, (2004), 44:1812–1818, see Tab 3.
Holmes–McNary, see Tab 2. Manna, Lopez–Velez, Critical Reviews in Food Science and Nutrition, (2003), 43:233–244.
Burns et al., J. Agric. Food Chem. (2002), 50:4096–4102.
Blanco–Colio, Manuscript Edigo 4 Dec. 12, 2005.
Giugliano, MD, To the Editor and Blanco–Colio et al., Response. [Egido 5 Dec. 12, 2005].
Nov. 11, 2005 Reply Expert Report–Dr. Jesus Egido [Egido 6 Dec. 12, 2005].
Leiro et al., International Immunopharmacology (2005), 5:393–406 Egido 7 Dec. 12, 2005.
Tsang et al., British Journal of Nutrition, (2005), 93:233–240 [Egido 8 Dec. 12, 2005].
Dec. 14, 2005 Condensed Deposition of David Latchman in Civil Case 02 CV 11280 RWZ including deposition Exhibits 1–10 attached with this Third Supplemental Information Disclosure Statement, Namely.
Curriculum Vitae of Professor David S. Latchman [Latchman 1 Dec. 14, 2005].
Sep. 9, 2005 Expert Report of David Latchman, DSc., Ph.D. [Latchman 2 Dec. 14, 2005].
Nov. 11, 2005 Reply Expert Report of David Latchman, DSc., Ph.D. [Latchman 3 Dec. 14, 2005].
Hand written notes [Latchman 5 Dec. 14, 2005].
Hand written notes [Latchman 4 Dec. 14, 2005].
Oct. 21, 2005 Rule 26(A) (2) Rebuttal Report of Thomas R. Kadesch, Ph.D. [Latchman 6 Dec. 14, 2005].
Hoyos et al., Science (1989), 244:457–460 [Latchman 7 Dec. 14, 2005].
Horuk, R., Journal of Immunological Methods, (1989), 119:255–258 [Latchman 8 Dec. 14, 2005].
Scott and Smith, Science, (1990), 249:386–390 [Latchman 9 Dec. 14, 2005].
Mar. 3, 2004 Memorandum of Decision and Order [Latchman 10 Dec. 14, 2005].
Dec. 16, 2005 Condensed Deposition of Laurie H. Glimcher in Civil Case 02 CV 11280 RWZ including deposition Exhibits 1–13 attached with this Third Supplemental Information Disclosure Statement, namely.
Cirriculum Vitae of Laurie H. Glimcher [DDX 385 Dec. 16, 2005].
Glick and Opal, Review Article Drugs, (2004), 837–859 [DDX388 Dec. 16, 2005 & Opal 105].
Opal and Huber, Critical Care, (2002), 6:125–136 [DDX389 Dec. 16, 2005].
Joyce et al., The Journal of Biological Chemistry, (2001), 276:11199–11203 [DDX390 Dec. 16, 2005].
Joyce and Grinnell, Crit. Care Med, (2002), 30:S288–S293 [DDX391 Dec. 16, 2005].
Brun–Buisson et al., JAMA, (1995), 274:968–974 [DDX392 Dec. 16, 2005].
Joyce et al., The Journal of Biological Chemistry, (2001), 276:11199–11203 [DDX393 Dec. 16, 2005].
Brueckmann et al., Inflamm. Res. (2004), 528–533 [DDX394 Dec. 16, 2005].
Leeuwen et al., Crit Care Med (2001), 29:1074–1077 [DDX395 Dec. 16, 2005].
Derhaschnig et al., Blood. (2003), 102:2093–2098 [DDX396 Dec. 16, 2005].
Kalil et al., Chock, (2004), 21:222–229 [DDX397 Dec. 16, 2005].
Nick et al., Blood, (2004), 104:3878–3885 [DDX398 Dec. 16, 2005].
Dhainaut, Crit Care Med. (2004) 32Supp:S194–S201 [DDX399 Dec. 16, 2005].

Dec. 17, 2005 Condensed Deposition of Brendan F. Boyce Civil Case 02 CV 11280 RWZ including deposition Exhibits 1–12 attached with this Third Supplemental Information Disclosure Statement, namely.
Curriculum Vitae of Brendan Franceis Boyce [DDX 400 Dec. 17, 2005].
Gianni et al., J. Clin. Endocrinol Metab., (2004), 89:6097–6099 [DDX403 Dec. 17, 2005].
Blum, et al., The American Journal of Cardiology Brief Reports, (2000), 86:892–895 [DDX404 Dec. 17, 2005].
Walsh et al., The American Journal of Cardiology, (2001), 88:825–828 [DDX405 Dec. 17, 2005].
Jimi et al., Nature Medicine (2004), 10:617–624 [DDX406 Dec. 17, 2005].
Compston, J.E., Physological Reviews, (2001), 31:419–447 [DDX407 Dec. 17, 2005].
Chadwick et al., PNAS, (2005), 102:2543–2548 [DDX408 Dec. 17, 2005].
Harnish, et al., Endocrinology, (2000), 141:3403–3411 [DDX409 Dec. 17, 2005].
Reifel–Miller et al., The Journal of Biological Chemistry, (1994), 269:23861–23864 [DDX411 Dec. 17, 2005].
Chen et al., Nature, (1998), 391:410–413 [DDX415 Dec. 17, 2005].
Olivier, et al., Presentation No. SU104 [DDX414 Dec. 17, 2005].
Dec. 20, 2005 Condensed Deposition of Thomas R. Kadesch Civil Case 02 CV 11280 RWZ including deposition Exhibits 1–12 attached with this Third Supplemental Information Disclosure Statement, namely.
Curriculum Vitae of Thomas Robert Kadesch [DDX 414 Dec. 20, 2005].
Oct. 21, 2005 Rule 26(A) (2) Rebuttal Report of Thomas R. Kadesch, Ph.D. [DDX 415 Dec. 20, 2005].
Sep. 9, 2005 Expert Report of David Latchman, DSc., Ph.D. [DDX416 Dec. 20, 2005].
Nov. 11, 2005 Reply Expert Report of David Latchman, DSc., Ph.D. [DDX417 Dec. 20, 2005].
Horuk R., Journal of Immunological Methods, (1989), 119:255–258 [DDX419 Dec. 20, 2005].
Gehrt, et al., The Journal of Antibiotics, (1998), 51:455–463 [DDX420 Dec. 20, 2005].
Kumar et al., Oncogene (1998), 17:913–918 [DDX421 Dec. 20, 2005].
Davis et al., Science, (1991), 253:1268–1271 [DDX422 Dec. 20, 2005].
Haskill et al., Cell, (1991), 65:1281–1289 [DDX423 Dec. 20, 2005].
Bielinska et al., Science, (1990), 250:997–1000 [DDX424 Dec. 20, 2005].
Hoyos et al., Science, (1989), 244:457–460 [DDX425 Dec. 20, 2005].
Dec. 23, 2005 Condensed Deposition of David M. Livingston Civil Case 02 CV 11280 RWZ including deposition Exhibits 1–6 attached with this Third Supplemental Information Disclosure Statement, namely.
Curriculum Vitae of David Morse Livingston [Livingston 450 Dec. 23, 2005].
Bernard et al., The New England Journal of Medicine, (2001), 344:699–709 [Livingston 453 Dec. 23, 2005].
Gianni et al., J. Clin. Endocrinol. Metab., (2004), 89:6097–6099 [Livingston 454 Dec. 23, 2005].
Taranta, et al., Bone, (2002) 30–368–376 [Livingston 455 Dec. 23, 2005].
Blum, et al, The American Journal of Cardiology, (2000), 86:892–895 [Livingston 456 Dec. 23, 2005].
Smith, C.L., Supplement ot Menopause Management, (Mar./Apr. 2005), pp. 40–43 [Livingston 465 Dec. 23, 2005].
Jan. 25, 2006 Condensed Deposition of Robert Lindsay Civil Case 02 CV 11280 RWZ including deposition Exhibits 1–14 attached with this Third Supplemental Information Disclosure Statement, namely.
Curriculum Vitae of Robert Lindsay [Lindsay 1 Jan. 25, 2006].
Mar. 3, 2004 Memorandum of Decision And Order [Lindsay 4 Jan. 25, 2006].
Dec. 21, 2005 Eli Lilly and Company To Pay U.S. $36 Million Relating To Off–Label Promotion [Lindsay 5 Jan. 25, 2006].
Cosman and Lindsay, Endocrine Reviews, (1999), 20:418–434 [Lindsay 6 Jan. 25, 2006].
Kousteni et al., J. Clin. Invest. (2003), 111:1651–1664 [Lindsay 7 Jan. 25, 2006].
Helvering et al., Molecular Pharamcology, (2005), 63:1225–1238 [Lindsay 8 Jan. 25, 2006]71.–77. Of deposition [Lindsay 9 Jan. 25, 2006].
Walsh et al., the American Journal of Cardiology, (2001), 88:825–828 [Lindsay 10 Jan. 25, 2006].
Gianni, et al., J. Clin. Endocrinal. Metab., (2004), 89:6097–6099 [Lindsay 11 Jan. 25, 2006].
Blum et al., The American Journal of Cardiology, (2000), 86:892–895 [Lindsay 12 Jan. 25, 2006].
Bone and Health and Osteoporosis: A Report of the Surgeon General 2004, Executive Summary <http://www.surgeongeneral.gov/library/bonehealth/Executive_summary.html> [Lindsay 14 Jan. 25, 2006].
Bone Health and Osteoporosis Chapter 9 pp. 219–253 [Lindsay 15 Jan. 25, 2006].
Baldwin, Jr. Annu. Rev. Immunol. (1996) 14:649–81.
Barnes, D.M., D.Sc., The New England Journal of Medicine 1997 336:1066–1071.
Beg, Nature, (1995) 376:167–170.
Blackwell, Am. J. Respir. Cell Mol. Biol. (1997) 17:3–9.
Brown, Proc. Natl. Acad. Sci. USA (1993) 90:2532–2536.
Collins, The Journal of Clinical Investigation (2001) 107:255–264.
Resume of Peter John Barnes. Han, The Journal of Biological Chemistry (1999) 274:939–947.
Han, The Journal of Biological Chemistry (1999) 274:939–947.
Hoffman, Science (2002) 298:1241–1245.
Ito, Nucleic Acids Research (1994) 22:3787–3792.
Klement, Molecular and Cellular Biology (1996) 16:2341–2349.
Li, J. Exp. Med. (1999) 11:1839–1845.
*Ariad et al. v. Eli Lilly and Company A Scientific Tutorial.*
*Ariad et al. v. Eli Lilly and Company* Markman Presentation.
Noble, J. Exp. Med. (1996) 183:2373–2378.
Scott, Genes & Development (1993) 7:1266–1276.
Selected pages of NF–κB Tutorial; and Sun, Science (1993) 259:1912–1915.
Expert Report of Stavros C. Manolagas, M.D., Ph.D., dated Sep. 9, 2005 including. Physicians' Desk Reference (1970) 24$^{th}$ Edition;
Adams, Journal of Bacteriology (2003) 185:1174–1180.
Aljada, The Journal of Clinical Endocrinology & Metabolism (1996) 84:3386–3389.

Cirriculum Vitae of Stavros C. Manolagas, M.D., Ph.D. last updated Aug. 1, 2005.
Declaration of Stavros Manolagas, M.D., Ph.D., Jan. 13, 2004 Markman Hearing.
Baeuerle, Advances in Immunology (1997) 65:111–137.
Baldwin, Jr., The Journal of Clinical Investigation (2001) 107:3–6.
Declaration of David Baltimore under Rule 1.132 and In re Brana (Feb. 2001).
Bantel, The American Journal of Gastroenterology (2000) 95:3452–3457.
Belido, The Journal of Clinical Investigation, Inc. (1995) 95:2886–2895.
Annual Meeting . . . Atlantic City Jun. 16–20, 1963, the Journal of the American Medical Association 183:166–169.
Brini, Eur. Cytokine Net, (1990) 1:131–139.
Caulin–Glaser, J. Clin. Invest (1996) 98:36–42.
Chadwick, PNAS (2005) 102:2543–2548.
Chen, The Journal of Biological Chemistry (2005) 280:4632–4638.
Deshpande, AJRI (1997) 38:46–54.
Hughes, British Medical Journal (1983) 287:23–24.
Emmel, Science (1989) 246:1617–1620.
Evans, Endocrinology (2002) 143:3785–3795.
Forsblad, Arthritis Research & Therapy (2003) 5:R202–R209.
Franta, The EMBO Journal (1994) 13:861–870.
Gao, PNAS (2004) 101:16618–16623.
Ghisletti, Molecular and Cellular Biology (2005) 25:2957–2968.
Hahn, (1950) pp. 274–281.
Harnish, Endocrinology (2000) 141:3403–3411.
Hench, Nobel Lecture (1950) 311–341.
Ide, J. Nutr. (2001) 131:1020S–1026S.
Jilka, Science (1992) 257:88–91.
Kopp, Science (1994) 265:956–959.
Kousteni, Cell (2001) 104:719–730.
Kousteni, Science (2002) 298:843–846.
Kousteni, The Journal of Clinical Investigation (2003) 111:1651–1664.
Krönke, Proc. Natl. Acad. Sci. USA (1984) 81:5214–5218.
Kurebayashi, J. Steroid Biochem. Molec. Biol. (1997) 60:11–17.
Lean, The Journal of Clinical Investigation (2003) 112:915–923.
Lefering, Critical Care Medicine (1995) 23:1294–1303.
Lin, The Journal of Clinical Investigation (1997) 100:1980–1990.
Luborsky, Human Reproduction (2002) 18:199–206.
Manolagas, Calcified Tissue International (1992) 50:199–202.
Manolagas, Osteoporosis Int. (1993) Suppl. 1:S114–S116.
Manolagas, Therapeutic Research (1994) 15:27–33.
Manolagas, Current Opinion in Endocrinology and Diabetes (1994) 275–281.
Manolagas, Int. J. Immunopharmac (1995) 17:109–116.
Manolagas, The New England Journal of Medicine (1995) 332:305–311.
Manolagas, Endocrine Reviews (2000) 21:115–137.
Manolagas, The Endocrine Society (2002) 57:385–409.
Manolagas, Kidney International (2004) 66:S41–S49.
Manson, Biochemical Society Transactions (2000) 28:7–12.
McCaffrey, Nucleic Acids Research (1994) 22:2134–2142.
Metka, Fertility and Sterility (1992) 57:37–41.

Nelson, JAMA (2002) 288:872–881.
Jun. 8, 2005 Order Granting/Denying Request For Ex Parte Reexamination issued by the PTO.
Pan, Biochemical Pharmacology (2000) 59:357–367.
A Modern Herbal Garlic <http://www.botanical.com/bontanical/mgmh/g/garlic06.html>.
Plotkin, The Journal of Biological Chemistry (2005) 280:7317–7325.
Pottratz, The Journal of Clinical Investigation, Inc. (1994) 93:944–950.
Ray, The Journal of Biological Chemistry (1994) 269:12940–12946.
Ray, FEBS Letters (1997) 409:79–85.
Apr. 4, 2005 Request For Reexamination Pursuant To 35 U.S.C. §302.
Scheinman, Science (1995) 270:283–286.
Scheinman, Molecular and Cellular Biology (1995) 15:943–953.
Schmidt, Journal of Virology (1990) 64:4037–4041.
Simoncini, Circ. Res. (2000) 87:19–25.
Singh, The Journal of Biological Chemistry (1995) 270:24995–25000.
Speir, Circ. Res. (2000) 87:1006–1011.
Stein, Molecular and Cellular Biology (1995) 15:4971–4979.
Sun, Biochemical and Biophysical Research Communications (1998) 244:691–695.
Synthetic Generic Conjugated Estrogens: Timeline <http://www.fda.gov/cder/news/cetimeline.htm>.
Nov. 18, 2005 Condensed Deposition of Carolyn Smith in Civil Case 02 CV 11280 RWZ including deposition Exhibits 1–11 attached with this Third Supplemental Information Disclosure Statement, namely.
Cirriculum Vitae of Carolyn Louise Smith, Ph.D., ADL Bates Nos. 0037187–0037205 [DDX 300 Nov. 18, 2005].
Sep. 8, 2005 Expert Report of Dr. Carolyn L. Smith Restricted Confidential [DDX 301 Nov. 18, 2005].
Nov. 11, 2005 Declaration of Carolyn Smith [DDX 302 Nov. 18, 2005].
Laboratory notebook of Dr. Carolyn Smith, Bates Nos. CLS 00001–00295 Confidential Information Under Protective Order [DDX 303 11/118/05].
Cavarretta, et al., Molecular Endocrinology (2002), 16(2):253–270 [DDX 304 Nov. 18, 2005].
Coleman, et al., The Journal of Biological Chemistry, (2003), 278 (15):12834–12845 [DDX 305 Nov. 18, 2005].
Dutertre and Smith, The Journal of Pharmacology and Experimental Therapeutics, (2000), 295(2):431–437 [DDX 307 Nov. 18, 2005].
Marino et al., Molecular and Cellular Endocrinology, (2001), 182:19–26 [DDX 308 Nov. 18, 2005].
Smith and Cummings, Supplement to Menopause Management, (Mar./Apr. 2005), pp. 40–43 [DDX 309 Nov. 18, 2005].
Abstract SA485–SA488 from Journal of Bone and Mineral Research, (2000), p. S325 [DDX 310 Nov. 18, 2005].
Abstract SA473–SA476 from Journal of Bone and Mineral Research (2003), [DDX 311 Nov. 18, 2005].
Nov. 22, 2005 Condensed Deposition of Stephen Prescott in Civil Case 02 CV 11280 RWZ including deposition Exhibits 1–29 attached with this Third Supplement Information Disclosure Statement, namely: Curriculum vitae of Stephen Michael Prescott [DDX 312].

Oct. 21, 2005 Expert Report of Dr. Stephen Prescott [DDX 313].
(The Reply Expert Report of Dr. Stephen Prescott [DDX314]is being submitted under separate cover).
Nov. 11, 2005 Reply Expert Report of Stavros C. Manolagas, M.D., Ph.D. Regarding Invalidity of the Asserted Claims [DDX 315].
Tsoukas, Science, (2004), 224:1438–1440 [DDX 317].
Manolagas, et al., Journal of Clinical Endocrinology and Metobolism, (1986), 63(2):394–400 [DX318].
Lemire et al., The Journal of Immunology, (1985), 134(5):3032–3035 [DX319].
Lemire et al., Rapid Publication, (1984), 74:657–661 [DDX320].
Rigby et al., J. Clin. Invest, (1984), 74:1451–1455 [DX321].
Rigby et al., The Journal of Immunology, (1985), 135:2279–2286 [DDX322].
Yu et al., Proc. Natl. Acad. Sci. USA, (1995), 92:10990–10994 [DDX323].
U.S. Appl. No. 10/037,341 Baltimore et al. filed Apr. 2002.
U.S. Appl. No. 10/037,415 Baltimore et al. filed Jan. 2002.
Jun. 28, 2004 Deposition of Jonathan H. Lebowitz in Civil Case 02 CV 11280 RWZ including deposition Exhibits 5–11 and 13 attached with this Supplemental Information Disclosure Statement, namely.
Oct. 28, 1987 correspondence from Barbara Bakal Greene [LeBowitz Jun. 28, 2004 Exh 5].
May 19, 1987 Notice of Grant Award [LeBowitz Jun. 28, 2004 Exh 6].
Jul. 26, 1988 Notice of Grant Award [LeBowitz Jun. 28, 2004 Exh 7].
Dec. 19, 1989 Notice of Grant Award [LeBowitz Jun. 28, 2004 Exh 8].
Apr. 23, 1990 Notice of Grant Award [LeBowitz Jun. 28, 2004 Exh 9].
Set of hand written notes [LeBowitz Jun. 28, 2004 Exh 10].
Set of hand written notes [LeBowitz Jun. 28, 2004 Exh 11].
Set of hand written notes [LeBowitz Jun. 28, 2004 Exh 13].
(Deposition Exhibits 2 and 14 are copies of the subject patent, deposition Exhibit 12 is plaintiffs' privileged log.
(Deposition Exhibits 1, 3 and 4 have been submitted as items 164, 2 and 167, respectively, in Patentees' Aug. 8, 2005 Information Disclosure Statement).
Jun. 30, 2004 Deposition of Harinder Singh, Ph.D. in Civil Case 02 CV 11280 RWZ including deposition Exhibits 21–25 attached with this Supplemental Information Disclosure Statement, namely.
Feb. 25, 2988 American Type Culture Collection [Singh Jun. 30, 2004 Exh 21].
Set of hand written notes [Singh Jun. 30, 2004 Exh 22].
Set of hand written notes [Singh Jun. 30, 2004 Exh 23].
Set of hand written notes [Singh Jun. 30, 2004 Exh 24].
Set of hand written notes [Singh Jun. 30, 2004 Exh 25].
(Deposition Exhibits 17, 18, 27, 28, 30 and 31 have been submitted as items 163, 1, 26, 27, 76 and 100, respectively in Patentees'Aug. 8, 2005 Information Disclosure Statement)..
Aug. 23, 2004 Deposition of Dr. David Baltimore in Civil Case 02 CV 11280 RWZ.
Sep. 30, 2004 Deposition of Dr. Phillip A. Sharp in Civil Case 02 CV 11280 RWZ including deposition Exhibits 87–89 attached with is Supplemental Information Disclosure Statement, namely.
Feb. 13, 1986 correspondence from Brian W. Kimes, Ph.D. [Sharp Sep. 30, 2004 Exh 87].
Apr. 30, 1986 Notice of Grant Award [Sharp Sep. 30, 2004 Exh 88].
Nov. 3, 1986 Notice of Grant Award [Sharp Sep. 30, 2004 Exh 89].
(Deposition Exhibits 85 and 86 have been submitted as items 29 and 28 in Patentees' Aug. 8, 2005 Information Disclosure Statement).
Oct. 12, 2004 Deposition of Ranjan Sen in Civil Case 02 CV 11280 RWZ.
Oct. 21, 2004 Deposition of Chen–Ming Fan in Civil Case 02 CV 11280 RWZ.
Oct. 22, 2004 Deposition of Michael J. Lenardo, M.D. in Civil Case 02 CV 11280 RWZ.
Oct. 26, 2004 Deposition of Albert S. Baldwin, Jr. Ph.D. in Civil Case 02 CV 11280 RWZ.
Nov. 10, 2004 Deposition of Thomas P. Maniatis, Ph.D. in Civil Case 02 CV 11280 RWZ.
Dec. 1, 2004 Deposition of Dr. Patrick Baeuerle in Civil Case 02 CV 11280 RWZ.
Aug. 20, 2003 Plaintiffs Ariad Pharmaceutical, Inc. et al., Response to Eli Lilly and Company's First Set of Rule 33 Interrogatories (Nos. 1–4).
Sep. 5, 2003 Eli Lilly & Company's Responses to Plaintiffs First Set of Interrogatories (Nos. 1–5).
Oct. 6, 2003 Plaintiffs Ariad Pharmaceuticals, Inc. et al. Responses to Eli Lilly & Company's Second Set of Rule 33 Interrogatories (No. 5).
Mar. 24, 2004 Plaintiffs Ariad Pharmaceuticals, Inc. et al., Supplemental Response to Eli Lilly & Company's First Set of Rule 33 Interrogatories (Nos. 1–5).
Mar. 24, 2004 Eli Lilly & Company's Supplemental Response to Plaintiffs' First Set of Interrogatories (Nos. 1–5).
Apr. 30, 2004 Plaintiffs Ariad Pharmaceuticals Inc. et al., Second Supplemental Response to Eli Lilly & Company's First Set of Rule 33 Interrogatories (Nos. 1–5).
Apr. 30, 2004 Eli Lilly & Company's Second Supplemental Responses to Plaintiffs' First Set of Interrogatories (Nos. 1–5).
Jun. 2, 2004 Plaintiffs Ariad Pharmaceuticals Inc. Et al. Responses to Eli Lilly & Company's Third Set of Rule 33 Interrogatories (No. 6).
Jun. 2, 2004 Plaintiffs Ariad Pharmaceuticals Inc. Et al Third Supplemental Response to Eli Lilly & Company's First Set of Rule 33 Interrogatories (Nos. 1–5).
Oct. 18, 2004 Eli Lilly & Company's Response to Plaintiffs Second Set of Requests for Admission to Eli Lilly & Company (Nos. 19–23).
Nov. 2, 2004 Eli Lilly & Company's Third Supplemental Responses to Plaintiffs First Set of Interrogatories (Nos. 1–5).
Nov. 12, 2004 Plaintiffs Ariad Pharmaceuticals, Inc. Et al., Responses to Eli Lilly & company's Fourth Set of Rule 33 Interrogatories (Nos. 7–8).
Dec. 13, 2004 Defendant's Response to Plaintiffs Fourth Set of Interrogatories (Nos. 8–18).
Dec. 15, 2004 Eli Lilly & Company's Responses to Plaintiffs Third Set of Requests for Admission (Nos. 24–45).
Dec. 15, 2004 Plaintiffs Ariad Pharmaceutical Response to Eli Lilly & Company's Fifth Set of Rule 33 Interrogatories.
Mar. 14, 2005 Plaintiffs Supplemental Response to Eli Lilly's Fourth Set of Rule 33 Interrogatories (Nos. 7–8).
Mar. 14, 2005 Eli Lilly & Company's Response to Plaintiffs Fifth Set of Interrogatories.

Sep. 15, 2005 Plaintiffs Third Supplemental Response to Eli Lilly & Company's First Set of Interrogatories (Nos. 1–4).
Expert Report of David Latchmann, Dsc., Ph.D., dated Sep. 5, 2005, including copies of the following referenced in the report.
Altavilla, Cardiovascular Research (2001) 52:143–152. Jan. 13, 2004 Markman Hearing.
Nov. 2, 2003 Tutorial Hearing.
Baldwin, Jr., Annu. Rev. Immunol. (1996) 14:649–81.
Baltimore, Nature (1988) 335:395–396.
Bielinska, Science (1990) 250:997–1000.
Blackwell, Arthritis & Rheumatism (2004) 50:2675–2684.
Böhnlein, Cell (1988) 53:827–836.
Budhram–Mahadeo, The Journal of Biological Chemistry (1996) 271:9108–9113.
Cavazzana–Calvo, Nature (2004) 427:779–781.
Cross, Science (1989) 244:466–469.
Dang, Clinical Cancer Research (1999) 5:471–474.
Davis, Science (1991) 253:1268–1271.
Fan, The EMBO Journal (1989) 8:101–110.
Fawell, Proc. Natl. Acad. Sci. USA (1994) 91:664–668.
Friedman, Nature (1988) 335:452–454.
Goodbourn, Proc. Natl. Acad. Sci. USA (1998) 85:1447–1451.
Hoag, Nature (2005) 435:530–531.
Hölschermann, Circulation (1997) 96:4232–4238.
Kabouridis, The Journal of Immunology (2002) 169:2587–2593.
Cirriculum Vitae Professor David S. Latchman.
Lenardo, Proc. Natl. Acad. Sci. USA (1988) 85:8825–8829.
Leung, Nature (1988) 333:776–778.
*Ariad et al.* v. *Eli Lilly and Company* Markman Presentation.
Mann, The Journal of Clinical Investigation (2000) 106:1071–1075.
Morishita, Proc. Natl. Acad. Sci. USA (1995) 92:5855–5859.
Morishita, Nature Medicine (1997) 3:894–899.
Morris, Molecular and Cellular Biology (1994) 14:6907–6914.
Mar. 3, 2004 Memorandum of Decision and Order.
Ruben, Science (1988) 241:89–92.
Sawa, Circulation (1997) 96[supp II]:II280–II285.
Scott, Genes & Development (1993) 7:1266–1276.
Selected pages of NF–κB Tutorials.
Ting, Science (2002) 298:1189–1190.
Tomita, Arthrities & Rheumatism (1999) 42:2532–2542.
Verma, Nature (1997) 389:239–242.
Latchman, Eukaryotic Transcription Factors, (2004) Fourth Edition Book.
Expert Report of Dr. Jesus Egido, dated Sep. 9, 2005, including: Report of the Dietary Guidelines <http://www.nal.usda.gov/fnic/Dietary/director.htm>.
Baldwin Jr., The Journal of Clinical Investigation (2001) 107:3–6.
Bellido, Am. J. Clin. Nutr. (2004) 80:1487–91.
The Holy Bible <hhtp://etext.lib.virginia.edu/kjv.browse.html>.
Blanco–Colio, Circulation (2000) 102:1020–1026.
Burns, J. Agric. Food Chem. (2002) 50:4096–4102.
Dell'Agli, Cardiovascular Research (2004) 63:593–602.
Deo, Journal of the American College of Cardiology (2004) 44:1812–8.
Abbreviated CV of Jesus Egido MD.
Manuscript.
Gaziano, The New England Journal of Medicine (1993) 329:1829–34.
Ghanim, Circulation (2004) 110:1564–1571.
Hofmann, Diabetologia (1999) 42:222–232.
Holmes–McNary, Cancer Research (2000) 60:3477–3483.
López–Vélez, Critical Reviews in Food Science and Nutrition (2003) 43:233–244.
Manna, The Journal of Immunology (2000) 164:6509–6519.
Martin–Ventura, Stroke (2004) 35:458–463.
Richie, Circulation (1998) 98:1707–1713.
Leger, Then Lancet (1979) 1:1017–1020.
Tsang, British Journal of Nutrition (2005) 94:170–181.
Expert Report of Peter Barnes, Ph.D., dated Sep. 9, 2005.
Appendix B Baltimore Deposition.
Appendix C Baldwin Deposition.
Jan. 13, 2004 Markman Hearing.
Nov. 3, 2003 Tutorial Hearing.
Baeuerle, Cell (1996) 87:13–20.
Colston, K. et al. "1, 25–Dihydroxyvitamin D3 and Malignant Melanoma: The Presence of Receptors and Inhibition of Cell Growth in Culture" Endocrinology (1981) 108:1083–1086.
Devary, Y. et al., "NF–κB Activation by Ultraviolet Light Not Dependent on a Nuclear Signal" Science (1993) 261:1442–1445.
Dew, MJ, "Maintenance of remission in ulcerative colitis with 5–amino salicylic acid in high doses by mouth" British Medical Journal (1983) 287:23–24.
Dobrilla, G. et al., "Is Ethanol Metabolism Affected by Oral Administration of Cimetidine and Ranitidine at Therapeutic Doses?" Hepato–gastorenterol (1984) 31:35–37.
Eck, S.D. et al., "Inhibition of Phorbol Ester–Induced Cellular Adhesion by Competitive Binding of NF–κB In Vivo" Molecular and Cellular Biology (1993) 13:6530–6536.
Edbrooke, M.R. et al., "Identification of cis–Acting Sequences Responsible for Phorbol Ester Induction of Human Serum Amyloid A Gene Expression via a Nuclear Factor κB–Like Transcription Factor" Molecular and Cellular Biology (1989) 9:1908–1916.
Emmel, E.A. et al., "Cyclosporin A Specifically Inhibits Function of Nuclear Proteins Involved in T Cell Activation" Science (1989) 246:1617–1620.
Giri, J.G. et al., "Interleukin 1–Mediated Induction of κ–Light Chain Synthesis And Surface Immunoglobulin Expression of Pre–B Cells" The Journal of Immunology (1984) 132:223–228.
Gray, T.K. et al., "17β–Estradiol acts directly on the clonal osteoblastic cell line UMR106" Proc. Natl. Acad. Sci. USA (1987) 84:6267–6271.
Griffith [1], B.P., et al., "Targeted blood levels of cyclosporine for cardiac transplantation" J. Thorac Cardiovasc Surg (1984) 88:952–957.
Griffith [2], B.P., et al., "Cardiac Transplantation with Cyclosporin A and Prednisone" Ann. Surg. (1982) 196:324–329.
Hahn, E.O. et al., "Effect of Cortisone on Acute Streptococcal Infections And Post–Streptococcal Complications[1]" Streptococcal Disease Laboratory (1950) pp. 274–281.
Holick, M.F. et al., "Identification of 1,25–Dihydroxycholecalciferol, a Form of Vitamin $D_3$ Metabolically Active in the Intestine" Proc. Nat. Acad. Sci. USA (1971) 68:803–804.
Hoyos, B. Et al., "Kappa B–Specific DNA Binding Proteins: Role in the Regulation of Human Interleukin–2 Gene Expression" Science (1989) 244:457–460.

Jones, A.W., "Elimination Half–life of Methanol During Hangover" Pharmacology & Toxicology (1987) 60:217–220.

Kohase, M. et al., "Dexamethasone Inhibits Feedback Regulation of the Mitogenic Activity of Tumor Necrosis Factor, Interleukin–1, and Epidermal Growth Factor in Human Fibroblasts" Journal of Cellular Physiology (1987) 132:271–278.

Koizumi, T. et al., "Inhibitors of IL–2 Production and IL–2 Receptor Expression in Human Leukemic T–Cell Line, Jurkat[1]" Cellular Immunology (1986) 103:469–475.

Kovacs, E.J., et al., "Differential Inhibition of IL–1 and TNF–α mRNA Expression By Agents Which Block Second Messenger Pathways In Murine Macrophages[1]" The Journal of Immunology (1988) 141:3101–3105.

Krönke, M. et al., "Cyclosporin A Inhibits T–cell Growth Factor Gene Expression At the Level of mRNA Transcription", Proc. Natl. Acad. Sci. USA (1984) 81:5214–5218.

Lawson, D.E.M., et al., "Identification of 1,25–Dihydroxycholecalciferol, a New Kidney Hormone controlling Calcium Metabolism" Nature (1971) 230:228–230.

Lemire, J.M., et al., "1,25–Dihydroxyvitamin $D_3$ Suppresses Human T Helper/Inducer Lymphosyte Activity in Virto[1]" The Journal of Immunology (1985) 134:3032–3035.

Lemire [2], J.M. et al., "1α, 25–Dihydroxyvitamin $D_3$ Suppresses Proliferation and Immunoglobulin Production by Normal Human Peripheral Blood Mononuclear Cells", J. Clin. Invest. (1984) 74:657–661.

Lipsky, P.E. et al., "The Role of Interleukin 1 in Human B Cell Activation: Inhibition of B Cell Proliferation and the Generation of Immunoglobulin–Secreting Cells By An Antibody Against Human Leukocytic Pyrogen[1]" The Journal of Immunology (1983) 130:2708–2714.

Männel, D.N., et al., "Inhibition of Nonspecific Tumoricidal Activity by Activated Macrophages with Antiserum Against a Soluble Cytotoxic Factor" Infection And Immunity (1981) 33:156–164.

Manolagas [1], S.C. et al., "The Antiproliferative Effect of Calcitriol on Human Peripheral Blood Mononuclear Cells" Journal of Clinical Endocrinology and Metabolism (1986) 63:394–400.

Manolagas [2], S.C. et al., Estrogen, Cytokines, and the Control of Osteoclast Formation and Bone Resorption In Vitro and In Vivo Osteoporosis Int (1993) Suppl. 1:S114–116.

Matthews [1], N., "Human Monocyte Killing of Tumor Cells: Contribution of an Extracellular Cytotoxin" Department of Medical Microbiology (1982) 721–729.

Matthews [2], N., "Effect on human monocyte killing of tumour cells of antibody raised against an extracellular monocyte cytotoxin" Immunology (1983) 48:321–327.

Meichle A. et al., "Protein Kinase C–independent Activation of Nuclear Factor κB by Tumor Necrosis Factor" The Journal of Biological Chemistry (1990) 265:8339–8343.

Mihm [1], S. And Droge, W., "Intracellular Glutathione Level Controls DNA–Binding Activity of NF–κB–Like Protein(s)" Institute of Immunology and Genetics, German Cancer Research Center, S.A.311.

Mihm [2], S. et al., "Inhibition of HIV–1 replication and NF–κB activity by cysteine and cysteine derivatives" Aids (1991) 5:497–503.

Miller, H.R. et al., "Reduction of Nonspecific Fluorescence in Respiratory Specimens By Pretreatment with N–Acetylcysteine" Journal of Clinical Microbiology (1986) 24:470–471.

Mukaida, N. et al., "Novel Mechanism of Glucocorticoid–Mediated Gene Repression", The Journal of Biological Chemistry (1994) 269:13289–13295.

Nagasawa, K. et al., "Inductio of Human Malignanat T–Lymphoblastic Cell Lines MOLT–3 and Jurkat by 12–0–Tetradecanoylphorbol–13–Acetate: Ciochemical, Physical, and Morphological Characterization" Journal of Cellular Physiology (1981) 109:181–192.

Norman, A.W. et al., "1,25–Dihydroxycholecalciferol: Indentification of the Proposed Active Form of Vitamin $D_3$ in the Intestine" Science (1971) 173:51–54.

Osborn, L. et al., "Tumor necrosis factor α and interleukin 1 stimulate the human immunodeficiency virus enhancer by activation of the nuclear factorκB" Proc. Natl. Acad. Sci. USA (1989) 86:2336–2340.

Provvedini, D.M. et al., "1,25–Dihydroxyvitamin $D_3$ Receptors in Humna Leukocytes" Science (1983) 221:1181–1183.

Reed, J.C. et al., "Effect of Cyclosporin A and Dexamethasone on Interleukin 2 Receptor Gene Expression[1]" The Journal of Immunology (1986) 137:150–154.

Reed [2], J.C. et al., "Regulation of c–myc mRNA levels in normal human lymphocytes by modulators of cell proliferation" Proc. Natl. Acad. Sci. USA (1985) 82:4221–4224.

Rigby [1], W.F.C. et al., "Regulation of Lymphokine Production and Human T Lymphocyte Activation by 1, 25–Dihydroxyvitamin $D_3$" J. Clin. Invest. (1987) 79:1659–1664.

Rigby [2], W.F.C. et al., "The Effects of 1,25–Dihydroxyvitamin $D_3$ on Human T Lymphocyte Activation and Proliferation: A cell cycle analysis" The Journal of Immunology (1985) 135:2279–2286.

Roederer, M. et al., "Cytokine–stimulated human immunodeficiency virus replication is inhibited by N–acetyl–L–cysteine" Proc. Natl. Acad. Sci. USA (1990) 87:4884–4888.

Rovera, G. et al., "Induction of Differentiation in Human Promyelocytic Leukemia Cells by Tumor Promoters" Science (1979) 204:868–870.

Ruben and Rosen, "Suppression of Signals Required for Activation of Transcription Factor NF–κB in Cells Constitutively Expressing the HTLV–I Tax Protein" The New Biologist (1990) 2:894–902.

Saito [Article], Y. et al., "Possible involvement of a novel protease in neurite outgrowth of PC12 cells" Neuroscience Research, Suppl. 13 (1990) S97–S101.

Saito [1], Y. et al., "Enhancement of neurite outgrowth in PC12h cells by a protease inhibitor" Neuroscience Letters (1988) 89:102–107.

Saito [2], Y. et al., "The Neurite–Initiating Effect of a Tripeptide Aldehyde Pretease Inhibitor on PC12h Cells" J. Biochem. (1989) 106:1035–1040.

Scheinman, R. et al., "Characterization of Mechanisms Involved In Transrepression of NF–κB by Activated Glucocorticoid Receptors", Molecular and Cellular Biology (1995) 15:943–953.

Schmidt, A. et al., "Inducible Nuclear Factor Binding to the κB Elements of the Human Immunodeficiency Virus Enhancer in T Cells Can Be Blocked by Cyclosporin A in a Signal–Dependent Manner", Journal of Virology (1990) 64:4037–4041.

Schreck [1], R. et al., "Dithiocarbamates as Potent Inhibitors of Nuclear Factor κB Activation in Intact Cells" J. Exp. Med. (1992) 175:1181–1194.

Schreck [2], R. et al., "Reactive oxygen intermediates as apparently widely used messengers in the activation of the NF–χB transcription factor and HIV–1" The EMBO Journal (1991) 10:2247–2258.

Semmler, E.J. et al., "The Synthesis of 1α, 25–Dihydroxycholecalciferol—A Metabolically Active Form of Vitamin $D_3$" Tetraheddron Letters No. 40 (1972) 4147–4150.

Shirakawa and Mizel, "In Vitro Activation and Nuclear Translocation of NF–κB Catalyzed by Cyclic AMP–Dependent Protein Kinase and Protein Kinase C", Molecular and Cellular Biology (1989) 9:2424–2430.

Siebenlist, U. et al., "Promoter Region of Interleukin–2 Gene Undergoes Chromatin Structure Changes and Confers Inducibility on Chloramphenicol Acetyltransferase Gene during Activation of T Cells" Molecular and Cellular Biology (1986) 6:3042–3049.

St. Ledger, et al., "Factors Associated With Cardiac Morality In Developed Countries With Particular Reference To The Consumption of Wine", Public Health.

Staal, F.J.T. et al., "Intracellular Thiols Regulate Activation of Nuclear FactorκB and Transcription of Human Immunodeficiency Virus", Proc. Natl. Acad. Sci. USA (1990) 87:9943–9947.

Tanaka, H. et al., "Sequence–specific interaction of α–β–anomeric couble–stranded DNA with the p50 subunit of NF–κB: application to the decoy approach" Nucleic Acids Research (1994) 22:3069–3074.

Thévenin, C. et al., "Induction of Nuclear Factor–κB and the Human Immunodeficiency Virus Long Terminal Repeat by Okadaic Acid, a Specific Inhibitor of Phosphatases 1 and 2A". The New Biologist (1990) 2:793–800.

Tong–Starksen, S.E. et al., "Signaling Through T Lymphocyte Surface Proteins, TCR/CD3 And CD28, Activates The HIV–1 Long Terminal Repeat" The Journal of Immunology (1989) 142:702–707.

Tracey, K.J. et al., "Anti–cachectin/TNF monoclonal antibodies prevent septic shock during lethal bacteraemia" Nature (1987) 330:662–664.

Tsoukas, C.D. et al., "1,25–Dihydrosyvitamin $D_3$: A Novel Immunoregulatory Hormone" Science (1984) 224:1438–1440.

Waage and Bakke, "Glucocorticoids suppress the production of tumour necrosis factor by lipoplysaccharide–stimulated human monocytes" Immunology (1988) 63:299–302.

Weissmann, G., "Aspirin: After more than 200 years, the mechanisms by which this venerable drug and its relatives achieve their wide range of effects have yet to be fully elucidated" Scientific American Journal (1991) pp. 84–90.

Physicians' Desk Reference 1970 $24^{th}$ Edition.

Physicians' Desk Reference 1980 $34^{th}$ Edition.

Physicians' Desk Reference 1985 $39^{th}$ Edition.

Arruda et al., Blood (2005) 105:3458–3464.

Kline et al., Int. J. Immunopharmac. (1984) 6:467–473.

Ballard et al., Cell (1990) 63:803–814.

Bass et al., Proteins: Structure, Function & Genetics (1990) 8:309–314.

Berns et al., Breast Cancer Research & Treatment (1984) 4:195–204.

Boda et al., Folia Biologica (1987) 33:93–97.

Bressler et al., Journal of Virology (1993) 67:288–293.

Brown et al., Methods in Enzymology (1979) 68:109–151.

Brown et al., Science (1995) 267:1485–1488.

Cai et al., The Journal of Biological Chemistry (1997) 272:96–101.

Cunningham and Wells, Science (1989) 244:1081–1085.

Esslinger et al., The Journal of Immunology (1997) 158:5075–5078.

Curriculum Vitae of Thomas Robert Kadesch dated Apr. 26, 2005.

Fenteany et al., Science (1995) 268:726–731.

Fujihara et al., The Journal of Immnology (2000) 165:1004–1012.

Gallop et al., J. Of Medicinal Chemistry (1994) 37:1233–1251.

Gehrt et al., The Journal of Antibiotics (1998) 51:455–463.

Gesner et al., Journal of Cellular Physiology (1988) 136:493–499.

Gill and Ptashne, Nature (1988) 334:721–724.

Haskill et al., Cell (1991) 65:1281–1289.

Horuk R., Journal of Immunological Methods (1989) 119:255–258.

Hoyos et al., Science (1989) 244:457–460.

Kawamura et al. Gene Therapy (2001) 905–912.

Khaled et al., Clinical Immunology (1998) 86:170–179.

Krappmann et al., The EMBO Journal (1996) 15:6716–6726.

Lenardo and Baltimore, Cell (1989) 58:227–229.

Lloyd et al., Nature (1991) 352:635–638.

Logeat et al., The EMBO Journal (1991) 10:1827–1832.

LyB et al., The Journal of Biological Chemistry (1998) 273:33508–33516.

McKinney et al., The Journal of Biological Chemistry (1997) 272:22377–22380.

McKnight and Kingsbury, Science (1982) 217:316–324.

Meng et al., Proc. Natl. Acad. Sci. USA, (1999) 96:10403–10408.

Morishita et al., Nature Medicine (1997) 3:894–899.

Nabel et al., Proc. Natl. Acad. Sci. USA, (1996) 93:15388–15393.

Nicolau et al., Cell Fusion (1984) pp. 254–267.

Palombella et al., Proc. Natl. Acad. Sci. USA, (1998) 95:16741–15676.

Ray et al., The Journal of Biological Chemistry (1995) 270:10680–10685.

Reisine et al., Proc. Natl. Acad. Sci. USA, (1985) 82:8261–8265.

Roberts K., Week in Review Desk (1985).

Baeuerle and Baltimore, "Phorbol–ester–induced Activation of the NF–κB Transcription Factor Involves Dissociation of an Apparently Cytoplasmic NF–κB/Inhibitor Complex", Cold Spring Harbor Symposia (1988c) LIII: 789–798.

Baltimore and Sharp, "Binding of a Nuclear Factor to a Regulatory Sequence in the Promoter of The Mouse H–2$\kappa^b$ Class I Major Histocompatibility Gene", Molecular and Cellular Biology (1987) 7:305–313.

Baltimore, D., "Intracellular immunization", Nature (1988) 335:395–396.

Banerji, S.S. et al., "The Immunosuppressant Fκ–506 Specifically Inhibits Mitogen–Induced Activation of the Interkeukin–2 Promoter and the Isolated Enhancer Elements NFIL–2A and NF–AT1", Molecular and Cellular Biology (1991) 11:4074–4087.

Blanar, M.A. et al., "A gamma–interferon–induced factor that binds the interferon response sequence of the MHC class I gene, H–2κ$^b$", The EMBO Journal (1989) 8:1139–1144.

Bohnlein E. et al., "The Same Inducible Nuclear Proteins Regulates Mitogen Activation of Both the Interleukin–2 Receptor–Alpha Gene and Type 1 HIV", Cell (1988) 53:827–836.

Clouse, K.A. et al., "Monokine Regulation of Human Immunodeficiency Virus–1 Expression in a Chronically Infrected Human T Cell Clone", The Journal of Immunology (1989) 142:431–438.

Collart, M.A. et al., "Modulations of Functional Activity in Differentiated Macrophages are Accompanied by Early And Transient Increase or Decrease in c–FOS Gene Transcription", The Journal of Immunology (1987) 139:949–955.

Collart, M.A. et al., "Regulation of Tumor Necrosis Factor Alpha Transcription in Macrophages: Involvement of Four κB–Like Motifs and of Constitutive and Inducible Forms of NF–κB", Molecullar and Cellular Biology (1990) 10:1498–1506.

Cross, S.L. et al., "Functionally Distinct NF–κB Binding Sites in the Immunoglobulin κ and IL–2 Receptor α Chain GEnes", Science (1989) 244:466–469.

Davis, N. et al., "Rel–Associated pp40: An Inhibitor of the Rel Family of Transcription Factors", Science (1991) 253:1268–1271.

Dew, M.J. et al., "Maintenance of remission in ulcerative colitis with 5–amino salicylic acid in high doses by mouth", British Medical Journal (1983) 287:23–24.

Dofferhoff, A.S.M., et al., "Effects of Different Types and Combinations of Antimicrobial Agents on Endotoxin Release from Gram–negative Bacteria: An In–Vitro and In–Vivo Study", Scandinavian Journal of Infectious Diseases (1991) 23:745–754.

Fan, Chen–Ming and Maniatis, T., "Two different virus–inducible elements are required for human β–interferon gene regulation", The EMBO Journal (1989) 8:101–110.

Fan, Chen–Ming and Maniatis, T., "A DNA–binding protein containing two widely separated zinc finger motifs that recognize the same DNA sequence", Genes and Development (1990) 4:29–42.

Fan, Chen–Ming and Maniatis, T., "Generation of p50 subunit of NF–κB by processing of p105 through an ATP–dependent pathway", Nature (1991) 354:395–398.

Friedman, A.D. et al., "Expression of a truncated viral trans–activator selectively impedes lytic infection by its cognate virus", Nature (1988) 335:452–454.

Gehrt, A. Et al., "Cycloepoxydon, 1–Hyrdoxy–2–hycroxymethyl–3–pent–1–enylbenzene and 1–Hydroxy–2–hydroxymethyl–3–pent–1, 3–dienylbenzene, New Inhibitors of Eukaryotic Signal Transduction", The Journal of Antibiotics (1998) 51:455–463.

Goldfelf, A.E. and Maniatis, T., "Coordiante viral induction of tumor necrosis factor α and interferon β cells and monocytes", Proc. Natl. Acad. Sci. USA (1989) 86:1490–1494.

Goldfeld, A. E. et al., "Human tumor necrosis factor α gene regulation by virus and lipopolysaccharide", Proc. Natl. Acad. Sci. USA (1990) 87:9769–9773.

Goodbourn, S. And Mantiatis, T., "Overlapping positive and negative regulatory domains of the human β–interferon gene", Proc. Natl. Acad. Sci. USA (1998) 85:1447–1451.

Haskill, S. et al., "Characterization of an Immediate—Early Gene Induced in Adherent Monocytes That Encodes IκB–like Activity", Cell (1991) 65:1261–1289.

Horuk, R., "A rapid and direct method for the detection and quantification of interleukin–1 receptors using 96 well filtration plates", Journal of Immunological Methods (1989) 119:255–258.

Hurley, J.C. et al., "Antibiotic–Induced Release of Endotoxin in Chronically Bacteriuric Patients", Antimicrobial Agents and Chemotherapy (1991) 35:2388–2394.

Keller, A.D. and Maniatis, T., "Identification of an inducible factor that binds to a positive regulatory element of the human β–interferon gene", Proc. Natl. Acad. Sci. USA (1988) 85:3309–3313.

Kerr, L.D. et al., "The Rel–associated pp40 protein prevents DNA binding of Rel and NF–κB: relationship wtih IκBβ and regulation by phosphorylation", Genes and Development (1991) 5:1464–1476.

St. Ledger, A.S. et al., "Factors Associated With Cardiac Mortality In Developed Countries With Particular Reference To The Consumption of Wine", The Lancet (1979) 1017–1020.

Lenardo, M. et al., "Protein–Binding Sites in Ig Gene Enhancers Determine Transcriptional Activity and Inducibility", Science (1987) 236:1573–1577.

Lenardo, M.J. et al., "NF–κB protein purification from bovine spleen: Nucleotide stimulation and binding site specificity", Proc. Natl. Acad. Sci. USA (1988) 85:8825–8829.

Lenardo, M.J. et al., "The Involvement of NF–κB in β–Interferon Gene Regulation Reveals Its Role as Widely Inducible Mediator of Signal Transduction", Cell (1989) 57:287–294.

Leung, K. and Nabel, G., "HTLV–1 transactivator induces interleukin–2 receptor expression through an NF–κB–like factor", Nature (1988) 333:776–778.

Logeat, F. et al., "Inhibition of transcription factors belonging to the rel/NF–χB family by trandominant negative mutant", The EMBO Journal (1991) 10:1827–1832.

Mauxion, F. et al., "Comparison of constitutive and inducible transcriptional enhancement mediated by κB–related sequences: Modulation of activity in B cells by human T–cell leukemia virus type I tax gene", Proc. Natl. Acad. Sci. USA (1991) 88:2141–2145.

Mauxion, F. And Sen, R., "Alteration of a Single Nucleotide Allows Efficient Binding of H2TF1/κBF1 to the Immunoglobulin κ Enhancer B Motif", Molecular and Cellular Biology (1989) 9:3548–3552.

Mustafa, M.M. et al., "Increased Endotoxin and Interleukin–1β Concentrations in Cerebrospinal Fluid of Infants with Coliform Meningitis and Ventriculitis Associated with Intraventricular Gentamicin Therapy", The Journal of Infectious Diseases (1989) 160:891–895.

Nabel, G. and Baltimore, D., "An inducible transcription factor activates expression of human immunodeficiency virus in T cells", Nature (1987) 326:711–713.

Nelsen, B. et al., "The NF–κB–Binding Site Mediates Phorbol Ester—Inducible Transcription in Nonlymphoid Cells", Molecular and Cellular Biology (1988) 8:3526–3531.

Rigby, W.F.C. et al., "Inhibition of T Lymphocyte Mitogenesis by 1,25–Dihydroxyvitamin D$_3$ (Calcitriol)", J. Clin. Invest. (1984) 74:1451–1455.

Rigby, W.F.C. et al., "The Effects of 1,25–Dihydroxyvitamin D$_3$ on Human T Lymphocyte Activation And Proliferation: A Cell Cycle Analysis", The Journal of Immunology (1985) 135:2279–2286.
Ruben, S. et al., "Cellular Transcription Factors and Regulation of IL–2 Receptor Gene Expression by HTLV–1 tax Gene Product", Science (1988) 241:89–92.
Schmitz, M.F., et al., "Proteins controlling the nuclear uptake of NF–κB, Rel and dorsal", Trends in Cell Biology (1991) 1:130–137.
Schreck, R. and Baeuerle, P., "A role for oxygen radicals as second messengers", Trends in Cell Biology (1991) 1:39–42.
Sen, R. and Baltimore, D., "Multiple Nuclear Factors Interact with the Immunoglobulin Enhancer Sequences", Cell (1986) 46:705–716.
Sen, R. and Baltimore, D., "Inducibility of κ Immunoglobulin Enhancer–Binding Protein NF–κB by a Posttranslational Mechanism", Cell (1986) 47:921–928.
Shenep, J.L. and Mogan, K.A., "Kinetics of Endoxtoin Release During Antibiotic Therapy For Experimental Gram–Negative Bacterial Sepsis", The Journal of Infectious Diseases (1984) 150:380–388.
Scott, J.K. and Smith, G.P., "Searching for Peptide Ligands with an Epitope Library", Science (1990) 249:386–390.
Tomita, T. et al., "Suppressed Severity of Collagen–Induced Arthritis By In Vivo Transfection of Nuclear Factor κB Decoy Oligodeoxynucleotides As A Gene Therapy", Arthritis & Rheumatism (1999) 42:2532–2542.
Yu, Xiao–Peng et al., "down–regulation on NF–κB protein levels in activated human lymphocytes by 1,25–dihydroxyvitamin D$_3$", Proc. Natl. Acad. Sci. USA (1995) 92:10990–10994.
Zabel, U., and Baeuerle, P.A., "Purified Human IκB Can Rapidly Dissociate the Complex of the NF–κB Transcription Factor with Its Cognate DNA", Cell (1990) 61:255–265.
Zinn, K. et al., "Identification of Two Distinct Regulatory Regions Adjacent to the Human β–Interferon Gene", Cell (1983) 34:865–879.
Pendurthi et al., Arterioscler Thromb Vasc. Biol. (1999) 19:419–426.
Reed et al., The Journal of Immunology (1986) 137:150–154.
Rigby et al., J. Clin. Invest. (1984) 74:1451–1455.
Ryu et al., Biochemical and Biophysical Research Communications (2000) 272:758–764.
Sadikot et al., Am. J. Respir. Crit. Care Med. (2001) 164:873–878.
Scheinman et al, Molecular and Cellular Biology (1995) 15:943–953.
Schmidt et al., Journal of Virology (1990) 64:4037–4041.
American Association for the Advancement of Science (1993).
Sica et al., The Journal of Biological Chemistry (1997) 272:30412–30420.
Singh and Aggarwal, J. Of Biological Chemistry (1995) 270:24995–25000.
Leger et al., The Lancet (1979) 1:1017–1020.
Stark et al., The FASEB Journal (2001) 15:1273–1275.
Takeuchi et al., The Journal of Immunology (1998) 160:209–218.
Tobler et al., Blood (1992) 79:45–51.
Tsoukas et al., Science (1984) 224:1438–1440.
Wadsworth and Koop, Biochemical Pharmacology (1999) 57:941–949.
Weismann G., Scientific American (1991) pp. 84–90.
Weissmann et al., Abstract (2002) 571–577.
Yan and Polk, the Journal of Biological Chemistry (1999) 274:36631–36636.
Yang et al., J. Nutr. (1998) 128:2334–2340.
Yin et al., Nature (1998) 396:77–80.
Yu et al, Proc. Natl. Acad. Sci. USA (1995) 92:10990–10994.
Yuan et al., Science (2001) 293:1673–1677.
Current Opinion in Cell Biology (1993) 5:477–487.
Schmitz et al. Trends in cell Biology (1991) 5:130–137.
Berkowitz et al., the Journal of Biological Chemistry (2002) 277:24694–24700.
Cappellen et al., The Journal of Biological Chemistry (2002) 277:21971–21982.
Chadwick et al., PNAS (2005) 102:2543–2548.
Chen et al., Nature (1998) 391:410–413.
Elices et al., Cell (1990) 60:577–584.
Ghisletti et al., Molecular and Cellular Biology (2005) 25:2957–2968.
Gianni et al., J. Clin. Endocrinol. Metab. (2004) 89:6097–6099.
Harnish et al., Endocrinology (2000) 141:3403–3411.
JBMR ASBMR 27th Annual Meeting SU103–SU106.
Liu et al., J. Natl. Cancer Inst. (2003) 95:1586–1597.
Macy et al., Clinical Chemistry (1997) 43:52–58.
Marino et al., Molecular and Cellular Endocrinology (2001) 182:19–26.
O'Brien et al., Am. J. Physiol. Endocrinol. Metab. (2005) 289:E784–E793.
O'Keefe et al., Lab. Invest. (1997) 76:457–465.
Reifel–Miller et al., The Journal of Biological Chemistry (1994) 269:23861–23864.
Sims et al., J. Clin. Invest. (2004) 113:379–389.
Sims et al., J. Bone Miner Res. (2005) 20:1093–1102.
Control No. 05–A–1610–ASBMR 1PG.
Walsh et al., The American Journal of Cardiology (2001) 88:825–828.
Walsh et al., JAMA (1998) 279:1445–1451.
Bertelli et al., Drugs Exptl. Clin. Res. (1998) XXIV:133–138.
Buffoli et al., JHC exPress (2005) pp. 2–33.
Hai–Hong et al., Journal of the Fourth Military Medical University (2003) 24:923–925.
Lee et al., J. Of Clinical Pharmacology (1998) 38:981–993.
Kundu and Surh, Mutation Research (2004) 555:65–80.
Leiro et al., International Immunophamacology (2005) 5:393–406.
Tsai et al., British Journal of Pharmacology (1999) 126:673–680.
Brueckmann et al., Inflamm. Res. (2004) 53:528–533.
Brun–Buisson et al., JAMA (1995) 274:968–974.
Derhaschnig et al., Blood (2003) 102:2093–2098.
Dhainaut et al., Thromb. Haemost (2003) 90:642–653.
Bernard et al., Intensive Care Med. (2003) 29:894–903.
Dhainaut et al., Crit. Care Med. (2004) 32[Suppl]: S194–S201.
Joyce et al., The Journal of Biological Chemistry (2001) 276:11199–11203.
Joyce et al., Crit. Care Med. (2002) 30 [Suppl]:S288–S293.
Kalil et al., Shock (2004) 21:222–229.
Kinasewitz et al., Critical Care (2004) 8:R82–R90.

Martin et al., N. Engl. J. Med. (2003) 348:1546–1554.
Nick et al., blood (2004) 104:3878–3885.
Opal et al., The Journal of Infectious Diseases (1999) 180:1584–1589.
Xigris drotrecogin alfa (activated) Drug Action 2pg.
Xigris drotrecogin alfo (activated) 1p.
Adams et al., Cancer Research (1999) 59:2615–2622.
Davis et al., Science (1991) 253:1268–1271.
Liou and Baltimore, Current Opinion in Cell Biology (1993) 5:477–487.
Schmitz et al. Trends in Cell Biology (1991) 1:130–137.
Chen et al. Nature (1998) 391:410–413.
Joyce and Grinnell, Crit. Care Med. (2002) 30[Suppl]: S288–S293.
Kalil et al. Shock (2004) 21:222–229.
Müller and Harrison, FEBS Letters (1995) 369:113–117.
Reifel–Miller et al., The Journal of Biological Chemistry (1994) 269:23861–23864.
Xigris drotrecogin alfa (activated) Drug Action 2pg..
Xigris drotrecogin alfa (activated) Emerging Understanding 1pg.
Gilston et al., Ann. Rheum. Dis. (2000) 59:303–307.
Kaltschmidt et al., Biol. Chem. Hoppe–Syler (1995) 376:9–16.
Kaltschmidt et al., Proc. Natl. Acad. Sci. USA, (1995) 92:9618–9622.
Kumar et al., Oncogene (1998) 17:913–918.
Palombella et al., Proc. Natl. Acad. Sci. USA, (1998) 95:15671–15676.
Zabel et al., The EMBO Journal (1993) 12:201–211.
Stein and Yang, Molecular and Cellular Biology (1995) 15:4971–4979.
Taranta et al., Bone (2002) 30:368–376.
Taylor et la., J. Clin. Invest. (1987) 79:918–925.
Helvering et al., Molecular Pharmacology (2005) 68:1225–1238.
Taylor et al., J. Clin. Invest. (1987) 79:918–925.
Baeuerle and Baltimore, Cell (1988) 53:211–217.
Baeuerle and Baltimore, Science (1988) 242:540–546.
Bass et al., Proteins: Structure, Function & Genetics (1990) 8:309—314.
Boda et al., Folia Biologica (Praha) (1987), 33:93–97.
Du et al., Molecular Brain Research (2005) 136:177–188.
Curriculum Vitae of George R. Stark, Ph. D. updated Sep. 12, 2005.
Fried and Crothers, Nucleic Acids Research (1981) 9:6505–6525.
Friedman et al., Nature (1988) 335:452–454.
Gallop et al., Journal of Medicinal chemistry (1994) 37:1233–1251.
Kawamurn et al., Gene Therapy (2001) 8:906–912.
Methods in Molecular and Cellular Biology (1989) 1:249.
McKinsey et al., The Journal of Biological Chemistry (1997) 272:22377–22380.
Morishta et al., Nature Medicine (1997) 1:894–899.
Myers et al., Research Articles (1986) 232:613–618.
Nicolau et al., Cell Cell Fusion (1984) pp. 254–267.
Sawa et al., Circulation (1997) 96[suppl] :II–280–II–285.
Scott and Smith, Science (1990) 249:386–390.
Siebenlist et al., Annu. Rev. Cell Biol. (1994) 10:405–455.
Tanaka et al., Nucleic Acids Research (1994) 22:3069–3074.
Tomita et al., Journal of Hypertension (1996) 16:993–1000.
Sawa et al., Circulation (1997) 96[suppl II] :II–280–II–285.
Schindler et al., The Journal of Immunology (1990) 144:2216–2222.
Holden C., Science (1985) 230:302.
Tomita et al., J. Hypertens (1998) 16:993–1000.
Tung et al., Proc. Natl. Acad. Sci. USA, (1988) 85:2479–2483.
PCT International Application No. WO 90/02809, International Publication Date Mar. 22, 1990.
PCT International Application No. WO 90/15070, International Publication Date Dec. 13, 1990.
Martino et al., J. Natl. Cancer Inst. (2004) 96:1751–1761.
McDonnell D.P., Endocrinology (2003) 144:4237–4240.
Metka et al., Fertility and Sterility (1992) 57:37–41.
Mundy et al., Osteoporosis (1996) pp. 301–313.
Physician's Guide to Prevention And Treatment of Osteoporosis (2003).
Nelson et al., JAMA (2002) 288:872–881.
Norfleet et al., FASEB J. (2000) 14:157–165.
O'Brien et al., Am. J. Physiol. Endorcinol. Metab (2005) 289:E784–E793.
Papapoulos S.E., Osteoporosis (1996) Chapter 64 1209–1234.
Parfitt A.M., Journal of Cellular Biochemistry (1994) 55:273–286.
Penolazzi et al., International Journal of Molecular Medicine (2004) 14:145–152.
Pfahl M., Endocrine Reviews (1993) 14:651–658.
Poli et al., EMBO Journal (1994) 13:1189–1196.
Power et al., Science (1991) 254:1636–1639.
Razandi et al., Molecular Endocrinology (1999) 13:307–319.
JAMA (2002) 288:321–333.
Rodan and Fleisch, J. Clin. Invest. (1996) 97:2692–2696.
Scheinman et al., Science (1995) 270:283–286.
Scheinman et al., Molecular and Cellular Biology (1995) 15:943–953.
Schindler and Baichwal, Molecular and Cellular Biology (1994) 14:5820–5831.
Sims et al., Journal of Bone and Mineral Research (2005) 20:1093–1102.
Smith et al., Molecular Endocrinology (1997) 11:657–666.
Tam et al., Science (1986) 234:1234–1237.
Tang et al., PNAS (2005) 102:5132–5137.
Tesarik and Mendoza, J. Clin. Endocrinol. Metab. (1995) 80:1438–1443.
Treilleux et al., Molecular Endocrinology (1997) 11:1319–1331.
Truss and Beato, Endocrine Reviews (1993) 14:459–479.
van de Stople et al., The Journal of Biological Chemistry (1994) 269:6185–6291.
Watson et al., Experimental Physiology (1999) 84:1013–1022.
Weigel and Zhang, J. Mol. Med. (1998) 76:469–479.
Whelan et al., Nucleic Acids Research (1991) 19:2645–2653.
Zang et al., Journal of Neuroimmunology (2002) 124:106–114.
Physicians' Desk Reference, 24$^{th}$ Ed. (1970) various pages of the Genetic and Chemical Name Index.
Declaration Under 37 C.F.R. §1.132 by David Baltimore singed Sep. 14, 1999; pp. 2–31.
Adams and Teegarden, J. Nutr. (2004) 134:2948–2952.
Aljada et al., The Journal of Clinical Endocrinology & Metabolism (1996) 84:3386–3389.

Alroy et al., Molecular and Cellular Biology (1995) 15:5789–5799.
Auphan et al., Science (1995) 270:286–290.
Baeuerle and Baichwal, Advances in Immunology (1997) 65:111–137.
Bantel et al., Am. J. Gastroenterol (2000) 95:3452–3457.
Bennett Jr. et al., JAMA (1963) 183:166–169.
Bergmann et al., Immunology (2004) 111:430–434.
Berry et al., Experimental Cell Research (2002) 272:176–184.
Björnström and Sjöberg, Molecular Endocrinology (2005) 19:833–842.
Blanco–Colio et al., Circulation (2000) 102:1020–1026.
Brini et al., Eur. Cytokine Net. (1990) 1:131–139.
Callejas et al., Hepatology (2002) 35:341–348.
Chaudhary and Avioli, The Journal of Biological Chemistry (1996) 271:16591–16596.
Cid et al., J. Clin. Invest. (1994) 93:17–25.
Delhase et al., Science (1999) 284:309–313.
Deshpande et al., AJRI (1997) 38:46–54; Dew et al., British Medical Journal (1983) 287:23–24.
Dew et al., British Medical Journal, (1983) 287:23–24.
Din et al., British Journal of Cancer (2004) 91:381–388.
Emmel et al., Science (1989) 246:1617–1620.
Curriculum Vitae of Stephen Michael Prescott dated Aug. 12, 2005.
Synthetic Generic Conjugated Estrogens <http://www.fda.gov/eder/news/cetimeline.htm>.
Forsblad et al., Arthritis Research & Therapy (2003) 5:R202–R209.
Fujihara et al., the Journal of Immumology (2000) 165:1004–1012.
Giffin et al., Nature Structural Biology (2003) 10:800–806.
Gilmore and Morin, Reviews (1993) 9:427–433.
Goodman & Gilman's The Pharmacological Basis of Therapeutics, $9^{th}$ Ed. pp. 625–631 and 1780 & 1712.
Griffith et al., Cardiac Transplantation (1982) 196:324–329.
Hahn et al., Journal of Clinical Investigation (1950) pp. 274–281.
Hämäläinen et al., European Journal of Pharmacology (2002) 448:239–244.
Han et al., Rheumatology (2001) 40:267–273.
Haynes et al., Circ. Res. (2000) 87:677–682.
Ho et al., Clinical Immunology and Immunopathology (1996) 80:S40–S45.
Hogan et al. Genes & Development (2003) 17:2205–2232.
Holmes–McNary and Baldwin Jr., Cancer Research (2000) 60:3477–3483.
Hölschermann et al., The Journal of Immunology (2001) 166:7112–7120.
Hölschermann et al., Circulation (1997) 96:4232–4238.
Ide and Lau, J. Nutr. (2001) 131:1020S–1026S.
Kayisli et al. Biology of Reproduction (2004) 71:714–721.
Kim and Leonard, The EMBO Journal (2002) 21:3051–3059.
Kinoshita et al., Immunity (1997) 6:235–244.
Kopp and Ghosh, Science (1994) 265:956–959.
Krönke et al., Proc. Natl. Acad. Sci. USA (1984) 81:5214–5218.
Lemire et al., J. Clin. Invest. (1984) 74:657–661.
Lemire et al., The Journal of Immunology (1985) 134:3032–3035.
Loh et al., The Journal of Biological Chemistry (1996) 271:10884–10891.
Liu et al., The Journal of Biological Chemistry (2002) 277:24353–24360.
Manna et al., The Journal of Immunology (2000) 164:6509–6519.
Manolagas et al., J. Clin. Endocrinol Metab. (1986) 63:394–400.
McCaffrey et al., Nucleic Acids Research (1994) 22:2134–2142.
Perez–G. et al., The Journal of Immunology (2002) 168:1428–1434.
Nagasawa et al., Journal of Cellular Physiology (1981) 109:181–192.
Nagpal et al., Current Medicinal Chemistry (2001) 8:1661–1679.
Park et al., Nephrol Dial Transplant (2004) 19:312–319.
Rigby et al., The Journal of Immunology (1985) 135:2279–2286.
Rovera et al., Science (1979) 204:868–870.
Ryu et al., Biochemical and Biophysical Research Communications (2000) 272:758–764.
Simoncini et al., Nature (2000) 407:538–541.
Physicians' Desk Reference, $24^{th}$ Ed. (1970) various pages of the Generic and Chemical Name Index.
Physisians' Desk Reference $39^{th}$ Ed. (1985) pp. 1811–1813.
Aljada et al., The Journal of Clinical Endocrinology & Metabolism (1996) 84:3386–3389.
Baldwin Jr., A.S., Annu. Rev. Immunol. (1996) 14:649–681.
Bergmann et al., Am. J. Respir. Cell Mol. Biol. (2004) 30:555–563.
Björnström and Sjöberg, Molecular Endocrinology (2005) 19:833–842.
Chaudhary and Avioli, The Journal of Biological Chemistry (1996) 271:16591–16596.
Deshpande et al., AJRI (1997) 38:46–54.
Dew et al., British Medical Journal (1983) 287:23–24.
Curriculum Vitae of Jeffrey V. Ravetch.
Synthetic Generic Conjugated Estrogens <http://www.fda.gov/eder/news/cetimeline.html>.
Fujihara et al., the Journal of Immunology (2000) 165:1004–1012.
Goodman & Gilman's The Pharmacological Basis of Therapeutics, $9^{th}$ Ed. pp. 625–631 and 1780 & 1712.
Griffith et al., J. Thorac Cardiovasc Surg. (1984) 88:952–957.
Hämäläinen et al., European Journal of Pharmacology (2002) 448:239–244.
Hölschermann et al., The Journal of Immunology (2001) 166:7112–7120.
Lefering and Neugebauer, Critical Care Medicine (1995) 23:1294–1303.
Annual Meeting, J. Am. Med. Assoc. (1963) 183:166–169.
Baeuerle and Baltimore, "IκB: A Specific Inhibitor of the NF–κB Transcription Factor", Science (1988a) 242:540–546.
Baeuerle and Baltimore, "Activation of DNA–Binding Activity in an Apparently Cytoplasmic Precursor of the NF–κB Transcription Factor", Cell (1988b) 53:211–217.
Trial Transcript—Apr. 27, 2006 Jury Trial Day 13, First Session pp. 1–86, in Civil Case 02 CV 11280 RWZ.
Trial Transcript—Apr. 27, 2006 Jury Trial Day 13, Second Session pp. 88–141, in Civil Case 02 CV 11280 RWZ.
Physicians' Desk Reference, $24^{th}$ Ed. (1970) various pages of The Generic and Chemical Name Index.
Abraham et al., JAMA (1995) 273:934–941.

Abraham et al., The Lancet (1998) 351:929–933.
Abraham et al., Am. J. Physiol. Lung Cell Mol. Physiol (2000) 279:L1137–L1145.
Abraham E., Crit. Care Med. (2003) 31[Suppl.]:S195–S199.
Alberti, et al., Intensive Care Med (2002) 28:108–121.
Aljada et al., The Journal of Clinical Endocrinology & Metabolism (1996) 84:3386–3389.
Angus et al., Crit Care Med (2001) 29:1303–1310.
Angus et al., Crit Care Med (2004) 32:2199–2206.
Djillali et al. JAMA (2005) 288:862–871.
Baumgartner et al. The Lancet (1985) pp. 59–63.
Bernard et al., N. Engl. J. Med. (2001) 344:699–709.
Bone et al., N. Engl. J. Med. (1987) 317:653–658.
Bone et al., Critical Care Medicine (1995) 23:994–1006.
Branson et al., The Lancet (1983) pp. 1165–1168.
Brueckmann M., Thromb Haemost (2003) 90:1123–1126.
Brun–Buisson C., Intensive Care Med (2004) 30:580–588.
Bryniarski et al., Inflammation (2003) 27:333–340.
Bunnell et al., Crit. Care Med. (2004) 28:2713–2720.
Cohen and Carlet, Crit. Care Med. (1996) 24:1431–1440.
Cohen J., Nature (2002) 420–885–891.
Collart et al., Molecular and Cellular Biology (1990) 10:1498–1506.
Colucci et al., J. Clin. Invest. (1984) 74:200–204.
Comp and Esmon, J. Clin. Invest. (1981) 68:1221–1228.
Cooper and Stewart, N. Engl. J. Med. (2003) 348:727–734.
Cronin et al., Crit. Care Med. (1995) 23:1430–1439.
de Kleijn et al., Crit. Care Med. (2003) 31:1839–1847.
de Hooge et al., Osteo. Arthritis and Cartilage (2005) 13:66–73.
de Pont et al., Critical Care (2005) 9:R490–R497.
Derkx, et al., Clinical Infectious Diseases (1999) 28:770–777.
Bernard G.R., Intensive Care Med. (2003) 29:894–903.
Dhainaut et al., Thromb Haemost (2003) 90:642–653.
Emerick et al., The Pharmacology and Toxicology of Proteins (1987) pp. 351–367.
Esmon et al., The Journal of Biological Chemistry (1976) 251:3052–3056.
Esmon C.T., J. Thromb. Haemost (2005) 3:1910–1911.
FDA Clinical Review BLA#125029/0 pp. 78–161.
Feistritzer and Riewald, Blood (2005) 105:3178–3184.
Finfer et al., Intensive Care Med. (2004) 30:589–596.
Fisher et al., N. Engl. J. Med. (1996) 334:1697–1702.
Giroir et al., Lancet (1997) 350:1439–1443.
Glick and Opal, Drugs (2004) 64:837–859.
Greenman et al., JAMA (1991) 266:1097–1102.
Griffin et al., J. Clin. Invest. (1981) 68:1370–1373.
Gruber and Griffin, Blood (1992) 79:2340–2348.
Gruber et al., Lancet (1993) 342:1275–1276.
Hahn et al., from the Streptococcal Disease Laboratory (1950) pp. 274–281.
Hinshaw et al., Circulatory Shock (1985) 16:265–277.
Hinshaw et al, Surgery Gynecology & Obstetrics (1986) 163:335–344.
Hiscott et al., Molecular and Cellular Biology (1993) 13:6231–6240.
Hooper et al., The Journal of Immunology (1998) 161:2567–2573.
Beckman et al., Intellectual Property Owners Association <http://www.ipo.org/Template.cfm?Section=National_Inventor_Of_The_Year_Award1&...>.
Joyce and Grinnell, Crit. Care Med. (2002) 30[Suppl]: S288–S293.
Joyce et al.,, The Journal of Biological Chemistry (2001) 276:11199–11203.
Keh et al., Am J. Respir. Crit. Care med. (2003) 167:512–520.
Kisiel et al., Biochemistry (1976) 15:4893–4900.
Klein et al., J. Clin. Invest. (2005) 115:860–869.
Kremer et al, Acta Maematol (1996) 95:268–273.
Levin et al., Lancet (2000) 356:961–967.
Macias et al., clin. Pharmacol. Ther. (2002) 72:391–402.
Mammen et al., Thrombosis et Diathesis Haemorrhagica (1961) 5:1–17.
Marsik et al., Clinical Immunology (2005) 114:293–298.
Martin et al., N. Engl. J. Med (2003) 348:1546–1554.
McCloskey et al., Ann. Intern. Med. (1994) 121:1–5.
Mifflin et al., Molecular Pharmacology (2004) 65:470–478.
Opal et al., Crit. Care Med. (1997) 25:1115–1124.
Owen and Esmon, The Journal of Biological Chemistry (1981) 256:5532–5535.
Padkin et al., Crit. Care Med. (2003) 31:2332–2338.
Panacek et al., crit. Care Med. (2004) 32:2173–2182.
Parrillo et al., Annals of Internal Medicine (1990) 113:227–242.
Parrillo J.E., The New England Journal of Medicine (1993) 328:1471–1477.
Patil et al., Immunol. Invest. (2004) 33:213–233.
Pedersen et al., Pflugers Arch—Eur. J. Physiol (2003) 446:9–16.
Phase 1 Clinical Studies <<file://S:William A/\Lindsay References\Phase 1 Clinical Studies.tm>.
Phase 2 Clinical Studies <<file://S:/William A\Lindsay References\Phase 2 Clinical Studies.htm>.
Phase 3 Clinical Studies <<file://S:/William A\Lindsay References\Phase 3 Clinical Studies.htm>.
Preas II et al., Blood (1996) 88:2465–2472.
Quesado et al., JAMA (1993) 269:2221–2227.
Sakata et al., Proc. Natl. Acad. Sci. USA (1985) 82:1121–1125.
Schlaak et al., Scand. J. Immunol. (2001) 54:396–403.
Seegers et al., Thrombosis Research (1976) 8:543–552.
Soop et al., Shock (2003) 19:503–507.
Sprung et al., N. Engl. J. Med. (1984) 311:1137–1143.
Stenflo J., the Journal of Biological Chemistry (1976) 251:355–363.
Suffredini et al, The Journal of Immunology (1995) 155:5038–5045.
Satoshi et al, Eur. J. Immunol. (2005) 35:460–468.
von der Möhlen et al., the Journal of Infectious Diseases (1995) 172:144–151.
van der Poll et al., J. Clin. Invest. (1996) 97:713–719.
van der Poll et al., J. Clin. Endocrinol. Metab. (1996) 81:3604–3606.
van der Poll et al., Blood (1997) 89:3727–3734.
van Hinsbergh et al., Blood (1985) 65:444–451.
Van Zee et al., The Journal of Immunology (1995) 154:1499–1507.
Verbon et al., The Journal of Immunology (2001) 166:3599–3605.
Hinshaw et al., N. Engl. J. Med. (1987) 317:659–665.
Wheeler and Bernard, N. Engl. J. Med. Current Concepts (2005) 340:207–214.
Wong et al., Arthritis & Rheumatism (2003) 48:1177–1189.
Wuestefeld et al., The Journal of Biological Chemistry (2003) 278:11281–11288.
XIGRIS™ Drotrecogin alfa (activated) pp. 1–9.

Macias et al., Critical Care (2005) 9[Suppl.]:S38–S45.
Zeng et al., Crit. Care Med. (2004) 32 [Suppl]:S302–S308.
Crit. Care Med. (1997) 25:1095–1100.
Ziegler et al., N. Engl. J. Med. (1982) 307:1225–1230.
Ziegler et al., N. Engl. J. Med. (1991) 324:429–436.
Adams et al., Journal of Bacteriology (2003) 185:1174–1180.
Aljada et al., The Journal of Clinical Endocrinology & Metabolism (1996) 84:3386–3389.
Azria and Avioli, Principles of Bone Biology (1996) Chapter 78 pp. 1083–1097.
Baldwin Jr. A. S., Annu. Rev. Immunol. (1996) 14:649–681.
Baldwin Jr. A. S., The Journal of Clinical Investigation (2001) 107:3–6.
Berg et al., The Journal of Biological Chemistry (1995) 270:15447–15450.
Biskobing D.M., Chest (2002) 121:609–620.
Black et al., J. Clin. Invest. (1994) 93:63–69.
Blum et al., The American Jurnal of Cardiology (2000) 86:892–895.
Bond et al., FEBS Letters (1998) 435:29–34.
Bunone et al., The EMBO Journal (1996) 15:2174–2183.
Chaisson et al., the Journal of Biological Chemistry (2004) 279:54841–54848.
Chen et al., The Journal of Biological Chemistry (2005) 280:4632–4638.
Coleman and Smith, Frontiers in Bioscience (2001) 6:1379–1391.
Coleman et al., The Journal of Biological Chemistry (2003) 278:12834–12845.
Coleman et al., Biochemical and Biophysical Research Communication (2004) 323:332–338.
Compston J.E., Physiological Reviews (2001) 81:419–447.
Cummings et al., JAMA (1999) 281:2189–2197.
Delmas et al., N. Engl. J. Med. (1997) 337:1641–1647.
Doran et al., Journal of Bone and Mineral Research (2001) 16:2118–2125.
Draper et al. Journal of Bone and Mineral Research (1996) 11:835–842.
El–Tanani and Green, Molecular Endocrinology (1997) 11:928–937.
Eriksen et al., Journal of Bone and Mineral Research (1999) 14:1217–1221.
Erlandsson et al., Journal of Endocrinology (2002) 175:319–327.
Synthetic Generic Conjugated Estrogens: Timeline (2003) <http://www.fda.gov/cder/news/cetimeline.htm>.
Evans et al., Endocrinology (1994) 134:2283–2288.
Franzoso et al., Genes & Development (1997) 11:3482–3496.
Farsetti et al., Endocrinology (1998) 139:4581–4889.
Fleisch H., Bisphosphonates in Bone Disease (1997) 3$^{rd}$ Ed. pp. 5–67.
Fleisch H., Bisphosphonates in Bone Disease (1997) 3$^{rd}$ Ed. pp. 5–163.
Horowitz et al., J. Clin. Invest. (1989) 83:149–157.
Hughes et al., Nature Medicine (1996) 2:1132–1136.
Jilka et al., Science (1992) 257:88–91.
Jimi et al. Nature Medicine (2004) 10:617–624.
Proceedings of ASCO vol. 17 (1998) p. 122a.
Kousteni et al., Cell (2001) 104:719–730.
Kousteni et al., Science (2002) 298:843–846.
Kousteni et al., J. Clin. Invest. (2003) 111:1651–1664.
Krämer et al., The Journal of Biological Chemistry (1995) 270:6577–6583.
Le Mellay et al., The Journal of Biological Chemistry (1997) 272:11902–11907.
Levin E.R., TEM (1999) 10:374–377.
Liu et al., The Journal of Immunology (2000) 164:4277–4285.
Liu et al., Journal of the National Cancer Institute (2003) 95:1586–1597.
Lubrosky et al., Human Reproduction (2002) 18:199–206.
Manolagas S. C., Endocrine Reviews (2000) 21:115–137.
Manolagas and Kousteni, Endocrinology (2001) 142:2200–2204.
Manolagas et al., Abstract The Endocrine Society (2002) pp. 385–409.
Deraschnig et al., Blood (2003) 102:2093–2098.
Joyce and Grinnell, Crit. Care Med. (2002) 30 [Suppl]: S288–S293.
Kali et al. Shock (2004) 21:222–229.
Reifel–Miller et al., The Journal of Biological Chemistry (1994) 269:23861–23864.
Curriculum Vitae of George R. Stark, Ph.D. updated Sep. 12, 2005.
Ghosh and Baltimore, Nature (1990) 344:678–682.
Khaled et al., Clinical Immunology (1988) 86:170–179.
McKinsey et al., The Journal of Biological Chemistry (1997) 272:22377–22380.
Nabel et al., Proc. Natl. Acad. Sci. USA (1996) 93:15388–15393.
Siebenlist et al., Annu. Rev. Cell. Biol. (1994) 10:405–455.
Trepicchio and Krontiris, Nucleic Acids Research (1993) 21:977–985.
Fiedler et al., Am. J. Respir. Cell Mol. Biol. (1998) 19:259–268.
McKinney et al., The Journal of Biological Chemistry (1997) 272:22377–22380.
Meng et al., Proc. Natl. Acad. Sci. USA, (1999) 96:10403–40408.
Myers et al., Science (1986) 232:613–618.
Roozemond et al., Immunobiol. (1987) 176:35–46.
Sawa et al., Circulation (1997) 96[suppl II]:II–280–II–285.
Shakhov et al., J. Exp. Med. (1990) 171:35–47.
PCT International Application No. WO 90/02809, International Publication Date Mar. 22, 1990.
PCT International Application No. WO 90/15070, International Publication Date Dec. 13, 1990.
Bottero et al. (2006) "NF–κB and the regulation of hematopoiesis," *Cell Death and Differentiation,* 13: 785–797.
Doucas et al. (2000) "Cytoplasmic catalytic subunit of protein kinase A mediates cross–repression by NF–κB and the glucocorticoid receptor," *PNAS,* 97 (22) : 11893–11898.
Withoff, S. et al. "Regulating the Master Regulator NF–κB: From Natural Strategies to Rationality Designed Superdrugs." in: Ghosh, S., *Handbook of Transcription Factor NF–kappaB* (Boca Raton, FL, CRC Press, 2007), pp. 195–211.
Azria and Avioli, Priniciples of Bone Biology (1996) Chapter 78 pp. 1083–1097.
Benten et al., Endocrinology (2001) 142:1669–1677.
Chaisson et al., the Journal of Biological Chemistry (2004) 279:54841–84848.
Cho and Katzenellenbogen, Molecular Endocrinology (1993) 7:441–452.

Coleman et al., The Journal of Biological Chemistry (2003) 278:12834–12845.
Coleman et al., Biochemical and Biophysical Research Communication (2004) 323:332–338.
Draper et al., Journal of Bone and Mineral Research (1996) 11:835–842.
Duan et al., Endocrinology (1998) 139:1981–1990.
Synthetic Generic Conjugated Estrogens: Timeline (2003) <http://www.fda.gov/cder/news/cetimeline.htm>.
Farsetti et al., Endocrinology (1998) 139:4581–4589.
Fleisch H., Bisphosphonates in Bone Disease (1997) $3^{rd}$ Ed. pp. 5–67.
Fleisch H., Bisphosphonates in Bone Disease (1997) $3^{rd}$ Ed. pp. 5–163.
Frolik et al., Bone (1996) 18:621–627.
Krämer et al., The Journal of Biological Chemistry (1995) 270:6577–6583.
Le Mellay et al., The Journal of Biological Chemistry (1997) 272:11902–11907.
Manolagas et al., Kidney International (2004) 66:S41–S49.
McDonnell D.P., TEM (1999) 10:301–311.
Parfitt et al., Journal of Bone and Mineral Research (1996) 11:150–159.
Penolazzi et al., International Journal of Molecular Medicine (2004) 14:145–152.
Reed et al., Anti–Cancer Drugs (2005) 16:559–567.
Schindler and Baichwal, Molecular and Cellular Biology (1994) 14:5820–5831.
Teitelbaum S.L., Science (2000) 289:1504–1508.
van de Stople et al., The Journal of Biological Chemistry (1994) 269:6185–6192.
Physicians' Desk Reference, $24^{th}$ Ed. (1970) various pages of the Generic and Chemical Name Index.
Declaration Under 37 C.F.R. §1.132 by David Baltimore singed Sep. 14, 1989, Examiner's Amendment pp. 2–31.
Aljada et al., The Journal of Clinical Endocrinology & Metabolism (1996) 84:3386–3389.
Björnström and Sjöberg, Molecular Endicronology (2005) 19:833–842.
Bochkov et al., Blood (2002) 99:199–206.
Chaudhary and Avioli, The Journal of Biological Chemistry (1996) 271:16591–16596.
Synthetic Generic Conjugated Estrogens <http://www.fda.gov/eder/news/cetimeline.htm>.
Goodman & Gilman's The Pharmacological Basis of Therapeutics, $9^{th}$ Ed. pp. 625–631 and 1780 & 1712.
Hämäläinen et al., European Journal of Pharmacology (2002) 448:239–244.
Ho et al, Clinical Immunology and Immunopathology (1996) 80:S40–S45.
Hölschermann et al., The Journal of Immunology (2001) 166:7112–7120.
Ide and Lau, J. Nutr. (2001) 131:1020S–S1026S.
Kayisli et al., Biology of Reproduction (2004) 71:714–721.
Liu et al., The Journal of Biological Chemistry (2002) 277:24353–24360,
Ryu et al., Biochemical and Biophysical Research Communications (2000) 272:758–764.
Siebenlist et al., Molecular and Cellular Biology (1986) 6:3042–3049.
Siebenlist et al., Annu. Rev. Cell Viol. (1994) 10:405–455.
Simoncini et al., Cir. Res. (2000) 87:19–25.
Tsoukas et al., Science (1984) 224:1438–1140.
Physicians' Desk Reference, $24^{th}$ Ed. (1970) various pages of the Generic and Chemical Name Index.
Physicians' Desk Reference $39^{th}$ Ed. (1985) pp. 1811–1813.
Aljada et al., The Journal of Clinical Endocrinology & Metabolism (1996) 84:3386–3389.
Baldwin Jr., A.S., Annu. Rev. Imminol. (1966) 14:649–681.
Björnström and Sjöberg, Molecular Endicronology (2005) 19:833–842.
Blanco Colio et al., Manuscript.
Chaudhary and Avioli, The Journal of Biological Chemistry (1996) 271:16591–16596.
Curriculum Vitae of Jeffey V. Ravetch.
Synthetic Generic Conjugated Estrogens <http://www.fda.gov/eder/news/cetimeline.htm>.
Goodman & Gilman's The Pharmacological Basis of Therapeutics, $9^{th}$ Ed. pp. 625–631 and 1780 & 1712.
Hämäläinen et al., European Journal of Pharmacology (2002) 448:239–244.
Hölschermann et al., The Journal of Immunology (2001) 166:7112–7120.
Ryu et al., Biochemical and Biophysical Research Communications (2000) 272:758–764.
Sienbenlist et al., Annu. Rev. Cell Viol. (1994) 10:405–455.
Simoncini et al., Nature (2000) 407:538–541;.
Yang et al.,, J. Nutr. (1998) 128:2334–2340.
Berkowitz et al., the Journal of Biological Chemistry (2002) 277:24694–24700.
Blum et al., the American Journal of Cardiology (2000) 86:892–895.
Cappellen et al., The Journal of Biological Chemistry (2002) 277:21971–21982.
Ghisletti et al., Molecular and Cellular Biology (2005)25:2957–2968.
Miller and Harrison, FEBS Letters (1995) 369:113–117.
Reifel–Miller et al., The Journal of Biological Chemistry (1994) 269:23861–23864.
Sims et al., J. Clin. Invest. (2001) 113:379–389.
Bertelli et al., Drugs Exptl. Clin. Res. (1998) XXIV: 133–138.
Hai–Hong et al., Journal of the Fourth Military Medical University (2003) 24:923–925.
Joyce et al., Crit. Care Med. (2002) 30[Suppl]:S288–S293.
Schmitz et al.. Trends in Cell Biology (1991) 1:130–137.
Banerji, J. et al., (1981) "Expression of a beta–globin gene is enhanced by remote SV40 DNA sequences," Cell, 27:299–308.
Cullen, (1986) "Trans–activation of human immunodeficiency virus occurs via a bimodal mechanism," Cell, 46:973–982.
Gescher et al., (1985) "Characterization of the growth inhibition induced by tumor–promoting phorbol esters and of their receptor binding in A549 human lung carcinoma cells," Cancer Res., 45:4315–4321.
Humphries et al., (1982) "Differences in human alpha–, beta–and delta–globin gene expression in monkey kidney cells," Cell, 30:173–183.
Hunter et al., (1984) "Protein kinase C phosphorylation of the EGF receptor at a threonine residue close to the cytoplasmic face of the plasma membrane," Nature, 311:480–483.
Jang et al., (2005) "Tetradecanoyl phorbol acetate induces expression of Toll–like receptor 2 in U937 cells: involvement of PKC, ERK, and NF–kappaB," Biochem. Biophys. Res. Commun., 328:70–77.

Kang et al., (2005) "Phorbol ester up–regulates aldose reductase expression in A549 cells: a potential role for aldose reductase in cell cycle modulation," Cell. Mol. Life Sci., 62:1146–1155.

Pasleau et al., (1985) "Growth hormone gene expression in eukaryotic cells directed by the Rous sarcoma virus long terminal repeat or cytomegalovirus immediate–early promoter," Gene, 38:227–232.

Withoff, S. et al. "Chapter 10: Regulating the Master Regulator NF–κB: From Natural Strategies to Rationally Designed Superdrugs," *Handbook of Transcription Factor NF–kappaB:* 195–221 (2007).

Doucas, V., et al. "Cytoplasmic catalytic subunit of protein kinase A mediates cross–repression of NF–κB and the glucocorticoid receptor," *PNAS Early Edition*: 2.

Bottero et al., "NF–κB and the regulation of hematopoiesis," *Cell Death and Differentiation* 13:785–797 (2006).

Israël, A. et al., "TNF stimulates expression of mouse MHC class I genes by inducing an NfχB–like enhancer binding activity which displaces constitutive factors", The EMBO Journal (1989) 8:3793–3800.

Lenardo, M.J. and Baltimore, D., "NF–κB: A Pleiotropic Mediator of Inducible and Tissue–Specific Gene Control", Cell (1989) 58:227–229.

Meager, A. et al., "Preparation and Characterization of Monoclonal Antibodies Directed Against Antigenic Determinants of Recombinant Human Tumour Necrosis Factor (rTNF)", Hybridoma (1987) 6:305–311.

Mercola, M. et al., "Immunoglobulin Heavy–Chain Enhancer Requires One or More Tissue–Specific Factors", Science (1985) 227:266–270.

Rothlein, R. et al., "Induction of Intercellular Adhesion Molecule 1 on Primary And Continuous Cell Lines By Pro–Inflammatory Cytokines", The Journal of Immunology (1988) 141:1665–1669.

Beutler, B. et al., "Passive Immunization Against Cachectin/Tumor Necrosis Factor Protects Mice from Lethal Effect of Endotoxin", Science (1985) 229:869–871.

Beutler, B. and Cerami, A., "Cachectin: More Than A Tumor Necrosis Factor", The New England Journal of Medicine (1987) 316:379–385.

Beutler, B. and Cerami, A., "Tumor Necrosis, Cachexia, Shock, And Inflammation: A Common Mediator", Ann. Rev. Biochem. (1988) 57:505–18.

Blasco, R. et al., "Variable and Constant Regions in African Swine Fever Virus DNA", Virology (1989) 168:330–338.

Brady, J. et al., "Interaction between two transcriptional control sequences required for tumor–antigen–mediated simian virus 40 late gene expression", Proc. Natl. Acad. Sci. USA (1985) 82:7299–7303.

Brady, J. and Khoury, G., "trans Acitivation of the Simian Virus 40 Late Transcription Unit by T–Antigen", Molecular and Cellular Biology (1985) 5:1391–1399.

Enjuanes, L. et al., "Titration of African Swine Fever (ASF) Virus", J. Gen. Virol. (1976) 32:471–477.

Enjuanes, L. et al., "Isolation and Properties of the DAN of African Swine Fever (ASF) Virus", J. Gen. Virol. (1976) 32:479–492.

Fendly, B.M. et al., "Murine Monoclonal Antibodies Defining Neutralizing Epitopes on Tumor Necrosis Factor", Hybridoma (1987) 6:359–370.

Israël, et al., "A common positive trans–acting factor binds to enhancer sequence in the promoters of mouse H–2 and $\beta_2$–microglobulin genes", Proc. Natl. Acad. Sci. USA (1987) 84:2653–2657.

Abraham et al., Am. J. Physiol. Lung Cell Mol. Physiol (2000) 279:L1137–L1145.

Aljada et al., The Journal of Clinical Endocrinology & Metabolism (1996) 84:3386–3389.

Brueckmann et al., Thromb Haemost (2003) 89:149–160.

Bunnell et al., Crit. Care Med. (2000) 28:2713–2720.

Emerick et al., The Pharmacology and Toxicology of Proteins (1987) pp. 351–367.

FDA Clinical Review BLA#125029/0 pp. 78–161.

Flournoy et al., Med. Microbiol. Immunol. (1986) 175:221–227.

Granowitz et al., Blood (1993) 82:2985–2990.

Hinshaw et al., Surgery Gynecology & Obstetrics (1986) 163:335–344.

Hotchkiss and Karl The New England Journal of Medicine (2003) 348:138–150.

Beckman et al., Intellectual Property Owners Association <http://www.ipo.org/Template.cfm?Section=National_Inventor_Of_The_Year_Award1&...>.

Keh et al., Am. J. Respir. Crit. Care med. (2003) 167:512–520.

McClosky et al., Ann. Intern. Med. (1994) 121:1–5.

Phase 1 Clinical Studies <<file:///S:/William A\LindsayReferences\Phase 1 Clinical Studies.htm>.

Phase 2 Clinical Studies <<file:///S:/William A\Lindsay References\Phase 2 Clinical Studies.htm>.

Phase 3 Clinical Studies <<file:///S:/William A\Lindsay References\Phase 3 Clinical Studies.htm>.

Rangel–Frausto et al., JAMA (1995) 273:117–123.

Van Amersfoort et al., Clincial Microbiology Reviews (2003) 16:379–414.

von der Möhlen et al., the Journal of Infectious Diseases (1995) 172:144–151.

Wuestefeld et al., The Journal of Biological Chemistry (2003) 278:11281–11288.

Aljada et al., The Journal of Clinical Endocrinology & Metabolism (1996) 84:3386–3389.

Aronica and Katzenellenbogen, Molecular Endocrinology (1993) 7:743–752.

Emmel et al., *Cyclosporin A Specifically Inhibits Function of Nuclear Proteins Involved in T Cell Activation,* Science, 246: 1617–20 (Dec. 1989).

Schmidt et al., *Inducible Nuclear Factor Binding to the κB Elements of the Human Immunodeficiency Virus Enhancer in T Cells Can be Blocked by Cyclosporin A In a Signal–Dependent Manner,* J. of Virology, 64:4037–4041 (Aug. 1990).

Brini et al., *Cyclosporin A Inhibits Induction of IL–2 Receptor α Chain Expression by Affecting Activation of NF–κ-B–Like Factor(s) in Cultured Human T Lymphocytes,* Eur. Cytokine Net., 1:131–139 (Sep. 1990).

The Physician's Desk Reference, 1811–13 (1985 Ed.).

Griffith et al., *Cardiac Transplantation with Cyclosporin A and Prednisone, Ann. Surg.* 196:324–329 (Sep. 1981).

Griffith et al., *Targeted Blood Levels of Cyclosporine for Cardiac Transplantation,* J. Thorac. Cardiovasc. Surg. 99:952–957 (Dec. 1984).

Baldwin, *The NF–κB and IκB Proteins: New Discoveries and Insights,* Annu. Rev. Immunol. 14:649–81 (1996).

Baldwin, *The Transcription Factor NF–κB and Human Disease,* J. Clin. Invest. 107:3 (Jan. 2001).

Baeuerle, *The Inducible Transcription Activator NF–κB: Regulation by Distinct Protein Subunits*, Biochimica et Biophysica Acta, 1072:63–80 (1991).

Baeuerle and Henkel, *Function and Activation of NF–κB in the Immune System*, Ann. Rev. Immunol., 12:141–79 (1994).

Reed et al., *Effect of Cyclosporin A and Dexamethasone on Interleukin 2 Receptor Gene Expression*, J. Immunol. 137:150–154 (Jul. 1986).

Krönke et al., *Cyclosporin A Inhibits T–Cell Growth Factor Gene Expression At the Level of Gene Expression*, Proc. Natl. Acad. Sci. USA 81:5214–5218 (Aug. 1984).

Siebenlist et al., *Promoter Region of Interleukin–2 Gene Undergoes Chromatin Structure Changes and Confers Inducibility on Chloramphenicol Acetyltransferase Gene During Activation of T Cells*, Molecular and Cell Biol. 6:3042–3049 (Sep. 1986).

Hölschermann et al., *Cyclosporin A Inhibits Monocyte Tissue Factor Activation in Cardiac Transplant Recipients*, Circulation, 96:4232–4238 (Dec. 1997).

Alkalay, et al., *In Vivo Stimulation of IκB Phosphorylation is Not Sufficient to Activate NF–κB*, Mol. Cell Biol. 15:1294–1301 (1995).

Hoyos et al., *Kappa B–Specific DNA Binding Proteins: Role in the Regulation of Human Interleukin–2 Gene Expression*, Science 244:457–460 (Apr. 1989).

Meichle et al., *Protein Kinase C–Independent Activation of Nuclear Factor κB by Tumor Necrosis Factor*, J. Biol. Chem. 265–8339–8343 (May 15, 1990).

Shirakawa et al., *In vitro Activation and Nuclear Translocation of NF–κB Catalyzed by Cyclic AMP–Dependent Protein Kinase and Protein Kinase C*, Mol. And Cell. Biol., 9: 2424–2430 (Jun. 1989).

Tsoukas, et al. *1,25–Dihydroxyvitamin $D_3$: A Novel Immunoregulatory Hormone*, Science 224:1438–40 (Jun. 1984).

Manolagas et al., *The Anti–Proliferative Effect of Calcitriol on Human Peripheral Blood Mononuclear Cells*, JCE&M, 63:394–400 (1986).

Yu et al., *Down–regulation of NF–κB Protein Levels in Activated Human Lymphocytes by 1,25–Dihydroxyvitamin $D_3$*, Proc. Natl. Acad. Sci., 92:10990–10994 (Nov. 1995).

Lemire et al., *1,25–Dihydroxyvitamin $D_3$ Suppresses Proliferation and Immunoglobulin Production by Normal Human Peripheral Blood Mononuclear Cells*, J. Clin. Invest., 74:657–661 (Aug. 1984).

Lemire et al., *1, 25–Dihydroxyvitamin $D_3$ Suppresses Human T Helper/Inducer Lymphocyte Activity in Vitro*, J. Immunol., 134:3032–3035 (May 1985).

Rigby et al., *Inhibition of T Lymphocyte Mitogenesis by 1,25–Dihydroxyvitamin D3 (Calcitriol)*, J. Clin. Invest. 74:1451–1455 (Oct. 1984).

Rigby et al., *The Effects of 1,25–Dihydroxyvitamin D3 on Human T Lymphocyte Activation and Proliferation: A Cell Cycle Analysis*, J. Immunol. 135:2279–2286 (Oct. 1985).

Colston et al., *1,25–Dihydroxyvitamin $D_3$ and Malignant Melanoma: The Presence of Receptors and Inhibition of Cell Growth in Culture*, Endocrinology 108:1083–1086 (1981).

Semmler, *The Synthesis of 1α,25–Dihydroxycholecalciferol—A Metabolically Active Form of Vitamin $D_3$*, Tetrahedron Lett. 40:4147–50 (1972).

Holick, *Identification of 1α,25–Dihydroxycholecalciferol, a Form of Vitamin $D_3$ Metabolically Active in the Intestine*, P.N.A.S. 68:803 (1971).

Norman, *1,25–Dihydroxycholecalciferol: Identification of the Proposed Active Form of Vitamin $D_3$ in the Intestine*, Science 173:51–54 (1971).

Lawson, *Identification of 1,25–Dihydroxycholecalciferol, a New Kidney Hormone Controlling Calcium Metabolism*, Nature 230:228–30 (1971).

Adams, et al., *1α,25–Dihydroxycholecalciferol Inhibits Apoptosis in C3H10T1/2 Murine Fibroblast Cells Through Activation of Nuclear Factor κB*, Am. Soc. Nut. Sci. 134:2948 (2004).

Ebert, et al., *Down–Regulation by Nuclear Factor κB of Human 25–Hydroxyvitamin $D_3$ 1α–Hydroxylase Promoter*, Mol. Endocrinology 18:2440–50 (2004).

Berry, et al., *1α,25–Dihydroxyvitamin $D_3$ Stimulates Phosphorylation of IκBα and Synergizes with TPA to Induce Nuclear Translocation of NF–κB During Monocytic Differentiation of NB4 Leukemia Cells*, Exp. Cell Res. 272, 176–84 (2002).

Xing, et al., *Distinctive Dendritic Cell Modulation by Vitamin $D_3$ and Glucocorticoid Pathways*, Biochem. and Biophys. Res. Comm. 297:645–652 (2002).

Komine, et al., *The Action of Novel Vitamin $D_3$ analogue, OCT, on Immunomodulatory Function of Keratinocytes and Lymphocytes*, Arch. Dermatol. Res. 291:500–06 (1999).

Harant, et al., *1α,25–Dihydroxyvitamin $D_3$ Decreases DNA Binding of Nuclear Factor–κB in Human Fibroblasts*, FEBS Lett. 436:329–34 (1998).

Harant, et al., *1α,25–Dihydroxyvitamin $D_3$ and a Variety of Its Natural Metabolites Transcriptionally Repress Nuclear–Factor–κB–Mediated Interleukin–8 Gene Expression*, Eur. J. Biochem., 250:63–71 (1997).

Provvedini et al., *1,25 dihydroxyvitamin $D_3$ Receptors in Human Leukocytes*, Science, 221:1181–83 (1983).

Dew et al., *Maintenance of Remission in Ulcerative Colitis With 5–Amino Salicylic Acid in High Doses By Mouth*, Br. Med. J. 287:23–24 (Jul. 1983).

Bantel et al., *Mesalazine Inhibits Activation of Transcription Factor NF–κB in Inflamed Mucosa of Patients with Ulcerative Colitis*, Arner. J. of Gastroenterology 287:3452 (2000).

Yan and Polk, *Aminosalicylic Acid Inhibits IκB Kinase α Phosphorylation of IκBα in Mouse Intestinal Epithelial Cells*, J. Biol Chem. 274:366631–36 (1999).

Physicians' Desk Reference, pp. 305, 307, 309, 312, 326, 328, 638–639, 809, 880–881, 1167, 1210–1211, 1309–1310, 1323, 1379–1380 (1970 Ed.).

Lefring and Neugebauer, *Steroid Controversy in Sepsis and Septic Shock: A Meta–Analysis;* Crit. Care. Med., 23:1294–1303 (Jul. 1995).

Nagasawa et al., *Induction of Human Malignant T–Lymphoblastic Cell Lines Molt–3 and Jurkat by 12–O–Tetradecaoylphorbol–13–Acetate: Biochemical, Physical and Morphological Characterization*, J. Cell. Phys. 109:181–192 (1981).

Rovera et al., *Induction of Differentiation in Human Promeolytic Leukemia Cells by Tumor Promoters*, Science 204:868–970 (1979).

Auphan et al., *Immunosuppression by Glucocorticoids: Inhibition of NF–κB Activity Through Induction of IκB Synthesis*, Science 270:286–290 (1995).

Scheinman et al., *Characterization of Mechanisms Involved in Transrepression of NF–κB by Activated Glucocorticoid Receptors*, Mol. Cell. Biol. 15:943–53 (Feb. 1995).

Scheinman et al., *Role of Transcriptional Activation of IκBα in Mediation of Immunosuppression by Glucocorticoids,* Science 270:283–186 (Oct. 1995).

Mukaida et al., *Novel Mechanism of Glucocorticoid–mediated Gene Repression,* J. Biol Chem. 269:13289–95 (May 1994).

Galdiero et al., *Porins From Salmonella Enterica Serovar Typhimurium Induce TNF–α, IL–6 and IL–8 Release By CD14–Independent And CD11a/CD18–Dependent Mechanisms,* Microbiology, 147:2697–2704 (2001).

Yang et al., *Toll–Like Receptor–2 Mediates Lipopolysaccharide–Induced Cellular Signaling,* Nature 395, 284–288 (1998).

Mori et al., *Activation of the Interleukin–10 Gene In The Human T Lymphoma Line Hut78: Identification And Characterization Of NF–κB Binding Sites In The Regulatory Region of the Interleukin–10 Gene.,* Eur. J. Haematol. 59:162–170 (1997).

Various excerpts from the Bible, King James Version (1611).

St. Leger et al., *Factors Associated with Cardiac Mortality in Developed Countries With Particular Reference to the Consumption of Wine,* The Lancet, 1017–1020 (May 1979).

Dobrilla et al., *Is Ethanol Metabolism Affected by Oral Administration of Cimetidine and Ranitidine at Therapeutic Doses?* Hepato–Gastroenterol., 31:35–37 (Feb. 1984).

Jones, *Elimination Half–Life of Methanol During Hangover,* Pharm. & Tox. 60:217–220 (Mar. 1987).

Blanco–Colio et al., *Red Wine Intake Prevents Nuclear Factor–κB Activation in Peripheral Blood Mononuclear Cells of Healthy Volunteers During Postprandial Lipemia,* Circulation, 102:1020–1026 (Aug. 2000).

Holmes–McNary and Baldwin, *Chemopreventive Properties of trans–Resveratrol are Associated with Inhibition of Activation of the IκB Kinase,* Cancer Res., 60:3477–483 (Jul. 2000).

Manna et al., *Resveratrol Suppresses TNF–Induced Activation of Nuclear Transcription Factors NF–κB, Activator Protein–1, and Apoptosis: Potential Role of Reactive Oxygen Intermediates and Lipid Peroxidation,* J. of Immunol., 164:6509–6519 (2000).

Weissmann, *Aspirin,* Sci. American, 84–90 (Jan. 1991).

Kopp and Ghosh, *Inhibition of NF–κB by Sodium Salicylate and Aspirin,* Science 265:956–959 (Aug. 1994).

Physicians' Desk Reference, pp. 1147–1149 (1980 Ed.).

Yamamoto, et al., *Sulindac Inhibits Activation of the NF–κB Pathway,* J. Biol. Chem. 274:27307 (1999).

Richards et al., *Gold and Its Relationship to Neurological/Glandular Conditions,* International Journal of Neuroscience, 112:31–53 (2002).

Jeon, et al., *Thiol–reactive Metal Compounds Inhibit NF–κB Activation by Blocking IκB kinase,* J. Immunol. 164:5981–5989 (Jun. 2000).

Yang, et al., *Green Tea Polyphenols Block Endotoxin–Induced Tumor Necrosis Factor–Production and Lethality in a Murine Model,* 128 J. Nutr. 2334 (1998).

Pan, *Suppression of Lipopolysaccharide–Induced Nuclear FactorκB Activity by Theaflavin–3,3'–Digallate from Black Tea and Other Polyphenols through Downregulation of IκB Kinase Activity in Macrophages,* Biochem. Pharmacol. 59:357 (2000).

Singh and Aggarwal, J. Biol. Chem. 270:24995–2500 (1995).

M.M. Manson, et al., *Modulation of signal–transduction pathways by chemopreventive agents,* 28 Biochem. Soc. Trans. 7,9 (2000).

Ide and Lau, *Garlic Compounds Minimize Intracellular Oxidative Stress and Inhibit Nuclear Factor–κB Activation,* 131 J. Nutr. 1020S (2001).

Apr. 20, 2006 Complaint For Declaratory Judgment of Patent Invalidity And Non–Infringement, *Amgen, Inc.* et al. V. *Ariad Pharmaceuticals, Inc.*, Civil Case 06–CV–00259–KAJ.

United States District Court fo the District of Massachusetts, Civil Action No. 02 CV 11280 RWZ, "*Lilly's Post–Trial Proposed Findings of Fact and Conclusions of Law Relating to (1) Invalidity Under 35 U.S.C. § 101, (2) Unenforceability for Inequitable Conduct, and (3) Unenforceability for Prosecution Laches*".

United States District Court for the District of Massachusetts, Civil Action No. 02 CV 11280 RWZ, "*Lilly's Response to Ariad's Proposed Findings of Fact and Conclusions of Law*".

Blanco Colio et al., Manuscript.

Bochkov et al., Blood (2002) 99: 199–206.

Frolik et al., Bone (1996) 18:621–627.

Ghisletti et al., Molecular and Cellular Biology (2005) 25:2957–2968.

\* cited by examiner

– US 6,410,516 C1 –

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 10, lines 16-17:

[FIG. 43 is the nucleotide sequence and the amino acid sequence of IkB-α.]

Column 28, lines 5-17:

The inhibitor fraction was treated with trypsin to test whether IκB is a protein (FIG. 35B). Tryptic digestion was stopped by the addition of bovine pancreas trypsin inhibitor (BPTI) and samples were analyzed for NF-κB inhibition. Trypsin treatment interfered with the activity of IκB, as shown by the complete inability of the treated sample to inhibit NF-κB activity (FIG. 35B, compare lanes 1 and 6). Trypsin that had been treated with BPTI had no effect (FIG. 35B, lane 5), demonstrating that the inactivation of IκB was specifically caused by the proteolytic activity of trypsin. It appears that IκB requires an intact polypeptide structure for its activity. [The nucleotide sequence of the IκB-α gene and the amino acid sequence of IκB-α are shown in FIG. 43.]

THE DRAWING FIGURES HAVE BEEN CHANGED AS FOLLOWS:

Cancel FIG. 43.

AS A RESULT OF REEXAMINATION, IT HAS BEEN DETERMINED THAT:

The patentability of claims 19, 30, 41, 44-46, 52, 63, 74, 87, 98, 101-103, 108, 111-113, 118, 121-123, 130-132, 138, 141-143, 148, 151-153, 158, 161-163, 169-171, 176, 179-181, 186-191, 194-196 and 202 is confirmed.

Claims 1-18, 20-29, 31-40, 42-43, 47-51, 53-62, 64-73, 75-86, 88-97, 99-100, 104-107, 109-110, 114-117, 119-120, 124-129, 133-137, 139-140, 144-147, 149-150, 154-157, 159-160, 164-168, 172-175, 177-178, 182-185, 192-193, 197-201 and 203-211 are cancelled.

* * * * *